US011279917B2

(12) United States Patent
Osborne et al.

(10) Patent No.: US 11,279,917 B2
(45) Date of Patent: *Mar. 22, 2022

(54) P450-BM3 VARIANTS WITH IMPROVED ACTIVITY

(71) Applicant: Codexis, Inc., Redwood City, CA (US)

(72) Inventors: Robert Osborne, Raleigh, NC (US); Vesna Mitchell, Santa Clara, CA (US); Khin Yu Naing Htwe, Daly City, CA (US); Xiyun Zhang, Fremont, CA (US); Erika M. Milczek, New York, NY (US); Jeffrey C. Moore, Westfield, NJ (US)

(73) Assignee: Codexis, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/931,310

(22) Filed: May 13, 2020

(65) Prior Publication Data

US 2020/0332268 A1 Oct. 22, 2020

Related U.S. Application Data

(60) Continuation of application No. 16/131,252, filed on Sep. 14, 2018, which is a continuation of application No. 15/619,176, filed on Jun. 9, 2017, now Pat. No. 10,100,289, which is a division of application No. 14/794,249, filed on Jul. 8, 2015, now Pat. No. 9,708,587.

(60) Provisional application No. 62/022,442, filed on Jul. 9, 2014.

(51) Int. Cl.
| | |
|---|---|
| *C12N 9/02* | (2006.01) |
| *C12N 1/20* | (2006.01) |
| *C12N 15/53* | (2006.01) |
| *C07K 14/80* | (2006.01) |
| *C12P 13/00* | (2006.01) |

(52) U.S. Cl.
CPC ............ *C12N 9/0071* (2013.01); *C07K 14/80* (2013.01); *C12N 9/0042* (2013.01); *C12P 13/001* (2013.01); *C12Y 114/14001* (2013.01); *C12Y 106/02004* (2013.01)

(58) Field of Classification Search
None
See application file for complete search history.

(56) References Cited

U.S. PATENT DOCUMENTS

| | | | |
|---|---|---|---|
| 5,538,867 A | 7/1996 | Durliat et al. |
| 5,605,793 A | 2/1997 | Stemmer |
| 5,811,238 A | 9/1998 | Stemmer et al. |
| 5,830,721 A | 11/1998 | Stemmer et al. |
| 5,834,252 A | 11/1998 | Stemmer et al. |
| 5,837,458 A | 11/1998 | Minshull et al. |
| 5,928,905 A | 7/1999 | Stemmer et al. |
| 6,096,548 A | 8/2000 | Stemmer |
| 6,117,679 A | 9/2000 | Stemmer |
| 6,132,970 A | 10/2000 | Stemmer |
| 6,165,793 A | 12/2000 | Stemmer |
| 6,180,406 B1 | 1/2001 | Stemmer |
| 6,251,674 B1 | 6/2001 | Tobin et al. |
| 6,277,638 B1 | 8/2001 | Stemmer |
| 6,287,861 B1 | 9/2001 | Stemmer et al. |
| 6,287,862 B1 | 9/2001 | delCardayre et al. |
| 6,291,242 B1 | 9/2001 | Stemmer |
| 6,297,053 B1 | 10/2001 | Stemmer |
| 6,303,344 B1 | 10/2001 | Patten et al. |
| 6,309,883 B1 | 10/2001 | Minshull et al. |
| 6,319,713 B1 | 11/2001 | Patten et al. |
| 6,319,714 B1 | 11/2001 | Crameri et al. |
| 6,323,030 B1 | 11/2001 | Stemmer |
| 6,326,204 B1 | 12/2001 | delCardayre et al. |
| 6,335,160 B1 | 1/2002 | Patten et al. |
| 6,335,198 B1 | 1/2002 | delCardayre et al. |
| 6,344,356 B1 | 2/2002 | Stemmer |
| 6,352,859 B1 | 3/2002 | delCardayre et al. |
| 6,355,484 B1 | 3/2002 | Patten et al. |
| 6,358,740 B1 | 3/2002 | Patten et al. |
| 6,358,742 B1 | 3/2002 | Stemmer |
| 6,365,377 B1 | 4/2002 | Patten et al. |
| 6,365,408 B1 | 4/2002 | Stemmer |
| 6,368,861 B1 | 4/2002 | Crameri et al. |
| 6,372,497 B1 | 4/2002 | Stemmer |
| 6,376,246 B1 | 4/2002 | Crameri et al. |
| 6,379,964 B1 | 4/2002 | delCardayre et al. |
| 6,387,702 B1 | 5/2002 | Stemmer |
| 6,391,552 B2 | 5/2002 | Stemmer |
| 6,391,640 B1 | 5/2002 | Minshull et al. |
| 6,395,547 B1 | 5/2002 | Stemmer |
| 6,406,855 B1 | 6/2002 | Patten et al. |

(Continued)

FOREIGN PATENT DOCUMENTS

| | | |
|---|---|---|
| WO | 95/22625 A1 | 8/1995 |
| WO | 95/33836 A1 | 12/1995 |

(Continued)

OTHER PUBLICATIONS

Singh et al., Curr. Protein Pept. Sci. 18:1-11,2017 (Year: 2017).*
Zhang et al., Structure 26:1474-1485, 2018 (Year: 2018).*
Goswami et al., Front. One. 9:297, 2019 (Year: 2019).*
Altschul, S., et al., "Basic local alignment search tool," J. Mol. Biol., 215: 403-410 (1990).
Altschul, S.F., et al., "Gapped BLAST and PSI-BLAST: a new generation of protein database search programs," Nucleic Acids Res., 25(17):3389-3402 (1997).
Beaucage, S.L., et al., "Deoxynucleoside phosphoamidites—A new class of key intermediates for deoxypolynucleotide synthesis," Tetrahedron Letters, 22(20):1859-62 (1981).

(Continued)

*Primary Examiner* — David Steadman
(74) *Attorney, Agent, or Firm* — Codexis, Inc.

(57) ABSTRACT

The present invention provides improved P450-BM3 variants with improved activity. In some embodiments, the P450-BM3 variants exhibit improved activity over a wide range of substrates.

13 Claims, 3 Drawing Sheets

Specification includes a Sequence Listing.

(56) References Cited

U.S. PATENT DOCUMENTS

| | | |
|---|---|---|
| 6,406,910 B1 | 6/2002 | Patten et al. |
| 6,413,745 B1 | 7/2002 | Patten et al. |
| 6,413,774 B1 | 7/2002 | Stemmer |
| 6,420,175 B1 | 7/2002 | Stemmer |
| 6,423,542 B1 | 7/2002 | Crameri et al. |
| 6,426,224 B1 | 7/2002 | Crameri et al. |
| 6,436,675 B1 | 8/2002 | Welch et al. |
| 6,444,468 B1 | 9/2002 | Stemmer et al. |
| 6,455,253 B1 | 9/2002 | Patten et al. |
| 6,479,652 B1 | 11/2002 | Crameri et al. |
| 6,482,647 B1 | 11/2002 | Stemmer |
| 6,489,146 B2 | 12/2002 | Stemmer et al. |
| 6,506,602 B1 | 1/2003 | Stemmer |
| 6,506,603 B1 | 1/2003 | Stemmer |
| 6,519,065 B1 | 2/2003 | Colbourne et al. |
| 6,521,453 B1 | 2/2003 | Crameri et al. |
| 6,528,311 B1 | 3/2003 | delCardayre et al. |
| 6,537,746 B2 | 3/2003 | Arnold et al. |
| 6,573,098 B1 | 6/2003 | Stemmer |
| 6,576,467 B1 | 6/2003 | Stemmer |
| 6,579,678 B1 | 6/2003 | Patten et al. |
| 6,586,182 B1 | 7/2003 | Patten et al. |
| 6,602,986 B1 | 8/2003 | Stemmer et al. |
| 6,613,514 B2 | 9/2003 | Patten et al. |
| 6,653,072 B1 | 11/2003 | Patten et al. |
| 6,716,631 B1 | 4/2004 | delCardayre et al. |
| 6,946,296 B2 | 9/2005 | Patten et al. |
| 6,961,664 B2 | 11/2005 | Selifonov et al. |
| 6,995,017 B1 | 2/2006 | Stemmer |
| 7,024,312 B1 | 4/2006 | Selifonov et al. |
| 7,058,515 B1 | 6/2006 | Selifonov et al. |
| 7,105,297 B2 | 9/2006 | Minshull et al. |
| 7,148,054 B2 | 12/2006 | delCardayre et al. |
| 7,288,375 B2 | 10/2007 | Stemmer et al. |
| 7,421,347 B2 | 9/2008 | Selifonov et al. |
| 7,430,477 B2 | 9/2008 | Selifonov et al. |
| 7,524,664 B2 | 4/2009 | Arnold et al. |
| 7,534,564 B2 | 5/2009 | Patten et al. |
| 7,620,500 B2 | 11/2009 | Mundorff et al. |
| 7,620,502 B2 | 11/2009 | Selifonov et al. |
| 7,629,170 B2 | 12/2009 | delCardayre et al. |
| 7,702,464 B1 | 4/2010 | Emig et al. |
| 7,747,391 B2 | 6/2010 | Gustafsson et al. |
| 7,747,393 B2 | 6/2010 | Fox |
| 7,751,986 B2 | 7/2010 | Gustafsson et al. |
| 7,776,598 B2 | 8/2010 | Patten et al. |
| 7,783,428 B2 | 8/2010 | Gustafsson et al. |
| 7,795,030 B2 | 9/2010 | Minshull et al. |
| 7,853,410 B2 | 12/2010 | Selifonov et al. |
| 7,868,138 B2 | 1/2011 | Stemmer et al. |
| 7,873,499 B2 | 1/2011 | Selifonov et al. |
| 7,904,249 B2 | 3/2011 | Selifonov et al. |
| 7,957,912 B2 | 6/2011 | Selifonov et al. |
| 9,683,220 B2 | 6/2017 | Osborne et al. |
| 9,708,587 B2 | 7/2017 | Osborne et al. |
| 10,100,289 B2 | 10/2018 | Osborne et al. |
| 10,113,153 B2 | 10/2018 | Osborne et al. |
| 10,689,627 B2* | 6/2020 | Osborne .............. C12N 9/0071 |
| 10,704,030 B2* | 7/2020 | Osborne ................ C12N 1/20 |
| 10,982,197 B2* | 4/2021 | Osborne ................ C12N 1/16 |
| 2008/0220990 A1 | 9/2008 | Fox |
| 2008/0268517 A1 | 10/2008 | Arnold et al. |
| 2009/0312196 A1 | 12/2009 | Colbeck et al. |
| 2010/0240106 A1 | 9/2010 | Wong et al. |
| 2011/0244537 A1 | 10/2011 | Arnold et al. |

FOREIGN PATENT DOCUMENTS

| | | |
|---|---|---|
| WO | 96/00787 A1 | 1/1996 |
| WO | 97/0078 A1 | 1/1997 |
| WO | 97/35966 A1 | 10/1997 |
| WO | 98/27230 A1 | 6/1998 |
| WO | 2000/42651 A1 | 7/2000 |
| WO | 2001/75767 A2 | 10/2001 |
| WO | 2005/017105 A2 | 2/2005 |
| WO | 2009/152336 A1 | 12/2009 |
| WO | 2014/070673 A1 | 5/2014 |

OTHER PUBLICATIONS

Black, M.E., et al., "Creation of drug-specific herpes simplex virus type 1 thymidine kinase mutants for gene therapy," Proc Natl Acad Sci USA, 93:3525-3529 (1996).

Botstein, D., et al., "Strategies and applications of in vitro mutagenesis," Science, 229(4719):1193-1201 [1985].

Caldwell, R.C., et al., "Mutagenic PCR," PCR Methods Appl., 3:S136-S140 (1994).

Capdevila, J.H., et al., "The Highly Stereoselective Oxidation of Polyunsaturated Fatty Acids by Cytochrome P450BM-3,"J. Biol. Chem., 271:22663-226671 [1996].

Carter, P., "Site-directed mutagenesis," Biochem. J., 237:1-7 (1986).

Christians, F.C., et al., "Directed evolution of thymidine kinase for AZT phosphorylation using DNA family shuffling," Mat. Biotechnol., 17:259-264 (1999).

Crameri, A., et al., "DNA shuffling of a family of genes from diverse species accelerates directed evolution", Nature, 391:288-291 (1998).

Crameri, A., et al., "Improved green fluorescent protein by molecular evolution using DNA shuffling," Nat. Biotechnol., 14(3):315-319 (1996).

Crameri, A., et al., "Molecular evolution of an arsenate detoxification pathway by DNA shuffling," Nat. Biotechnol., 15(5):436-438 (1997).

Dale, S.J., et al., "Oligonucleotide-directed random mutagenesis using the phosphorothioate method," Methods Mol. Biol., 57:369-74 (1996).

Damsten, M.C., et al., "Application of drug metabolising mutants of cytochrome P450 BM3 (CYP102A1) as biocatalysts for the generation of reactive metabolites," Chem. Biol. Interact., 171:96-107 [2008].

De Boer, H.A., et al., "The tac promoter: A functional hybrid derived from the trp and lac promoters," Proc. Natl Acad. Sci. USA, 80: 21-25(1983).

Di Nardo, G., et al., "Optimization of the Bacterial Cytochrome P450 BM3 System for the Production of Human Drug Metabolites," Int. J. Mol. Sci., 13(12):15901-15924 [2012].

Guo, Z., et al., "3'-End-Forming Signals of Yeast mRNA," Mol. Cell. Biol., 15(11):5983-5990 [1995].

Henikoff, S., et al., "Amino acid substitution matrices from protein blocks," Proc. Natl. Acad. Sci., 89:10915-10919 (1992).

Kramer, B., et al., "Different base/base mismatches are corrected with different efficiencies by the methyl-directed DNA mismatch-repair system of E. coli," Cell, 38(3):879-887,1984.

Ling, M., et al., "Approaches to DNA Mutagenesis:An Overview," Anal. Biochem., 254:157-78 (1997).

Matthes, H.W.D., et al., "Simultaneous rapid chemical synthesis of over one hundred oligonucleotides on a microscale," EMBO J., 3(4):801-05 (1984).

Minshull, J., et al., "Protein evolution by molecular breeding," Curr. Op. Chem. Biol., 3(3):284-290 (1999).

Munro, A.W., et al., "Probing electron transfer in flavocytochrome P-450 BM3 and its component domains," Eur. J. Biochem., 239:403-409 [1996].

Narhi, L.O., et al., "Characterization of a catalytically self-sufficient 119,000-dalton cytochrome P-450 monooxygenase induced by barbiturates in Bacillus megaterium," J. Biol. Chem., 261(18):7160-7169 [1986].

Needleman, S., et al., "A general method applicable to the search for similarities in the amino acid sequence of two proteins," J. Mol. Biol. 48:443-453 (1970).

Noble, M.A., et al., "Roles of key active-site residues in flavocytochrome P450 BM3," Biochem. J., 339:371-379 [1999].

Otey, C.R., et al., "Preparation of human metabolites of propranolol using laboratory-evolved bacterial cytochromes P450," Biotechnol. Bioeng., 93(3):494-499 [2006].

Pearson, W.R., "Improved tools for biological sequence comparison," Proc. Natl. Acad. Sci. USA, 85:2444-2448 (1988).

(56) References Cited

OTHER PUBLICATIONS

Romanos, M.A., et al., "Foreign gene expression in yeast: a review," Yeast 8:423-488 [1992].

Sawayama, A.M., et al., "A panel of cytochrome P450 BM3 variants to produce drug metabolites and diversify lead compounds," Chem., 15(43):11723-11729 [2009].

Simonen, M., et al., "Protein Secretion in Bacillus Species," Microbiological Reviews, 57:109-137 (1993).

Smith, M., "In vitro mutagenesis," Ann. Rev. Genet., 19:423-462 (1985).

Smith, T., et al., "Comparison of Biosequences," Adv. Appl. Math, 2:482-489 (1981).

Stemmer, W., "DNA Shuffling by Random Fragmentation and Reassembly: In vitro Recombination for Molecular Evolution," Proc. Natl. Acad. Sci. USA, 91:10747-10751 (1994).

Stemmer, W.P.C., "Rapid evolution of a protein in vitro by DNA shuffling", Nature, 370:389-391 (1994).

Villa-Komaroff, L., et al., "A bacterial clone synthesizing proinsulin," Proc. Natl Acad. Sci. USA, 75:3727-3731 (1978).

Wells, J.A., et al., "Cassette mutagenesis: an efficient method for generation of multiple mutations at defined sites," Gene, 34:315-323 (1985).

Zhang, J-H., et al., "Directed evolution of a fucosidase from a galactosidase by DNA shuffling and screening ," Proc. Nat. Acad. Sci., U.S.A., 94:4504-4509 (1997).

Zhao, H., et al., "Molecular evolution by staggered extension process (StEP) in vitro recombination," Nat. Biotechnol., 16:258-261 (1998).

Ruettinger, R.T., et al., "Coding nucleotide, 5' regulatory, and deduced amino acid sequences of P-450BM-3, a single peptide cytochrome P-450:NADPH-P-450 reductase from Bacillus megaterium," J. Biol. Chem., 264(19):10987-10995 [1989].

Wen, L-P., et al., "Cloning of the gene encoding a catalytically self-sufficient cytochrome P-450 fatty acid monooxygenase induced by barbiturates in Bacillus megaterium and its functional expression and regulation in heterologous (*Escherichia coli*) and homologous (Bacillus megaterium) hosts," J. Biol. Chem., 262(14):6676-6682 [1987].

Tsotsou, G.E., et al., "Identification of Mutant Asp251Gly/ Gln307His of Cytochrome P450 BM3 for the Generation of Metabolites of Diclofenac, Ibuprofen and Tolbutamide," Chem. Eur. J., 18:3582-3588 [2012].

Sang, H., "Prospects for transgenesis in the chick," Mechanisms of Development, 121:1179-1186 [2004].

Yun, C., et al., "The bacterial P450 BM3: a prototype for a biocatalyst with human P450 activities," TRENDS in Biotechnology, 25(7):289-298 [2007].

\* cited by examiner p-Nitroanisole

Diclofenac

Nifedipine

Propranolol

Verapamil

P450-BM3 VARIANTS WITH IMPROVED ACTIVITY

CROSS-REFERENCE TO RELATED APPLICATION

This application is a continuation of U.S. patent application Ser. No. 16/131,252, filed Sep. 18, 2018, now U.S. Pat. No. 10,689,627, which is a continuation of U.S. patent application Ser. No. 15/619,176, filed Jun. 9, 2017, now U.S. Pat. No. 10,100,289, which is a Divisional of U.S. patent application Ser. No. 14/794,249, filed Jul. 8, 2015, now U.S. Pat. No. 9,708,587, which claims the benefit of U.S. Provisional Application Ser. No. 62/022,442, filed Jul. 9, 2014, the contents of each of which are incorporated herein by reference in their entireties and for all purposes.

FIELD OF THE INVENTION

The present invention provides improved P450-BM3 variants with improved activity. In some embodiments, the P450-BM3 variants exhibit improved activity over a wide range of substrates.

REFERENCE TO SEQUENCE LISTING, TABLE OR COMPUTER PROGRAM

The official copy of the Sequence Listing is submitted concurrently with the specification as an ASCII formatted text file via EFS-Web, with a file name of "CX2-144USP1_ST25_substitute.txt", a creation date of Sep. 16, 2015, and a size of 433 kilobytes. The Sequence Listing filed via EFS-Web is part of the specification and is incorporated in its entirety by reference herein.

BACKGROUND OF THE INVENTION

The cytochrome P450 monooxgenases ("P450s") comprise a large group of widely-distributed heme enzymes that are ubiquitous in the natural world. Cytochrome P450-BM3 ("P450-BM3"), obtained from *Bacillus megaterium* catalyzes the NADPH-dependent hydroxylation of long-chain fatty acids, alcohols, and amides, as well as the epoxidation of unsaturated fatty acids (See e.g., Narhi and Fulco, J. Biol. Chem., 261:7160-7169 [1986]; and Capdevila et al., J. Biol. Chem., 271:2263-22671 [1996]). P450-BM3 is unique, in that the reductase (65 kDa) and monooxygenase (55 kDa) domains of the enzyme are fused and produced as a catalytically self-sufficient 120 kDa enzyme. Although these enzymes have been the subject of numerous studies, there remains a need in the art for improved P450s that exhibit high levels of enzymatic activity over a wide range of substrates.

SUMMARY OF THE INVENTION

The present invention provides improved P450-BM3 variants with improved activity. In some embodiments, the P450-BM3 variants exhibit improved activity over a wide range of substrates.

The present invention provides recombinant cytochrome P450-BM3 variants comprising the sequences set forth in SEQ ID NO:4, 6, 8, 10, 12, 14, 16, 18, 20, 22, 24, 26, 28, 30, 32, 34, 36, 38, 40, 44, 46, 48, 50, 52, 54, 56, 58, 60, 62, 64, 66, and 68. In some additional embodiments, the recombinant cytochrome P450-BM3 variant is set forth in SEQ ID NO:4, 6, 8, 10, 12, 14, 16, 18, 20, 22, 24, 26, 28, 30, 32, 34, 36, 38, 40, 44, 46, 48, 50, 52, 54, 56, 58, 60, 62, 64, 66, or 68. In some embodiments, the recombinant cytochrome P450-BM3 variant comprises a sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO:4, 6, 8, 10, 12, 14, 16, 18, 20, 22, 24, 26, 28, 30, 32, 34, 36, 38, 40, 44, 46, 48, 50, 52, 54, 56, 58, 60, 62, 64, 66, and/or 68. In some embodiments, the recombinant cytochrome P450-BM3 variants oxidize at least three organic substrates. In some additional embodiments, the organic substrate is selected from nifedipine, propranolol, verapamil, diclofenac, and para-nitroanisol.

The present invention also provides isolated polynucleotide sequence encoding the recombinant cytochrome P450-BM3 variants. In some embodiments, the isolated polynucleotide sequence comprises SEQ ID NO:3, 5, 7, 9, 11, 13, 15, 17, 19, 21, 23, 25, 27, 29, 31, 33, 35, 37, 39, 43, 45, 47, 49, 51, 53, 55, 57, 59, 61, 63, 65, or 67. In some additional embodiments, the isolated polynucleotide sequence is set forth in SEQ ID NO:3, 5, 7, 9, 11, 13, 15, 17, 19, 21, 23, 25, 27, 29, 31, 33, 35, 37, 39, 43, 45, 47, 49, 51, 53, 55, 57, 59, 61, 63, 65, or 67. In some further embodiments, the isolated polynucleotide sequence comprises a sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO:3, 5, 7, 9, 11, 13, 15, 17, 19, 21, 23, 25, 27, 29, 31, 33, 35, 37, 39, 43, 45, 47, 49, 51, 53, 55, 57, 59, 61, 63, 65, and/or 67.

The present invention also provides expression vectors comprising at least one polynucleotide sequence provided herein. In some additional embodiments, the vector comprises at least one polynucleotide sequence that is operably linked with at least one regulatory sequence suitable for expression of the polynucleotide sequence in a suitable host cell. In some embodiments, the host cell is a prokaryotic or eukaryotic cell. In some additional embodiments, the host cell is a prokaryotic cell. In some further embodiments, the host cell is *E. coli*. The present invention also provides host cells comprising the vectors provided herein.

The present invention also provides methods for producing at least one recombinant cytochrome P450-BM3 variant comprising culturing the host cell provided herein under conditions such that at least one of the recombinant cytochrome P450-BM3 variants provided herein is produced by the host cell. In some additional embodiments, the methods further comprise the step of recovering at least one recombinant cytochrome P450 variant.

DESCRIPTION OF THE INVENTION

Figure 1:
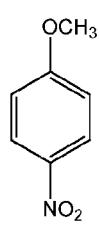
FIG. 1 provides the structures of the substrates used in the screening methods described herein. Diclofenac was used for HTP screening to detect/rank beneficial diversity. The remaining substrates were used to validate that the evolved BM3 variants were active on substrates that were not used for HTP screening.
Figure 1:
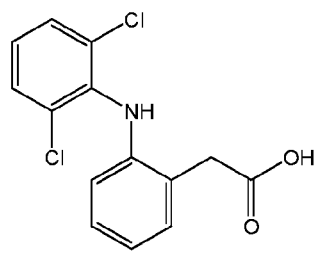
Figure 1:
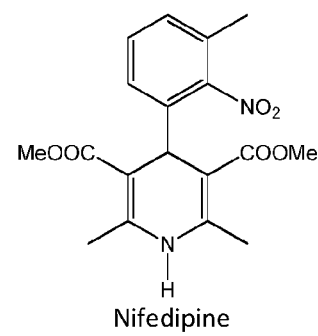
Figure 1:
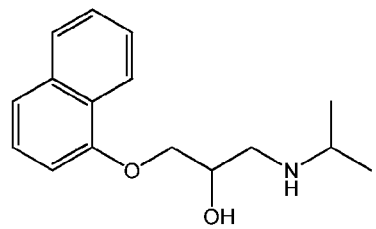
Figure 1:
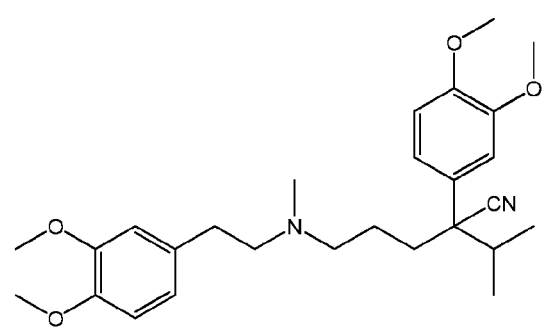

The present invention provides improved P450-BM3 variants with improved activity. In some embodiments, the P450-BM3 variants exhibit improved activity over a wide range of substrates. P450-BM3 enzymes exhibit the highest rate of catalysis amongst P450 monooxygenases due to the efficient electron transfer between the fused reductase and heme domains (See e.g., Noble et al., Biochem. J., 339:371-379 [1999]; and Munro et al., Eur. J. Biochem., 239:403-409 [2009]). Thus, P450-BM3 is a highly desirable enzyme for the manipulation of biotechnological processes (See e.g., Sawayama et al., Chem., 15:11723-11729 [2009]; Otey et al., Biotechnol. Bioeng., 93:494-499 [2006]; Damsten et al., Biol. Interact., 171:96-107 [2008]; and Di Nardo and Gilardi, Int. J. Mol. Sci., 13:15901-15924). However, there still remains a need in the art for P450 enzymes that exhibit activity over a broad range of substrates. The present invention provides P450-BM3 variants that have improved enzymatic activity over a broad range of substrates, as compared to a parental P450-BM3 sequence (i.e., SEQ ID NO:2).

In some embodiments, the present invention provides P450-BM3 variants that provide improved total percent conversion/turnover number for the oxidation of multiple organic substrates (e.g., diclofenac, para-nitroanisol, verpamil, nifedipine, and propranolol; See FIG. 1). In particular, during the development of the present invention, beneficial diversity was identified and recombined based on HTP screening results.

Abbreviations and Definitions:

Unless defined otherwise, all technical and scientific terms used herein generally have the same meaning as commonly understood by one of ordinary skill in the art to which this invention pertains. Generally, the nomenclature used herein and the laboratory procedures of cell culture, molecular genetics, microbiology, organic chemistry, analytical chemistry and nucleic acid chemistry described below are those well-known and commonly employed in the art. Such techniques are well-known and described in numerous texts and reference works well known to those of skill in the art. Standard techniques, or modifications thereof, are used for chemical syntheses and chemical analyses. All patents, patent applications, articles and publications mentioned herein, both supra and infra, are hereby expressly incorporated herein by reference.

Although any suitable methods and materials similar or equivalent to those described herein find use in the practice of the present invention, some methods and materials are described herein. It is to be understood that this invention is not limited to the particular methodology, protocols, and reagents described, as these may vary, depending upon the context they are used by those of skill in the art. Accordingly, the terms defined immediately below are more fully described by reference to the application as a whole. All patents, patent applications, articles and publications mentioned herein, both supra and infra, are hereby expressly incorporated herein by reference.

Also, as used herein, the singular "a", "an," and "the" include the plural references, unless the context clearly indicates otherwise.

Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein.

The term "about" means an acceptable error for a particular value. In some instances "about" means within 0.05%, 0.5%, 1.0%, or 2.0%, of a given value range. In some instances, "about" means within 1, 2, 3, or 4 standard deviations of a given value.

Furthermore, the headings provided herein are not limitations of the various aspects or embodiments of the invention which can be had by reference to the application as a whole. Accordingly, the terms defined immediately below are more fully defined by reference to the application as a whole. Nonetheless, in order to facilitate understanding of the invention, a number of terms are defined below.

Unless otherwise indicated, nucleic acids are written left to right in 5' to 3' orientation; amino acid sequences are written left to right in amino to carboxy orientation, respectively.

As used herein, the term "comprising" and its cognates are used in their inclusive sense (i.e., equivalent to the term "including" and its corresponding cognates).

"EC" number refers to the Enzyme Nomenclature of the Nomenclature Committee of the International Union of Biochemistry and Molecular Biology (NC-IUBMB). The IUBMB biochemical classification is a numerical classification system for enzymes based on the chemical reactions they catalyze.

"ATCC" refers to the American Type Culture Collection whose biorepository collection includes genes and strains.

"NCBI" refers to National Center for Biological Information and the sequence databases provided therein.

As used herein "cytochrome P450-BM3" and "P450-BM3" refer to the cytochrome P450 enzyme obtained from *Bacillus megaterium* that catalyzes the NADPH-dependent hydroxylation of long-chain fatty acids, alcohols, and amides, as well as the epoxidation of unsaturated fatty acids.

"Protein," "polypeptide," and "peptide" are used interchangeably herein to denote a polymer of at least two amino acids covalently linked by an amide bond, regardless of length or post-translational modification (e.g., glycosylation or phosphorylation).

"Amino acids" are referred to herein by either their commonly known three-letter symbols or by the one-letter symbols recommended by IUPAC-IUB Biochemical Nomenclature Commission. Nucleotides, likewise, may be referred to by their commonly accepted single letter codes.

The term "engineered," "recombinant," "non-naturally occurring," and "variant," when used with reference to a cell, a polynucleotide or a polypeptide refers to a material or a material corresponding to the natural or native form of the material that has been modified in a manner that would not otherwise exist in nature or is identical thereto but produced or derived from synthetic materials and/or by manipulation using recombinant techniques.

As used herein, "wild-type" and "naturally-occurring" refer to the form found in nature. For example a wild-type polypeptide or polynucleotide sequence is a sequence present in an organism that can be isolated from a source in nature and which has not been intentionally modified by human manipulation.

"Coding sequence" refers to that part of a nucleic acid (e.g., a gene) that encodes an amino acid sequence of a protein.

The term "percent (%) sequence identity" is used herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman (Smith and Waterman, Adv. Appl. Math., 2:482 [1981]), by the homology alignment algorithm of Needleman and Wunsch (Needleman and Wunsch, J. Mol. Biol., 48:443 [1970]), by the search for similarity method of Pearson and Lipman (Pearson and Lipman, Proc. Natl. Acad. Sci. USA 85:2444 [1988]), by computerized implementations of these algorithms (e.g., GAP, BESTFIT, FASTA, and TFASTA in the GCG Wisconsin Software Package), or by visual inspection, as known in the art. Examples of algorithms that are suitable for determining percent sequence identity and sequence similarity include, but are not limited to the BLAST and BLAST 2.0 algorithms, which are described by Altschul et al. (See, Altschul et al., J. Mol. Biol., 215: 403-410 [1990]; and Altschul et al., 1977, Nucl. Acids Res., 3389-3402 [1977], respectively). Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (See, Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=-4, and a comparison of both strands. For amino acid sequences, the BLASTP program uses as defaults a wordlength (W) of 3, an expectation (E) of 10, and the BLOSUM62 scoring matrix (See, Henikoff and Henikoff, Proc. Natl. Acad. Sci. USA 89:10915 [1989]). Exemplary determination of sequence alignment and % sequence identity can employ the BESTFIT or GAP programs in the GCG Wisconsin Software package (Accelrys, Madison Wis.), using default parameters provided.

"Reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, at least 100 residues in length or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptides are typically performed by comparing sequences of the two polynucleotides or polypeptides over a "comparison window" to identify and compare local regions of sequence similarity. In some embodiments, a "reference sequence" can be based on a primary amino acid sequence, where the reference sequence is a sequence that can have one or more changes in the primary sequence. "Comparison window" refers to a conceptual segment of at least about 20 contiguous nucleotide positions or amino acid residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

"Corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered P450-BM3, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Amino acid difference" or "residue difference" refers to a difference in the amino acid residue at a position of a polypeptide sequence relative to the amino acid residue at a corresponding position in a reference sequence. The positions of amino acid differences generally are referred to herein as "Xn," where n refers to the corresponding position in the reference sequence upon which the residue difference is based. For example, a "residue difference at position X93 as compared to SEQ ID NO:2" refers to a difference of the amino acid residue at the polypeptide position corresponding to position 93 of SEQ ID NO:2. Thus, if the reference polypeptide of SEQ ID NO:2 has a serine at position 93, then a "residue difference at position X93 as compared to SEQ ID NO:2" an amino acid substitution of any residue other than serine at the position of the polypeptide corresponding to position 93 of SEQ ID NO:2. In most instances herein, the specific amino acid residue difference at a position is indicated as "XnY" where "Xn" specified the corresponding position as described above, and "Y" is the single letter identifier of the amino acid found in the engineered polypeptide (i.e., the different residue than in the reference polypeptide). In some instances (e.g., in Table 2-1), the present disclosure also provides specific amino acid differences denoted by the conventional notation "AnB", where A is the single letter identifier of the residue in the reference sequence, "n" is the number of the residue position in the reference sequence, and B is the single letter identifier of the residue substitution in the sequence of the engineered polypeptide. In some instances, a polypeptide of the present disclosure can include one or more amino acid residue differences relative to a reference sequence, which is indicated by a list of the specified positions where residue differences are present relative to the reference sequence. In some embodiments, where more than one amino acid can be used in a specific residue position of a polypeptide, the various amino acid residues that can be used are separated by a "/" (e.g., X307H/X307P or X307H/P). The present application includes engineered polypeptide sequences comprising one or more amino acid differences that include either/or both conservative and non-conservative amino acid substitutions.

"Conservative amino acid substitution" refers to a substitution of a residue with a different residue having a similar side chain, and thus typically involves substitution of the amino acid in the polypeptide with amino acids within the same or similar defined class of amino acids. By way of example and not limitation, an amino acid with an aliphatic side chain may be substituted with another aliphatic amino acid (e.g., alanine, valine, leucine, and isoleucine); an amino acid with hydroxyl side chain is substituted with another amino acid with a hydroxyl side chain (e.g., serine and threonine); an amino acids having aromatic side chains is substituted with another amino acid having an aromatic side chain (e.g., phenylalanine, tyrosine, tryptophan, and histidine); an amino acid with a basic side chain is substituted with another amino acid with a basis side chain (e.g., lysine and arginine); an amino acid with an acidic side chain is substituted with another amino acid with an acidic side chain (e.g., aspartic acid or glutamic acid); and/or a hydrophobic or hydrophilic amino acid is replaced with another hydrophobic or hydrophilic amino acid, respectively.

"Non-conservative substitution" refers to substitution of an amino acid in the polypeptide with an amino acid with significantly differing side chain properties. Non-conservative substitutions may use amino acids between, rather than within, the defined groups and affects (a) the structure of the peptide backbone in the area of the substitution (e.g., proline for glycine) (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

"Deletion" refers to modification to the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the reference enzyme while retaining enzymatic activity and/or retaining the improved properties of an engineered P450-BM3 enzyme. Deletions can be directed to the internal portions and/or terminal portions of the polypeptide. In various embodiments, the deletion can comprise a continuous segment or can be discontinuous.

"Insertion" refers to modification to the polypeptide by addition of one or more amino acids from the reference polypeptide. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

A "functional fragment" or a "biologically active fragment" used interchangeably herein refers to a polypeptide that has an amino-terminal and/or carboxy-terminal deletion(s) and/or internal deletions, but where the remaining amino acid sequence is identical to the corresponding positions in the sequence to which it is being compared (e.g., a full-length engineered P450-BM3 of the present invention) and that retains substantially all of the activity of the full-length polypeptide.

"Isolated polypeptide" refers to a polypeptide which is substantially separated from other contaminants that naturally accompany it, e.g., protein, lipids, and polynucleotides. The term embraces polypeptides which have been removed or purified from their naturally-occurring environment or expression system (e.g., host cell or in vitro synthesis). The recombinant P450-BM3 polypeptides may be present within a cell, present in the cellular medium, or prepared in various forms, such as lysates or isolated preparations. As such, in some embodiments, the recombinant P450-BM3 polypeptides can be an isolated polypeptide.

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. However, in some embodiments, the composition comprising P450-BM3 comprises P450-BM3 that this less than 50% pure (e.g., about 10%, about 20%, about 30%, about 40%, or about 50%) Generally, a substantially pure P450-BM3 composition comprises about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species. In some embodiments, the isolated recombinant P450-BM3 polypeptides are substantially pure polypeptide compositions.

"Improved enzyme property" refers to an engineered P450-BM3 polypeptide that exhibits an improvement in any enzyme property as compared to a reference P450-BM3 polypeptide and/or a wild-type P450-BM3 polypeptide or another engineered P450-BM3 polypeptide. Improved properties include but are not limited to such properties as increased protein expression, increased thermoactivity, increased thermostability, increased pH activity, increased stability, increased enzymatic activity, increased substrate specificity or affinity, increased specific activity, increased resistance to substrate or end-product inhibition, increased chemical stability, improved chemoselectivity, improved solvent stability, increased tolerance to acidic pH, increased tolerance to proteolytic activity (i.e., reduced sensitivity to proteolysis), reduced aggregation, increased solubility, and altered temperature profile.

"Increased enzymatic activity" or "enhanced catalytic activity" refers to an improved property of the engineered P450-BM3 polypeptides, which can be represented by an increase in specific activity (e.g., product produced/time/weight protein) or an increase in percent conversion of the substrate to the product (e.g., percent conversion of starting amount of substrate to product in a specified time period using a specified amount of P450-BM3) as compared to the reference P450-BM3 enzyme. Exemplary methods to determine enzyme activity are provided in the Examples. Any property relating to enzyme activity may be affected, including the classical enzyme properties of $K_m$, $V_{max}$ or $k_{cat}$, changes of which can lead to increased enzymatic activity. Improvements in enzyme activity can be from about 1.1 fold the enzymatic activity of the corresponding wild-type enzyme, to as much as 2-fold, 5-fold, 10-fold, 20-fold, 25-fold, 50-fold, 75-fold, 100-fold, 150-fold, 200-fold or more enzymatic activity than the naturally occurring P450-BM3 or another engineered P450-BM3 from which the P450-BM3 polypeptides were derived.

"Conversion" refers to the enzymatic conversion (or biotransformation) of a substrate(s) to the corresponding product(s). "Percent conversion" refers to the percent of the substrate that is converted to the product within a period of time under specified conditions. Thus, the "enzymatic activity" or "activity" of a P450-BM3 polypeptide can be expressed as "percent conversion" of the substrate to the product in a specific period of time.

"Hybridization stringency" relates to hybridization conditions, such as washing conditions, in the hybridization of nucleic acids. Generally, hybridization reactions are performed under conditions of lower stringency, followed by washes of varying but higher stringency. The term "moderately stringent hybridization" refers to conditions that permit target-DNA to bind a complementary nucleic acid that has about 60% identity, preferably about 75% identity, about 85% identity to the target DNA, with greater than about 90% identity to target-polynucleotide. Exemplary moderately stringent conditions are conditions equivalent to hybridization in 50% formamide, 5×Denhart's solution, 5×SSPE, 0.2% SDS at 42° C., followed by washing in 0.2×SSPE, 0.2% SDS, at 42° C. "High stringency hybridization" refers generally to conditions that are about 10° C. or less from the thermal melting temperature $T_m$ as determined under the solution condition for a defined polynucleotide sequence. In some embodiments, a high stringency condition refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in conditions equivalent to 50% formamide, 5×Denhart's solution, 5×SSPE, 0.2% SDS at 42° C., followed by washing in 0.1×SSPE, and 0.1% SDS at 65° C. Another high stringency condition is hybridizing in conditions equivalent to hybridizing in 5×SSC containing 0.1% (w:v) SDS at 65° C. and washing in 0.1×SSC containing 0.1% SDS at 65° C. Other high stringency hybridization conditions, as well as moderately stringent conditions, are described in the references cited above.

"Codon optimized" refers to changes in the codons of the polynucleotide encoding a protein to those preferentially used in a particular organism such that the encoded protein is more efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding the P450-BM3 enzymes may be codon optimized for optimal production from the host organism selected for expression.

"Control sequence" refers herein to include all components, which are necessary or advantageous for the expression of a polynucleotide and/or polypeptide of the present application. Each control sequence may be native or foreign to the nucleic acid sequence encoding the polypeptide. Such control sequences include, but are not limited to, a leader, polyadenylation sequence, propeptide sequence, promoter sequence, signal peptide sequence, initiation sequence and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

"Operably linked" is defined herein as a configuration in which a control sequence is appropriately placed (i.e., in a functional relationship) at a position relative to a polynucleotide of interest such that the control sequence directs or regulates the expression of the polynucleotide and/or polypeptide of interest.

"Promoter sequence" refers to a nucleic acid sequence that is recognized by a host cell for expression of a polynucleotide of interest, such as a coding sequence. The promoter sequence contains transcriptional control sequences, which mediate the expression of a polynucleotide of interest. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

"Suitable reaction conditions" refers to those conditions in the enzymatic conversion reaction solution (e.g., ranges of enzyme loading, substrate loading, temperature, pH, buffers, co-solvents, etc.) under which a P450-BM3 polypeptide of the present application is capable of converting a substrate to the desired product compound, Exemplary "suitable reaction conditions" are provided in the present application and illustrated by the Examples. "Loading", such as in "compound loading" or "enzyme loading" refers to the concentration or amount of a component in a reaction mixture at the start of the reaction. "Substrate" in the context of an enzymatic conversion reaction process refers to the compound or molecule acted on by the P450-BM3 polypeptide. "Product" in the context of an enzymatic conversion process refers to the compound or molecule resulting from the action of the P450-BM3 polypeptide on a substrate.

As used herein the term "culturing" refers to the growing of a population of microbial cells under any suitable conditions (e.g., using a liquid, gel or solid medium).

Recombinant polypeptides can be produced using any suitable methods known in the art. Genes encoding the wild-type polypeptide of interest can be cloned in vectors, such as plasmids, and expressed in desired hosts, such as *E. coli*, etc. Variants of recombinant polypeptides can be generated by various methods known in the art. Indeed, there is a wide variety of different mutagenesis techniques well known to those skilled in the art. In addition, mutagenesis kits are also available from many commercial molecular biology suppliers. Methods are available to make specific substitutions at defined amino acids (site-directed), specific or random mutations in a localized region of the gene (regio-specific), or random mutagenesis over the entire gene (e.g., saturation mutagenesis). Numerous suitable methods are known to those in the art to generate enzyme variants, including but not limited to site-directed mutagenesis of single-stranded DNA or double-stranded DNA using PCR, cassette mutagenesis, gene synthesis, error-prone PCR, shuffling, and chemical saturation mutagenesis, or any other suitable method known in the art. Non-limiting examples of methods used for DNA and protein engineering are provided in the following patents: U.S. Pat. Nos. 6,117,679; 6,420,175; 6,376,246; 6,586,182; 7,747,391; 7,747,393; 7,783,428; and 8,383,346. After the variants are produced, they can be screened for any desired property (e.g., high or increased activity, or low or reduced activity, increased thermal activity, increased thermal stability, and/or acidic pH stability, etc.). In some embodiments, "recombinant P450-BM3 polypeptides" (also referred to herein as "engineered P450-BM3 polypeptides," "variant P450-BM3 enzymes," and "P450-BM3 variants") find use.

As used herein, a "vector" is a DNA construct for introducing a DNA sequence into a cell. In some embodiments, the vector is an expression vector that is operably linked to a suitable control sequence capable of effecting the expression in a suitable host of the polypeptide encoded in the DNA sequence. In some embodiments, an "expression vector" has a promoter sequence operably linked to the DNA sequence (e.g., transgene) to drive expression in a host cell, and in some embodiments, also comprises a transcription terminator sequence.

As used herein, the term "expression" includes any step involved in the production of the polypeptide including, but not limited to, transcription, post-transcriptional modification, translation, and post-translational modification. In some embodiments, the term also encompasses secretion of the polypeptide from a cell.

As used herein, the term "produces" refers to the production of proteins and/or other compounds by cells. It is intended that the term encompass any step involved in the production of polypeptides including, but not limited to, transcription, post-transcriptional modification, translation, and post-translational modification. In some embodiments, the term also encompasses secretion of the polypeptide from a cell.

As used herein, an amino acid or nucleotide sequence (e.g., a promoter sequence, signal peptide, terminator sequence, etc.) is "heterologous" to another sequence with which it is operably linked if the two sequences are not associated in nature.

As used herein, the terms "host cell" and "host strain" refer to suitable hosts for expression vectors comprising DNA provided herein (e.g., the polynucleotides encoding the P450-BM3 variants). In some embodiments, the host cells are prokaryotic or eukaryotic cells that have been transformed or transfected with vectors constructed using recombinant DNA techniques as known in the art.

The term "analogue" means a polypeptide having more than 70% sequence identity but less than 100% sequence identity (e.g., more than 75%, 78%, 80%, 83%, 85%, 88%, 90%, 91%, 92%, 93%, 94%, 95%, 96%, 97%, 98%, 99% sequence identity) with a reference polypeptide. In some embodiments, analogues means polypeptides that contain one or more non-naturally occurring amino acid residues including, but not limited, to homoarginine, ornithine and norvaline, as well as naturally occurring amino acids. In some embodiments, analogues also include one or more D-amino acid residues and non-peptide linkages between two or more amino acid residues.

The term "effective amount" means an amount sufficient to produce the desired result. One of general skill in the art may determine what the effective amount by using routine experimentation.

The terms "isolated" and "purified" are used to refer to a molecule (e.g., an isolated nucleic acid, polypeptide, etc.) or other component that is removed from at least one other component with which it is naturally associated. The term "purified" does not require absolute purity, rather it is intended as a relative definition.

Engineered P450-BM3 Polypeptides:

In some embodiments, engineered P450-BM3 polypeptides are produced by cultivating a microorganism comprising at least one polynucleotide sequence encoding at least one engineered P450-BM3 polypeptide under conditions which are conducive for producing the engineered P450-BM3 polypeptide(s). In some embodiments, the engineered P450-BM3 polypeptide is recovered from the resulting culture medium and/or cells.

The present invention provides exemplary engineered P450-BM3 polypeptides having P450-BM3 activity. The Examples provide Tables showing sequence structural information correlating specific amino acid sequence features with the functional activity of the engineered P450-BM3 polypeptides. This structure-function correlation information is provided in the form of specific amino acid residues differences relative to a reference engineered polypeptide, as indicated in the Examples. The Examples further provide experimentally determined activity data for the exemplary engineered P450-BM3 polypeptides.

In some embodiments, the engineered P450-BM3 polypeptides of the invention having P450-BM3 activity comprise: a) an amino acid sequence having at least 85% sequence identity to reference sequence SEQ ID NO:2; b) an amino acid residue difference as compared to SEQ ID NO:2 at one or more amino acid positions; and c) which exhibits an improved property selected from i) enhanced catalytic activity, ii) reduced proteolytic sensitivity, iii) increased tolerance to acidic pH, iv) reduced aggregation, v) increased activity on a range of substrates (i.e., enzymes with a broad substrate range), or a combination of any of i), ii), iii) or iv), as compared to the reference sequence.

In some embodiments the engineered P450-BM3 which exhibits an improved property has at least about 85%, at least about 88%, at least about 90%, at least about 91%, at least about 92%, at least about 93%, at least about 94%, at least about 95%, at least about 96%, at least about 97%, at least about 98%, at least about 99%, or at about 100% amino acid sequence identity with SEQ ID NO:2, and an amino acid residue difference as compared to SEQ ID NO:2, at one or more amino acid positions (such as at 1, 2, 3, 4, 5, 6, 7, 8, 9, 10, 11, 12, 14, 15, 20 or more amino acid positions compared to SEQ ID NO:2, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:2). In some embodiment the residue difference as compared to SEQ ID NO:2, at one or more positions will include at least 1, 2, 3, 4, 5, 6, 7, 8, 9, 10 or more conservative amino acid substitutions. In some embodiments, the engineered P450-BM3 polypeptide is a polypeptide listed in Table 2-1.

In some embodiments the engineered P450-BM3 which exhibits an improved property has at least 85%, at least 88%, at least 90%, at least 91%, at least 92%, at least 93%, at least 94%, at least 95%, at least 96%, at least 97%, at least 98%, or at least 99% amino acid sequence identity with SEQ ID NO:2.

In some embodiments, the engineered P450-BM3 polypeptide comprises a functional fragment of an engineered P450-BM3 polypeptide encompassed by the invention. Functional fragments have at least 95%, 96%, 97%, 98%, or 99% of the activity of the engineered P450-BM3 polypeptide from which is was derived (i.e., the parent engineered P450-BM3). A functional fragment comprises at least 90%, 91%, 92%, 93%, 94%, 95%, 96%, 97%, 98% and even 99% of the parent sequence of the engineered P450-BM3. In some embodiments the functional fragment is truncated by less than 5, less than 10, less than 15, less than 10, less than 25, less than 30, less than 35, less than 40, less than 45, and less than 50 amino acids.

Variants with Improved Activity:

In some embodiments, the engineered P450-BM3 polypeptides of the invention having P450-BM3 activity comprise a) an amino acid sequence having at least 85% sequence identity to reference sequence SEQ ID NO:2, or a fragment thereof; b) an amino acid residue difference as compared to SEQ ID NO:2, at one or more amino acid positions; and c) which exhibits improved activity, as compared to SEQ ID NO:2.

In some embodiments, the engineered P450-BM3 that exhibits improved activity has at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:2 and an amino acid residue difference as compared to SEQ ID NO:2, at one or more amino acid positions (such as at 1, 2, 3, 4, 5, 6, 7, 8, 9, 10, 11, 12, 14, 15, 20 or more amino acid positions compared to SEQ ID NO:2, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:2.

In some embodiments, when all other assay conditions are essentially the same, the engineered P450-BM3 polypeptide has improved activity as compared to a reference P450-BM3 polypeptide. In some embodiments this activity can be measured under conditions that monitor enzymatic activity using any suitable assay system to assess the maximum activity of the enzyme (e.g., the $k_{cat}$). In other embodiments this activity can be measured under substrate concentrations resulting in one-half, one-fifth, one-tenth or less of maximal activity. Under either method of analysis, the engineered polypeptide has improved activity levels about 1.0 fold, 1.5-fold, 2-fold, 5-fold, 10-fold, 20-fold, 25-fold, 50-fold, 75-fold, 100-fold, or more of the enzymatic activity of the reference P450-BM3 In some embodiments, the engineered P450-BM3 polypeptide having improved activity as compared to a reference P450-BM3 when measured by any standard assay, including, but not limited to the assays described in the Examples.

In light of the guidance provided herein, it is further contemplated that any of the exemplary engineered polypeptides can be used as the starting amino acid sequence for synthesizing other engineered P450-BM3 polypeptides, for example by subsequent rounds of evolution by adding new combinations of various amino acid differences from other polypeptides and other residue positions described herein. Further improvements may be generated by including amino acid differences at residue positions that had been maintained as unchanged throughout earlier rounds of evolution.

Polynucleotides Encoding Engineered Polypeptides, Expression Vectors and Host Cells:

The present invention provides polynucleotides encoding the engineered P450-BM3 polypeptides described herein. In some embodiments, the polynucleotides are operatively linked to one or more heterologous regulatory sequences that control gene expression to create a recombinant polynucleotide capable of expressing the polypeptide. Expression constructs containing a heterologous polynucleotide encoding the engineered P450-BM3 polypeptides can be introduced into appropriate host cells to express the corresponding P450-BM3 polypeptide.

As will be apparent to the skilled artisan, availability of a protein sequence and the knowledge of the codons corresponding to the various amino acids provide a description of all the polynucleotides capable of encoding the subject polypeptides. The degeneracy of the genetic code, where the same amino acids are encoded by alternative or synonymous codons, allows an extremely large number of nucleic acids to be made, all of which encode the engineered P450-BM3 polypeptide. Thus, having knowledge of a particular amino acid sequence, those skilled in the art could make any number of different nucleic acids by simply modifying the sequence of one or more codons in a way which does not change the amino acid sequence of the protein. In this regard, the present invention specifically contemplates each and every possible variation of polynucleotides that could be made encoding the polypeptides described herein by selecting combinations based on the possible codon choices, and all such variations are to be considered specifically disclosed for any polypeptide described herein, including the variants provided in Table 2-1, as well as SEQ ID NO:2.

In various embodiments, the codons are preferably selected to fit the host cell in which the protein is being produced. For example, preferred codons used in bacteria are used for expression in bacteria. Consequently, codon optimized polynucleotides encoding the engineered P450-BM3 polypeptides contain preferred codons at about 40%, 50%, 60%, 70%, 80%, or greater than 90% of codon positions of the full length coding region.

In some embodiments, as described above, the polynucleotide encodes an engineered polypeptide having P450-BM3 activity with the properties disclosed herein, wherein the polypeptide comprises an amino acid sequence having at least 80%, 85%, 86%, 87%, 88%, 89%, 90%, 91%, 92%, 93%, 94%, 95%, 96%, 97%, 98%, 99% or more identity to a reference sequence (e.g., SEQ ID NO:2), or the amino acid sequence of any variant as disclosed in Table 2-1, and one or more residue differences as compared to the reference polypeptide of SEQ ID NO:2 or the amino acid sequence of any variant as disclosed in Table 2-1 (for example 1, 2, 3, 4, 5, 6, 7, 8, 9, 10 or more amino acid residue positions). In some embodiments, the reference sequence is selected from SEQ ID NO:2.

In some embodiments, the polynucleotides are capable of hybridizing under highly stringent conditions to a reference polynucleotide sequence selected from SEQ ID NO:1, or a complement thereof, or a polynucleotide sequence encoding any of the variant P450-BM3 polypeptides provided herein. In some embodiments, the polynucleotide capable of hybridizing under highly stringent conditions encodes a P450-BM3 polypeptide comprising an amino acid sequence that has one or more residue differences as compared to SEQ ID NO:2.

In some embodiments, an isolated polynucleotide encoding any of the engineered P450-BM3 polypeptides provided herein is manipulated in a variety of ways to provide for expression of the polypeptide. In some embodiments, the polynucleotides encoding the polypeptides are provided as expression vectors where one or more control sequences is present to regulate the expression of the polynucleotides and/or polypeptides. Manipulation of the isolated polynucleotide prior to its insertion into a vector may be desirable or necessary depending on the expression vector. The techniques for modifying polynucleotides and nucleic acid sequences utilizing recombinant DNA methods are well known in the art.

In some embodiments, the control sequences include among other sequences, promoters, leader sequences, polyadenylation sequences, propeptide sequences, signal peptide sequences, and transcription terminators. As known in the art, suitable promoters can be selected based on the host cells used. For bacterial host cells, suitable promoters for directing transcription of the nucleic acid constructs of the present application, include, but are not limited to the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (See e.g., Villa-Kamaroff et al., Proc. Natl Acad. Sci. USA 75: 3727-3731 [1978]), as well as the tac promoter (See e.g., DeBoer et al., Proc. Natl Acad. Sci. USA 80: 21-25 [1983]). Exemplary promoters for filamentous fungal host cells, include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (See e.g., WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof. Exemplary yeast cell promoters can be from the genes can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are known in the art (See e.g., Romanos et al., Yeast 8:423-488 [1992]).

In some embodiments, the control sequence is a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice finds use in the present invention. For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease. Exemplary terminators for yeast host cells can be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are known in the art (See e.g., Romanos et al., supra).

In some embodiments, the control sequence is a suitable leader sequence, a non-translated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells include, but are not limited to those obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells include, but are not limited to those from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are also known in the art (See e.g., Guo and Sherman, Mol. Cell. Bio., 15:5983-5990 [1995]).

In some embodiments, the control sequence is a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. Any signal peptide coding region that directs the expressed polypeptide into the secretory pathway of a host cell of choice finds use for expression of the engineered P450-BM3 polypeptides provided herein. Effective signal peptide coding regions for bacterial host cells include, but are not limited to the signal peptide coding regions obtained from the genes for *Bacillus* NClB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are known in the art (See e.g., Simonen and Palva, Microbiol. Rev., 57:109-137 [1993]). Effective signal peptide coding regions for filamentous fungal host cells include, but are not limited to the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase. Useful signal peptides for yeast host cells include, but are not limited to those from the genes for *Saccharomyces cerevisiae* alpha-factor and *Saccharomyces cerevisiae* invertase.

In some embodiments, the control sequence is a propeptide coding region that codes for an amino acid sequence positioned at the amino terminus of a polypeptide. The resultant polypeptide is referred to as a "proenzyme," "propolypeptide," or "zymogen," in some cases). A propolypeptide can be converted to a mature active polypeptide by catalytic or autocatalytic cleavage of the propeptide from the propolypeptide. The propeptide coding region includes, but is not limited to the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (See e.g., WO 95/33836). Where both signal peptide and propeptide regions are present at the amino terminus of a polypeptide, the propeptide region is positioned next to the amino terminus of a polypeptide and the signal peptide region is positioned next to the amino terminus of the propeptide region.

In some embodiments, regulatory sequences are also utilized. These sequences facilitate the regulation of the expression of the polypeptide relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include, but are not limited to the lac, tac, and trp operator systems. In yeast host cells, suitable regulatory systems include, but are not limited to the ADH2 system or GAL1 system. In filamentous fungi, suitable regulatory sequences include, but are not limited to the TAKA alpha-amylase promoter, *Aspergillus niger* glucoamylase promoter, and *Aspergillus oryzae* glucoamylase promoter.

In another aspect, the present invention also provides a recombinant expression vector comprising a polynucleotide encoding an engineered P450-BM3 polypeptide, and one or more expression regulating regions such as a promoter and a terminator, a replication origin, etc., depending on the type of hosts into which they are to be introduced, in some embodiments, the various nucleic acid and control sequences described above are joined together to produce a recombinant expression vector which includes one or more convenient restriction sites to allow for insertion or substitution of the nucleic acid sequence encoding the variant P450-BM3 polypeptide at such sites. Alternatively, the polynucleotide sequence(s) of the present invention are expressed by inserting the polynucleotide sequence or a nucleic acid construct comprising the polynucleotide sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus), that can be conveniently subjected to recombinant DNA procedures and can result in the expression of the variant P450-BM3 polynucleotide sequence. The choice of the vector will typically depend on the compatibility of the vector with the host cell into which the vector is to be introduced. The vectors may be linear or closed circular plasmids.

In some embodiments, the expression vector is an autonomously replicating vector (i.e., a vector that exists as an extra-chromosomal entity, the replication of which is independent of chromosomal replication, such as a plasmid, an extra-chromosomal element, a minichromosome, or an artificial chromosome). The vector may contain any means for assuring self-replication. In some alternative embodiments, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

In some embodiments, the expression vector preferably contains one or more selectable markers, which permit easy selection of transformed cells. A "selectable marker" is a gene the product of which provides for biocide or viral resistance, resistance to heavy metals, prototrophy to auxotrophs, and the like. Examples of bacterial selectable markers include, but are not limited to the dal genes from *Bacillus subtilis* or *Bacillus licheniformis*, or markers, which confer antibiotic resistance such as ampicillin, kanamycin, chloramphenicol or tetracycline resistance. Suitable markers for yeast host cells include, but are not limited to ADE2, HIS3, LEU2, LYS2, MET3, TRP1, and URA3. Selectable markers for use in a filamentous fungal host cell include, but are not limited to, amdS (acetamidase), argB (ornithine carbamoyltransferases), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. In another aspect, the present invention provides a host cell comprising a polynucleotide encoding at least one engineered P450-BM3 polypeptide of the present application, the polynucleotide being operatively linked to one or more control sequences for expression of the engineered P450-BM3 enzyme(s) in the host cell. Host cells for use in expressing the polypeptides encoded by the expression vectors of the present invention are well known in the art and include but are not limited to, bacterial cells, such as *E. coli, Vibrio fluvialis, Streptomyces* and *Salmonella typhimurium* cells; fungal cells, such as yeast cells (e.g., *Saccharomyces cerevisiae* and *Pichia pastoris* (ATCC Accession No. 201178)); insect cells such as *Drosophila* S2 and *Spodoptera* Sf9 cells; animal cells such as CHO, COS, BHK, 293, and Bowes melanoma cells; and plant cells. Exemplary host cells are *Escherichia coli* strains (such as W3110 (AfhuA) and BL21).

Accordingly, in another aspect, the present invention provides methods for producing the engineered P450-BM3 polypeptides, where the methods comprise culturing a host cell capable of expressing a polynucleotide encoding the engineered P450-BM3 polypeptide under conditions suitable for expression of the polypeptide. In some embodiments, the methods further comprise the steps of isolating and/or purifying the P450-BM3 polypeptides, as described herein.

Appropriate culture media and growth conditions for the above-described host cells are well known in the art. Polynucleotides for expression of the P450-BM3 polypeptides may be introduced into cells by various methods known in the art. Techniques include, among others, electroporation, biolistic particle bombardment, liposome mediated transfection, calcium chloride transfection, and protoplast fusion.

The engineered P450-BM3 with the properties disclosed herein can be obtained by subjecting the polynucleotide encoding the naturally occurring or engineered P450-BM3 polypeptide to mutagenesis and/or directed evolution methods known in the art, and as described herein. An exemplary directed evolution technique is mutagenesis and/or DNA shuffling (See e.g., Stemmer, Proc. Natl. Acad. Sci. USA 91:10747-10751 [1994]; WO 95/22625; WO 97/0078; WO 97/35966; WO 98/27230; WO 00/42651; WO 01/75767 and U.S. Pat. No. 6,537,746). Other directed evolution procedures that can be used include, among others, staggered extension process (StEP), in vitro recombination (See e.g., Zhao et al., Nat. Biotechnol., 16:258-261 [1998]), mutagenic PCR (See e.g., Caldwell et al., PCR Methods Appl., 3:S136-S140 [1994]), and cassette mutagenesis (See e.g., Black et al., Proc. Natl. Acad. Sci. USA 93:3525-3529 [1996]).

For example, mutagenesis and directed evolution methods can be readily applied to polynucleotides to generate variant libraries that can be expressed, screened, and assayed. Mutagenesis and directed evolution methods are well known in the art (See e.g., U.S. Pat. Nos. 5,605,793, 5,830,721, 6,132,970, 6,420,175, 6,277,638, 6,365,408, 6,602,986, 7,288,375, 6,287,861, 6,297,053, 6,576,467, 6,444,468, 5,811238, 6,117,679, 6,165,793, 6,180,406, 6,291,242, 6,995,017, 6,395,547, 6,506,602, 6,519,065, 6,506,603, 6,413,774, 6,573,098, 6,323,030, 6,344,356, 6,372,497, 7,868,138, 5,834,252, 5,928,905, 6,489,146, 6,096,548, 6,387,702, 6,391,552, 6,358,742, 6,482,647, 6,335,160, 6,653,072, 6,355,484, 6,303,344, 6,319,713, 6,613,514, 6,455,253, 6,579,678, 6,586,182, 6,406,855, 6,946,296, 7,534,564, 7,776,598, 5,837,458, 6,391,640, 6,309,883, 7,105,297, 7,795,030, 6,326,204, 6,251,674, 6,716,631, 6,528,311, 6,287,862, 6,335,198, 6,352,859, 6,379,964, 7,148,054, 7,629,170, 7,620,500, 6,365,377, 6,358,740, 6,406,910, 6,413,745, 6,436,675, 6,961,664, 7,430,477, 7,873,499, 7,702,464, 7,783,428, 7,747,391, 7,747,393, 7,751,986, 6,376,246, 6,426,224, 6,423,542, 6,479,652, 6,319,714, 6,521,453, 6,368,861, 7,421,347, 7,058,515, 7,024,312, 7,620,502, 7,853,410, 7,957,912, 7,904,249, and all related non-US counterparts; Ling et al., Anal. Biochem., 254:157-78 [1997]; Dale et al., Meth. Mol. Biol., 57:369-74 [1996]; Smith, Ann. Rev. Genet., 19:423-462 [1985]; Botstein et al., Science, 229:1193-1201 [1985]; Carter, Biochem. J., 237:1-7 [1986]; Kramer et al., Cell, 38:879-887 [1984]; Wells et al., Gene, 34:315-323 [1985]; Minshull et al., Curr. Op. Chem. Biol., 3:284-290 [1999]; Christians et al., Nat. Biotechnol., 17:259-264 [1999]; Crameri et al., Nature, 391:288-291 [1998]; Crameri, et al., Nat. Biotechnol., 15:436-438 [1997]; Zhang et al., Proc. Nat. Acad. Sci. U.S.A., 94:4504-4509 [1997]; Crameri et al., Nat. Biotechnol., 14:315-319 [1996]; Stemmer, Nature, 370:389-391 [1994]; Stemmer, Proc. Nat. Acad. Sci. USA, 91:10747-10751 [1994]; WO 95/22625; WO 97/0078; WO 97/35966; WO 98/27230; WO 00/42651; WO 01/75767; WO 2009/152336, and U.S. Pat. No. 6,537,746, all of which are incorporated herein by reference).

In some embodiments, the enzyme clones obtained following mutagenesis treatment are screened by subjecting the enzymes to a defined temperature (or other assay conditions, such as testing the enzyme's activity over a broad range of substrates) and measuring the amount of enzyme activity remaining after heat treatments or other assay conditions. Clones containing a polynucleotide encoding a P450-BM3 polypeptide are then sequenced to identify the nucleotide sequence changes (if any), and used to express the enzyme in a host cell. Measuring enzyme activity from the expression libraries can be performed using any suitable method known in the art (e.g., standard biochemistry techniques, such as HPLC analysis).

For engineered polypeptides of known sequence, the polynucleotides encoding the enzyme can be prepared by standard solid-phase methods, according to known synthetic methods. In some embodiments, fragments of up to about 100 bases can be individually synthesized, then joined (e.g., by enzymatic or chemical ligation methods, or polymerase mediated methods) to form any desired continuous sequence. For example, polynucleotides and oligonucleotides disclosed herein can be prepared by chemical synthesis using the classical phosphoramidite method (See e.g., Beaucage et al., Tetra. Lett., 22:1859-69 [1981]; and Matthes et al., EMBO J., 3:801-05 [1984]), as it is typically practiced in automated synthetic methods. According to the phosphoramidite method, oligonucleotides are synthesized (e.g., in an automatic DNA synthesizer), purified, annealed, ligated and cloned in appropriate vectors.

Accordingly, in some embodiments, a method for preparing the engineered P450-BM3 polypeptide can comprise: (a) synthesizing a polynucleotide encoding a polypeptide comprising an amino acid sequence selected from the amino acid sequence of any variant provided in Table 2-1, as well as SEQ ID NO:2, and (b) expressing the P450-BM3 polypeptide encoded by the polynucleotide. In some embodiments of the method, the amino acid sequence encoded by the polynucleotide can optionally have one or several (e.g., up to 3, 4, 5, or up to 10) amino acid residue deletions, insertions and/or substitutions. In some embodiments, the amino acid sequence has optionally 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, or 1-50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 17, 18, 19, 20, 21, 22, 23, 24, 25, 30, 30, 35, 40, 45, or 50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 18, 20, 21, 22, 23, 24, or 25 amino acid residue deletions, insertions and/or substitutions. In some embodiments, the substitutions can be conservative or non-conservative substitutions.

The expressed engineered P450-BM3 polypeptide can be measured for any desired improved property (e.g., activity, selectivity, stability, acid tolerance, protease sensitivity, etc.), using any suitable assay known in the art, including but not limited to the assays and conditions described herein.

In some embodiments, any of the engineered P450-BM3 polypeptides expressed in a host cell are recovered from the cells and/or the culture medium using any one or more of the well-known techniques for protein purification, including, among others, lysozyme treatment, sonication, filtration, salting-out, ultra-centrifugation, and chromatography.

Chromatographic techniques for isolation of the P450-BM3 polypeptides include, among others, reverse phase chromatography high performance liquid chromatography, ion exchange chromatography, hydrophobic interaction chromatography, gel electrophoresis, and affinity chromatography. Conditions for purifying a particular enzyme depends, in part, on factors such as net charge, hydrophobicity, hydrophilicity, molecular weight, molecular shape, etc., and will be apparent to those having skill in the art. In some embodiments, affinity techniques may be used to isolate the improved variant P450-BM3 enzymes. In some embodiments utilizing affinity chromatography purification, any antibody which specifically binds the variant P450-BM3 polypeptide finds use. For the production of antibodies, various host animals, including but not limited to rabbits, mice, rats, etc., are immunized by injection with a P450-BM3 polypeptide (e.g., a P450-BM3 variant), or a fragment thereof. In some embodiments, the P450-BM3 polypeptide or fragment is attached to a suitable carrier, such as BSA, by means of a side chain functional group or linkers attached to a side chain functional group.

In some embodiments, the engineered P450-BM3 polypeptide is produced in a host cell by a method comprising culturing a host cell (e.g., an *E. coli* strain) comprising a polynucleotide sequence encoding an engineered P450-BM3 polypeptide as described herein under conditions conducive to the production of the engineered P450-BM3 polypeptide and recovering the engineered P450-BM3 polypeptide from the cells and/or culture medium.

In some embodiments, the engineered P450-BM3 polypeptides are recovered from the recombinant host cells or cell culture and they are further purified by any suitable method(s) known in the art. In some additional embodiments, the purified P450-BM3 polypeptides are combined with other ingredients and compounds to provide compositions and formulations comprising the engineered P450-BM3 polypeptide as appropriate for different applications and uses (e.g., pharmaceutical compositions).

The foregoing and other aspects of the invention may be better understood in connection with the following non-limiting examples. The examples are provided for illustrative purposes only and are not intended to limit the scope of the present invention in any way.

EXPERIMENTAL

The following Examples, including experiments and results achieved, are provided for illustrative purposes only and are not to be construed as limiting the present invention.

In the experimental disclosure below, the following abbreviations apply: ppm (parts per million); M (molar); mM (millimolar), uM and µM (micromolar); nM (nanomolar); mol (moles); gm and g (gram); mg (milligrams); ug and µg (micrograms); L and l (liter); ml and mL (milliliter); cm (centimeters); mm (millimeters); um and µm (micrometers); sec. (seconds); min(s) (minute(s)); h(s) and hr(s) (hour(s)); U (units); MW (molecular weight); rpm (rotations per minute); ° C. (degrees Centigrade); CDS (coding sequence); DNA (deoxyribonucleic acid); RNA (ribonucleic acid); NA (nucleic acid; polynucleotide); AA (amino acid; polypeptide); *E. coli* W3110 (commonly used laboratory *E. coli* strain, available from the Coli Genetic Stock Center [CGSC], New Haven, Conn.); HPLC (high pressure liquid chromatography); SDS-PAGE (sodium dodecyl sulfate polyacrylamide gel electrophoresis); PES (polyethersulfone); CFSE (carboxyfluorescein succinimidyl ester); IPTG (isopropyl beta-D-1-thiogalactopyranoside); PMBS (polymyxin B sulfate); NADPH (nicotinamide adenine dinucleotide phosphate); GDH (glucose dehydrogenase); FIOPC (fold improvement over positive control); ESI (electrospray ionization); LB (Luria broth);TB (terrific broth); MeOH (methanol); Athens Research (Athens Research Technology, Athens, Ga.); ProSpec (ProSpec Tany Technogene, East Brunswick, N.J.); Sigma-Aldrich (Sigma-Aldrich, St. Louis, Mo.); Ram Scientific (Ram Scientific, Inc., Yonkers, N.Y.); Pall Corp. (Pall, Corp., Pt. Washington, N.Y.); Millipore (Millipore, Corp., Billerica Mass.); Difco (Difco Laboratories, BD Diagnostic Systems, Detroit, Mich.); Molecular Devices (Molecular Devices, LLC, Sunnyvale, Calif.); Kuhner (Adolf Kuhner, AG, Basel, Switzerland); Cambridge Isotope Laboratories, (Cambridge Isotope Laboratories, Inc., Tewksbury, Mass.); Applied Biosystems (Applied Biosystems, part of Life Technologies, Corp., Grand Island, N.Y.), Agilent (Agilent Technologies, Inc., Santa Clara, Calif.); Thermo Scientific (part of Thermo Fisher Scientific, Waltham, Mass.); Fisher (Fisher Scientific, Waltham, Mass.); Corning (Corning, Inc., Palo Alto, Calif.); Waters (Waters Corp., Milford, Mass.); GE Healthcare (GE Healthcare Bio-Sciences, Piscataway, N.J.); Pierce (Pierce Biotechnology (now part of Thermo Fisher Scientific), Rockford, Ill.); Phenomenex (Phenomenex, Inc., Torrance, Calif.); Optimal (Optimal Biotech Group, Belmont, Calif.); and Bio-Rad (Bio-Rad Laboratories, Hercules, Calif.).

EXAMPLE 1

P450-BM3 Gene Acquisition and Construction of Expression Vectors

Libraries of P450-BM3 variants were produced using standard methods known in the art, based on the parental sequence of SEQ ID NO:2 (SEQ ID NO:1 is the corresponding polynucleotide sequence) and SEQ ID NO:42 (SEQ ID NO:41 is the corresponding polynucleotide sequence). These variants, cloned into an IPTG-inducible vector were transformed into *E. coli* BL21 strain and plated on LB agar plates supplemented with chloramphenicol (30 µg/mL). The plates were grown at 37° C. for 16 hrs before single clones were picked and added to 96-well AXYGEN® plates (Corning), containing LB medium (250 µL/well) supplemented with chloramphenicol (30 µg/mL). After the plates were shaken at 250 rpm, 30° C., and 85% humidity for 20-24 h to grow the cultures to saturation, an aliquot (50 µL) was used to inoculate 2 mL 96-well COSTAR® deep plates (Corning) containing TB medium (900 µL) supplemented with chloramphenicol (30 µg/mL), trace element solution (740 ug/L ammonium molybdate tetrahydrate, 5.8 mgs/L zinc sulfate heptahydrate, 620 ug/L boric acid anhydrous, 1 mg/L copper sulfate pentahydrate, and 4 mgs/L manganese chloride tetrahydrate), and 0.05 g/L ammonium iron (III) citrate. After being shaken at 250 rpm, 30° C., and 85% humidity to an $OD_{600}$ of 0.8-1.2, P450 expression was induced by addition of IPTG (500 uM) and the heme precursor 5-aminolevulinic acid (5-ALA) to a final concentration of 500 uM. The cultures were shaken at 250 rpm, 26° C., 85% humidity for 24 hrs before the cells were centrifuged and stored at −80° C.

Cell lysis was accomplished by resuspending cell pellets in 96-well COSTAR® plates (Corning) with lysis buffer (200-300 µL/well) containing potassium phosphate, pH 8.0 (100 mM), $MgSO_4$ (10 mM), DTT (1 mM), lysozyme (1 mg/mL), PMBS (0.5 mg/mL), and DNAseI (3 µgs/mL). The lysis reactions were shaken using a Thermo Scientific titer shaker (model 4625 and setting 8-10) at room temperature for 1-2 hrs. The lysis reaction was centrifuged to pellet cellular debris and the supernatant was used in the activity assays described in Example 2.

For the production of lyophilized protein powders, LB agar plates supplemented with chloramphenicol (30 µg/mL) were streaked with *E. coli* containing a desired *B. megaterium* P450-BM3 variant in the IPTG-inducible pCK200 vector. The plates were grown at 37° C. for 16 hrs before single clones were selected to inoculate a 15 mL FALCON™ tube (Fisher) containing TB media (3 mL) supplemented with chloramphenicol (30 µg/mL). The tube was shaken at 200 rpm, 30° C., and 85% humidity for 20-24 h to grow the cultures to saturation. Then, 2.5 mL of the overnight culture was used to inoculate sterile 1 L flasks containing TB medium (250 mL) supplemented with chloramphenicol (30 µg/mL), trace element solution (as indicated above), and 0.05 g/L ammonium iron (III) citrate. After being shaken at 250 rpm, 30° C., and 85% humidity to an $OD_{600}$ of 0.8-1.2, P450 expression was induced by addition of IPTG (500 uM) and the heme precursor 5-aminolevulinic acid (5-ALA) to a final concentration of 500 uM. The cultures were centrifuged in pre-weighed 250 mL centrifuge bottles for 20 minutes at 4000 rpm, 4° C. The supernatants were discarded, and the centrifuge bottles containing cell pellets were weighed. The pellets were resuspended in 50 mM potassium phosphate buffer with 2 mM DTT, pH 8.0 (5 mL of buffer per gram of cell pellet). The cells were lysed using a microfluidics homogenizer, and the suspension of cells and lysate was collected in sterile 50 mL centrifuge tubes. The samples were centrifuged for 30 minutes at 10,000 rpm, 4° C. The clarified lysate was collected into a plastic petri plate and frozen at −80° C. prior to lyophilization. The enzyme-containing lysates were lyophilized using standard methods known in the art.

EXAMPLE 2

Assay Systems & Results

In this Example, the test systems used to assess the activities and generalist properties (i.e., activity on a broad substrate range) are described.

I. Activity-Based High Throughput Screening (HTP) for Enzymatic Activity:

Diclofenac (See, FIG. 1) was used as a substrate for high throughput (HTP) screening assays to detect variants with improved activity. Enzymatic activity screens were initiated by adding 60 µL lysate and 120 µL of the reaction mixture to each well of a 96-well (2 mL) plate. The reaction mixture contained the recycling system (120 mM potassium phosphate, 1.2 mM NADP+, 30 mM glucose, and 0.6 mg/mL glucose dehydrogenase), co-solvent (7.5% DMSO), and substrate (3 mM diclofenac). The reactions were shaken at 250 rpm, 30° C., 85% humidity for 4-24 hrs. The reactions were quenched by the addition of acetonitrile (400 µL to 1 ml) to each well. The quenched reactions were centrifuged to remove precipitated proteins prior to analysis with HPLC and LCMS, as described below.

II. Validation of Generalist Properties:

Lyophilized powders produced as described in Example 1, were dissolved in 100 mM potassium phosphate buffer, pH 7.5 (~12 mgs/mL), and the UV-visible absorption spectrum of each variant was determined. The stock solution of each variant was normalized to ~6 µM. In a 96-well (2 mL) plate, enzymatic activity screens were initiated by adding 50 µL of each lyophilized powder solution (1 µM final) and 250 µL of the reaction mixture to each well. The reaction mixture contained the recycling system (120 mM potassium phosphate, 1.2 mM NADP+, 30 mM glucose, and 0.6 mg/mL glucose dehydrogenase), co-solvent (7.5% DMSO), and substrate (0.6-3 mM). Lyophilized protein powders were first validated using diclofenac to confirm the observations in HTP. Nifedipine, verapamil, and propranolol were selected as substrates to confirm that the BM3 mutants evolved for generalist properties (i.e., broad substrate range) were improved for substrates not used for HTP screening to identify beneficial diversity. The reactions were shaken at 250 rpm, 30° C., 85% humidity for 18 hrs. The reactions were quenched by the addition of acetonitrile (400-1000 µL) to each well. The quenched reactions were centrifuged to remove precipitated proteins prior to analysis with HPLC and LCMS, as described below.

III. HPLC and LCMS Analysis:

For analysis, 150 µL of the quenched reaction sample to be assessed were transferred to 96-well round bottom plates for analysis by HPLC on an Agilent 1200 series equipped with an autosampler. Then, a 10 µL aliquot of the quenched sample was injected onto an ONYX™ Monolithic C18 column (2×50 mm) (Phenomenex). The column was eluted at a constant flow rate of 0.5 mL/min; conditions with solvent A (0.1% formic acid v/v, in $H_2O$) and solvent B (0.1% formic acid v/v, in acetonitrile) used to elute the products of the reaction were: 0-1 min, A/B 90:10; 1-2 min, A/B 80:20; 2-4 min, A/B 70:30; 4-4.5 min, A/B 60:40; 4.5-4.9 min, A/B 10:90, and 4.9-5.3 min, A/B 90:10. The column eluent was monitored by UV at 270 nm.

Alternatively, analysis by LC-UV-MS was performed for some substrates on a Thermo LXQ ion trap system using a SURVEYOR PLUS™ LC-PDA (Thermo Scientific) system for sample separation. For this analysis 0.01 mL of quenched sample was injected into an XBRIDGE® C18 column (3 x 50 mm, 5µ) (Waters). The column was eluted at a constant flow rate of 0.5 mL/min; the conditions with solvent A (0.1% formic acid v/v, in H2O) and solvent B (0.1% formic acid v/v, in acetonitrile) used to elute the products of the reaction were: 0-1.5 min, A/B 90:10; 1.5-5.5 min, A/B 20:80; 5.5-6.0 min, A/B 1:99; 6.0-6.25 min, A/B 90:10; 6.25-7.5 min, A/B 90:10. Column eluent was monitored by PDA (200-600 nm) prior to MS analysis in positive ESI mode (capillary temperature 350° C., 5 kV spray voltage). The column eluent was diverted to waste for the first 1.5 minutes of the run. For the remainder of the LC run, both MS (m/z 125-1000 scan range) and MS/MS were collected. MS/MS spectra were acquired in a data-dependent manner for the nth most intense ions employing dynamic exclusion for dominate ions after the 5th occurrence with an exclusion duration of 30 seconds. The data were analyzed using XCALIBUR™ software (Thermo Scientific) for substrate and product base peaks and MS/MS transitions.

Figure 2:
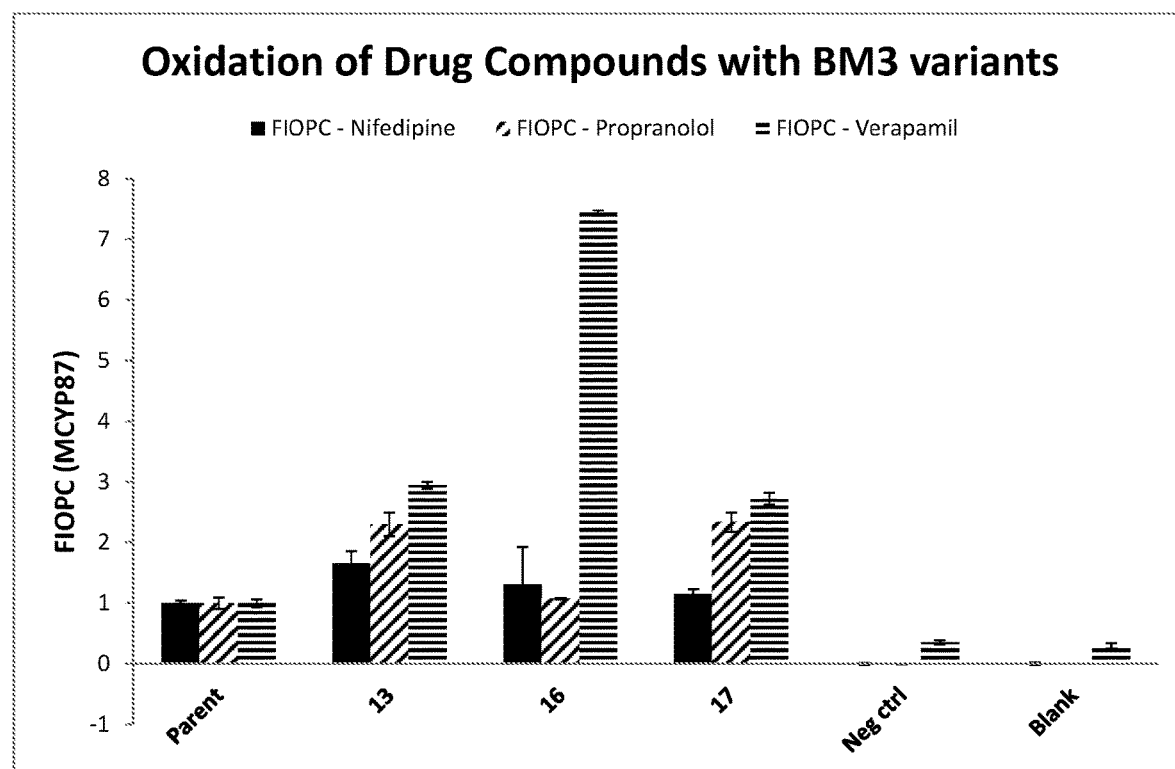
FIG. 2 provides a graph showing the performance of three BM3 variants and the positive control (i.e., the parental BM3 sequence; SEQ ID NO:2) on nifedipine, propranolol and verapamil.

IV. Results:

Variants of P450-BM3 were identified that improve the total % conversion/turnover number for the oxidation of multiple organic substrates (diclofenac, nifedipine, propranolol, and verapamil; See, FIG. 2). In FIG. 2, the fold improvement over positive control (FIOPC; positive control: SEQ ID NOS: 1/2) is plotted as a function of each enzyme's performance using nifedipine, propranolol, and verapamil as substrates. During the development of the present invention, beneficial diversity was identified and recombined as a result of HTP screening using diclofenac or p-nitroanisole as the substrate. Subsequently, lyophilized powders of the best performing BM3 variants were generated and validated using diclofenac as the substrate (enzyme samples were normalized to 1 µM). The results are provided in Table 2-1, below. For variants 1-16, the FIOPC is calculated using MCYP87 as the positive control/parental gene (SEQ ID NOS: 1/2). The FIOPC for variant 17 (SEQ ID NO: 35/36) is calculated using variant 13 (SEQ ID NOS: 15/16) as the positive control/parental gene. The FIOPC for variants 18 and 19 (SEQ ID NOS: 37/38 and 39/40) is calculated using variant 17 (SEQ ID NOS: 35/36) as the positive control/parental gene. Then, a subset of these variants (variants 13, 16, and 17; SEQ ID NOS: 15/16, 33/34, and 35/36) were screened against additional substrates (i.e., substrates that were not used to rank diversity) to determine their performance when screened against additional substrates (FIG. 2).

In Table 2-1, the results are shown based on the following:

| % Conversion | Notation | FIOPC | Notation |
|---|---|---|---|
| 5-10 | + | 0.7-1.0 | * |
| 10.01-15 | ++ | 1.01-1.50 | ** |
| 15.01-20 | +++ | 1.51-2.0 | *** |
| 20.01-25 | ++++ | 2.01-2.5 | **** |
| 25.01-30 | +++++ | 2.51-3.0 | ***** |
| >30 | ++++++ | >3.0 | ****** |

TABLE 2-1

Results for P450-BM3 Variants

| Substrate -- Conc. | Variant # | % Conv. | FIOPC | Mutations (Compared to SEQ ID NO: 2); SEQ ID NOS: (NA/AA) |
|---|---|---|---|---|
| Diclofenac - 1 mM | 1 | +++++ | **** | K32R; I95P; G115R; D232H; E349H (SEQ ID NOS: 5/6) |
| Diclofenac - 1 mM | 2 | ++++ | *** | I95P; L105G; D232H; S724P; A1009T (SEQ ID NOS: 13/14) |
| Diclofenac - 1 mM | 3 | ++++ | **** | L105A; Q110H; K114I; L216Y; Y346W; E349R; Q547N; T613R; L729V (SEQ ID NOS: 21/22) |
| Diclofenac - 1 mM | 4 | ++++ | *** | L105A; Q110H; Y346W; T577H; T613R; L729V (SEQ ID NOS: 23/24) |
| Diclofenac - 1 mM | 5 | +++ | ** | I176Q; D218Q; P347Q; E349S; G458F; D550R; T577P; D600R (SEQ ID NOS: 25/26) |
| Diclofenac - 1 mM | 6 | + | * | P347Q; E349S; G458F; D550R; K771T; A1027Y (SEQ ID NOS: 27/28) |
| Diclofenac - 1 mM | 7 | ++++ | *** | I176V; S231R; E349A; T577A; T613N; D722G; L795M; D992G; A1048M (SEQ ID NOS: 29/30) |
| Diclofenac - 1 mM | 8 | ++++ | **** | S231R; D433K; T613N; A1048M (SEQ ID NOS: 31/32) |
| Diclofenac - 1 mM | 9 | +++++ | **** | K32R; I95P; L105G; A198R; D232H; D433V; T577G; N597L; T613P; L795S; A1009T (SEQ ID NOS: 7/8) |
| Diclofenac - 1 mM | 10 | ++++ | ++++ | I95P; D232H; L795S (SEQ ID NOS: 9/10) |
| Diclofenac - 1 mM | 11 | +++ | *** | I95P; L105G; G115R; D232H; T577G; N597L; T613P; S724P (SEQ ID NOS: 3/4) |
| Diclofenac - 1 mM | 12 | ++ | ** | K32R; I95P; A198R; D232H; S724P; A1009T (SEQ ID NOS: 11/12) |
| Diclofenac - 1 mM | 13 | +++++ | ***** | K32R; G115R; D232H (SEQ ID NOS: 15/16) |
| Diclofenac - 1 mM | 14 | +++ | **** | I95P; L105G; A198R; Q547G; T577G; N597L; S724P (SEQ ID NOS: 17/18) |
| Diclofenac - 1 mM | 15 | +++++ | ****** | K32R; I95P; L105G; D232H; D433V; T577G; N597L; K791H (SEQ ID NOS: 19/20) |
| Diclofenac - 1 mM | 16 | ++++++ | ****** | Y52F; L216Y; K219R; D433R; E616V (SEQ ID NOS: 33/34) |
| Diclofenac - 2 mM | 17 | ++++ | *** | K32R; I95P; G115R; I176V; D232H; M491A (SEQ ID NOS: 35/36) |
| Diclofenac - 2 mM | 18 | +++++ | ** | K32R; L48S; Y52F; I95P; G115R; I176V; L216Y; D232H; E349K; M491A; N574T; T577A; E619D (SEQ ID NOS 37/38) |
| Diclofenac - 2 mM | 19 | +++++ | ** | K32R; L48S; I95P; G115R; I176V; D232H; E349K; K453G; M491A; T577A; E619D (SEQ ID NOS 39/40) |

EXAMPLE 3

Assay Systems & Results

In this Example, the test systems used to assess the activities and generalist properties (i.e., activity on a broad substrate range) transferred to a parental backbone differing by at least 7 mutations compared to the parental gene defined in Example 2 are described.

I. Activity-Based High Throughput Screening (HTP) for Enzymatic Activity:

Diclofenac (See, FIG. 1) was used as a substrate for high throughput (HTP) screening assays to detect variants with improved activity. Enzymatic activity screens were initiated by adding 60 µL lysate and 120 µL of the reaction mixture to each well of a 96-well (2 mL) plate. The reaction mixture contained the recycling system (120 mM potassium phosphate, 1.2 mM NADP+, 30 mM glucose, and 0.6 mg/mL glucose dehydrogenase), co-solvent (7.5% DMSO), and substrate (3 mM diclofenac). The reactions were shaken at 250 rpm, 30° C., 85% humidity for 4-24 hrs. The reactions were quenched by the addition of acetonitrile (400 µL to 1 ml) to each well. The quenched reactions were centrifuged to remove precipitated proteins prior to analysis with HPLC and LCMS, as described below.

II. Validation of Generalist Properties:

Lyophilized powders produced as described in Example 1 were dissolved in 100 mM potassium phosphate buffer, pH 7.5 (~12 mg/mL), and the UV-visible absorption spectrum of each variant was determined. The stock solution of each variant was normalized to ~6 µM. In a 96-well (2 mL) plate, enzymatic activity screens were initiated by adding 50 µL of each lyophilized powder solution (1 µM final) and 250 µL of the reaction mixture to each well. The reaction mixture contained the recycling system (120 mM potassium phosphate, 1.2 mM NADP+, 30 mM glucose, and 0.6 mg/mL glucose dehydrogenase), co-solvent (7.5% DMSO), and substrate (0.6-3 mM). Lyophilized protein powders were first validated using diclofenac to confirm the observations in HTP. Nifedipine, verapamil, and propranolol were selected as substrates to confirm that the beneficial diversity for generalist properties (i.e., applicable to a broad substrate range) transferred to a different parental backbone retained the property of being improved on substrates not used for HTP screening. The reactions were shaken at 250 rpm, 30° C., 85% humidity for 18 hrs. The reactions were quenched by the addition of acetonitrile (400-1000 µL) to each well. The quenched reactions were centrifuged to remove precipitated proteins prior to analysis with HPLC and LCMS, as described below.

III. HPLC and LCMS Analysis:

For analysis, 150 µL of the quenched reaction sample to be assessed were transferred to 96-well round bottom plates for analysis by HPLC on an Agilent 1200 series equipped with an autosampler. Then, a 10 µL aliquot of the quenched sample was injected onto an ONYX™ Monolithic C18 column (2×50 mm) (Phenomenex). The column was eluted at a constant flow rate of 0.5 mL/min; conditions with solvent A (0.1% formic acid v/v, in $H_2O$) and solvent B (0.1% formic acid v/v, in acetonitrile) used to elute the products of the reaction were: 0-1 min, A/B 90:10; 1-2 min, A/B 80:20; 2-4 min, A/B 70:30; 4-4.5 min, A/B 60:40; 4.5-4.9 min, A/B 10:90, and 4.9-5.3 min, A/B 90:10. The column eluent was monitored by UV at 270 nm.

Alternatively, analysis by LC-UV-MS was performed for some substrates on a Thermo LXQ ion trap system using a SURVEYOR PLUS™ LC-PDA (Thermo Scientific) system for sample separation. For this analysis 0.01 mL of quenched sample was injected into an XBRIDGE® C18 column (3×50 mm, 5µ) (Waters). The column was eluted at a constant flow rate of 0.5 mL/min; the conditions with solvent A (0.1% formic acid v/v, in $H_2O$) and solvent B (0.1% formic acid v/v, in acetonitrile) used to elute the products of the reaction were: 0-1.5 min, A/B 90:10; 1.5-5.5 min, A/B 20:80; 5.5-6.0 min, A/B 1:99; 6.0-6.25 min, A/B 90:10; 6.25-7.5 min, A/B 90:10. Column eluent was monitored by PDA (200-600 nm) prior to MS analysis in positive ESI mode (capillary temperature 350° C., 5 kV spray voltage). The column eluent was diverted to waste for the first 1.5 minutes of the run. For the remainder of the LC run, both MS (m/z 125-1000 scan range) and MS/MS were collected. MS/MS spectra were acquired in a data-dependent manner for the nth most intense ions employing dynamic exclusion for dominate ions after the $5^{th}$ occurrence with an exclusion duration of 30 seconds. The data were analyzed using x™ software (Thermo Scientific) for substrate and product base peaks and MS/MS transitions.

IV. Results:

Diversity beneficial for broadening the substrate scope was previously identified over several rounds of evolution leading to the variant MCYP87 (SEQ ID NO:2). Six beneficial mutations were identified and combinations of these mutations were transferred to MCYP P-1.2-A07 (SEQ ID NO: 42) as the parental gene. MCYP P-1.2-A07 differs from MCYP87 by seven mutations, including mutations in the active site and substrate channel that have a significant impact on substrate recognition. The ability to transfer diversity to a different yet related backbone is significant owing to the fact that the identification of beneficial diversity is often rather specific to the reference backbone. The demonstration of transferrable beneficial diversity is important as initial improvements may be manifest without the requirement of initial directed evolution-based HTP screening.

Figure 3:
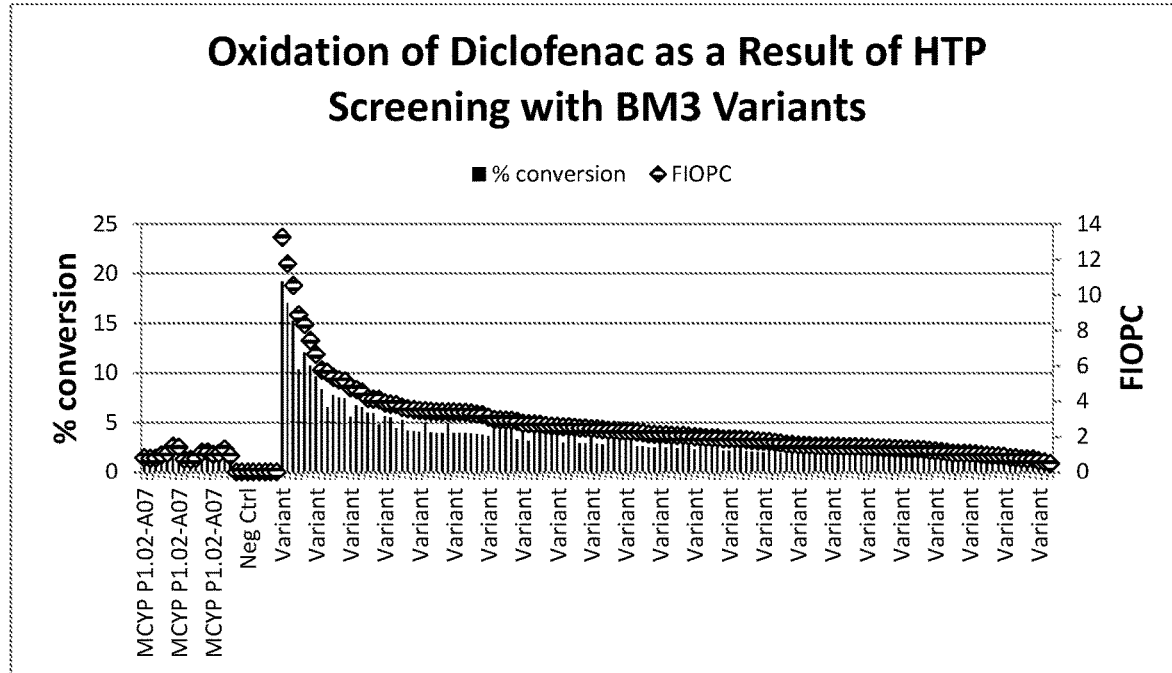
FIG. 3 provides a graph showing the HTP performance of 135 BM3 variants, the negative control (pCK200 vector only), and the positive control (i.e., the parental BM3 sequence; SEQ ID NO:42) on diclofenac.
Figure 4:
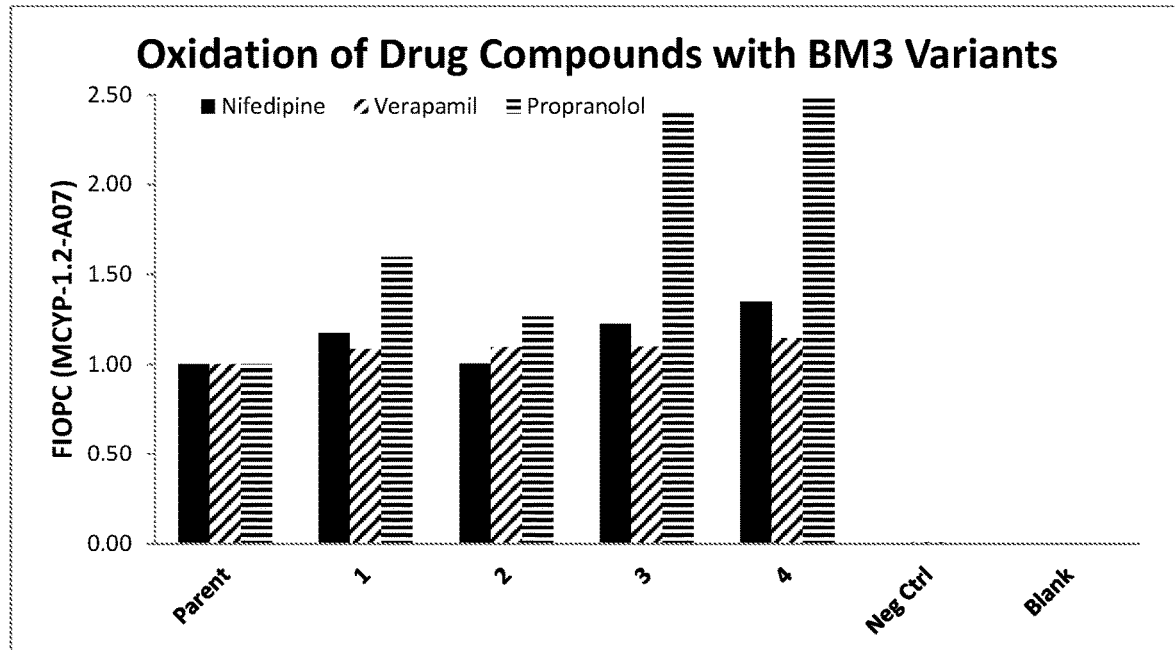
FIG. 4 provides a graph showing the performance of four BM3 variants and the positive control (i.e., the parental BM3 sequence; SEQ ID NO:42) on nifedipine, propranolol and verapamil.

HTP screening of variants of MCYP P1.2-A07 (i.e., SEQ ID NO: 42) was completed using diclofenac as the substrate to test the transferability of the diversity (See, FIG. 1 and FIG. 3). The results are provided in Table 3-1, below. The FIOPC in table 3-1 were calculated using MCYP-1.2-A07 (SEQ ID NOS: 41/42) as the positive control. Then, lyophilized protein powders for a subset of these variants (variants 1, 2, 3, and 4; SEQ ID NOS: 43/44, 45/46, 47/48, and 49/50) were generated and screened against multiple organic substrates (nifedipine, propranolol, and verapamil; See, FIG. 4). These variants of P450-BM3 retain their ability to improve the total % conversion/turnover number for the oxidation of the substrates evaluated. In FIG. 4, the fold improvement over positive control (FIOPC, as compared to MCYP P1.2-A07 [SEQ ID NO:42]) is plotted as a function of each enzyme's performance using nifedipine, propranolol, and verapamil as substrates.

In Table 3-1, the results are shown based on the following:

| % Conversion | Notation | FIOPC | Notation |
|---|---|---|---|
| 0-5.00 | + | 1.0-3.0 | * |
| 5.01-10.00 | ++ | 3.01-5.0 | ** |
| 10.01-15.00 | +++ | 5.01-10.0 | *** |
| 15.01-20.00 | ++++ | 10.01-15.00 | **** |

TABLE 3-1

Results for P450-BM3 Variants

| Substrate - Conc. | Variant # | % Conv. | FIOPC | Mutations (Compared to SEQ ID NO: 42)[a] |
|---|---|---|---|---|
| Diclofenac - 2 mM | [b]1 | ++++ | **** | I95P; G115R; I176V; D232H (SEQ ID NOS: 43/44) |
| Diclofenac - 2 mM | [b]2 | ++++ | *** | K32R; I95P; G115R; I176V; M491A (SEQ ID NOS: 45/46) |
| Diclofenac - 2 mM | [b]3 | ++++ | **** | I95P; G115R; M491A (SEQ ID NOS: 47/48) |
| Diclofenac - 2 mM | [b]4 | ++++ | *** | I95P; G115R; I176V; D232H; M491A (SEQ ID NOS: 49/50) |
| Diclofenac - 2 mM | 5 | + | * | K32R; G115R; D232H; M491A (SEQ ID NOS: 51/52) |
| Diclofenac - 2 mM | 6 | + | * | K32R; G115R; M491A (SEQ ID NOS: 53/54) |
| Diclofenac - 2 mM | 7 | + | * | K32R; I95P; G115R; D232H; M491A (SEQ ID NOS: 55/56) |
| Diclofenac - 2 mM | 8 | ++++ | *** | K32R; I95P; G115R; I176V; D232H; M491A (SEQ ID NOS: 57/58) |
| Diclofenac - 2 mM | 9 | + | * | G115R; I176V; D232H; M491A (SEQ ID NOS: 59/60) |
| Diclofenac - 2 mM | 10 | + | * | I176V; M491A; (SEQ ID NOS: 61/62) |
| Diclofenac - 2 mM | 11 | + | ** | I95P; G115R; D232H (SEQ ID NOS: 63/64) |
| Diclofenac - 2 mM | 12 | ++ | ** | I95P; G115R; I176V; D232H; T516P (SEQ ID NOS: 65/66) |
| Diclofenac - 2 mM | 13 | + | * | I95P; I176V; D232H; M491A (SEQ ID NOS: 67/68) |

[a]Sequence ID NO: 42 corresponds to MCYP-1.2-A07.
[b]Shake flask powders validated.

While the invention has been described with reference to the specific embodiments, various changes can be made and equivalents can be substituted to adapt to a particular situation, material, composition of matter, process, process step or steps, thereby achieving benefits of the invention without departing from the scope of what is claimed.

For all purposes in the United States of America, each and every publication and patent document cited in this disclosure is incorporated herein by reference as if each such publication or document was specifically and individually indicated to be incorporated herein by reference. Citation of publications and patent documents is not intended as an indication that any such document is pertinent prior art, nor does it constitute an admission as to its contents or date.

What is claimed is:

1. A recombinant cytochrome P450-BM3 variant having cytochrome P450-BM3 activity and comprising the amino acid sequence of SEQ ID NO: 48.

2. The recombinant cytochrome P450-BM3 variant of claim 1, wherein said variant oxidizes at least three organic substrates.

3. The recombinant cytochrome P450-BM3 variant of claim 2, wherein the at least three organic substrates are selected from the group consisting of nifedipine, propranolol, verapamil, and diclofenac.

4. An isolated polynucleotide comprising a polynucleotide sequence encoding the recombinant cytochrome P450-BM3 variant of claim 1.

5. The isolated polynucleotide of claim 4, wherein said polynucleotide comprises the polynucleotide sequence of SEQ ID NO: 47.

6. An expression vector comprising the polynucleotide of claim 4.

7. The vector of claim 6, wherein said polynucleotide sequence is operably linked with regulatory sequences suitable for expression of said polynucleotide sequence in a suitable host cell.

8. The vector of claim 7, wherein said host cell is a prokaryotic or eukaryotic cell.

9. The vector of claim 8, wherein said host cell is a prokaryotic cell.

10. The vector of claim 8, wherein said host cell is *E. coli*.

11. An isolated host cell comprising the vector of claim 6.

12. A method for producing at least one recombinant cytochrome P450-BM3 variant comprising culturing the host cell of claim 11 under conditions such that the recombinant cytochrome P450-BM3 variant is produced.

13. The method of claim 12, further comprising the step of recovering said at least one recombinant cytochrome P450-BM3 variant.

* * * * *

SEQUENCE LISTING

```
<160> NUMBER OF SEQ ID NOS: 68

<210> SEQ ID NO 1
<211> LENGTH: 3150
<212> TYPE: DNA
<213> ORGANISM: Artificial Sequence
<220> FEATURE:
<223> OTHER INFORMATION: synthetic P450-BM3 variant polynucleotide

<400> SEQUENCE: 1
atgacaataa aggaaatgcc gcagccgaaa acgtttggag aacttaaaaa tttaccgtta      60
ttaaacacag ataaaccggt tcaagctttg atgaaaattg cggatgaatt aggagaaatc     120
tttaaattcg aggcgcctgg tttggtaacg atttacttat caagtcagcg tctaattaaa     180
gaagcatgcg atgaatcacg ctttgataaa aacttaagtc aggcgatgaa atttgcacgt     240
gattttctgg gagacgggtt agcaacaagc tggacgcatg aaataaattg gaaaaaagcg     300
cataatatct tacttccaag ctttagtcag caggcaatga aaggctatca tgcgatgatg     360
gtcgatatcg ccgtgcagct tgttcaaaag tgggagcgtc taaatgcaga tgagcatatt     420
gaagtatcgg aagacatgac acgtttaacg cttgatacaa ttggtctttg cggctttaac     480
tatcgcttta acagctttta ccgagatcag cctcatccat ttattataag tatggtccgt     540
```

```
gcactggatg aagtaatgaa caagcgtcag cgagcaaatc cagacgaccc agcttatgat    600
gaaaacaagc gccagtgtca agaagatatc aaggtgatga acgacctagt agataaaatt    660
attgcagatc gcaaagcaag gggtgaacaa agcgatgatt tattaacgca gatgctaaac    720
ggaaaagatc cagaaacggg tgagccgctt gatgacggga acattagcta tcaaattatt    780
acattcttaa ttgcgggaca cgaaacaaca agtggtcttt tatcatttgc gctgtatttc    840
ttagtgaaaa atccacatgt attacaaaaa gtagcagaag aagcagcacg agttctagta    900
gatcctgttc caagctacaa acaagtcaaa cagcttaaat atgtcggcat ggtcttaaac    960
gaagcgctgc gcttatggcc aactgctcct gcgttttccc tatatgcaaa agaagatacg   1020
gtgcttggag gagaatatcc tttagaaaaa ggcgacgaag taaatgttct gattcctcag   1080
cttcaccgtg ataaaacaat ttggggagac gatgtggagg agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact ttgaagatca tacaaactac gagctcgata ttaaagaaac tttaacgtta   1320
aaacctgaag gctttgtggt aaaagcaaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat atgggaacag ctgaaggaac ggcgcgtgat   1500
ttagcagata ttgcaatgag caaaggattt gcaccgcagg tcgcaacgct tgattcacac   1560
gccggaaatc ttccgcgcga aggagctgta ttaattgtaa cggcgtctta taacggtcat   1620
ccgcctgata acgcaaagca atttgtcgac tggttagacc aagcgtctgc tgatgaagta   1680
aaaggcgttc gctactccgt atttggatgc ggcgataaaa actgggctac tacgtatcaa   1740
aaagtgcctg cttttatcga tgaaacgctt gccgctaaag gggcagaaaa catcgctgac   1800
cgcggtgaag cagatgcaag cgacgacttt gaaggcacat atgaagaatg gcgtgaacat   1860
atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctggaa gcagaagaag aaaaattagc tcatttgcca   2220
ctcgctaaaa cagtatccgt agaagagctt ctgcaatacg tggagcttca agatcctgcg   2280
acgcgcacgc agcttcgcgc aatggctgct aaaacggtct gcccgccgca taaagtagag   2340
cttgaagcct tgcttgaaaa gcaagcctac aaagaacaag tgctggcaaa cgtttaaca    2400 atgcttgaac tgcttgaaaa atacccggcg tgtgaaatga aattcagcga atttatcgcc   2460
cttctgccaa gcatacgccc gcgctattac tcgatttctt catcacctcg tgtcgatgaa   2520
aaacaagcaa gcatcacggt cagcgttgtc tcaggagaag cgtggagcgg atatggagaa   2580
tataaaggaa ttgcgtcgaa ctatcttgcc gagctgcaag aaggagatac gattacgtgc   2640
tttatttcca caccgcagtc agaatttacg ctgccaaaag accctgaaac gccgcttatc   2700
atggtcggac cgggaacagg cgtcgcgccg tttagaggct tgtgcaggc gcgcaaacag   2760 ctaaaagaac aaggacagtc acttggagaa gcacatttat acttcggctg ccgttcacct   2820
catgaagact atctgtatca agaagagctt gaaaacgccc aaagcgaagg catcattacg   2880
```

```
cttcatac cg cttttt ctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctgggtaa                                     3150
```

<210> SEQ ID NO 2
<211> LENGTH: 1049
<212> TYPE: PRT
<213> ORGANISM: Artificial Sequence
<220> FEATURE:
<223> OTHER INFORMATION: synthetic P450-BM3 variant polypeptide

<400> SEQUENCE: 2

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Leu
        35                  40                  45

Val Thr Ile Tyr Leu Ser Ser Gln Arg Leu Ile Lys Glu Ala Cys Asp
    50                  55                  60

Glu Ser Arg Phe Asp Lys Asn Leu Ser Gln Ala Met Lys Phe Ala Arg
65                  70                  75                  80

Asp Phe Leu Gly Asp Gly Leu Ala Thr Ser Trp Thr His Glu Ile Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Ala Leu Asp Glu Val Met Asn Lys Arg Gln Arg Ala
            180                 185                 190

Asn Pro Asp Asp Pro Ala Tyr Asp Glu Asn Lys Arg Gln Cys Gln Glu
        195                 200                 205

Asp Ile Lys Val Met Asn Asp Leu Val Asp Lys Ile Ile Ala Asp Arg
    210                 215                 220

Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Val Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320
```

Glu Ala Leu Arg Leu Trp Pro Thr Ala Pro Ala Phe Ser Leu Tyr Ala
            325                 330                 335

Lys Glu Asp Thr Val Leu Gly Gly Glu Tyr Pro Leu Glu Lys Gly Asp
            340                 345                 350

Glu Val Asn Val Leu Ile Pro Gln Leu His Arg Asp Lys Thr Ile Trp
            355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
            405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
            435                 440                 445

Ala Lys Ser Lys Lys Ile Pro Leu Gly Gly Ile Pro Ser Pro Ser Thr
            450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
            485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
            565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
            595                 600                 605

Asp Phe Glu Gly Thr Tyr Glu Glu Trp Arg Glu His Met Trp Ser Asp
            610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
            645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
            675                 680                 685

Leu Pro Lys Glu Ala Ser Tyr Gln Glu Gly Asp His Leu Gly Val Ile
            690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Glu Lys Leu
            725                 730                 735

Ala His Leu Pro Leu Ala Lys Thr Val Ser Val Glu Glu Leu Leu Gln
            740                 745                 750

Tyr Val Glu Leu Gln Asp Pro Ala Thr Arg Thr Gln Leu Arg Ala Met
        755                 760                 765

Ala Ala Lys Thr Val Cys Pro His Lys Val Glu Leu Glu Ala Leu
770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Ala Gly
    1040                1045

<210> SEQ ID NO 3
<211> LENGTH: 3150
<212> TYPE: DNA
<213> ORGANISM: Artificial Sequence
<220> FEATURE:
<223> OTHER INFORMATION: synthetic P450-BM3 variant polynucleotide

<400> SEQUENCE: 3
atgacaataa aggaaatgcc gcagccgaaa acgtttggag aacttaaaaa tttaccgtta      60
ttaaacacag ataaaccggt tcaagctttg atgaaaattg cggatgaatt aggagaaatc     120
tttaaattcg aggcgcctgg tttggtaacg atttacttat caagtcagcg tctaattaaa     180
gaagcatgcg atgaatcacg ctttgataaa aacttaagtc aggcgatgaa atttgcacgt     240
gattttctgg gagacgggtt agcaacaagc tggacgcatg aaccgaattg gaaaaagcg      300

```
cataatatct taggcccaag ctttagtcag caggcaatga aacgttatca tgcgatgatg    360
gtcgatatcg ccgtgcagct tgttcaaaag tgggagcgtc taaatgcaga tgagcatatt    420
gaagtatcgg aagacatgac acgtttaacg cttgatacaa ttggtctttg cggctttaac    480
tatcgcttta acagctttta ccgagatcag cctcatccat ttattataag tatggtccgt    540
gcactggatg aagtaatgaa caagcgtcag cgagcaaatc cagacgaccc agcttatgat    600
gaaaacaagc gccagtgtca agaagatatc aaggtgatga acgacctagt agataaaatt    660
attgcagatc gcaaagcaag gggtgaacaa agccatgatt tattaacgca gatgctaaac    720
ggaaaagatc cagaaacggg tgagccgctt gatgacggga acattagcta tcaaattatt    780
acattcttaa ttgcgggaca cgaaacaaca agtggtcttt tatcatttgc gctgtatttc    840
ttagtgaaaa atccacatgt attacaaaaa gtagcagaag aagcagcacg agttctagta    900
gatcctgttc caagctacaa acaagtcaaa cagcttaaat atgtcggcat ggtcttaaac    960
gaagcgctgc gcttatggcc aactgctcct gcgttttccc tatatgcaaa agaagatacg   1020
gtgcttggag gagaatatcc tttagaaaaa ggcgacgaag taaatgttct gattcctcag   1080
cttcaccgtg ataaaacaat ttggggagac gatgtggagg agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact ttgaagatca tacaaactac gagctcgata ttaaagaaac tttaacgtta   1320
aaacctgaag gctttgtggt aaaagcaaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat atgggaacag ctgaaggaac ggcgcgtgat   1500
ttagcagata ttgcaatgag caaaggattt gcaccgcagg tcgcaacgct tgattcacac   1560
gccggaaatc ttccgcgcga aggagctgta ttaattgtaa cggcgtctta taacggtcat   1620
ccgcctgata acgcaaagca atttgtcgac tggttagacc aagcgtctgc tgatgaagta   1680
aaaggcgttc gctactccgt atttggatgc ggcgataaaa actgggctgg cacgtatcaa   1740
aaagtgcctg cttttatcga tgaaacgctt gccgctaaag gggcagaact gatcgctgac   1800
cgcggtgaag cagatgcaag cgacgacttt gaaggcccgt atgaagaatg gcgtgaacat   1860
atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctagatgcac cgcagcaaat ccgtctggaa gcagaagaag aaaaattagc tcatttgcca   2220
ctcgctaaaa cagtatccgt agaagagctt ctgcaatacg tggagcttca agatcctgcg   2280
acgcgcacgc agcttcgcgc aatggctgct aaaacggtct gcccgccgca taaagtagag   2340
cttgaagcct tgcttgaaaa gcaagcctac aaagaacaag tgctggcaaa acgtttaaca   2400
atgcttgaac tgcttgaaaa atacccggcg tgtgaaatga aattcagcga atttatcgcc   2460
cttctgccaa gcatacgccc gcgctattac tcgatttctt catcacctcg tgtcgatgaa   2520
aaacaagcaa gcatcacggt cagcgttgtc tcaggagaag cgtggagcgg atatggaaaa   2580
tataaaggaa ttgcgtcgaa ctatcttgcc gagctgcaag aaggagatac gattacgtgc   2640
```

-continued

```
tttatttcca caccgcagtc agaatttacg ctgccaaaag accctgaaac gccgcttatc    2700
atggtcggac cgggaacagg cgtcgcgccg tttagaggct tgtgcaggc gcgcaaacag    2760 ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg cttttctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctgggtaa                                     3150
```

<210> SEQ ID NO 4
<211> LENGTH: 1049
<212> TYPE: PRT
<213> ORGANISM: Artificial Sequence
<220> FEATURE:
<223> OTHER INFORMATION: synthetic P450-BM3 variant polypeptide

<400> SEQUENCE: 4

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Leu
        35                  40                  45

Val Thr Ile Tyr Leu Ser Ser Gln Arg Leu Ile Lys Glu Ala Cys Asp
    50                  55                  60

Glu Ser Arg Phe Asp Lys Asn Leu Ser Gln Ala Met Lys Phe Ala Arg
65                  70                  75                  80

Asp Phe Leu Gly Asp Gly Leu Ala Thr Ser Trp Thr His Glu Pro Asn
                85                  90                  95

Trp Lys Lys Ala His Asn Ile Leu Gly Pro Ser Phe Ser Gln Gln Ala
            100                 105                 110

Met Lys Arg Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Ala Leu Asp Glu Val Met Asn Lys Arg Gln Arg Ala
            180                 185                 190

Asn Pro Asp Asp Pro Ala Tyr Asp Glu Asn Lys Arg Gln Cys Gln Glu
        195                 200                 205

Asp Ile Lys Val Met Asn Asp Leu Val Asp Lys Ile Ile Ala Asp Arg
    210                 215                 220

Lys Ala Arg Gly Glu Gln Ser His Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
            260                 265                 270
```

-continued

```
Leu Leu Ser Phe Ala Leu Tyr Phe Leu Val Lys Asn Pro His Val Leu
            275                 280                 285
Gln Lys Val Ala Glu Ala Ala Arg Val Leu Val Asp Pro Val Pro
        290                 295                 300
Ser Tyr Lys Gln Val Lys Gln Leu Lys Tyr Val Gly Met Val Leu Asn
305                 310                 315                 320
Glu Ala Leu Arg Leu Trp Pro Thr Ala Pro Ala Phe Ser Leu Tyr Ala
                325                 330                 335
Lys Glu Asp Thr Val Leu Gly Gly Glu Tyr Pro Leu Glu Lys Gly Asp
            340                 345                 350
Glu Val Asn Val Leu Ile Pro Gln Leu His Arg Asp Lys Thr Ile Trp
        355                 360                 365
Gly Asp Asp Val Glu Glu Phe Arg Pro Glu Arg Phe Glu Asn Pro Ser
370                 375                 380
Ala Ile Pro Gln His Ala Phe Lys Pro Phe Gly Asn Gly Gln Arg Ala
385                 390                 395                 400
Cys Ile Gly Gln Gln Phe Ala Leu His Glu Ala Thr Leu Val Leu Gly
                405                 410                 415
Met Met Leu Lys His Phe Asp Phe Glu Asp His Thr Asn Tyr Glu Leu
            420                 425                 430
Asp Ile Lys Glu Thr Leu Thr Leu Lys Pro Glu Gly Phe Val Val Lys
        435                 440                 445
Ala Lys Ser Lys Lys Ile Pro Leu Gly Gly Ile Pro Ser Pro Ser Thr
        450                 455                 460
Glu Gln Ser Ala Lys Lys Val Arg Lys Lys Ala Glu Asn Ala His Asn
465                 470                 475                 480
Thr Pro Leu Leu Val Leu Tyr Gly Ser Asn Met Gly Thr Ala Glu Gly
                485                 490                 495
Thr Ala Arg Asp Leu Ala Asp Ile Ala Met Ser Lys Gly Phe Ala Pro
            500                 505                 510
Gln Val Ala Thr Leu Asp Ser His Ala Gly Asn Leu Pro Arg Glu Gly
        515                 520                 525
Ala Val Leu Ile Val Thr Ala Ser Tyr Asn Gly His Pro Pro Asp Asn
530                 535                 540
Ala Lys Gln Phe Val Asp Trp Leu Asp Gln Ala Ser Ala Asp Glu Val
545                 550                 555                 560
Lys Gly Val Arg Tyr Ser Val Phe Gly Cys Gly Asp Lys Asn Trp Ala
                565                 570                 575
Gly Thr Tyr Gln Lys Val Pro Ala Phe Ile Asp Glu Thr Leu Ala Ala
            580                 585                 590
Lys Gly Ala Glu Leu Ile Ala Asp Arg Gly Glu Ala Asp Ala Ser Asp
        595                 600                 605
Asp Phe Glu Gly Pro Tyr Glu Glu Trp Arg Glu His Met Trp Ser Asp
610                 615                 620
Val Ala Ala Tyr Phe Asn Leu Asp Ile Glu Asn Ser Glu Asp Asn Lys
625                 630                 635                 640
Ser Thr Leu Ser Leu Gln Phe Val Asp Ser Ala Ala Asp Met Pro Leu
                645                 650                 655
Ala Lys Met His Gly Ala Phe Ser Thr Asn Val Val Ala Ser Lys Glu
            660                 665                 670
Leu Gln Gln Pro Gly Ser Ala Arg Ser Thr Arg His Leu Glu Ile Glu
        675                 680                 685
Leu Pro Lys Glu Ala Ser Tyr Gln Glu Gly Asp His Leu Gly Val Ile
```

```
                690                 695                 700
Pro Arg Asn Tyr Glu Gly Ile Val Asn Arg Val Thr Ala Arg Phe Gly
705                 710                 715                 720

Leu Asp Ala Pro Gln Gln Ile Arg Leu Glu Ala Glu Glu Lys Leu
            725                 730                 735

Ala His Leu Pro Leu Ala Lys Thr Val Ser Val Glu Leu Leu Gln
            740                 745                 750

Tyr Val Glu Leu Gln Asp Pro Ala Thr Arg Thr Gln Leu Arg Ala Met
        755                 760                 765

Ala Ala Lys Thr Val Cys Pro Pro His Lys Val Glu Leu Glu Ala Leu
770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln
    1010            1015            1020

Val Ser Glu Ala Asp Ala Arg Leu Trp Leu Gln Gln Leu Glu Glu
    1025            1030            1035

Lys Gly Arg Tyr Ala Lys Asp Val Trp Ala Gly
    1040            1045

<210> SEQ ID NO 5
<211> LENGTH: 3150
<212> TYPE: DNA
<213> ORGANISM: Artificial Sequence
<220> FEATURE:
<223> OTHER INFORMATION: synthetic P450-BM3 variant polynucleotide

<400> SEQUENCE: 5
atgacaataa aggaaatgcc gcagccgaaa acgtttggag aacttaaaaa tttaccgtta        60
```

```
ttaaacacag ataaaccggt tcaagctttg atgcgtattg cggatgaatt aggagaaatc    120
tttaaattcg aggcgcctgg tttggtaacg atttacttat caagtcagcg tctaattaaa    180
gaagcatgcg atgaatcacg ctttgataaa aacttaagtc aggcgatgaa atttgcacgt    240
gattttctgg gagacgggtt agcaacaagc tggacgcatg aaccgaattg gaaaaaagcg    300
cataatatct tacttccaag ctttagtcag caggcaatga aacgttatca tgcgatgatg    360
gtcgatatcc ccgtgcagct tgttcaaaag tgggagcgtc taaatgcaga tgagcatatt    420
gaagtatcgg aagacatgac acgtttaacg cttgatacaa ttggtctttg cggctttaac    480
tatcgcttta acagctttta ccgagatcag cctcatccat ttattataag tatggtccgt    540
gcactggatg aagtaatgaa caagcgtcag cgagcaaatc cagacgaccc agcttatgat    600
gaaaacaagc gccagtgtca agaagatatc aaggtgatga acgacctagt agataaaatt    660
attgcagatc gcaaagcaag gggtgaacaa agccatgatt tattaacgca gatgctaaac    720
ggaaaagatc cagaaacggg tgagccgctt gatgacggga acattagcta tcaaattatt    780
acattcttaa ttgcgggaca cgaaacaaca agtggtcttt tatcatttgc gctgtatttc    840
ttagtgaaaa atccacatgt attacaaaaa gtagcagaag aagcagcacg agttctagta    900
gatcctgttc caagctacaa acaagtcaaa cagcttaaat atgtcggcat ggtcttaaac    960
gaagcgctgc gcttatggcc aactgctcct gcgttttccc tatatgcaaa agaagatacg   1020
gtgcttggag gagaatatcc tttacataaa ggcgacgaag taaatgttct gattcctcag   1080
cttcaccgtg ataaacaat ttggggagac gatgtggagg agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact tgaagatca tacaaactac gagctcgata ttaaagaaac tttaacgtta   1320
aaacctgaag gctttgtggt aaaagcaaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat atgggaacag ctgaaggaac ggcgcgtgat   1500
ttagcagata ttgcaatgag caaaggattt gcaccgcagg tcgcaacgct tgattcacac   1560
gccggaaatc ttccgcgcga aggagctgta ttaattgtaa cggcgtctta taacggtcat   1620
ccgcctgata acgcaaagca atttgtcgac tggttagacc aagcgtctgc tgatgaagta   1680
aaaggcgttc gctactccgt atttggatgc ggcgataaaa actgggctac tacgtatcaa   1740
aaagtgcctg cttttatcga tgaaacgctt gccgctaaag gggcagaaaa catcgctgac   1800
cgcggtgaag cagatgcaag cgacgacttt gaaggcacat atgaagaatg cgtgaacat    1860 atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctggaa gcagaagaag aaaaattagc tcatttgcca   2220
ctcgctaaaa cagtatccgt agaagagctt ctgcaatacg tggagcttca agatcctgcg   2280
acgcgcacgc agcttcgcgc aatggctgct aaaacggtct gcccgccgca taagtagag    2340 cttgaagcct tgcttgaaaa gcaagcctac aaagaacaag tgttagcaaa acgtttaaca   2400
```

-continued

```
atgcttgaac tgcttgaaaa atacccggcg tgtgaaatga aattcagcga atttatcgcc    2460
cttctgccaa gcatacgccc gcgctattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct tgtgcaggc gcgcaaacag    2760 ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg cttttctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctgggtaa                                    3150
```

<210> SEQ ID NO 6
<211> LENGTH: 1049
<212> TYPE: PRT
<213> ORGANISM: Artificial Sequence
<220> FEATURE:
<223> OTHER INFORMATION: synthetic P450-BM3 variant polypeptide

<400> SEQUENCE: 6

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Arg
            20                  25                  30

Ile Ala Asp Glu Leu Gly Glu Ile Phe Lys Phe Glu Ala Pro Gly Leu
        35                  40                  45

Val Thr Ile Tyr Leu Ser Ser Gln Arg Leu Ile Lys Glu Ala Cys Asp
    50                  55                  60

Glu Ser Arg Phe Asp Lys Asn Leu Ser Gln Ala Met Lys Phe Ala Arg
65                  70                  75                  80

Asp Phe Leu Gly Asp Gly Leu Ala Thr Ser Trp Thr His Glu Pro Asn
                85                  90                  95

Trp Lys Lys Ala His Asn Ile Leu Leu Pro Ser Phe Ser Gln Gln Ala
            100                 105                 110

Met Lys Arg Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Ala Leu Asp Glu Val Met Asn Lys Arg Gln Arg Ala
            180                 185                 190

Asn Pro Asp Asp Pro Ala Tyr Asp Glu Asn Lys Arg Gln Cys Gln Glu
        195                 200                 205

Asp Ile Lys Val Met Asn Asp Leu Val Asp Lys Ile Ile Ala Asp Arg
    210                 215                 220

Lys Ala Arg Gly Glu Gln Ser His Asp Leu Leu Thr Gln Met Leu Asn
```

-continued

```
             225                 230                 235                 240
Gly Lys Asp Pro Glu Thr Gly Glu Pro Leu Asp Asp Gly Asn Ile Ser
                 245                 250                 255

Tyr Gln Ile Ile Thr Phe Leu Ile Ala Gly His Glu Thr Thr Ser Gly
                 260                 265                 270

Leu Leu Ser Phe Ala Leu Tyr Phe Leu Val Lys Asn Pro His Val Leu
                 275                 280                 285

Gln Lys Val Ala Glu Ala Ala Arg Val Leu Val Asp Pro Val Pro
            290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                 325                 330                 335

Lys Glu Asp Thr Val Leu Gly Gly Glu Tyr Pro Leu His Lys Gly Asp
                 340                 345                 350

Glu Val Asn Val Leu Ile Pro Gln Leu His Arg Asp Lys Thr Ile Trp
                 355                 360                 365

Gly Asp Asp Val Glu Glu Phe Arg Pro Glu Arg Phe Glu Asn Pro Ser
            370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                 405                 410                 415

Met Met Leu Lys His Phe Asp Phe Glu Asp His Thr Asn Tyr Glu Leu
                 420                 425                 430

Asp Ile Lys Glu Thr Leu Thr Leu Lys Pro Glu Gly Phe Val Val Lys
            435                 440                 445

Ala Lys Ser Lys Lys Ile Pro Leu Gly Gly Ile Pro Ser Pro Ser Thr
            450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                 485                 490                 495

Thr Ala Arg Asp Leu Ala Asp Ile Ala Met Ser Lys Gly Phe Ala Pro
                 500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
            530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                 565                 570                 575

Thr Thr Tyr Gln Lys Val Pro Ala Phe Ile Asp Glu Thr Leu Ala Ala
                 580                 585                 590

Lys Gly Ala Glu Asn Ile Ala Asp Arg Gly Glu Ala Asp Ala Ser Asp
            595                 600                 605

Asp Phe Glu Gly Thr Tyr Glu Glu Trp Arg Glu His Met Trp Ser Asp
            610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                 645                 650                 655
```

```
Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Ala Thr Arg Thr Gln Leu Arg Ala Met
        755                 760                 765

Ala Ala Lys Thr Val Cys Pro Pro His Lys Val Glu Leu Glu Ala Leu
    770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Ala Gly
    1040                1045

<210> SEQ ID NO 7
<211> LENGTH: 3150
```

```
<212> TYPE: DNA
<213> ORGANISM: Artificial Sequence
<220> FEATURE:
<223> OTHER INFORMATION: synthetic P450-BM3 variant polynucleotide

<400> SEQUENCE: 7
atgacaataa aggaaatgcc gcagccgaaa acgtttggag aacttaaaaa tttaccgtta      60
ttaaacacag ataaaccggt tcaagctttg atgcgtattg cggatgaatt aggagaaatc     120
tttaaattcg aggcgcctgg tttggtaacg atttacttat caagtcagcg tctaattaaa     180
gaagcatgcg atgaatcacg ctttgataaa aacttaagtc aggcgatgaa atttgcacgt     240
gattttctgg agacgggttt agcaacaagc tggacgcatg aaccgaattg gaaaaaagcg     300
cataatatct taggcccaag ctttagtcag caggcaatga aaggctatca tgcgatgatg     360
gtcgatatcg ccgtgcagct tgttcaaaag tgggagcgtc taaatgcaga tgagcatatt     420
gaagtatcgg aagacatgac acgtttaacg cttgatacaa ttggtctttg cggctttaac     480
tatcgcttta acagctttta ccgagatcag cctcatccat ttattataag tatggtccgt     540
gcactggatg aagtaatgaa caagcgtcag cgagcaaatc cagacgaccc acgttatgat     600
gaaaacaagc gccagtgtca agaagatatc aaggtgatga cgacctagt agataaaatt     660
attgcagatc gcaaagcaag gggtgaacaa agccatgatt tattaacgca gatgctaaac     720
ggaaaagatc cagaaacggg tgagccgctt gatgacggga acattagcta tcaaattatt     780
acattcttaa ttgcgggaca cgaaacaaca agtggtcttt tatcatttgc gctgtatttc     840
ttagtgaaaa atccacatgt attacaaaaa gtagcagaag aagcagcacg agttctagta     900
gatcctgttc caagctacaa acaagtcaaa cagcttaaat atgtcggcat ggtcttaaac     960
gaagcgctgc gcttatggcc aactgctcct gcgttttccc tatatgcaaa agaagatacg    1020
gtgcttggag gagaatatcc tttagaaaaa gcgacgaagt aaatgttct gattcctcag    1080
cttcaccgtg ataaacaat tggggagac gatgtggagg agttccgtcc agagcgtttt    1140
gaaaatccaa gtgcgattcc gcagcatgcg tttaaaccgt ttggaaacgg tcagcgtgcg    1200
tgtatcggtc agcagttcgc tcttcatgaa gcaacgctgg tacttggtat gatgctaaaa    1260
cactttgact ttgaagatca tacaaactac gagctcgtga ttaaagaaac tttaacgtta    1320
aaacctgaag gctttgtggt aaaagcaaaa tcgaaaaaaa ttccgcttgg cggtattcct    1380
tcacctagca ctgaacagtc tgctaaaaaa gtacgcaaaa aggcagaaaa cgctcataat    1440
acgccgctgc ttgtgctata cggttcaaat atgggaacag ctgaaggaac ggcgcgtgat    1500
ttagcagata ttgcaatgag caaaggattt gcaccgcagg tcgcaacgct tgattcacac    1560
gccggaaatc ttccgcgcga aggagctgta ttaattgtaa cggcgtctta taacggtcat    1620
ccgcctgata acgcaaagca atttgtcgac tggttagacc aagcgtctgc tgatgaagta    1680
aaaggcgttc gctactccgt atttggatgc ggcgataaaa actgggctgg cacgtatcaa    1740
aaagtgcctg ctttatcga tgaaacgctt gccgctaaag gggcagaact gatcgctgac    1800
cgcggtgaag cagatgcaag cgacgacttt gaaggcccgt atgaagaatg gcgtgaacat    1860
atgtggagtg acgtagcagc ctactttaac ctcgacattg aaaacagtga agataataaa    1920
tctactcttt cacttcaatt tgtcgacagc gccgcggata tgccgcttgc gaaaatgcac    1980
ggtgcgtttt caacgaacgt cgtagcaagc aaagaacttc aacagccagg cagtgcacga    2040
agcacgcgac atcttgaaat tgaacttcca aaagaagctt cttatcaaga aggagatcat    2100
ttaggtgtta ttcctcgcaa ctatgaagga atagtaaacc gtgtaacagc aaggttcggc    2160
```

```
ctagatgcat cacagcaaat ccgtctggaa gcagaagaag aaaaattagc tcatttgcca    2220
ctcgctaaaa cagtatccgt agaagagctt ctgcaatacg tggagcttca agatcctgcg    2280
acgcgcacgc agcttcgcgc aatggctgct aaaacggtct gcccgccgca taaagtagag    2340
cttgaagcct tgcttgaaaa gcaagcctac aaagaacaag tgtcagcaaa acgtttaaca    2400
atgcttgaac tgcttgaaaa atacccggcg tgtgaaatga aattcagcga atttatcgcc    2460
cttctgccaa gcatacgccc gcgctattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct ttgtgcaggc gcgcaaacag    2760
ctaaaagaac aaggacagtc acttggagaa gcacatttat acttcggctg ccgttcacct    2820
catgaagact atctgtatca agaagagctt gaaacgcccc aaagcgaagg catcattacg    2880
cttcataccg cttttctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc acctaccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctgggtaa                                    3150

<210> SEQ ID NO 8
<211> LENGTH: 1049
<212> TYPE: PRT
<213> ORGANISM: Artificial Sequence
<220> FEATURE:
<223> OTHER INFORMATION: synthetic P450-BM3 variant polypeptide

<400> SEQUENCE: 8

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Arg
            20                  25                  30

Ile Ala Asp Glu Leu Gly Glu Ile Phe Lys Phe Glu Ala Pro Gly Leu
        35                  40                  45

Val Thr Ile Tyr Leu Ser Ser Gln Arg Leu Ile Lys Glu Ala Cys Asp
    50                  55                  60

Glu Ser Arg Phe Asp Lys Asn Leu Ser Gln Ala Met Lys Phe Ala Arg
65                  70                  75                  80

Asp Phe Leu Gly Asp Gly Leu Ala Thr Ser Trp Thr His Glu Pro Asn
                85                  90                  95

Trp Lys Lys Ala His Asn Ile Leu Gly Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Ala Leu Asp Glu Val Met Asn Lys Arg Gln Arg Ala
            180                 185                 190
```

```
Asn Pro Asp Asp Pro Arg Tyr Asp Glu Asn Lys Arg Gln Cys Gln Glu
            195                 200                 205

Asp Ile Lys Val Met Asn Asp Leu Val Asp Lys Ile Ile Ala Asp Arg
210                 215                 220

Lys Ala Arg Gly Glu Gln Ser His Asp Leu Leu Thr Gln Met Leu Asn
225                 230                 235                 240

Gly Lys Asp Pro Glu Thr Gly Glu Pro Leu Asp Asp Gly Asn Ile Ser
            245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
            275                 280                 285

Gln Lys Val Ala Glu Ala Ala Arg Val Leu Val Asp Pro Val Pro
            290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
            325                 330                 335

Lys Glu Asp Thr Val Leu Gly Gly Glu Tyr Pro Leu Glu Lys Gly Asp
            340                 345                 350

Glu Val Asn Val Leu Ile Pro Gln Leu His Arg Asp Lys Thr Ile Trp
            355                 360                 365

Gly Asp Asp Val Glu Glu Phe Arg Pro Glu Arg Phe Glu Asn Pro Ser
            370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
            405                 410                 415

Met Met Leu Lys His Phe Asp Phe Glu Asp His Thr Asn Tyr Glu Leu
            420                 425                 430

Val Ile Lys Glu Thr Leu Thr Leu Lys Pro Glu Gly Phe Val Val Lys
            435                 440                 445

Ala Lys Ser Lys Lys Ile Pro Leu Gly Gly Ile Pro Ser Pro Ser Thr
            450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
            485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
            530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
            565                 570                 575

Gly Thr Tyr Gln Lys Val Pro Ala Phe Ile Asp Glu Thr Leu Ala Ala
            580                 585                 590

Lys Gly Ala Glu Leu Ile Ala Asp Arg Gly Glu Ala Asp Ala Ser Asp
            595                 600                 605
```

-continued

```
Asp Phe Glu Gly Pro Tyr Glu Glu Trp Arg Glu His Met Trp Ser Asp
610                 615                 620
Val Ala Ala Tyr Phe Asn Leu Asp Ile Glu Asn Ser Glu Asp Asn Lys
625                 630                 635                 640
Ser Thr Leu Ser Leu Gln Phe Val Asp Ser Ala Ala Asp Met Pro Leu
                645                 650                 655
Ala Lys Met His Gly Ala Phe Ser Thr Asn Val Val Ala Ser Lys Glu
                660                 665                 670
Leu Gln Gln Pro Gly Ser Ala Arg Ser Thr Arg His Leu Glu Ile Glu
                675                 680                 685
Leu Pro Lys Glu Ala Ser Tyr Gln Glu Gly Asp His Leu Gly Val Ile
            690                 695                 700
Pro Arg Asn Tyr Glu Gly Ile Val Asn Arg Val Thr Ala Arg Phe Gly
705                 710                 715                 720
Leu Asp Ala Ser Gln Gln Ile Arg Leu Glu Ala Glu Glu Lys Leu
                725                 730                 735
Ala His Leu Pro Leu Ala Lys Thr Val Ser Val Glu Glu Leu Leu Gln
                740                 745                 750
Tyr Val Glu Leu Gln Asp Pro Ala Thr Arg Thr Gln Leu Arg Ala Met
            755                 760                 765
Ala Ala Lys Thr Val Cys Pro Pro His Lys Val Glu Leu Glu Ala Leu
770                 775                 780
Leu Glu Lys Gln Ala Tyr Lys Glu Gln Val Ser Ala Lys Arg Leu Thr
785                 790                 795                 800
Met Leu Glu Leu Leu Glu Lys Tyr Pro Ala Cys Glu Met Lys Phe Ser
                805                 810                 815
Glu Phe Ile Ala Leu Leu Pro Ser Ile Arg Pro Arg Tyr Tyr Ser Ile
                820                 825                 830
Ser Ser Ser Pro Arg Val Asp Glu Lys Gln Ala Ser Ile Thr Val Ser
            835                 840                 845
Val Val Ser Gly Glu Ala Trp Ser Gly Tyr Gly Glu Tyr Lys Gly Ile
850                 855                 860
Ala Ser Asn Tyr Leu Ala Glu Leu Gln Glu Gly Asp Thr Ile Thr Cys
865                 870                 875                 880
Phe Ile Ser Thr Pro Gln Ser Glu Phe Thr Leu Pro Lys Asp Pro Glu
                885                 890                 895
Thr Pro Leu Ile Met Val Gly Pro Gly Thr Gly Val Ala Pro Phe Arg
            900                 905                 910
Gly Phe Val Gln Ala Arg Lys Gln Leu Lys Glu Gln Gly Gln Ser Leu
                915                 920                 925
Gly Glu Ala His Leu Tyr Phe Gly Cys Arg Ser Pro His Glu Asp Tyr
930                 935                 940
Leu Tyr Gln Glu Glu Leu Glu Asn Ala Gln Ser Glu Gly Ile Ile Thr
945                 950                 955                 960
Leu His Thr Ala Phe Ser Arg Met Pro Asn Gln Pro Lys Thr Tyr Val
                965                 970                 975
Gln His Val Met Glu Gln Asp Gly Lys Lys Leu Ile Glu Leu Leu Asp
                980                 985                 990
Gln Gly Ala His Phe Tyr Ile Cys Gly Asp Gly Ser Gln Met Ala Pro
            995                 1000                1005
Thr Val Glu Ala Thr Leu Met Lys Ser Tyr Ala Asp Val His Gln
            1010                1015                1020
Val Ser Glu Ala Asp Ala Arg Leu Trp Leu Gln Gln Leu Glu Glu
```

Lys Gly  Arg Tyr Ala Lys Asp  Val Trp Ala Gly
   1040              1045

<210> SEQ ID NO 9
<211> LENGTH: 3150
<212> TYPE: DNA
<213> ORGANISM: Artificial Sequence
<220> FEATURE:
<223> OTHER INFORMATION: synthetic P450-BM3 variant polynucleotide

<400> SEQUENCE: 9

| | | | | | |
|---|---|---|---|---|---|
| atgacaataa | aggaaatgcc | gcagccgaaa | acgtttggag | aacttaaaaa | tttaccgtta | 60 |
| ttaaacacag | ataaaccggt | tcaagctttg | atgaaaattg | cggatgaatt | aggagaaatc | 120 |
| tttaaattcg | aggcgcctgg | tttggtaacg | atttacttat | caagtcagcg | tctaattaaa | 180 |
| gaagcatgcg | atgaatcacg | ctttgataaa | aacttaagtc | aggcgatgaa | atttgcacgt | 240 |
| gattttctgg | agacgggtt | agcaacaagc | tggacgcatg | aaccgaattg | aaaaaaagcg | 300 |
| cataatatct | tacttccaag | ctttagtcag | caggcaatga | aaggctatca | tgcgatgatg | 360 |
| gtcgatatcg | ccgtgcagct | tgttcaaaag | tgggagcgtc | taaatgcaga | tgagcatatt | 420 |
| gaagtatcgg | aagacatgac | acgtttaacg | cttgatacaa | ttggtctttg | cggctttaac | 480 |
| tatcgcttta | acagctttta | ccgagatcag | cctcatccat | ttattataag | tatggtccgt | 540 |
| gcactggatg | aagtaatgaa | caagcgtcag | cgagcaaatc | cagacgaccc | agcttatgat | 600 |
| gaaaacaagc | gccagtgtca | agaagatatc | aaggtgatga | cgacctagt | agataaaatt | 660 |
| attgcagatc | gcaaagcaag | gggtgaacaa | agccatgatt | tattaacgca | gatgctaaac | 720 |
| ggaaaagatc | cagaaacggg | tgagccgctt | gatgacggga | acattagcta | tcaaattatt | 780 |
| acattcttaa | ttgcgggaca | cgaaacaaca | agtggtcttt | tatcatttgc | gctgtatttc | 840 |
| ttagtgaaaa | atccacatgt | attacaaaaa | gtagcagaag | aagcagcacg | agttctagta | 900 |
| gatcctgttc | caagctacaa | acaagtcaaa | cagcttaaat | atgtcggcat | ggtcttaaac | 960 |
| gaagcgctgc | gcttatggcc | aactgctcct | gcgttttccc | tatatgcaaa | agaagatacg | 1020 |
| gtgcttggag | gagaatatcc | tttagaaaaa | ggcgacgaag | taaatgttct | gattcctcag | 1080 |
| cttcaccgtg | ataaaacaat | ttggggagac | gatgtggagg | agttccgtcc | agagcgtttt | 1140 |
| gaaaatccaa | gtgcgattcc | gcagcatgcg | tttaaaccgt | ttggaaacgg | tcagcgtgcg | 1200 |
| tgtatcggtc | agcagttcgc | tcttcatgaa | gcaacgctgg | tacttggtat | gatgctaaaa | 1260 |
| cactttgact | ttgaagatca | tacaaactac | gagctcgata | ttaaagaaac | tttaacgtta | 1320 |
| aaacctgaag | gctttgtggt | aaaagcaaaa | tcgaaaaaaa | ttccgcttgg | cggtattcct | 1380 |
| tcacctagca | ctgaacagtc | tgctaaaaaa | gtacgcaaaa | aggcagaaaa | cgctcataat | 1440 |
| acgccgctgc | ttgtgctata | cggttcaaat | atgggaacag | ctgaaggaac | ggcgcgtgat | 1500 |
| ttagcagata | ttgcaatgag | caaaggattt | gcaccgcagg | tcgcaacgct | tgattcacac | 1560 |
| gccggaaatc | ttccgcgcga | aggagctgta | ttaattgtaa | cggcgtctta | taacggtcat | 1620 |
| ccgcctgata | acgcaaagca | atttgtcgac | tggttagacc | aagcgtctgc | tgatgaagta | 1680 |
| aaaggcgttc | gctactccgt | atttggatgc | ggcgataaaa | actgggctac | tacgtatcaa | 1740 |
| aaagtgcctg | ctttttatcga | tgaaacgctt | gccgctaaag | gggcagaaaa | catcgctgac | 1800 |
| cgcggtgaag | cagatgcaag | cgacgacttt | gaaggcacat | atgaagaatg | gcgtgaacat | 1860 |
| atgtggagtg | acgtagcagc | ctactttaac | ctcgacattg | aaaacagtga | agataataaa | 1920 |

```
tctactcttt cacttcaatt tgtcgacagc gccgcggata tgccgcttgc gaaaatgcac    1980
ggtgcgtttt caacgaacgt cgtagcaagc aaagaacttc aacagccagg cagtgcacga    2040
agcacgcgac atcttgaaat tgaacttcca aaagaagctt cttatcaaga aggagatcat    2100
ttaggtgtta ttcctcgcaa ctatgaagga atagtaaacc gtgtaacagc aaggttcggc    2160
ctagatgcat cacagcaaat ccgtctggaa gcagaagaag aaaaattagc tcatttgcca    2220
ctcgctaaaa cagtatccgt agaagagctt ctgcaatacg tggagcttca agatcctgcg    2280
acgcgcacgc agcttcgcgc aatggctgct aaaacggtct gcccgccgca taagtagag     2340 cttgaagcct tgcttgaaaa gcaagcctac aaagaacaag tgtcagcaaa acgtttaaca    2400
atgcttgaac tgcttgaaaa atacccggcg tgtgaaatga aattcagcga atttatcgcc    2460
cttctgccaa gcatacgccc gcgctattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct tgtgcaggc gcgcaaacag     2760 ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg ctttttctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctgggtaa                                     3150
```

<210> SEQ ID NO 10
<211> LENGTH: 1049
<212> TYPE: PRT
<213> ORGANISM: Artificial Sequence
<220> FEATURE:
<223> OTHER INFORMATION: synthetic P450-BM3 variant polypeptide

<400> SEQUENCE: 10

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Leu
        35                  40                  45

Val Thr Ile Tyr Leu Ser Ser Gln Arg Leu Ile Lys Glu Ala Cys Asp
    50                  55                  60

Glu Ser Arg Phe Asp Lys Asn Leu Ser Gln Ala Met Lys Phe Ala Arg
65                  70                  75                  80

Asp Phe Leu Gly Asp Gly Leu Ala Thr Ser Trp Thr His Glu Pro Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

```
Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
            165                 170                 175

Ser Met Val Arg Ala Leu Asp Glu Val Met Asn Lys Arg Gln Arg Ala
        180                 185                 190

Asn Pro Asp Asp Pro Ala Tyr Asp Glu Asn Lys Arg Gln Cys Gln Glu
    195                 200                 205

Asp Ile Lys Val Met Asn Asp Leu Val Asp Lys Ile Ala Asp Arg
210                 215                 220

Lys Ala Arg Gly Glu Gln Ser His Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Val Ala Glu Ala Ala Arg Val Leu Val Asp Pro Val Pro
290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Val Asn Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
    530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
```

```
                    565                 570                 575
Thr Thr Tyr Gln Lys Val Pro Ala Phe Ile Asp Glu Thr Leu Ala Ala
                580                 585                 590

Lys Gly Ala Glu Asn Ile Ala Asp Arg Gly Glu Ala Asp Ala Ser Asp
                595                 600                 605

Asp Phe Glu Gly Thr Tyr Glu Glu Trp Arg Glu His Met Trp Ser Asp
                610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
                660                 665                 670

Leu Gln Gln Pro Gly Ser Ala Arg Ser Thr Arg His Leu Glu Ile Glu
                675                 680                 685

Leu Pro Lys Glu Ala Ser Tyr Gln Glu Gly Asp His Leu Gly Val Ile
                690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
                740                 745                 750

Tyr Val Glu Leu Gln Asp Pro Ala Thr Arg Thr Gln Leu Arg Ala Met
                755                 760                 765

Ala Ala Lys Thr Val Cys Pro Pro His Lys Val Glu Leu Glu Ala Leu
                770                 775                 780

Leu Glu Lys Gln Ala Tyr Lys Glu Gln Val Ser Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
                820                 825                 830

Ser Ser Ser Pro Arg Val Asp Glu Lys Gln Ala Ser Ile Thr Val Ser
                835                 840                 845

Val Val Ser Gly Glu Ala Trp Ser Gly Tyr Gly Glu Tyr Lys Gly Ile
                850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
                900                 905                 910

Gly Phe Val Gln Ala Arg Lys Gln Leu Lys Glu Gln Gly Gln Ser Leu
                915                 920                 925

Gly Glu Ala His Leu Tyr Phe Gly Cys Arg Ser Pro His Glu Asp Tyr
                930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
                980                 985                 990
```

Gln Gly Ala His Phe Tyr Ile Cys Gly Asp Gly Ser Gln Met Ala Pro
           995                1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Ala Gly
    1040                1045

<210> SEQ ID NO 11
<211> LENGTH: 3150
<212> TYPE: DNA
<213> ORGANISM: Artificial Sequence
<220> FEATURE:
<223> OTHER INFORMATION: synthetic P450-BM3 variant polynucleotide

<400> SEQUENCE: 11

| | |
|---|---|
| atgacaataa aggaaatgcc gcagccgaaa acgtttggag aacttaaaaa tttaccgtta | 60 |
| ttaaacacag ataaaccggt tcaagctttg atgcgtattg cggatgaatt aggagaaatc | 120 |
| tttaaattcg aggcgcctgg tttggtaacg atttacttat caagtcagcg tctaattaaa | 180 |
| gaagcatgcg atgaatcacg ctttgataaa aacttaagtc aggcgatgaa atttgcacgt | 240 |
| gattttctgg agacgggtt agcaacaagc tggacgcatg aaccgaattg gaaaaaagcg | 300 |
| cataatatct tacttccaag ctttagtcag caggcaatga aaggctatca tgcgatgatg | 360 |
| gtcgatatcg ccgtgcagct tgttcaaaag tgggagcgtc taaatgcaga tgagcatatt | 420 |
| gaagtatcgg aagacatgac acgtttaacg cttgatacaa ttggtctttg cggctttaac | 480 |
| tatcgcttta acagcttta ccagatcag cctcatccat ttattataag tatggtccgt | 540 |
| gcactggatg aagtaatgaa caagcgtcag cgagcaaatc cagacgaccc acgttatgat | 600 |
| gaaaacaagc gccagtgtca agaagatatc aaggtgatga cgacctagt agataaaatt | 660 |
| attgcagatc gcaaagcaag gggtgaacaa agccatgatt tattaacgca gatgctaaac | 720 |
| ggaaaagatc cagaaacggg tgagccgctt gatgacggga acattagcta tcaaattatt | 780 |
| acattcttaa ttgcgggaca cgaaacaaca agtggtcttt tatcatttgc gctgtatttc | 840 |
| ttagtgaaaa atccacatgt attacaaaaa gtagcagaag aagcagcacg agttctagta | 900 |
| gatcctgttc aagctacaa acaagtcaaa cagcttaaat atgtcggcat ggtcttaaac | 960 |
| gaagcgctgc gcttatggcc aactgctcct gcgttttccc tatatgcaaa agaagatacg | 1020 |
| gtgcttggag gagaatatcc tttagaaaaa ggcgacgaag taatgttct gattcctcag | 1080 |
| cttcaccgtg ataaaacaat ttggggagac gatgtggagg agttccgtcc agagcgtttt | 1140 |
| gaaaatccaa gtgcgattcc gcagcatgcg tttaaaccgt ttggaaacgg tcagcgtgcg | 1200 |
| tgtatcggtc agcagttcgc tcttcatgaa gcaacgctgg tacttggtat gatgctaaaa | 1260 |
| cactttgact tgaagatca tacaaactac gagctcgata ttaagaaac tttaacgtta | 1320 |
| aaacctgaag gctttgtggt aaaagcaaaa tcgaaaaaaa ttccgcttgg cggtattcct | 1380 |
| tcacctagca ctgaacagtc tgctaaaaaa gtacgcaaaa aggcagaaaa cgctcataat | 1440 |
| acgccgctgc ttgtgctata cggttcaaat atgggaacag ctgaaggaac ggcgcgtgat | 1500 |
| ttagcagata ttgcaatgag caaaggattt gcaccgcagg tcgcaacgct tgattcacac | 1560 |
| gccggaaatc ttccgcgcga aggagctgta ttaattgtaa cggcgtctta taacggtcat | 1620 |
| ccgcctgata acgcaaagca atttgtcgac tggttagacc aagcgtctgc tgatgaagta | 1680 |

```
aaaggcgttc gctactccgt atttggatgc ggcgataaaa actgggctac tacgtatcaa    1740
aaagtgcctg cttttatcga tgaaacgctt gccgctaaag gggcagaaaa catcgctgac    1800
cgcggtgaag cagatgcaag cgacgacttt gaaggcacat atgaagaatg cgtgaacat    1860
atgtggagtg acgtagcagc ctactttaac ctcgacattg aaacagtga agataataaa    1920
tctactcttt cacttcaatt tgtcgacagc gccgcggata tgccgcttgc gaaaatgcac    1980
ggtgcgtttt caacgaacgt cgtagcaagc aaagaacttc aacagccagg cagtgcacga    2040
agcacgcgac atcttgaaat tgaacttcca aaagaagctt cttatcaaga aggagatcat    2100
ttaggtgtta ttcctcgcaa ctatgaagga atagtaaacc gtgtaacagc aaggttcggc    2160
ctagatgcac cgcagcaaat ccgtctggaa gcagaagaag aaaaattagc tcatttgcca    2220
ctcgctaaaa cagtatccgt agaagagctt ctgcaatacg tggagcttca agatcctgcg    2280
acgcgcacgc agcttcgcgc aatggctgct aaaacggtct gcccgccgca taagtagag    2340
cttgaagcct tgcttgaaaa gcaagcctac aaagaacaag tgctggcaaa cgtttaaca    2400
atgcttgaac tgcttgaaaa atacccggcg tgtgaaatga attcagcga atttatcgcc    2460
cttctgccaa gcatacgccc gcgctattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct tgtgcaggc gcgcaaacag    2760
ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg ctttttctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc acctaccgtt gaagcaacgc ttatgaaaag ctatgctgac    3060
gttcaccaag tgagtgaagc agacgctcgc ttatggctgc agcagctaga agaaaaaggc    3120
cgatacgcaa agacgtgtg ggctgggtaa                                    3150
```

<210> SEQ ID NO 12
<211> LENGTH: 1049
<212> TYPE: PRT
<213> ORGANISM: Artificial Sequence
<220> FEATURE:
<223> OTHER INFORMATION: synthetic P450-BM3 variant polypeptide

<400> SEQUENCE: 12

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Arg
            20                  25                  30

Ile Ala Asp Glu Leu Gly Glu Ile Phe Lys Phe Glu Ala Pro Gly Leu
        35                  40                  45

Val Thr Ile Tyr Leu Ser Ser Gln Arg Leu Ile Lys Glu Ala Cys Asp
    50                  55                  60

Glu Ser Arg Phe Asp Lys Asn Leu Ser Gln Ala Met Lys Phe Ala Arg
65                  70                  75                  80

Asp Phe Leu Gly Asp Gly Leu Ala Thr Ser Trp Thr His Glu Pro Asn
                85                  90                  95

Trp Lys Lys Ala His Asn Ile Leu Leu Pro Ser Phe Ser Gln Gln Ala
```

```
                100             105             110
Met Lys Gly Tyr His Ala Met Met Val Asp Ile Ala Val Gln Leu Val
            115             120             125
Gln Lys Trp Glu Arg Leu Asn Ala Asp Glu His Ile Glu Val Ser Glu
            130             135             140
Asp Met Thr Arg Leu Thr Leu Asp Thr Ile Gly Leu Cys Gly Phe Asn
145             150             155             160
Tyr Arg Phe Asn Ser Phe Tyr Arg Asp Gln Pro His Pro Phe Ile Ile
            165             170             175
Ser Met Val Arg Ala Leu Asp Glu Val Met Asn Lys Arg Gln Arg Ala
            180             185             190
Asn Pro Asp Asp Pro Arg Tyr Asp Glu Asn Lys Arg Gln Cys Gln Glu
            195             200             205
Asp Ile Lys Val Met Asn Asp Leu Val Asp Lys Ile Ile Ala Asp Arg
            210             215             220
Lys Ala Arg Gly Glu Gln Ser His Asp Leu Leu Thr Gln Met Leu Asn
225             230             235             240
Gly Lys Asp Pro Glu Thr Gly Glu Pro Leu Asp Asp Gly Asn Ile Ser
            245             250             255
Tyr Gln Ile Ile Thr Phe Leu Ile Ala Gly His Glu Thr Thr Ser Gly
            260             265             270
Leu Leu Ser Phe Ala Leu Tyr Phe Leu Val Lys Asn Pro His Val Leu
            275             280             285
Gln Lys Val Ala Glu Glu Ala Ala Arg Val Leu Val Asp Pro Val Pro
            290             295             300
Ser Tyr Lys Gln Val Lys Gln Leu Lys Tyr Val Gly Met Val Leu Asn
305             310             315             320
Glu Ala Leu Arg Leu Trp Pro Thr Ala Pro Ala Phe Ser Leu Tyr Ala
            325             330             335
Lys Glu Asp Thr Val Leu Gly Gly Glu Tyr Pro Leu Glu Lys Gly Asp
            340             345             350
Glu Val Asn Val Leu Ile Pro Gln Leu His Arg Asp Lys Thr Ile Trp
            355             360             365
Gly Asp Asp Val Glu Glu Phe Arg Pro Glu Arg Phe Glu Asn Pro Ser
            370             375             380
Ala Ile Pro Gln His Ala Phe Lys Pro Phe Gly Asn Gly Gln Arg Ala
385             390             395             400
Cys Ile Gly Gln Gln Phe Ala Leu His Glu Ala Thr Leu Val Leu Gly
            405             410             415
Met Met Leu Lys His Phe Asp Phe Glu Asp His Thr Asn Tyr Glu Leu
            420             425             430
Asp Ile Lys Glu Thr Leu Thr Leu Lys Pro Glu Gly Phe Val Val Lys
            435             440             445
Ala Lys Ser Lys Lys Ile Pro Leu Gly Gly Ile Pro Ser Pro Ser Thr
            450             455             460
Glu Gln Ser Ala Lys Lys Val Arg Lys Lys Ala Glu Asn Ala His Asn
465             470             475             480
Thr Pro Leu Leu Val Leu Tyr Gly Ser Asn Met Gly Thr Ala Glu Gly
            485             490             495
Thr Ala Arg Asp Leu Ala Asp Ile Ala Met Ser Lys Gly Phe Ala Pro
            500             505             510
Gln Val Ala Thr Leu Asp Ser His Ala Gly Asn Leu Pro Arg Glu Gly
            515             520             525
```

-continued

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
690                 695                 700

Pro Arg Asn Tyr Glu Gly Ile Val Asn Arg Val Thr Ala Arg Phe Gly
705                 710                 715                 720

Leu Asp Ala Pro Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Ala Thr Arg Thr Gln Leu Arg Ala Met
        755                 760                 765

Ala Ala Lys Thr Val Cys Pro Pro His Lys Val Glu Leu Glu Ala Leu
770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
930                 935                 940

-continued

```
Leu Tyr Gln Glu Glu Leu Glu Asn Ala Gln Ser Glu Gly Ile Ile Thr
945                 950                 955                 960
Leu His Thr Ala Phe Ser Arg Met Pro Asn Gln Pro Lys Thr Tyr Val
                965                 970                 975
Gln His Val Met Glu Gln Asp Gly Lys Lys Leu Ile Glu Leu Leu Asp
            980                 985                 990
Gln Gly Ala His Phe Tyr Ile Cys Gly Asp Gly Ser Gln Met Ala Pro
        995                 1000                1005
Thr Val  Glu Ala Thr Leu Met  Lys Ser Tyr Ala Asp  Val His Gln
    1010                1015                1020
Val Ser  Glu Ala Asp Ala Arg  Leu Trp Leu Gln Gln  Leu Glu Glu
    1025                1030                1035
Lys Gly  Arg Tyr Ala Lys Asp  Val Trp Ala Gly
    1040                1045

<210> SEQ ID NO 13
<211> LENGTH: 3150
<212> TYPE: DNA
<213> ORGANISM: Artificial Sequence
<220> FEATURE:
<223> OTHER INFORMATION: synthetic P450-BM3 variant polynucleotide

<400> SEQUENCE: 13
atgacaataa aggaaatgcc gcagccgaaa acgtttggag aacttaaaaa tttaccgtta       60
ttaaacacag ataaaccggt tcaagctttg atgaaaattg cggatgaatt aggagaaatc      120
tttaaattcg aggcgcctgg tttggtaacg atttacttat caagtcagcg tctaattaaa      180
gaagcatgcg atgaatcacg ctttgataaa aacttaagtc aggcgatgaa atttgcacgt      240
gattttctgg agacgggtt agcaacaagc tggacgcatg aaccgaattg aaaaaagcg       300 cataatatct taggcccaag ctttagtcag caggcaatga aggctatca tgcgatgatg       360 gtcgatatcg ccgtgcagct tgttcaaaag tgggagcgtc taaatgcaga tgagcatatt      420
gaagtatcgg aagacatgac acgtttaacg cttgatacaa ttggtctttg cggctttaac      480
tatcgcttta acagctttta ccagatcag cctcatccat ttattataag tatggtccgt      540
gcactggatg aagtaatgaa caagcgtcag cgagcaaatc cagacgaccc agcttatgat      600
gaaaacaagc gccagtgtca agaagatatc aaggtgatga cgacctagt agataaaatt      660 attgcagatc gcaaagcaag gggtgaacaa agccatgatt tattaacgca gatgctaaac      720
ggaaaagatc cagaaacggg tgagccgctt gatgacggga acattagcta tcaaattatt      780
acattcttaa ttgcgggaca cgaaacaaca agtggtcttt tatcatttgc gctgtatttc      840
ttagtgaaaa atccacatgt attacaaaaa gtagcagaag aagcagcacg agttctagta      900
gatcctgttc caagctacaa acaagtcaaa cagcttaaat atgtcggcat ggtcttaaac      960
gaagcgctgc gcttatggcc aactgctcct gcgttttccc tatatgcaaa agaagatacg     1020
gtgcttggag agaatatcc tttagaaaaa ggcgacgaag taatgttct gattcctcag      1080 cttcaccgtg ataaaacaat tgggggagac gatgtggagg agttccgtcc agagcgtttt      1140
gaaaatccaa gtgcgattcc gcagcatgcg tttaaaccgt ttggaaacgg tcagcgtgcg     1200
tgtatcggtc agcagttcgc tcttcatgaa gcaacgctgg tacttggtat gatgctaaaa     1260
cactttgact ttgaagatca tacaaactac gagctcgata ttaaagaaac tttaacgtta     1320
aaacctgaag gctttgtggt aaaagcaaaa tcgaaaaaaa ttccgcttgg cggtattcct     1380
tcacctagca ctgaacagtc tgctaaaaaa gtacgcaaaa aggcagaaaa cgctcataat     1440
```

-continued

```
acgccgctgc ttgtgctata cggttcaaat atgggaacag ctgaaggaac ggcgcgtgat    1500
ttagcagata ttgcaatgag caaaggattt gcaccgcagg tcgcaacgct tgattcacac    1560
gccggaaatc ttccgcgcga aggagctgta ttaattgtaa cggcgtctta taacggtcat    1620
ccgcctgata acgcaaagca atttgtcgac tggttagacc aagcgtctgc tgatgaagta    1680
aaaggcgttc gctactccgt atttggatgc ggcgataaaa actgggctac tacgtatcaa    1740
aaagtgcctg cttttatcga tgaaacgctt gccgctaaag gggcagaaaa catcgctgac    1800
cgcggtgaag cagatgcaag cgacgacttt gaaggcacat atgaagaatg cgtgaacat    1860 atgtggagtg acgtagcagc ctactttaac ctcgacattg aaaacagtga agataataaa    1920
tctactcttt cacttcaatt tgtcgacagc gccgcggata tgccgcttgc gaaaatgcac    1980
ggtgcgtttt caacgaacgt cgtagcaagc aaagaacttc aacagccagg cagtgcacga    2040
agcacgcgac atcttgaaat tgaacttcca aaagaagctt cttatcaaga aggagatcat    2100
ttaggtgtta ttcctcgcaa ctatgaagga atagtaaacc gtgtaacagc aaggttcggc    2160
ctagatgcac cgcagcaaat ccgtctggaa gcagaagaag aaaaattagc tcatttgcca    2220
ctcgctaaaa cagtatccgt agaagagctt ctgcaatacg tggagcttca agatcctgcg    2280
acgcgcacgc agcttcgcgc aatggctgct aaaacggtct gccgccgcca taagtagag    2340 cttgaagcct tgcttgaaaa gcaagcctac aaagaacaag tgttagcaaa acgtttaaca    2400
atgcttgaac tgcttgaaaa atacccggcg tgtgaaatga attcagcga atttatcgcc    2460 cttctgccaa gcatacgccc gcgctattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct ttgtgcaggc gcgcaaacag    2760
ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg cttttttctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc acctaccgtt gaagcaacgc ttatgaaaag ctatgctgac    3060
gttcaccaag tgagtgaagc agacgctcgc ttatggctgc agcagctaga agaaaaaggc    3120
cgatacgcaa agacgtgtg ggctgggtaa                                       3150
```

<210> SEQ ID NO 14
<211> LENGTH: 1049
<212> TYPE: PRT
<213> ORGANISM: Artificial Sequence
<220> FEATURE:
<223> OTHER INFORMATION: synthetic P450-BM3 variant polypeptide

<400> SEQUENCE: 14

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Leu
        35                  40                  45

Val Thr Ile Tyr Leu Ser Ser Gln Arg Leu Ile Lys Glu Ala Cys Asp
    50                  55                  60
```

```
Glu Ser Arg Phe Asp Lys Asn Leu Ser Gln Ala Met Lys Phe Ala Arg
 65                  70                  75                  80

Asp Phe Leu Gly Asp Gly Leu Ala Thr Ser Trp Thr His Glu Pro Asn
                 85                  90                  95

Trp Lys Lys Ala His Asn Ile Leu Gly Pro Ser Phe Ser Gln Gln Ala
                100                 105                 110

Met Lys Gly Tyr His Ala Met Met Val Asp Ile Ala Val Gln Leu Val
                115                 120                 125

Gln Lys Trp Glu Arg Leu Asn Ala Asp Glu His Ile Glu Val Ser Glu
                130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Ala Leu Asp Glu Val Met Asn Lys Arg Gln Arg Ala
                180                 185                 190

Asn Pro Asp Asp Pro Ala Tyr Asp Glu Asn Lys Arg Gln Cys Gln Glu
                195                 200                 205

Asp Ile Lys Val Met Asn Asp Leu Val Asp Lys Ile Ile Ala Asp Arg
210                 215                 220

Lys Ala Arg Gly Glu Gln Ser His Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
                260                 265                 270

Leu Leu Ser Phe Ala Leu Tyr Phe Leu Val Lys Asn Pro His Val Leu
                275                 280                 285

Gln Lys Val Ala Glu Glu Ala Ala Arg Val Leu Val Asp Pro Val Pro
                290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
                340                 345                 350

Glu Val Asn Val Leu Ile Pro Gln Leu His Arg Asp Lys Thr Ile Trp
                355                 360                 365

Gly Asp Asp Val Glu Glu Phe Arg Pro Glu Arg Phe Glu Asn Pro Ser
                370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
                420                 425                 430

Asp Ile Lys Glu Thr Leu Thr Leu Lys Pro Glu Gly Phe Val Val Lys
                435                 440                 445

Ala Lys Ser Lys Lys Ile Pro Leu Gly Gly Ile Pro Ser Pro Ser Thr
                450                 455                 460

Glu Gln Ser Ala Lys Lys Val Arg Lys Lys Ala Glu Asn Ala His Asn
465                 470                 475                 480
```

```
Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
        530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
            595                 600                 605

Asp Phe Glu Gly Thr Tyr Glu Glu Trp Arg Glu His Met Trp Ser Asp
        610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
        690                 695                 700

Pro Arg Asn Tyr Glu Gly Ile Val Asn Arg Val Thr Ala Arg Phe Gly
705                 710                 715                 720

Leu Asp Ala Pro Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Ala Thr Arg Thr Gln Leu Arg Ala Met
        755                 760                 765

Ala Ala Lys Thr Val Cys Pro Pro His Lys Val Glu Leu Glu Ala Leu
        770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
            835                 840                 845

Val Val Ser Gly Glu Ala Trp Ser Gly Tyr Gly Glu Tyr Lys Gly Ile
        850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
```

-continued

```
                     900                 905                    910
Gly Phe Val Gln Ala Arg Lys Gln Leu Lys Glu Gln Gly Gln Ser Leu
                915                    920                 925

Gly Glu Ala His Leu Tyr Phe Gly Cys Arg Ser Pro His Glu Asp Tyr
            930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys  Gly Asp Gly Ser Gln  Met Ala Pro
        995                 1000                1005

Thr Val  Glu Ala Thr Leu Met  Lys Ser Tyr Ala Asp  Val His Gln
    1010                1015                1020

Val Ser  Glu Ala Asp Ala Arg  Leu Trp Leu Gln Gln  Leu Glu Glu
    1025                1030                1035

Lys Gly  Arg Tyr Ala Lys Asp  Val Trp Ala Gly
    1040                1045
```

<210> SEQ ID NO 15
<211> LENGTH: 3150
<212> TYPE: DNA
<213> ORGANISM: Artificial Sequence
<220> FEATURE:
<223> OTHER INFORMATION: synthetic P450-BM3 variant polynucleotide

<400> SEQUENCE: 15

```
atgacaataa aggaaatgcc gcagccgaaa acgtttggag aacttaaaaa tttaccgtta      60
ttaaacacag ataaaccggt tcaagctttg atgcgtattg cggatgaatt aggagaaatc     120
tttaaattcg aggcgcctgg tttggtaaca atttacttat caagtcagcg tctaattaaa     180
gaagcatgcg atgaatcacg ctttgataaa aacttaagtc aggcgatgaa atttgcacgt     240
gattttctgg agacgggttt agcaacaagc tggacgcatg aaataaattg gaaaaaagcg     300
cataatatct tacttccaag ctttagtcag caggcaatga acgttatca tgcgatgatg     360
gtcgatatcg ccgtgcagct tgttcaaaag tgggagcgtc taaatgcaga tgagcatatt     420
gaagtatcgg aagacatgac acgtttaacg cttgatacaa ttggtctttg cggctttaac     480
tatcgcttta acagctttta ccgagatcag cctcatccat ttattataag tatggtccgt     540
gcactggatg aagtaatgaa caagcgtcag cgagcaaatc cagacgaccc agcttatgat     600
gaaaacaagc gccagtgtca agaagatatc aaggtgatga cgacctagt agataaaatt     660
attgcagatc gcaaagcaag gggtgaacaa agccatgatt tattaacgca gatgctaaac     720
ggaaaagatc cagaaacggg tgagccgctt gatgacggga acattagcta tcaaattatt     780
acattcttaa ttgcgggaca cgaaacaaca agtggtcttt tatcatttgc gctgtatttc     840
ttagtgaaaa atccacatgt attacaaaaa gtagcagaag aagcagcacg agttctagta     900
gatcctgttc caagctacaa acaagtcaaa cagcttaaat atgtcggcat ggtcttaaac     960
gaagcgctgc gcttatggcc aactgctcct gcgttttccc tatatgcaaa agaagatacg    1020
gtgcttggag agaatatcc tttagaaaaa ggcgacgaag taatgttct gattcctcag    1080
cttcaccgtg ataaacaat tggggagac gatgtgagg agttccgtcc agagcgtttt    1140
gaaaatccaa gtgcgattcc gcagcatgcg tttaaaccgt ttggaaacgg tcagcgtgcg    1200
```

```
tgtatcggtc agcagttcgc tcttcatgaa gcaacgctgg tacttggtat gatgctaaaa   1260
cactttgact tgaagatca tacaaactac gagctcgata ttaaagaaac tttaacgtta    1320
aaacctgaag ctttgtggt aaaagcaaaa tcgaaaaaaa ttccgcttgg cggtattcct    1380
tcacctagca ctgaacagtc tgctaaaaaa gtacgcaaaa aggcagaaaa cgctcataat    1440
acgccgctgc ttgtgctata cggttcaaat atgggaacag ctgaaggaac ggcgcgtgat    1500
ttagcagata ttgcaatgag caaaggattt gcaccgcagg tcgcaacgct tgattcacac    1560
gccggaaatc ttccgcgcga aggagctgta ttaattgtaa cggcgtctta taacggtcat    1620
ccgcctgata acgcaaagca atttgtcgac tggttagacc aagcgtctgc tgatgaagta    1680
aaaggcgttc gctactccgt atttggatgc ggcgataaaa actgggctac tacgtatcaa    1740
aaagtgcctg cttttatcga tgaaacgctt gccgctaaag gggcagaaaa catcgctgac    1800
cgcggtgaag cagatgcaag cgacgacttt gaaggcacat atgaagaatg gcgtgaacat    1860
atgtggagtg acgtagcagc ctactttaac ctcgacattg aaaacagtga agataataaa    1920
tctactcttt cacttcaatt tgtcgacagc gccgcggata tgccgcttgc gaaaatgcac    1980
ggtgcgtttt caacgaacgt cgtagcaagc aaagaacttc aacagccagg cagtgcacga    2040
agcacgcgac atcttgaaat tgaacttcca aagaagctt cttatcaaga aggagatcat    2100
ttaggtgtta ttcctcgcaa ctatgaagga atagtaaacc gtgtaacagc aaggttcggc    2160
ctagatgcat cacagcaaat ccgtctggaa gcagaagaag aaaaattagc tcatttgcca    2220
ctcgctaaaa cagtatccgt agaagagctt ctgcaatacg tggagcttca agatcctgcg    2280
acgcgcacgc agcttcgcgc aatggctgct aaaacggtct gcccgccgca taagtagag    2340 cttgaagcct tgcttgaaaa gcaagcctac aaagaacaag tgctggcaaa acgtttaaca    2400
atgcttgaac tgcttgaaaa atacccggcg tgtgaaatga aattcagcga atttatcgcc    2460
cttctgccaa gcatacgccc gcgctattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct ttgtgcaggc gcgcaaacag    2760
ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg cttttctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctgggtaa                                    3150
```

<210> SEQ ID NO 16
<211> LENGTH: 1049
<212> TYPE: PRT
<213> ORGANISM: Artificial Sequence
<220> FEATURE:
<223> OTHER INFORMATION: synthetic P450-BM3 variant polypeptide

<400> SEQUENCE: 16

```
Met Thr Ile Lys Glu Met Pro Gln Pro Lys Thr Phe Gly Glu Leu Lys
1               5                   10                  15
```

-continued

Asn Leu Pro Leu Leu Asn Thr Asp Lys Pro Val Gln Ala Leu Met Arg
                20                  25                  30

Ile Ala Asp Glu Leu Gly Glu Ile Phe Lys Phe Glu Ala Pro Gly Leu
         35                  40                  45

Val Thr Ile Tyr Leu Ser Ser Gln Arg Leu Ile Lys Glu Ala Cys Asp
     50                  55                  60

Glu Ser Arg Phe Asp Lys Asn Leu Ser Gln Ala Met Lys Phe Ala Arg
65                  70                  75                  80

Asp Phe Leu Gly Asp Gly Leu Ala Thr Ser Trp Thr His Glu Ile Asn
                 85                  90                  95

Trp Lys Lys Ala His Asn Ile Leu Leu Pro Ser Phe Ser Gln Gln Ala
                100                 105                 110

Met Lys Arg Tyr His Ala Met Met Val Asp Ile Ala Val Gln Leu Val
            115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Ala Leu Asp Glu Val Met Asn Lys Arg Gln Arg Ala
            180                 185                 190

Asn Pro Asp Asp Pro Ala Tyr Asp Glu Asn Lys Arg Gln Cys Gln Glu
    195                 200                 205

Asp Ile Lys Val Met Asn Asp Leu Val Asp Lys Ile Ile Ala Asp Arg
210                 215                 220

Lys Ala Arg Gly Glu Gln Ser His Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
                260                 265                 270

Leu Leu Ser Phe Ala Leu Tyr Phe Leu Val Lys Asn Pro His Val Leu
            275                 280                 285

Gln Lys Val Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
                340                 345                 350

Glu Val Asn Val Leu Ile Pro Gln Leu His Arg Asp Lys Thr Ile Trp
            355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
                420                 425                 430

Asp Ile Lys Glu Thr Leu Thr Leu Lys Pro Glu Gly Phe Val Val Lys

```
                435                 440                 445
Ala Lys Ser Lys Lys Ile Pro Leu Gly Gly Ile Pro Ser Pro Ser Thr
450                 455                 460
Glu Gln Ser Ala Lys Lys Val Arg Lys Lys Ala Glu Asn Ala His Asn
465                 470                 475                 480
Thr Pro Leu Leu Val Leu Tyr Gly Ser Asn Met Gly Thr Ala Glu Gly
                485                 490                 495
Thr Ala Arg Asp Leu Ala Asp Ile Ala Met Ser Lys Gly Phe Ala Pro
            500                 505                 510
Gln Val Ala Thr Leu Asp Ser His Ala Gly Asn Leu Pro Arg Glu Gly
            515                 520                 525
Ala Val Leu Ile Val Thr Ala Ser Tyr Asn Gly His Pro Pro Asp Asn
530                 535                 540
Ala Lys Gln Phe Val Asp Trp Leu Asp Gln Ala Ser Ala Asp Glu Val
545                 550                 555                 560
Lys Gly Val Arg Tyr Ser Val Phe Gly Cys Gly Asp Lys Asn Trp Ala
                565                 570                 575
Thr Thr Tyr Gln Lys Val Pro Ala Phe Ile Asp Glu Thr Leu Ala Ala
            580                 585                 590
Lys Gly Ala Glu Asn Ile Ala Asp Arg Gly Glu Ala Asp Ala Ser Asp
            595                 600                 605
Asp Phe Glu Gly Thr Tyr Glu Glu Trp Arg Glu His Met Trp Ser Asp
610                 615                 620
Val Ala Ala Tyr Phe Asn Leu Asp Ile Glu Asn Ser Glu Asp Asn Lys
625                 630                 635                 640
Ser Thr Leu Ser Leu Gln Phe Val Asp Ser Ala Ala Asp Met Pro Leu
                645                 650                 655
Ala Lys Met His Gly Ala Phe Ser Thr Asn Val Val Ala Ser Lys Glu
            660                 665                 670
Leu Gln Gln Pro Gly Ser Ala Arg Ser Thr Arg His Leu Glu Ile Glu
            675                 680                 685
Leu Pro Lys Glu Ala Ser Tyr Gln Glu Gly Asp His Leu Gly Val Ile
            690                 695                 700
Pro Arg Asn Tyr Glu Gly Ile Val Asn Arg Val Thr Ala Arg Phe Gly
705                 710                 715                 720
Leu Asp Ala Ser Gln Gln Ile Arg Leu Glu Ala Glu Glu Lys Leu
                725                 730                 735
Ala His Leu Pro Leu Ala Lys Thr Val Ser Val Glu Glu Leu Leu Gln
            740                 745                 750
Tyr Val Glu Leu Gln Asp Pro Ala Thr Arg Thr Gln Leu Arg Ala Met
            755                 760                 765
Ala Ala Lys Thr Val Cys Pro Pro His Lys Val Glu Leu Glu Ala Leu
            770                 775                 780
Leu Glu Lys Gln Ala Tyr Lys Glu Gln Val Leu Ala Lys Arg Leu Thr
785                 790                 795                 800
Met Leu Glu Leu Leu Glu Lys Tyr Pro Ala Cys Glu Met Lys Phe Ser
                805                 810                 815
Glu Phe Ile Ala Leu Leu Pro Ser Ile Arg Pro Arg Tyr Tyr Ser Ile
            820                 825                 830
Ser Ser Ser Pro Arg Val Asp Glu Lys Gln Ala Ser Ile Thr Val Ser
            835                 840                 845
Val Val Ser Gly Glu Ala Trp Ser Gly Tyr Gly Glu Tyr Lys Gly Ile
850                 855                 860
```

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
            885                 890                 895

Thr Pro Leu Ile Met Val Gly Pro Gly Thr Gly Val Ala Pro Phe Arg
        900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
        930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Ala Gly
    1040                1045

<210> SEQ ID NO 17
<211> LENGTH: 3150
<212> TYPE: DNA
<213> ORGANISM: Artificial Sequence
<220> FEATURE:
<223> OTHER INFORMATION: synthetic P450-BM3 variant polynucleotide

<400> SEQUENCE: 17

```
atgacaataa aggaaatgcc gcagccgaaa acgtttggag aacttaaaaa tttaccgtta     60
ttaaacacag ataaaccggt tcaagctttg atgaaaattg cggatgaatt aggagaaatc    120
tttaaattcg aggcgcctgg tttggtaacg atttacttat caagtcagcg tctaattaaa    180
gaagcatgcg atgaatcacg ctttgataaa aacttaagtc aggcgatgaa atttgcacgt    240
gattttctgg agacgggtt agcaacaagc tggacgcatg aaccgaattg gaaaaaagcg    300
cataatatct taggcccaag ctttagtcag caggcaatga aaggctatca tgcgatgatg    360
gtcgatatcg ccgtgcagct tgttcaaaag tgggagcgtc taaatgcaga tgagcatatt    420
gaagtatcgg aagacatgac acgtttaacg cttgatacaa ttggtctttg cggctttaac    480
tatcgcttta acagcttta ccgagatcag cctcatccat ttattataag tatggtccgt    540
gcactggatg aagtaatgaa caagcgtcag cgagcaaatc cagacgaccc acgttatgat    600
gaaaacaagc gccagtgtca agaagatatc aaggtgatga cgacctagt agataaaatt    660
attgcagatc gcaaagcaag gggtgaacaa agcgatgatt tattaacgca gatgctaaac    720
ggaaaagatc cagaaacggg tgagccgctt gatgacggga cattagcta tcaaattatt    780
acattcttaa ttgcgggaca cgaaacaaca agtggtcttt tatcatttgc gctgtatttc    840
ttagtgaaaa atccacatgt attacaaaaa gtagcagaag aagcagcacg agttctagta    900
gatcctgttc caagctacaa acaagtcaaa cagcttaaat atgtcggcat ggtcttaaac    960
```

```
gaagcgctgc gcttatggcc aactgctcct gcgttttccc tatatgcaaa agaagatacg   1020
gtgcttggag gagaatatcc tttagaaaaa ggcgacgaag taaatgttct gattcctcag   1080
cttcaccgtg ataaaacaat tggggagac gatgtggagg agttccgtcc agagcgtttt    1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact ttgaagatca tacaaactac gagctcgata ttaaagaaac tttaacgtta   1320
aaacctgaag gctttgtggt aaaagcaaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat atgggaacag ctgaaggaac ggcgcgtgat   1500
ttagcagata ttgcaatgag caaaggattt gcaccgcagg tcgcaacgct tgattcacac   1560
gccggaaatc ttccgcgcga aggagctgta ttaattgtaa cggcgtctta taacggtcat   1620
ccgcctgata acgcaaaggg ctttgtcgac tggttagacc aagcgtctgc tgatgaagta   1680
aaaggcgttc gctactccgt atttggatgc ggcgataaaa actgggctgg cacgtatcaa   1740
aaagtgcctg cttttatcga tgaaacgctt gccgctaaag gggcagaact gatcgctgac   1800
cgcggtgaag cagatgcaag cgacgacttt gaaggcacat atgaagaatg gcgtgaacat   1860
atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aagaagcttc ttatcaaga aggagatcat    2100 ttaggtgtta ttcctcgcaa ctatgaagga atagtaaacc gtgtaacagc aaggttcggc   2160
ctagatgcac cgcagcaaat ccgtctggaa gcagaagaag aaaaattagc tcatttgcca   2220
ctcgctaaaa cagtatccgt agaagagctt ctgcaatacg tggagcttca agatcctgcg   2280
acgcgcacgc agcttcgcgc aatggctgct aaaacggtct gcccgccgca taagtagag    2340 cttgaagcct tgcttgaaaa gcaagcctac aaagaacaag tgttagcaaa acgtttaaca   2400
atgcttgaac tgcttgaaaa atacccggcg tgtgaaatga aattcagcga atttatcgcc   2460
cttctgccaa gcatacgccc gcgctattac tcgatttctt catcacctcg tgtcgatgaa   2520
aaacaagcaa gcatcacggt cagcgttgtc tcaggagaag cgtggagcgg atatggagaa   2580
tataaaggaa ttgcgtcgaa ctatcttgcc gagctgcaag aaggagatac gattacgtgc   2640
tttatttcca caccgcagtc agaatttacg ctgccaaaag accctgaaac gccgcttatc   2700
atggtcggac cgggaacagg cgtcgcgccg tttagaggct ttgtgcaggc gcgcaaacag   2760
ctaaaagaac aaggacagtc acttggagaa gcacatttat acttcggctg ccgttcacct   2820
catgaagact atctgtatca agaagagctt gaaaacgccc aaagcgaagg catcattacg   2880
cttcataccg cttttctcg catgccaaat cagccgaaaa catacgttca gcacgtaatg    2940
gaacaagacg gcaagaaatt gattgaactt cttgatcaag gagcgcactt ctatatttgc   3000
ggagacggaa gccaaatggc acctgccgtt gaagcaacgc ttatgaaaag ctatgctgac   3060
gttcaccaag tgagtgaagc agacgctcgc ttatggctgc agcagctaga agaaaaggc    3120 cgatacgcaa aagacgtgtg ggctgggtaa                                    3150
```

<210> SEQ ID NO 18
<211> LENGTH: 1049
<212> TYPE: PRT
<213> ORGANISM: Artificial Sequence
<220> FEATURE:
<223> OTHER INFORMATION: synthetic P450-BM3 variant polypeptide

<400> SEQUENCE: 18

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Leu
        35                  40                  45

Val Thr Ile Tyr Leu Ser Ser Gln Arg Leu Ile Lys Glu Ala Cys Asp
    50                  55                  60

Glu Ser Arg Phe Asp Lys Asn Leu Ser Gln Ala Met Lys Phe Ala Arg
65                  70                  75                  80

Asp Phe Leu Gly Asp Gly Leu Ala Thr Ser Trp Thr His Glu Pro Asn
                85                  90                  95

Trp Lys Lys Ala His Asn Ile Leu Gly Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Ala Leu Asp Glu Val Met Asn Lys Arg Gln Arg Ala
            180                 185                 190

Asn Pro Asp Asp Pro Arg Tyr Asp Glu Asn Lys Arg Gln Cys Gln Glu
        195                 200                 205

Asp Ile Lys Val Met Asn Asp Leu Val Asp Lys Ile Ile Ala Asp Arg
    210                 215                 220

Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Val Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Val Asn Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400
```

```
Cys Ile Gly Gln Gln Phe Ala Leu His Glu Ala Thr Leu Val Leu Gly
                405                 410                 415
Met Met Leu Lys His Phe Asp Phe Glu Asp His Thr Asn Tyr Glu Leu
                420                 425                 430
Asp Ile Lys Glu Thr Leu Thr Leu Lys Pro Glu Gly Phe Val Val Lys
                435                 440                 445
Ala Lys Ser Lys Lys Ile Pro Leu Gly Gly Ile Pro Ser Pro Ser Thr
            450                 455                 460
Glu Gln Ser Ala Lys Lys Val Arg Lys Lys Ala Glu Asn Ala His Asn
465                 470                 475                 480
Thr Pro Leu Leu Val Leu Tyr Gly Ser Asn Met Gly Thr Ala Glu Gly
                485                 490                 495
Thr Ala Arg Asp Leu Ala Asp Ile Ala Met Ser Lys Gly Phe Ala Pro
                500                 505                 510
Gln Val Ala Thr Leu Asp Ser His Ala Gly Asn Leu Pro Arg Glu Gly
            515                 520                 525
Ala Val Leu Ile Val Thr Ala Ser Tyr Asn Gly His Pro Pro Asp Asn
530                 535                 540
Ala Lys Gly Phe Val Asp Trp Leu Asp Gln Ala Ser Ala Asp Glu Val
545                 550                 555                 560
Lys Gly Val Arg Tyr Ser Val Phe Gly Cys Gly Asp Lys Asn Trp Ala
                565                 570                 575
Gly Thr Tyr Gln Lys Val Pro Ala Phe Ile Asp Glu Thr Leu Ala Ala
                580                 585                 590
Lys Gly Ala Glu Leu Ile Ala Asp Arg Gly Glu Ala Asp Ala Ser Asp
            595                 600                 605
Asp Phe Glu Gly Thr Tyr Glu Glu Trp Arg Glu His Met Trp Ser Asp
            610                 615                 620
Val Ala Ala Tyr Phe Asn Leu Asp Ile Glu Asn Ser Glu Asp Asn Lys
625                 630                 635                 640
Ser Thr Leu Ser Leu Gln Phe Val Asp Ser Ala Ala Asp Met Pro Leu
                645                 650                 655
Ala Lys Met His Gly Ala Phe Ser Thr Asn Val Val Ala Ser Lys Glu
                660                 665                 670
Leu Gln Gln Pro Gly Ser Ala Arg Ser Thr Arg His Leu Glu Ile Glu
            675                 680                 685
Leu Pro Lys Glu Ala Ser Tyr Gln Glu Gly Asp His Leu Gly Val Ile
            690                 695                 700
Pro Arg Asn Tyr Glu Gly Ile Val Asn Arg Val Thr Ala Arg Phe Gly
705                 710                 715                 720
Leu Asp Ala Pro Gln Gln Ile Arg Leu Glu Ala Glu Glu Lys Leu
                725                 730                 735
Ala His Leu Pro Leu Ala Lys Thr Val Ser Val Glu Glu Leu Leu Gln
                740                 745                 750
Tyr Val Glu Leu Gln Asp Pro Ala Thr Arg Thr Gln Leu Arg Ala Met
            755                 760                 765
Ala Ala Lys Thr Val Cys Pro Pro His Lys Val Glu Leu Glu Ala Leu
770                 775                 780
Leu Glu Lys Gln Ala Tyr Lys Glu Gln Val Leu Ala Lys Arg Leu Thr
785                 790                 795                 800
Met Leu Glu Leu Leu Glu Lys Tyr Pro Ala Cys Glu Met Lys Phe Ser
                805                 810                 815
```

Glu Phe Ile Ala Leu Leu Pro Ser Ile Arg Pro Arg Tyr Tyr Ser Ile
                820                 825                 830

Ser Ser Ser Pro Arg Val Asp Glu Lys Gln Ala Ser Ile Thr Val Ser
            835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
                900                 905                 910

Gly Phe Val Gln Ala Arg Lys Gln Leu Lys Glu Gln Gly Gln Ser Leu
                915                 920                 925

Gly Glu Ala His Leu Tyr Phe Gly Cys Arg Ser Pro His Glu Asp Tyr
            930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
                980                 985                 990

Gln Gly Ala His Phe Tyr Ile Cys Gly Asp Gly Ser Gln Met Ala Pro
            995                 1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Ala Gly
    1040                1045

<210> SEQ ID NO 19
<211> LENGTH: 3150
<212> TYPE: DNA
<213> ORGANISM: Artificial Sequence
<220> FEATURE:
<223> OTHER INFORMATION: synthetic P450-BM3 variant polynucleotide

<400> SEQUENCE: 19
atgacaataa aggaaatgcc gcagccgaaa acgtttggag aacttaaaaa tttaccgtta      60
ttaaacacag ataaaccggt tcaagctttg atgcgtattg cggatgaatt aggagaaatc     120
tttaaattcg aggcgcctgg tttggtaacg atttacttat caagtcagcg tctaattaaa     180
gaagcatgcg atgaatcacg ctttgataaa aacttaagtc aggcgatgaa atttgcacgt     240
gattttctgg agacgggtt agcaacaagc tggacgcatg aaccgaattg gaaaaaagcg     300
cataatatct taggcccaag ctttagtcag caggcaatga aaggctatca tgcgatgatg     360
gtcgatatcg ccgtgcagct tgttcaaaag tgggagcgtc taaatgcaga tgagcatatt     420
gaagtatcgg aagacatgac acgtttaacg cttgatacaa ttggtctttg cggctttaac     480
tatcgcttta cagcttttta ccgagatcag cctcatccat ttattataag tatggtccgt     540
gcactggatg aagtaatgaa caagcgtcag cgagcaaatc cagacgaccc agcttatgat     600
gaaaacaagc gccagtgtca agaagatatc aaggtgatga cgaccctagt agataaaatt     660
attgcagatc gcaaagcaag gggtgaacaa agccatgatt tattaacgca gatgctaaac     720

```
ggaaaagatc cagaaacggg tgagccgctt gatgacggga acattagcta tcaaattatt    780
acattcttaa ttgcgggaca cgaaacaaca agtggtcttt tatcatttgc gctgtatttc    840
ttagtgaaaa atccacatgt attacaaaaa gtagcagaag aagcagcacg agttctagta    900
gatcctgttc caagctacaa acaagtcaaa cagcttaaat atgtcggcat ggtcttaaac    960
gaagcgctgc gcttatggcc aactgctcct gcgttttccc tatatgcaaa agaagatacg   1020
gtgcttggag gagaatatcc tttagaaaaa ggcgacgaag taaatgttct gattcctcag   1080
cttcaccgtg ataaaacaat tgggggagac gatgtggagg agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact tgaagatca tacaaactac gagctcgtga ttaaagaaac tttaacgtta   1320
aaacctgaag gctttgtggt aaaagcaaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat atgggaacag ctgaaggaac ggcgcgtgat   1500
ttagcagata ttgcaatgag caaaggattt gcaccgcagg tcgcaacgct tgattcacac   1560
gccggaaatc ttccgcgcga aggagctgta ttaattgtaa cggcgtctta taacggtcat   1620
ccgcctgata acgcaaagca atttgtcgac tggttagacc aagcgtctgc tgatgaagta   1680
aaaggcgttc gctactccgt atttggatgc ggcgataaaa actgggctgg cacgtatcaa   1740
aaagtgcctg cttttatcga tgaaacgctt gccgctaaag gggcagaact gatcgctgac   1800
cgcggtgaag cagatgcaag cgacgacttt gaaggcacat atgaagaatg gcgtgaacat   1860
atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctggaa gcagaagaag aaaaattagc tcatttgcca   2220
ctcgctaaaa cagtatccgt agaagagctt ctgcaatacg tggagcttca agatcctgcg   2280
acgcgcacgc agcttcgcgc aatggctgct aaaacggtct gcccgccgca taaagtagag   2340
cttgaagcct tgcttgaaaa gcaagcctac catgaacaag tgttagcaaa acgtttaaca   2400
atgcttgaac tgcttgaaaa ataccccggcg tgtgaaatga aattcagcga atttatcgcc   2460
cttctgccaa gcatacgccc gcgctattac tcgatttctt catcacctcg tgtcgatgaa   2520
aaacaagcaa gcatcacggt cagcgttgtc tcaggagaag cgtggagcgg atatggagaa   2580
tataaaggaa ttgcgtcgaa ctatcttgcc gagctgcaag aaggagatac gattacgtgc   2640
tttatttcca caccgcagtc agaatttacg ctgccaaaag accctgaaac gccgcttatc   2700
atggtcggac cgggaacagg cgtcgcgccg tttagaggct tgtgcaggc gcgcaaacag   2760 ctaaaagaac aaggacagtc acttggagaa gcacatttat acttcggctg ccgttcacct   2820
catgaagact atctgtatca agaagagctt gaaaacgccc aaagcgaagg catcattacg   2880
cttcataccg cttttctcg catgccaaat cagccgaaaa catacgttca gcacgtaatg   2940
gaacaagacg gcaagaaatt gattgaactt cttgatcaag agcgcacttc tatatttgc   3000 ggagacggaa gccaaatggc acctgccgtt gaagcaacgc ttatgaaaag ctatgctgac   3060
gttcaccaag tgagtgaagc agacgctcgc ttatggctgc agcagctaga agaaaaaggc   3120
```
cgatacgcaa aagacgtgtg ggctgggtaa    3150

<210> SEQ ID NO 20
<211> LENGTH: 1049
<212> TYPE: PRT
<213> ORGANISM: Artificial Sequence
<220> FEATURE:
<223> OTHER INFORMATION: synthetic P450-BM3 variant polypeptide

<400> SEQUENCE: 20

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Arg
            20                  25                  30

Ile Ala Asp Glu Leu Gly Glu Ile Phe Lys Phe Glu Ala Pro Gly Leu
        35                  40                  45

Val Thr Ile Tyr Leu Ser Ser Gln Arg Leu Ile Lys Glu Ala Cys Asp
    50                  55                  60

Glu Ser Arg Phe Asp Lys Asn Leu Ser Gln Ala Met Lys Phe Ala Arg
65                  70                  75                  80

Asp Phe Leu Gly Asp Gly Leu Ala Thr Ser Trp Thr His Glu Pro Asn
                85                  90                  95

Trp Lys Lys Ala His Asn Ile Leu Gly Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Ala Leu Asp Glu Val Met Asn Lys Arg Gln Arg Ala
            180                 185                 190

Asn Pro Asp Asp Pro Ala Tyr Asp Glu Asn Lys Arg Gln Cys Gln Glu
        195                 200                 205

Asp Ile Lys Val Met Asn Asp Leu Val Asp Lys Ile Ile Ala Asp Arg
    210                 215                 220

Lys Ala Arg Gly Glu Gln Ser His Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Val Ala Glu Glu Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

```
Glu Val Asn Val Leu Ile Pro Gln Leu His Arg Asp Lys Thr Ile Trp
            355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
            405                 410                 415

Met Met Leu Lys His Phe Asp Phe Glu Asp His Thr Asn Tyr Glu Leu
            420                 425                 430

Val Ile Lys Glu Thr Leu Thr Leu Lys Pro Glu Gly Phe Val Val Lys
            435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
            530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Gly Thr Tyr Gln Lys Val Pro Ala Phe Ile Asp Glu Thr Leu Ala Ala
            580                 585                 590

Lys Gly Ala Glu Leu Ile Ala Asp Arg Gly Glu Ala Asp Ala Ser Asp
            595                 600                 605

Asp Phe Glu Gly Thr Tyr Glu Glu Trp Arg Glu His Met Trp Ser Asp
610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
            675                 680                 685

Leu Pro Lys Glu Ala Ser Tyr Gln Glu Gly Asp His Leu Gly Val Ile
            690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Ala Thr Arg Thr Gln Leu Arg Ala Met
            755                 760                 765

Ala Ala Lys Thr Val Cys Pro Pro His Lys Val Glu Leu Glu Ala Leu
```

```
                770            775            780
Leu Glu Lys Gln Ala Tyr His Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
                820                 825                 830

Ser Ser Ser Pro Arg Val Asp Glu Lys Gln Ala Ser Ile Thr Val Ser
                835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
                900                 905                 910

Gly Phe Val Gln Ala Arg Lys Gln Leu Lys Glu Gln Gly Gln Ser Leu
                915                 920                 925

Gly Glu Ala His Leu Tyr Phe Gly Cys Arg Ser Pro His Glu Asp Tyr
930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
                980                 985                 990

Gln Gly Ala His Phe Tyr Ile Cys Gly Asp Gly Ser Gln Met Ala Pro
                995                 1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Ala Gly
    1040                1045
```

<210> SEQ ID NO 21
<211> LENGTH: 3150
<212> TYPE: DNA
<213> ORGANISM: Artificial Sequence
<220> FEATURE:
<223> OTHER INFORMATION: synthetic P450-BM3 variant polynucleotide

<400> SEQUENCE: 21

```
atgacaataa aggaaatgcc gcagccgaaa acgtttggag aacttaaaaa tttaccgtta    60
ttaaacacag ataaaccggt tcaagctttg atgaaaattg cggatgaatt aggagaaatc   120
tttaaattcg aggcgcctgg tttggtaacg atttacttat caagtcagcg tctaattaaa   180
gaagcatgcg atgaatcacg ctttgataaa aacttaagtc aggcgatgaa atttgcacgt   240
gattttctgg agacgggggtt agcaacaagc tggacgcatg aaataaattg gaaaaaagcg   300
cataatatct tagcgccaag ctttagtcac caggcaatga taggctatca tgcgatgatg   360
gtcgatatcg ccgtgcagct tgttcaaaag tgggagcgtc taaatgcaga tgagcatatt   420
gaagtatcgg aagacatgac acgtttaacg cttgatacaa ttggtctttg cggctttaac   480
```

| | |
|---|---|
| tatcgcttta acagctttta ccgagatcag cctcatccat ttattataag tatggtccgt | 540 |
| gcactggatg aagtaatgaa caagcgtcag cgagcaaatc cagacgaccc agcttatgat | 600 |
| gaaaacaagc gccagtgtca agaagatatc aaggtgatga acgactatgt agataaaatt | 660 |
| attgcagatc gcaaagcaag gggtgaacaa agcgatgatt tattaacgca gatgctaaac | 720 |
| ggaaaagatc cagaaacggg tgagccgctt gatgacggga acattagcta tcaaattatt | 780 |
| acattcttaa ttgcgggaca cgaaacaaca agtggtcttt tatcatttgc gctgtatttc | 840 |
| ttagtgaaaa atccacatgt attacaaaaa gtagcagaag aagcagcacg agttctagta | 900 |
| gatcctgttc caagctacaa acaagtcaaa cagcttaaat atgtcggcat ggtcttaaac | 960 |
| gaagcgctgc gcttatggcc aactgctcct gcgttttccc tatatgcaaa agaagatacg | 1020 |
| gtgcttggag gagaatggcc tttacgtaaa ggcgacgaag taaatgttct gattcctcag | 1080 |
| cttcaccgtg ataaaacaat ttggggagac gatgtggagg agttccgtcc agagcgtttt | 1140 |
| gaaaatccaa gtgcgattcc gcagcatgcg tttaaaccgt ttggaaacgg tcagcgtgcg | 1200 |
| tgtatcggtc agcagttcgc tcttcatgaa gcaacgctgg tacttggtat gatgctaaaa | 1260 |
| cactttgact ttgaagatca tacaaactac gagctcgata ttaaagaaac tttaacgtta | 1320 |
| aaacctgaag gctttgtggt aaaagcaaaa tcgaaaaaaa ttccgcttgg cggtattcct | 1380 |
| tcacctagca ctgaacagtc tgctaaaaaa gtacgcaaaa aggcagaaaa cgctcataat | 1440 |
| acgccgctgc ttgtgctata cggttcaaat atgggaacag ctgaaggaac ggcgcgtgat | 1500 |
| ttagcagata ttgcaatgag caaaggattt gcaccgcagg tcgcaacgct tgattcacac | 1560 |
| gccgaaaatc ttccgcgcga aggagctgta ttaattgtaa cggcgtctta taacggtcat | 1620 |
| ccgcctgata acgcaaagaa ctttgtcgac tggttagacc aagcgtctgc tgatgaagta | 1680 |
| aaaggcgttc gctactccgt atttggatgc ggcgataaaa actgggctac tacgtatcaa | 1740 |
| aaagtgcctg cttttatcga tgaaacgctt gccgctaaag gggcagaaaa catcgctgac | 1800 |
| cgcggtgaag cagatgcaag cgacgacttt gaaggccgtt atgaagaatg gcgtgaacat | 1860 |
| atgtggagtg acgtagcagc ctactttaac ctcgacattg aaaacagtga agataataaa | 1920 |
| tctactcttt cacttcaatt tgtcgacagc gccgcggata tgccgcttgc gaaaatgcac | 1980 |
| ggtgcgtttt caacgaacgt cgtagcaagc aaagaacttc aacagccagg cagtgcacga | 2040 |
| agcacgcgac atcttgaaat tgaacttcca aaagaagctt cttatcaaga aggagatcat | 2100 |
| ttaggtgtta ttcctcgcaa ctatgaagga atagtaaacc gtgtaacagc aaggttcggc | 2160 |
| ctagatgcat cacagcaaat ccgtgtggaa gcagaagaag aaaaattagc tcatttgcca | 2220 |
| ctcgctaaaa cagtatccgt agaagagctt ctgcaatacg tggagcttca agatcctgcg | 2280 |
| acgcgcacgc agcttcgcgc aatggctgct aaaacggtct gcccgccgca taagtagag | 2340 |
| cttgaagcct tgcttgaaaa gcaagcctac aaagaacaag tgctggcaaa acgtttaaca | 2400 |
| atgcttgaac tgcttgaaaa ataccccggcg tgtgaaatga aattcagcga atttatcgcc | 2460 |
| cttctgccaa gcatacgccc gcgctattac tcgatttctt catcacctcg tgtcgatgaa | 2520 |
| aaacaagcaa gcatcacggt cagcgttgtc tcaggagaag cgtggagcgg atatggagaa | 2580 |
| tataaaggaa ttgcgtcgaa ctatcttgcc gagctgcaag aaggagatac gattacgtgc | 2640 |
| tttatttcca caccgcagtc agaatttacg ctgccaaaag accctgaaac gccgcttatc | 2700 |
| atggtcggac cgggaacagg cgtcgcgccg tttagaggct tgtgcaggc gcgcaaacag | 2760 |
| ctaaaagaac aaggacagtc acttggagaa gcacatttat acttcggctg ccgttcacct | 2820 |
| catgaagact atctgtatca agaagagctt gaaaacgccc aaagcgaagg catcattacg | 2880 |

```
cttcataccg cttttctctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctgggtaa                                     3150
```

<210> SEQ ID NO 22
<211> LENGTH: 1049
<212> TYPE: PRT
<213> ORGANISM: Artificial Sequence
<220> FEATURE:
<223> OTHER INFORMATION: synthetic P450-BM3 variant polypeptide

<400> SEQUENCE: 22

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Leu
        35                  40                  45

Val Thr Ile Tyr Leu Ser Ser Gln Arg Leu Ile Lys Glu Ala Cys Asp
    50                  55                  60

Glu Ser Arg Phe Asp Lys Asn Leu Ser Gln Ala Met Lys Phe Ala Arg
65                  70                  75                  80

Asp Phe Leu Gly Asp Gly Leu Ala Thr Ser Trp Thr His Glu Ile Asn
                85                  90                  95

Trp Lys Lys Ala His Asn Ile Leu Ala Pro Ser Phe Ser His Gln Ala
            100                 105                 110

Met Ile Gly Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Ala Leu Asp Glu Val Met Asn Lys Arg Gln Arg Ala
            180                 185                 190

Asn Pro Asp Asp Pro Ala Tyr Asp Glu Asn Lys Arg Gln Cys Gln Glu
        195                 200                 205

Asp Ile Lys Val Met Asn Asp Tyr Val Asp Lys Ile Ile Ala Asp Arg
    210                 215                 220

Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Val Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
```

-continued

```
                305                 310                 315                 320
        Glu Ala Leu Arg Leu Trp Pro Thr Ala Pro Ala Phe Ser Leu Tyr Ala
                        325                 330                 335

Lys Glu Asp Thr Val Leu Gly Gly Glu Trp Pro Leu Arg Lys Gly Asp
                        340                 345                 350

Glu Val Asn Val Leu Ile Pro Gln Leu His Arg Asp Lys Thr Ile Trp
                        355                 360                 365

Gly Asp Asp Val Glu Glu Phe Arg Pro Glu Arg Phe Glu Asn Pro Ser
                        370                 375                 380

Ala Ile Pro Gln His Ala Phe Lys Pro Phe Gly Asn Gly Gln Arg Ala
        385                 390                 395                 400

Cys Ile Gly Gln Gln Phe Ala Leu His Glu Ala Thr Leu Val Leu Gly
                        405                 410                 415

Met Met Leu Lys His Phe Asp Phe Glu Asp His Thr Asn Tyr Glu Leu
                        420                 425                 430

Asp Ile Lys Glu Thr Leu Thr Leu Lys Pro Glu Gly Phe Val Val Lys
                        435                 440                 445

Ala Lys Ser Lys Lys Ile Pro Leu Gly Gly Ile Pro Ser Pro Ser Thr
                        450                 455                 460

Glu Gln Ser Ala Lys Lys Val Arg Lys Lys Ala Glu Asn Ala His Asn
        465                 470                 475                 480

Thr Pro Leu Leu Val Leu Tyr Gly Ser Asn Met Gly Thr Ala Glu Gly
                        485                 490                 495

Thr Ala Arg Asp Leu Ala Asp Ile Ala Met Ser Lys Gly Phe Ala Pro
                        500                 505                 510

Gln Val Ala Thr Leu Asp Ser His Ala Gly Asn Leu Pro Arg Glu Gly
                        515                 520                 525

Ala Val Leu Ile Val Thr Ala Ser Tyr Asn Gly His Pro Pro Asp Asn
                        530                 535                 540

Ala Lys Asn Phe Val Asp Trp Leu Asp Gln Ala Ser Ala Asp Glu Val
        545                 550                 555                 560

Lys Gly Val Arg Tyr Ser Val Phe Gly Cys Gly Asp Lys Asn Trp Ala
                        565                 570                 575

Thr Thr Tyr Gln Lys Val Pro Ala Phe Ile Asp Glu Thr Leu Ala Ala
                        580                 585                 590

Lys Gly Ala Glu Asn Ile Ala Asp Arg Gly Glu Ala Asp Ala Ser Asp
                        595                 600                 605

Asp Phe Glu Gly Arg Tyr Glu Glu Trp Arg Glu His Met Trp Ser Asp
                        610                 615                 620

Val Ala Ala Tyr Phe Asn Leu Asp Ile Glu Asn Ser Glu Asp Asn Lys
        625                 630                 635                 640

Ser Thr Leu Ser Leu Gln Phe Val Asp Ser Ala Ala Asp Met Pro Leu
                        645                 650                 655

Ala Lys Met His Gly Ala Phe Ser Thr Asn Val Val Ala Ser Lys Glu
                        660                 665                 670

Leu Gln Gln Pro Gly Ser Ala Arg Ser Thr Arg His Leu Glu Ile Glu
                        675                 680                 685

Leu Pro Lys Glu Ala Ser Tyr Gln Glu Gly Asp His Leu Gly Val Ile
                        690                 695                 700

Pro Arg Asn Tyr Glu Gly Ile Val Asn Arg Val Thr Ala Arg Phe Gly
        705                 710                 715                 720

Leu Asp Ala Ser Gln Gln Ile Arg Val Glu Ala Glu Glu Glu Lys Leu
                        725                 730                 735
```

```
Ala His Leu Pro Leu Ala Lys Thr Val Ser Val Glu Leu Leu Gln
            740                 745                 750

Tyr Val Glu Leu Gln Asp Pro Ala Thr Arg Thr Gln Leu Arg Ala Met
            755                 760                 765

Ala Ala Lys Thr Val Cys Pro His Lys Val Glu Leu Glu Ala Leu
770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
                820                 825                 830

Ser Ser Ser Pro Arg Val Asp Glu Lys Gln Ala Ser Ile Thr Val Ser
                835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
                900                 905                 910

Gly Phe Val Gln Ala Arg Lys Gln Leu Lys Glu Gln Gly Gln Ser Leu
                915                 920                 925

Gly Glu Ala His Leu Tyr Phe Gly Cys Arg Ser Pro His Glu Asp Tyr
                930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
                980                 985                 990

Gln Gly Ala His Phe Tyr Ile Cys Gly Asp Gly Ser Gln Met Ala Pro
                995                 1000                1005

Ala Val Glu Ala Thr Leu Met Lys Ser Tyr Ala Asp Val His Gln
        1010            1015                1020

Val Ser Glu Ala Asp Ala Arg Leu Trp Leu Gln Gln Leu Glu Glu
        1025            1030                1035

Lys Gly Arg Tyr Ala Lys Asp Val Trp Ala Gly
        1040            1045

<210> SEQ ID NO 23
<211> LENGTH: 3150
<212> TYPE: DNA
<213> ORGANISM: Artificial Sequence
<220> FEATURE:
<223> OTHER INFORMATION: synthetic P450-BM3 variant polynucleotide

<400> SEQUENCE: 23
atgacaataa aggaaatgcc gcagccgaaa acgtttggag aacttaaaaa tttaccgtta      60
ttaaacacag ataaaccggt tcaagctttg atgaaaattg cggatgaatt aggagaaatc     120
tttaaattcg aggcgcctgg tttggtaacg atttacttat caagtcagcg tctaattaaa     180
gaagcatgcg atgaatcacg ctttgataaa aacttaagtc aggcgatgaa atttgcacgt     240
```

```
gattttctgg gagacgggtt agcaacaagc tggacgcatg aaataaattg gaaaaaagcg      300
cataatatct tagcgccaag ctttagtcac caggcaatga aaggctatca tgcgatgatg      360
gtcgatatcg ccgtgcagct tgttcaaaag tgggagcgtc taaatgcaga tgagcatatt      420
gaagtatcgg aagacatgac acgtttaacg cttgatacaa ttggtctttg cggctttaac      480 tatcgctttta acagctttta ccgagatcag cctcatccat ttattataag tatggtccgt      540
gcactggatg aagtaatgaa caagcgtcag cgagcaaatc cagacgaccc agcttatgat      600
gaaaacaagc gccagtgtca agaagatatc aaggtgatga acgacctagt agataaaatt      660
attgcagatc gcaaagcaag gggtgaacaa agcgatgatt tattaacgca gatgctaaac      720
ggaaaagatc cagaaacggg tgagccgctt gatgacggga acattagcta tcaaattatt      780
acattcttaa ttgcgggaca cgaaacaaca agtggtcttt tatcatttgc gctgtatttc      840
ttagtgaaaa atccacatgt attacaaaaa gtagcagaag aagcagcacg agttctagta      900
gatcctgttc caagctacaa acaagtcaaa cagcttaaat atgtcggcat ggtcttaaac      960
gaagcgctgc gcttatggcc aactgctcct gcgttttccc tatatgcaaa agaagatacg     1020
gtgcttggag gagaatggcc tttagagaaa ggcgacgaag taaatgttct gattcctcag     1080
cttcaccgtg ataaaacaat ttggggagac gatgtggagg agttccgtcc agagcgtttt     1140
gaaaatccaa gtgcgattcc gcagcatgcg tttaaaccgt ttggaaacgg tcagcgtgcg     1200
tgtatcggtc agcagttcgc tcttcatgaa gcaacgctgg tacttggtat gatgctaaaa     1260
cactttgact tgaagatca tacaaactac gagctcgata ttaaagaaac tttaacgtta     1320
aaacctgaag gctttgtggt aaaagcaaaa tcgaaaaaaa ttccgcttgg cggtattcct     1380
tcacctagca ctgaacagtc tgctaaaaaa gtacgcaaaa aggcagaaaa cgctcataat     1440
acgccgctgc ttgtgctata cggttcaaat atgggaacag ctgaaggaac ggcgcgtgat     1500
ttagcagata ttgcaatgag caaaggattt gcaccgcagg tcgcaacgct tgattcacac     1560
gccggaaaat ttccgcgcga aggagctgta ttaattgtaa cggcgtctta taacggtcat     1620
ccgcctgata acgcaaagca atttgtcgac tggttagacc aagcgtctgc tgatgaagta     1680
aaaggcgttc gctactccgt atttggatgc ggcgataaaa actgggctca tacgtatcaa     1740
aaagtgcctg cttttatcga tgaaacgctt gccgctaaag gggcagaaaa catcgctgac     1800
cgcggtgaag cagatgcaag cgacgacttt gaaggccgtt atgaagaatg gcgtgaacat     1860
atgtggagtg acgtagcagc ctactttaac ctcgacattg aaaacagtga agataataaa     1920
tctactcttt cacttcaatt tgtcgacagc gccgcggata tgccgcttgc gaaaatgcac     1980
ggtgcgtttt caacgaacgt cgtagcaagc aaagaacttc aacagccagg cagtgcacga     2040
agcacgcgac atcttgaaat tgaacttcca aaagaagctt cttatcaaga aggagatcat     2100
ttaggtgtta ttcctcgcaa ctatgaagga atagtaaacc gtgtaacagc aaggttcggc     2160
ctagatgcat cacagcaaat ccgtgtggaa gcagaagaag aaaaattagc tcatttgcca     2220
ctcgctaaaa cagtatccgt agaagagctt ctgcaatacg tggagcttca agatcctgcg     2280
acgcgcacgc agcttcgcgc aatggctgct aaaacggtct gcccgccgca taaagtagag     2340
cttgaagcct tgcttgaaaa gcaagcctac aaagaacaag tgctggcaaa cgtttaaca      2400 atgcttgaac tgcttgaaaa atacccggcg tgtgaaatga aattcagcga atttatcgcc     2460
cttctgccaa gcatacgccc gcgctattac tcgatttctt catcacctcg tgtcgatgaa     2520
aaacaagcaa gcatcacggt cagcgttgtc tcaggagaag cgtggagcgg atatggagaa     2580
tataaaggaa ttgcgtcgaa ctatcttgcc gagctgcaag aaggagatac gattacgtgc     2640
```

-continued

```
tttatttcca caccgcagtc agaatttacg ctgccaaaag accctgaaac gccgcttatc    2700
atggtcggac cgggaacagg cgtcgcgccg tttagaggct ttgtgcaggc gcgcaaacag    2760
ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg cttttctcg catgccaaat cagccgaaaa catacgttca gcacgtaatg    2940
gaacaagacg caagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga gaaaaaggc    3120 cgatacgcaa aagacgtgtg ggctgggtaa                                     3150
```

<210> SEQ ID NO 24
<211> LENGTH: 1049
<212> TYPE: PRT
<213> ORGANISM: Artificial Sequence
<220> FEATURE:
<223> OTHER INFORMATION: synthetic P450-BM3 variant polypeptide

<400> SEQUENCE: 24

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Leu
        35                  40                  45

Val Thr Ile Tyr Leu Ser Ser Gln Arg Leu Ile Lys Glu Ala Cys Asp
    50                  55                  60

Glu Ser Arg Phe Asp Lys Asn Leu Ser Gln Ala Met Lys Phe Ala Arg
65                  70                  75                  80

Asp Phe Leu Gly Asp Gly Leu Ala Thr Ser Trp Thr His Glu Ile Asn
                85                  90                  95

Trp Lys Lys Ala His Asn Ile Leu Ala Pro Ser Phe Ser His Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Ala Leu Asp Glu Val Met Asn Lys Arg Gln Arg Ala
            180                 185                 190

Asn Pro Asp Asp Pro Ala Tyr Asp Glu Asn Lys Arg Gln Cys Gln Glu
        195                 200                 205

Asp Ile Lys Val Met Asn Asp Leu Val Asp Lys Ile Ile Ala Asp Arg
    210                 215                 220

Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
            260                 265                 270
```

```
Leu Leu Ser Phe Ala Leu Tyr Phe Leu Val Lys Asn Pro His Val Leu
        275                 280                 285

Gln Lys Val Ala Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Trp Pro Leu Glu Lys Gly Asp
                340                 345                 350

Glu Val Asn Val Leu Ile Pro Gln Leu His Arg Asp Lys Thr Ile Trp
            355                 360                 365

Gly Asp Asp Val Glu Glu Phe Arg Pro Glu Arg Phe Glu Asn Pro Ser
        370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
    450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
                500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
        530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

His Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Arg Tyr Glu Glu Trp Arg Glu His Met Trp Ser Asp
610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
                660                 665                 670

Leu Gln Gln Pro Gly Ser Ala Arg Ser Thr Arg His Leu Glu Ile Glu
        675                 680                 685
```

Leu Pro Lys Glu Ala Ser Tyr Gln Glu Gly Asp His Leu Gly Val Ile
690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Val Glu Ala Glu Glu Lys Leu
        725                 730                 735

Ala His Leu Pro Leu Ala Lys Thr Val Ser Val Glu Leu Leu Gln
        740                 745                 750

Tyr Val Glu Leu Gln Asp Pro Ala Thr Arg Thr Gln Leu Arg Ala Met
        755                 760                 765

Ala Ala Lys Thr Val Cys Pro Pro His Lys Val Glu Leu Glu Ala Leu
770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
            805                 810                 815

Glu Phe Ile Ala Leu Leu Pro Ser Ile Arg Pro Arg Tyr Tyr Ser Ile
        820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
            885                 890                 895

Thr Pro Leu Ile Met Val Gly Pro Gly Thr Gly Val Ala Pro Phe Arg
        900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
            965                 970                 975

Gln His Val Met Glu Gln Asp Gly Lys Lys Leu Ile Glu Leu Leu Asp
        980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Ala Gly
    1040                1045

<210> SEQ ID NO 25
<211> LENGTH: 3150
<212> TYPE: DNA
<213> ORGANISM: Artificial Sequence
<220> FEATURE:
<223> OTHER INFORMATION: synthetic P450-BM3 variant polynucleotide

<400> SEQUENCE: 25

```
atgacaataa aggaaatgcc gcagccgaaa acgtttggag aacttaaaaa tttaccgtta      60
ttaaacacag ataaaccggt tcaagctttg atgaaaattg cggatgaatt aggagaaatc     120
tttaaattcg aggcgcctgg tttggtaacg atttacttat caagtcagcg tctaattaaa     180
gaagcatgcg atgaatcacg cttttgataaa aacttaagtc aggcgatgaa atttgcacgt    240
gattttctgg gagacgggtt agcaacaagc tggacgcatg aaataaattg gaaaaaagcg     300
cataatatct tacttccaag cttttagtcag caggcaatga aaggctatca tgcgatgatg     360
gtcgatatcg ccgtgcagct tgttcaaaag tgggagcgtc taaatgcaga tgagcatatt     420
gaagtatcgg aagacatgac acgtttaacg cttgatacaa ttggtctttg cggctttaac     480
tatcgctttta acagctttta ccgagatcag cctcatccat ttattcagag tatggtccgt    540
gcactggatg aagtaatgaa caagcgtcag cgagcaaatc cagacgaccc agcttatgat    600
gaaaacaagc gccagtgtca agaagatatc aaggtgatga acgacctagt acagaaaatt    660
attgcagatc gcaaagcaag gggtgaacaa agcgatgatt tattaacgca gatgctaaac    720
ggaaaagatc cagaaacggg tgagccgctt gatgacggga acattagcta tcaaattatt    780
acattcttaa ttgcgggaca cgaaacaaca agtggtcttt tatcatttgc gctgtatttc    840
ttagtgaaaa atccacatgt attacaaaaa gtagcagaag aagcagcacg agttctagta    900
gatcctgttc caagctacaa acaagtcaaa cagcttaaat atgtcggcat ggtcttaaac    960
gaagcgctgc gcttatggcc aactgctcct gcgttttccc tatatgcaaa agaagatacg   1020
gtgcttggag gagaatatca attatccaaa ggcgacgaag taaatgttct gattcctcag   1080
cttcaccgtg ataaaacaat ttggggagac gatgtggagg agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact ttgaagatca tacaaactac gagctcgata ttaaagaaac tttaacgtta   1320
aaacctgaag gctttgtggt aaaagcaaaa tcgaaaaaaa ttccgcttgg ctttattcct   1380
tcacctagca ctgaacagtc tgctaaaaaa gtacgcaaaa aggcagaaaa cgctcataat   1440
acgccgctgc ttgtgctata cggttcaaat atgggaacag ctgaaggaac ggcgcgtgat   1500
ttagcagata ttgcaatgag caaaggattt gcaccgcagg tcgcaacgct tgattcacac   1560
gccggaaatc ttccgcgcga aggagctgta ttaattgtaa cggcgtctta taacggtcat   1620
ccgcctgata acgcaaagca atttgtccgt tggttagacc aagcgtctgc tgatgaagta   1680
aaaggcgttc gctactccgt atttggatgc ggcgataaaa actgggctcc gacgtatcaa   1740
aaagtgcctg cttttatcga tgaaacgctt gccgctaaag gggcagaaaa catcgctcgt   1800
cgcggtgaag cagatgcaag cgacgacttt gaaggcacat atgaagaatg gcgtgaacat   1860
atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcaagc aagaacttc aacagccagg cagtgcacga    2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctggaa gcagaagaag aaaaattagc tcatttgcca   2220
ctcgctaaaa cagtatccgt agaagagctt ctgcaatacg tggagcttca agatcctgcg   2280
acgcgcacgc agcttcgcgc aatggctgct aaaacggtct gcccgccgca taaagtagag   2340
cttgaagcct tgcttgaaaa gcaagcctac aaagaacaag tgctggcaaa acgtttaaca   2400
```

```
atgcttgaac tgcttgaaaa atacccggcg tgtgaaatga aattcagcga atttatcgcc    2460
cttctgccaa gcatacgccc gcgctattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct ttgtgcaggc gcgcaaacag    2760
ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg cttttctctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctgggtaa                                     3150
```

<210> SEQ ID NO 26  
<211> LENGTH: 1049  
<212> TYPE: PRT  
<213> ORGANISM: Artificial Sequence  
<220> FEATURE:  
<223> OTHER INFORMATION: synthetic P450-BM3 variant polypeptide

<400> SEQUENCE: 26

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Leu
        35                  40                  45

Val Thr Ile Tyr Leu Ser Ser Gln Arg Leu Ile Lys Glu Ala Cys Asp
    50                  55                  60

Glu Ser Arg Phe Asp Lys Asn Leu Ser Gln Ala Met Lys Phe Ala Arg
65                  70                  75                  80

Asp Phe Leu Gly Asp Gly Leu Ala Thr Ser Trp Thr His Glu Ile Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Gln
                165                 170                 175

Ser Met Val Arg Ala Leu Asp Glu Val Met Asn Lys Arg Gln Arg Ala
            180                 185                 190

Asn Pro Asp Asp Pro Ala Tyr Asp Glu Asn Lys Arg Gln Cys Gln Glu
        195                 200                 205

Asp Ile Lys Val Met Asn Asp Leu Val Gln Lys Ile Ile Ala Asp Arg
    210                 215                 220
```

```
Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Ser
            245                 250                 255

Tyr Gln Ile Ile Thr Phe Leu Ile Ala Gly His Glu Thr Thr Ser Gly
        260                 265                 270

Leu Leu Ser Phe Ala Leu Tyr Phe Leu Val Lys Asn Pro His Val Leu
    275                 280                 285

Gln Lys Val Ala Glu Glu Ala Arg Val Leu Val Asp Pro Val Pro
290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Gln Leu Ser Lys Gly Asp
                340                 345                 350

Glu Val Asn Val Leu Ile Pro Gln Leu His Arg Asp Lys Thr Ile Trp
            355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
            435                 440                 445

Ala Lys Ser Lys Lys Ile Pro Leu Gly Phe Ile Pro Ser Pro Ser Thr
450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
                500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
530                 535                 540

Ala Lys Gln Phe Val Arg Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Pro Thr Tyr Gln Lys Val Pro Ala Phe Ile Asp Glu Thr Leu Ala Ala
                580                 585                 590

Lys Gly Ala Glu Asn Ile Ala Arg Arg Gly Glu Ala Asp Ala Ser Asp
            595                 600                 605

Asp Phe Glu Gly Thr Tyr Glu Glu Trp Arg Glu His Met Trp Ser Asp
            610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
```

```
            645                 650                 655
Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
            675                 680                 685

Leu Pro Lys Glu Ala Ser Tyr Gln Glu Gly Asp His Leu Gly Val Ile
            690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
            725                 730                 735

Ala His Leu Pro Leu Ala Lys Thr Val Ser Val Glu Glu Leu Leu Gln
            740                 745                 750

Tyr Val Glu Leu Gln Asp Pro Ala Thr Arg Thr Gln Leu Arg Ala Met
            755                 760                 765

Ala Ala Lys Thr Val Cys Pro Pro His Lys Val Glu Leu Glu Ala Leu
            770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                    805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
            835                 840                 845

Val Val Ser Gly Glu Ala Trp Ser Gly Tyr Gly Glu Tyr Lys Gly Ile
            850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                    885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
            915                 920                 925

Gly Glu Ala His Leu Tyr Phe Gly Cys Arg Ser Pro His Glu Asp Tyr
            930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                    965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
            995                 1000                1005

Ala Val Glu Ala Thr Leu Met Lys Ser Tyr Ala Asp Val His Gln
            1010                1015                1020

Val Ser Glu Ala Asp Ala Arg Leu Trp Leu Gln Gln Leu Glu Glu
            1025                1030                1035

Lys Gly Arg Tyr Ala Lys Asp Val Trp Ala Gly
            1040                1045
```

<210> SEQ ID NO 27

<211> LENGTH: 3150
<212> TYPE: DNA
<213> ORGANISM: Artificial Sequence
<220> FEATURE:
<223> OTHER INFORMATION: synthetic P450-BM3 variant polynucleotide

<400> SEQUENCE: 27

| | | | | | |
|---|---|---|---|---|---|
| atgacaataa | aggaaatgcc | gcagccgaaa | acgtttggag | aacttaaaaa | tttaccgtta | 60 |
| ttaaacacag | ataaaccggt | tcaagctttg | atgaaaattg | cggatgaatt | aggagaaatc | 120 |
| tttaaattcg | aggcgcctgg | tttggtaacg | atttacttat | caagtcagcg | tctaattaaa | 180 |
| gaagcatgcg | atgaatcacg | ctttgataaa | aacttaagtc | aggcgatgaa | atttgcacgt | 240 |
| gattttctgg | agacgggtt | agcaacaagc | tggacgcatg | aaataaattg | gaaaaaagcg | 300 |
| cataatatct | tacttccaag | ctttagtcag | caggcaatga | aaggctatca | tgcgatgatg | 360 |
| gtcgatatcg | ccgtgcagct | tgttcaaaag | tgggagcgtc | taaatgcaga | tgagcatatt | 420 |
| gaagtatcgg | aagacatgac | acgtttaacg | cttgatacaa | ttggtctttg | cggctttaac | 480 |
| tatcgcttta | acagcttta | ccgagatcag | cctcatccat | ttattataag | tatggtccgt | 540 |
| gcactggatg | aagtaatgaa | caagcgtcag | cgagcaaatc | cagacgaccc | agcttatgat | 600 |
| gaaaacaagc | gccagtgtca | agaagatatc | aaggtgatga | cgacctagt | agataaaatt | 660 |
| attgcagatc | gcaaagcaag | gggtgaacaa | agcgatgatt | tattaacgca | gatgctaaac | 720 |
| ggaaaagatc | cagaaacggg | tgagccgctt | gatgacggga | acattagcta | tcaaattatt | 780 |
| acattcttaa | ttgcgggaca | cgaaacaaca | agtggtcttt | tatcatttgc | gctgtatttc | 840 |
| ttagtgaaaa | atccacatgt | attacaaaaa | gtagcagaag | aagcagcacg | agttctagta | 900 |
| gatcctgttc | aagctacaa | acaagtcaaa | cagcttaaat | atgtcggcat | ggtcttaaac | 960 |
| gaagcgctgc | gcttatggcc | aactgctcct | gcgttttccc | tatatgcaaa | agaagatacg | 1020 |
| gtgcttggag | agaatatca | attatccaaa | ggcgacgaag | taatgttct | gattcctcag | 1080 |
| cttcaccgtg | ataaaacaat | tggggagac | gatgtggagg | agttccgtcc | agagcgtttt | 1140 |
| gaaaatccaa | gtgcgattcc | gcagcatgcg | tttaaaccgt | ttggaacgg | tcagcgtgcg | 1200 |
| tgtatcggtc | agcagttcgc | tcttcatgaa | gcaacgctgg | tacttggtat | gatgctaaaa | 1260 |
| cactttgact | ttgaagatca | tacaaactac | gagctcgata | ttaaagaaac | tttaacgtta | 1320 |
| aaacctgaag | ctttgtggt | aaaagcaaaa | tcgaaaaaaa | ttccgcttgg | ctttattcct | 1380 |
| tcacctagca | ctgaacagtc | tgctaaaaaa | gtacgcaaaa | aggcagaaaa | cgctcataat | 1440 |
| acgccgctgc | ttgtgctata | cggttcaaat | atgggaacag | ctgaaggaac | ggcgcgtgat | 1500 |
| ttagcagata | ttgcaatgag | caaaggatt | gcaccgcagg | tcgcaacgct | tgattcacac | 1560 |
| gccggaaatc | ttccgcgcga | aggagctgta | ttaattgtaa | cggcgtctta | taacggtcat | 1620 |
| ccgcctgata | acgcaaagca | atttgtccgt | tggttagacc | aagcgtctgc | tgatgaagta | 1680 |
| aaaggcgttc | gctactccgt | atttggatgc | ggcgataaaa | actgggctac | tacgtatcaa | 1740 |
| aaagtgcctg | cttttatcga | tgaaacgctt | gccgctaaag | gggcagaaaa | catcgctgac | 1800 |
| cgcggtgaag | cagatgcaag | cgacgacttt | gaaggcacat | atgaagaatg | gcgtgaacat | 1860 |
| atgtggagtg | acgtagcagc | ctactttaac | ctcgacattg | aaaacagtga | agataataaa | 1920 |
| tctactcttt | cacttcaatt | tgtcgacagc | gccgcggata | tgccgcttgc | gaaaatgcac | 1980 |
| ggtgcgtttt | caacgaacgt | cgtagcaagc | aaagaacttc | aacagccagg | cagtgcacga | 2040 |
| agcacgcgac | atcttgaaat | tgaacttcca | aagaagcttt | cttatcaaga | aggagatcat | 2100 |
| ttaggtgtta | ttcctcgcaa | ctatgaagga | atagtaaacc | gtgtaacagc | aaggttcggc | 2160 |

```
ctagatgcat acacagcaaat ccgtctggaa gcagaagaag aaaaattagc tcatttgcca   2220
ctcgctaaaa cagtatccgt agaagagctt ctgcaatacg tggagcttca agatcctgcg   2280
acgcgcacgc agcttcgcgc aatggctgct accacggtct gcccgccgca taaagtagag   2340
cttgaagcct tgcttgaaaa gcaagcctac aaagaacaag tgctggcaaa acgtttaaca   2400
atgcttgaac tgcttgaaaa atacccggcg tgtgaaatga aattcagcga atttatcgcc   2460
cttctgccaa gcatacgccc gcgctattac tcgatttctt catcacctcg tgtcgatgaa   2520
aaacaagcaa gcatcacggt cagcgttgtc tcaggagaag cgtggagcgg atatggagaa   2580
tataaaggaa ttgcgtcgaa ctatcttgcc gagctgcaag aaggagatac gattacgtgc   2640
tttatttcca caccgcagtc agaatttacg ctgccaaaag accctgaaac gccgcttatc   2700
atggtcggac cgggaacagg cgtcgcgccg tttagaggct tgtgcaggc gcgcaaacag   2760 ctaaaagaac aaggacagtc acttggagaa gcacatttat acttcggctg ccgttcacct   2820
catgaagact atctgtatca agaagagctt gaaaacgccc aaagcgaagg catcattacg   2880
cttcataccg cttttctcg catgccaaat cagccgaaaa catacgttca gcacgtaatg   2940
gaacaagacg gcaagaaatt gattgaactt cttgatcaag gagcgcactt ctatatttgc   3000
ggagacggaa gccaaatggc acctgccgtt gaagcaacgc ttatgaaaag ctatgctgac   3060
gttcaccaag tgagtgaata tgacgctcgc ttatggctgc agcagctaga agaaaaaggc   3120
cgatacgcaa aagacgtgtg ggctgggtaa                                    3150
```

<210> SEQ ID NO 28
<211> LENGTH: 1049
<212> TYPE: PRT
<213> ORGANISM: Artificial Sequence
<220> FEATURE:
<223> OTHER INFORMATION: synthetic P450-BM3 variant polypeptide

<400> SEQUENCE: 28

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Leu
        35                  40                  45

Val Thr Ile Tyr Leu Ser Ser Gln Arg Leu Ile Lys Glu Ala Cys Asp
    50                  55                  60

Glu Ser Arg Phe Asp Lys Asn Leu Ser Gln Ala Met Lys Phe Ala Arg
65                  70                  75                  80

Asp Phe Leu Gly Asp Gly Leu Ala Thr Ser Trp Thr His Glu Ile Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Ala Leu Asp Glu Val Met Asn Lys Arg Gln Arg Ala
```

```
                180                 185                 190
Asn Pro Asp Asp Pro Ala Tyr Asp Glu Asn Lys Arg Gln Cys Gln Glu
            195                 200                 205

Asp Ile Lys Val Met Asn Asp Leu Val Asp Lys Ile Ile Ala Asp Arg
            210                 215                 220

Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
                260                 265                 270

Leu Leu Ser Phe Ala Leu Tyr Phe Leu Val Lys Asn Pro His Val Leu
            275                 280                 285

Gln Lys Val Ala Glu Ala Ala Arg Val Leu Val Asp Pro Val Pro
            290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Gln Leu Ser Lys Gly Asp
                340                 345                 350

Glu Val Asn Val Leu Ile Pro Gln Leu His Arg Asp Lys Thr Ile Trp
            355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
            435                 440                 445

Ala Lys Ser Lys Lys Ile Pro Leu Gly Phe Ile Pro Ser Pro Ser Thr
450                 455                 460

Glu Gln Ser Ala Lys Lys Val Arg Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
                500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
530                 535                 540

Ala Lys Gln Phe Val Arg Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
                580                 585                 590

Lys Gly Ala Glu Asn Ile Ala Asp Arg Gly Glu Ala Asp Ala Ser Asp
            595                 600                 605
```

```
Asp Phe Glu Gly Thr Tyr Glu Glu Trp Arg Glu His Met Trp Ser Asp
610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
                660                 665                 670

Leu Gln Gln Pro Gly Ser Ala Arg Ser Thr Arg His Leu Glu Ile Glu
            675                 680                 685

Leu Pro Lys Glu Ala Ser Tyr Gln Glu Gly Asp His Leu Gly Val Ile
690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
            725                 730                 735

Ala His Leu Pro Leu Ala Lys Thr Val Ser Val Glu Leu Leu Gln
                740                 745                 750

Tyr Val Glu Leu Gln Asp Pro Ala Thr Arg Thr Gln Leu Arg Ala Met
        755                 760                 765

Ala Ala Thr Thr Val Cys Pro His Lys Val Glu Leu Glu Ala Leu
770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln
    1010                1015                1020
```

Val Ser Glu Tyr Asp Ala Arg Leu Trp Leu Gln Gln Leu Glu Glu
    1025                1030                1035

Lys Gly Arg Tyr Ala Lys Asp Val Trp Ala Gly
    1040                1045

<210> SEQ ID NO 29
<211> LENGTH: 3150
<212> TYPE: DNA
<213> ORGANISM: Artificial Sequence
<220> FEATURE:
<223> OTHER INFORMATION: synthetic P450-BM3 variant polynucleotide

<400> SEQUENCE: 29

```
atgacaataa aggaaatgcc gcagccgaaa acgtttggag aacttaaaaa tttaccgtta    60
ttaaacacag ataaaccggt tcaagctttg atgaaaattg cggatgaatt aggagaaatc   120
tttaaattcg aggcgcctgg tttggtaacg atttacttat caagtcagcg tctaattaaa   180
gaagcatgcg atgaatacg ctttgataaa aacttaagtc aggcgatgaa atttgcacgt   240
gattttctgg agacgggtt agcaacaagc tggacgcatg aaataaattg gaaaaaagcg   300
cataatatct acttccaag ctttagtcag caggcaatga aaggctatca tgcgatgatg   360
gtcgatatcg ccgtgcagct tgttcaaaag tgggagcgtc taaatgcaga tgagcatatt   420
gaagtatcgg aagacatgac acgtttaacg cttgatacaa ttggtctttg cggctttaac   480
tatcgcttta cagctttta ccgagatcag cctcatccat ttattgtgag tatggtccgt   540
gcactggatg aagtaatgaa caagcgtcag cgagcaaatc agacgaccc agcttatgat   600
gaaaacaagc gccagtgtca agaagatatc aaggtgatga cgacctagt agataaaatt   660
attgcagatc gcaaagcaag gggtgaacaa cgtgatgatt tattaacgca gatgctaaac   720
ggaaaagatc cagaaacggg tgagccgctt gatgacggga acattagcta tcaaattatt   780
acattcttaa ttgcgggaca cgaaacaaca agtggtcttt tatcatttgc gctgtatttc   840
ttagtgaaaa atccacatgt attacaaaaa gtagcagaag aagcagcacg agttctagta   900
gatcctgttc aagctacaa acaagtcaaa cagcttaaat atgtcggcat ggtcttaaac   960
gaagcgctgc gcttatggcc aactgctcct gcgttttccc tatatgcaaa agaagatacg  1020
gtgcttggag agaatatcc tttagcgaaa ggcgacgaag taatgttcct gattcctcag  1080
cttcaccgtg ataaaacaat tggggagac gatgtggagg agttccgtcc agagcgtttt  1140
gaaaatccaa gtgcgattcc gcagcatgcg tttaaaccgt ttggaaacgg tcagcgtgcg  1200
tgtatcggtc agcagttcgc tcttcatgaa gcaacgctgg tacttggtat gatgctaaaa  1260
cactttgact ttgaagatca tacaaactac gagctcgata ttaagaaac tttaacgtta  1320
aaacctgaag ctttgtggt aaaagcaaaa tcgaaaaaaa ttccgcttgg cggtattcct  1380
tcacctagca ctgaacagtc tgctaaaaaa gtacgcaaaa aggcagaaaa cgctcataat  1440
acgccgctgc ttgtgctata cggttcaaat atgggaacag ctgaaggaac ggcgcgtgat  1500
ttagcagata ttgcaatgag caaaggattt gcaccgcagg tcgcaacgct tgattcacac  1560
gccggaaatc ttccgcgcga aggagctgta ttaattgtaa cggcgtctta taacggtcat  1620
ccgcctgata cgcaaagca atttgtcgac tggttagacc aagcgtctgc tgatgaagta  1680
aaaggcgttc gctactccgt atttggatgc ggcgataaaa actgggctgc gacgtatcaa  1740
aaagtgcctg cttttatcga tgaaacgctt gccgctaaag gggcagaaaa catcgctgac  1800
cgcggtgaag cagatgcaag cgacgacttt gaaggcaact atgaagaatg gcgtgaacat  1860
atgtggagtg acgtagcagc ctactttaac ctcgacattg aaaacagtga agataataaa  1920
```

```
tctactctttt cacttcaatt tgtcgacagc gccgcggata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctaggcgcat cacagcaaat ccgtctggaa gcagaagaag aaaaattagc tcatttgcca   2220
ctcgctaaaa cagtatccgt agaagagctt ctgcaatacg tggagcttca agatcctgcg   2280
acgcgcacgc agcttcgcgc aatggctgct aaaacggtct gcccgccgca taaagtagag   2340
cttgaagcct tgcttgaaaa gcaagcctac aaagaacaag tgatggcaaa cgtttaaca   2400 atgcttgaac tgcttgaaaa ataccccggcg tgtgaaatga aattcagcga atttatcgcc   2460
cttctgccaa gcatacgccc gcgctattac tcgatttctt catcacctcg tgtcgatgaa   2520
aaacaagcaa gcatcacggt cagcgttgtc tcaggagaag cgtggagcgg atatggagaa   2580
tataaaggaa ttgcgtcgaa ctatcttgcc gagctgcaag aaggagatac gattacgtgc   2640
tttatttcca caccgcagtc agaatttacg ctgccaaaag accctgaaac gccgcttatc   2700
atggtcggac cgggaacagg cgtcgcgccg tttagaggct ttgtgcaggc gcgcaaacag   2760
ctaaaagaac aaggacagtc acttggagaa gcacatttat acttcggctg ccgttcacct   2820
catgaagact atctgtatca agaagagctt gaaaacgccc aaagcgaagg catcattacg   2880
cttcataccg ctttttctcg catgccaaat cagccgaaaa catacgttca gcacgtaatg   2940
gaacaagacg gcaagaaatt gattgaactt cttggccaag gagcgcactt ctatatttgc   3000
ggagacggaa gccaaatggc acctgccgtt gaagcaacgc ttatgaaaag ctatgctgac   3060
gttcaccaag tgagtgaagc agacgctcgc ttatggctgc agcagctaga agaaaaaggc   3120
cgatacgcaa aagacgtgtg gatggggtaa                                    3150
```

<210> SEQ ID NO 30
<211> LENGTH: 1049
<212> TYPE: PRT
<213> ORGANISM: Artificial Sequence
<220> FEATURE:
<223> OTHER INFORMATION: synthetic P450-BM3 variant polypeptide

<400> SEQUENCE: 30

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Leu
        35                  40                  45

Val Thr Ile Tyr Leu Ser Ser Gln Arg Leu Ile Lys Glu Ala Cys Asp
    50                  55                  60

Glu Ser Arg Phe Asp Lys Asn Leu Ser Gln Ala Met Lys Phe Ala Arg
65                  70                  75                  80

Asp Phe Leu Gly Asp Gly Leu Ala Thr Ser Trp Thr His Glu Ile Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140
```

```
Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Val
            165                 170                 175

Ser Met Val Arg Ala Leu Asp Glu Val Met Asn Lys Arg Gln Arg Ala
        180                 185                 190

Asn Pro Asp Asp Pro Ala Tyr Asp Glu Asn Lys Arg Gln Cys Gln Glu
    195                 200                 205

Asp Ile Lys Val Met Asn Asp Leu Val Asp Lys Ile Ala Asp Arg
210                 215                 220

Lys Ala Arg Gly Glu Gln Arg Asp Asp Leu Leu Thr Gln Met Leu Asn
225                 230                 235                 240

Gly Lys Asp Pro Glu Thr Gly Glu Pro Leu Asp Asp Gly Asn Ile Ser
            245                 250                 255

Tyr Gln Ile Ile Thr Phe Leu Ile Ala Gly His Glu Thr Thr Ser Gly
        260                 265                 270

Leu Leu Ser Phe Ala Leu Tyr Phe Leu Val Lys Asn Pro His Val Leu
    275                 280                 285

Gln Lys Val Ala Glu Ala Ala Arg Val Leu Val Asp Pro Val Pro
290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
            325                 330                 335

Lys Glu Asp Thr Val Leu Gly Gly Glu Tyr Pro Leu Ala Lys Gly Asp
        340                 345                 350

Glu Val Asn Val Leu Ile Pro Gln Leu His Arg Asp Lys Thr Ile Trp
    355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
            405                 410                 415

Met Met Leu Lys His Phe Asp Phe Glu Asp His Thr Asn Tyr Glu Leu
        420                 425                 430

Asp Ile Lys Glu Thr Leu Thr Leu Lys Pro Glu Gly Phe Val Val Lys
    435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
            485                 490                 495

Thr Ala Arg Asp Leu Ala Asp Ile Ala Met Ser Lys Gly Phe Ala Pro
        500                 505                 510

Gln Val Ala Thr Leu Asp Ser His Ala Gly Asn Leu Pro Arg Glu Gly
    515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Glu Val
545                 550                 555                 560
```

-continued

```
Lys Gly Val Arg Tyr Ser Val Phe Gly Cys Gly Asp Lys Asn Trp Ala
                565                 570                 575
Ala Thr Tyr Gln Lys Val Pro Ala Phe Ile Asp Glu Thr Leu Ala Ala
            580                 585                 590
Lys Gly Ala Glu Asn Ile Ala Asp Arg Gly Glu Ala Asp Ala Ser Asp
        595                 600                 605
Asp Phe Glu Gly Asn Tyr Glu Glu Trp Arg Glu His Met Trp Ser Asp
    610                 615                 620
Val Ala Ala Tyr Phe Asn Leu Asp Ile Glu Asn Ser Glu Asp Asn Lys
625                 630                 635                 640
Ser Thr Leu Ser Leu Gln Phe Val Asp Ser Ala Ala Asp Met Pro Leu
                645                 650                 655
Ala Lys Met His Gly Ala Phe Ser Thr Asn Val Val Ala Ser Lys Glu
            660                 665                 670
Leu Gln Gln Pro Gly Ser Ala Arg Ser Thr Arg His Leu Glu Ile Glu
        675                 680                 685
Leu Pro Lys Glu Ala Ser Tyr Gln Glu Gly Asp His Leu Gly Val Ile
    690                 695                 700
Pro Arg Asn Tyr Glu Gly Ile Val Asn Arg Val Thr Ala Arg Phe Gly
705                 710                 715                 720
Leu Gly Ala Ser Gln Gln Ile Arg Leu Glu Ala Glu Glu Lys Leu
                725                 730                 735
Ala His Leu Pro Leu Ala Lys Thr Val Ser Val Glu Glu Leu Leu Gln
            740                 745                 750
Tyr Val Glu Leu Gln Asp Pro Ala Thr Arg Thr Gln Leu Arg Ala Met
        755                 760                 765
Ala Ala Lys Thr Val Cys Pro Pro His Lys Val Glu Leu Glu Ala Leu
    770                 775                 780
Leu Glu Lys Gln Ala Tyr Lys Glu Gln Val Met Ala Lys Arg Leu Thr
785                 790                 795                 800
Met Leu Glu Leu Leu Glu Lys Tyr Pro Ala Cys Glu Met Lys Phe Ser
                805                 810                 815
Glu Phe Ile Ala Leu Leu Pro Ser Ile Arg Pro Arg Tyr Tyr Ser Ile
            820                 825                 830
Ser Ser Ser Pro Arg Val Asp Glu Lys Gln Ala Ser Ile Thr Val Ser
        835                 840                 845
Val Val Ser Gly Glu Ala Trp Ser Gly Tyr Gly Glu Tyr Lys Gly Ile
    850                 855                 860
Ala Ser Asn Tyr Leu Ala Glu Leu Gln Glu Gly Asp Thr Ile Thr Cys
865                 870                 875                 880
Phe Ile Ser Thr Pro Gln Ser Glu Phe Thr Leu Pro Lys Asp Pro Glu
                885                 890                 895
Thr Pro Leu Ile Met Val Gly Pro Gly Thr Gly Val Ala Pro Phe Arg
            900                 905                 910
Gly Phe Val Gln Ala Arg Lys Gln Leu Lys Glu Gln Gly Gln Ser Leu
        915                 920                 925
Gly Glu Ala His Leu Tyr Phe Gly Cys Arg Ser Pro His Glu Asp Tyr
    930                 935                 940
Leu Tyr Gln Glu Glu Leu Glu Asn Ala Gln Ser Glu Gly Ile Ile Thr
945                 950                 955                 960
Leu His Thr Ala Phe Ser Arg Met Pro Asn Gln Pro Lys Thr Tyr Val
                965                 970                 975
Gln His Val Met Glu Gln Asp Gly Lys Lys Leu Ile Glu Leu Leu Gly
```

```
            980             985             990
Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Met Gly
    1040                1045
```

<210> SEQ ID NO 31
<211> LENGTH: 3150
<212> TYPE: DNA
<213> ORGANISM: Artificial Sequence
<220> FEATURE:
<223> OTHER INFORMATION: synthetic P450-BM3 variant polynucleotide

<400> SEQUENCE: 31

| | |
|---|---|
| atgacaataa aggaaatgcc gcagccgaaa acgtttggag aacttaaaaa tttaccgtta | 60 |
| ttaaacacag ataaaccggt tcaagctttg atgaaaattg cggatgaatt aggagaaatc | 120 |
| tttaaattcg aggcgcctgg tttggtaacg atttacttat caagtcagcg tctaattaaa | 180 |
| gaagcatgcg atgaatcacg ctttgataaa aacttaagtc aggcgatgaa atttgcacgt | 240 |
| gattttctgg agacgggtt agcaacaagc tggacgcatg aaataaattg gaaaaaagcg | 300 |
| cataatatct tacttccaag ctttagtcag caggcaatga aaggctatca tgcgatgatg | 360 |
| gtcgatatcg ccgtgcagct tgttcaaaag tgggagcgtc taaatgcaga tgagcatatt | 420 |
| gaagtatcgg aagacatgac acgtttaacg cttgatacaa ttggtctttg cggctttaac | 480 |
| tatcgcttta cagcttttta ccgagatcag cctcatccat ttattataag tatggtccgt | 540 |
| gcactggatg aagtaatgaa caagcgtcag cgagcaaatc cagacgaccc agcttatgat | 600 |
| gaaaacaagc gccagtgtca agaagatatc aaggtgatga cgacctagt agataaaatt | 660 |
| attgcagatc gcaaagcaag gggtgaacaa cgtgatgatt tattaacgca gatgctaaac | 720 |
| ggaaaagatc cagaaacggg tgagccgctt gatgacggga acattagcta tcaaattatt | 780 |
| acattcttaa ttgcgggaca cgaaacaaca agtggtcttt tatcatttgc gctgtatttc | 840 |
| ttagtgaaaa atccacatgt attacaaaaa gtagcagaag aagcagcacg agttctagta | 900 |
| gatcctgttc caagctacaa acaagtcaaa cagcttaaat atgtcggcat ggtcttaaac | 960 |
| gaagcgctgc gcttatggcc aactgctcct gcgttttccc tatatgcaaa agaagatacg | 1020 |
| gtgcttggag gagaatatcc tttagaaaaa ggcgacgaag taatgttcct gattcctcag | 1080 |
| cttcaccgtg ataaacaat tggggagac gatgtggagg agttccgtcc agagcgtttt | 1140 |
| gaaaatccaa gtgcgattcc gcagcatgcg tttaaaccgt ttggaaacgg tcagcgtgcg | 1200 |
| tgtatcggtc agcagttcgc tcttcatgaa gcaacgctgg tacttggtat gatgctaaaa | 1260 |
| cactttgact ttgaagatca tacaaactac gagctcaaaa ttaagaaaac tttaacgtta | 1320 |
| aaacctgaag gctttgtggt aaaagcaaaa tcgaaaaaaa ttccgcttgg cggtattcct | 1380 |
| tcacctagca ctgaacagtc tgctaaaaaa gtacgcaaaa aggcagaaaa cgctcataat | 1440 |
| acgccgctgc ttgtgctata cggttcaaat atgggaacag ctgaaggaac ggcgcgtgat | 1500 |
| ttagcagata ttgcaatgag caaaggattt gcaccgcagg tcgcaacgct tgattcacac | 1560 |
| gccggaaatc ttccgcgcga aggagctgta ttaattgtaa cggcgtctta taacggtcat | 1620 |
| ccgcctgata acgcaaagca atttgtcgac tggttagacc aagcgtctgc tgatgaagta | 1680 |

```
aaaggcgttc gctactccgt atttggatgc ggcgataaaa actgggctac tacgtatcaa      1740
aaagtgcctg cttttatcga tgaaacgctt gccgctaaag gggcagaaaa catcgctgac      1800
cgcggtgaag cagatgcaag cgacgacttt gaaggcaact atgaagaatg cgtgaacat       1860 atgtggagtg acgtagcagc ctactttaac ctcgacattg aaaacagtga agataataaa      1920
tctactcttt cacttcaatt tgtcgacagc gccgcggata tgccgcttgc gaaaatgcac      1980
ggtgcgtttt caacgaacgt cgtagcaagc aaagaacttc aacagccagg cagtgcacga      2040
agcacgcgac atcttgaaat tgaacttcca aaagaagctt cttatcaaga aggagatcat      2100
ttaggtgtta ttcctcgcaa ctatgaagga atagtaaacc gtgtaacagc aaggttcggc      2160
ctagatgcat cacagcaaat ccgtctggaa gcagaagaag aaaaattagc tcatttgcca      2220
ctcgctaaaa cagtatccgt agaagagctt ctgcaatacg tggagcttca agatcctgcg      2280
acgcgcacgc agcttcgcgc aatggctgct aaaacggtct gcccgccgca taagtagag       2340 cttgaagcct tgcttgaaaa gcaagcctac aaagaacaag tgctggcaaa cgtttaaca       2400 atgcttgaac tgcttgaaaa atacccggcg tgtgaaatga aattcagcga atttatcgcc      2460
cttctgccaa gcatacgccc gcgctattac tcgatttctt catcacctcg tgtcgatgaa      2520
aaacaagcaa gcatcacggt cagcgttgtc tcaggagaag cgtggagcgg atatggagaa      2580
tataaaggaa ttgcgtcgaa ctatcttgcc gagctgcaag aaggagatac gattacgtgc      2640
tttatttcca caccgcagtc agaatttacg ctgccaaaag accctgaaac gccgcttatc      2700
atggtcggac cgggaacagg cgtcgcgccg tttagaggct ttgtgcaggc gcgcaaacag      2760
ctaaaagaac aaggacagtc acttggagaa gcacatttat acttcggctg ccgttcacct      2820
catgaagact atctgtatca agaagagctt gaaaacgccc aaagcgaagg catcattacg      2880
cttcataccg ctttttctcg catgccaaat cagccgaaaa catacgttca gcacgtaatg      2940
gaacaagacg gcaagaaatt gattgaactt cttgatcaag gagcgcactt ctatatttgc      3000
ggagacggaa gccaaatggc acctgccgtt gaagcaacgc ttatgaaaag ctatgctgac      3060
gttcaccaag tgagtgaagc agacgctcgc ttatggctgc agcagctaga agaaaaaggc      3120
cgatacgcaa aagacgtgtg gatggggtaa                                       3150
```

<210> SEQ ID NO 32
<211> LENGTH: 1049
<212> TYPE: PRT
<213> ORGANISM: Artificial Sequence
<220> FEATURE:
<223> OTHER INFORMATION: synthetic P450-BM3 variant polypeptide

<400> SEQUENCE: 32

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Leu
        35                  40                  45

Val Thr Ile Tyr Leu Ser Ser Gln Arg Leu Ile Lys Glu Ala Cys Asp
    50                  55                  60

Glu Ser Arg Phe Asp Lys Asn Leu Ser Gln Ala Met Lys Phe Ala Arg
65                  70                  75                  80

Asp Phe Leu Gly Asp Gly Leu Ala Thr Ser Trp Thr His Glu Ile Asn
                85                  90                  95
```

```
Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
            115                 120                 125

Gln Lys Trp Glu Arg Leu Asn Ala Asp Glu His Ile Glu Val Ser Glu
        130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                    165                 170                 175

Ser Met Val Arg Ala Leu Asp Glu Val Met Asn Lys Arg Gln Arg Ala
                180                 185                 190

Asn Pro Asp Asp Pro Ala Tyr Asp Glu Asn Lys Arg Gln Cys Gln Glu
            195                 200                 205

Asp Ile Lys Val Met Asn Asp Leu Val Asp Lys Ile Ile Ala Asp Arg
210                 215                 220

Lys Ala Arg Gly Glu Gln Arg Asp Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
                260                 265                 270

Leu Leu Ser Phe Ala Leu Tyr Phe Leu Val Lys Asn Pro His Val Leu
                275                 280                 285

Gln Lys Val Ala Glu Glu Ala Ala Arg Val Leu Val Asp Pro Val Pro
            290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                    325                 330                 335

Lys Glu Asp Thr Val Leu Gly Gly Glu Tyr Pro Leu Glu Lys Gly Asp
                340                 345                 350

Glu Val Asn Val Leu Ile Pro Gln Leu His Arg Asp Lys Thr Ile Trp
            355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
                420                 425                 430

Lys Ile Lys Glu Thr Leu Thr Leu Lys Pro Glu Gly Phe Val Val Lys
            435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
                500                 505                 510

Gln Val Ala Thr Leu Asp Ser His Ala Gly Asn Leu Pro Arg Glu Gly
```

```
            515                 520                 525
Ala Val Leu Ile Val Thr Ala Ser Tyr Asn Gly His Pro Pro Asp Asn
        530                 535                 540
Ala Lys Gln Phe Val Asp Trp Leu Asp Gln Ala Ser Ala Asp Glu Val
545                 550                 555                 560
Lys Gly Val Arg Tyr Ser Val Phe Gly Cys Gly Asp Lys Asn Trp Ala
                565                 570                 575
Thr Thr Tyr Gln Lys Val Pro Ala Phe Ile Asp Glu Thr Leu Ala Ala
                580                 585                 590
Lys Gly Ala Glu Asn Ile Ala Asp Arg Gly Glu Ala Asp Ala Ser Asp
                595                 600                 605
Asp Phe Glu Gly Asn Tyr Glu Glu Trp Arg Glu His Met Trp Ser Asp
        610                 615                 620
Val Ala Ala Tyr Phe Asn Leu Asp Ile Glu Asn Ser Glu Asp Asn Lys
625                 630                 635                 640
Ser Thr Leu Ser Leu Gln Phe Val Asp Ser Ala Ala Asp Met Pro Leu
                645                 650                 655
Ala Lys Met His Gly Ala Phe Ser Thr Asn Val Val Ala Ser Lys Glu
                660                 665                 670
Leu Gln Gln Pro Gly Ser Ala Arg Ser Thr Arg His Leu Glu Ile Glu
                675                 680                 685
Leu Pro Lys Glu Ala Ser Tyr Gln Gly Asp His Leu Gly Val Ile
        690                 695                 700
Pro Arg Asn Tyr Glu Gly Ile Val Asn Arg Val Thr Ala Arg Phe Gly
705                 710                 715                 720
Leu Asp Ala Ser Gln Gln Ile Arg Leu Glu Ala Glu Glu Lys Leu
                725                 730                 735
Ala His Leu Pro Leu Ala Lys Thr Val Ser Val Glu Glu Leu Leu Gln
                740                 745                 750
Tyr Val Glu Leu Gln Asp Pro Ala Thr Arg Thr Gln Leu Arg Ala Met
        755                 760                 765
Ala Ala Lys Thr Val Cys Pro Pro His Lys Val Glu Leu Glu Ala Leu
        770                 775                 780
Leu Glu Lys Gln Ala Tyr Lys Glu Gln Val Leu Ala Lys Arg Leu Thr
785                 790                 795                 800
Met Leu Glu Leu Leu Glu Lys Tyr Pro Ala Cys Glu Met Lys Phe Ser
                805                 810                 815
Glu Phe Ile Ala Leu Leu Pro Ser Ile Arg Pro Arg Tyr Tyr Ser Ile
                820                 825                 830
Ser Ser Ser Pro Arg Val Asp Glu Lys Gln Ala Ser Ile Thr Val Ser
        835                 840                 845
Val Val Ser Gly Glu Ala Trp Ser Gly Tyr Gly Glu Tyr Lys Gly Ile
        850                 855                 860
Ala Ser Asn Tyr Leu Ala Glu Leu Gln Glu Gly Asp Thr Ile Thr Cys
865                 870                 875                 880
Phe Ile Ser Thr Pro Gln Ser Glu Phe Thr Leu Pro Lys Asp Pro Glu
                885                 890                 895
Thr Pro Leu Ile Met Val Gly Pro Gly Thr Gly Val Ala Pro Phe Arg
                900                 905                 910
Gly Phe Val Gln Ala Arg Lys Gln Leu Lys Glu Gln Gly Gln Ser Leu
                915                 920                 925
Gly Glu Ala His Leu Tyr Phe Gly Cys Arg Ser Pro His Glu Asp Tyr
        930                 935                 940
```

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Met Gly
    1040                1045

<210> SEQ ID NO 33
<211> LENGTH: 3150
<212> TYPE: DNA
<213> ORGANISM: Artificial Sequence
<220> FEATURE:
<223> OTHER INFORMATION: synthetic P450-BM3 variant polynucleotide

<400> SEQUENCE: 33
atgacaataa ggaaatgcc gcagccgaaa acgtttggag aacttaaaaa tttaccgtta      60
ttaaacacag ataaaccggt tcaagctttg atgaaaattg cggatgaatt aggagaaatc    120
tttaaattcg aggcgcctgg tttggtaacg atttttttat caagtcagcg tctaattaaa    180
gaagcatgcg atgaatcacg ctttgataaa aacttaagtc aggcgatgaa atttgcacgt    240
gattttctgg agacggggtt agcaacaagc tggacgcatg aaataaattg gaaaaaagcg    300
cataatatct acttccaag ctttagtcag caggcaatga aaggctatca tgcgatgatg    360
gtcgatatcg ccgtgcagct tgttcaaaag tgggagcgtc taaatgcaga tgagcatatt    420
gaagtatcgg aagacatgac acgtttaacg cttgatacaa ttggtctttg cggctttaac    480
tatcgcttta acagcttta ccgagatcag cctcatccat ttattataag tatggtccgt    540
gcactggatg aagtaatgaa caagcgtcag cgagcaaatc cagacgaccc agcttatgat    600
gaaaacaagc gccagtgtca agaagatatc aaggtgatga cgactatgt agatcgtatt    660 attgcagatc gcaaagcaag gggtgaacaa agcgatgatt tattaacgca gatgctaaac    720
ggaaaagatc cagaaacggg tgagccgctt gatgacggga cattagcta tcaaattatt    780 acattcttaa ttgcgggaca cgaaacaaca agtggtcttt tatcatttgc gctgtatttc    840
ttagtgaaaa atccacatgt attacaaaaa gtagcagaag aagcagcacg agttctagta    900
gatcctgttc caagctacaa acaagtcaaa cagcttaaat atgtcggcat ggtcttaaac    960
gaagcgctgc gcttatggcc aactgctcct gcgttttccc tatatgcaaa agaagatacg   1020
gtgcttggag gagaatatcc tttagaaaaa ggcgacgaag taaatgttct gattcctcag   1080
cttcaccgtg ataaaacaat ttggggagac gatgtggagg agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact ttgaagatca tacaaactac gagctccgta ttaagaaac tttaacgtta   1320 aaacctgaag gctttgtggt aaaagcaaaa tcgaaaaaaa ttccgcttgg cggtattcct   1380
tcacctagca ctgaacagtc tgctaaaaaa gtacgcaaaa aggcagaaaa cgctcataat   1440

-continued

```
acgccgctgc ttgtgctata cggttcaaat atgggaacag ctgaaggaac ggcgcgtgat   1500
ttagcagata ttgcaatgag caaaggattt gcaccgcagg tcgcaacgct tgattccacc   1560
gccggaaatc ttccgcgcga aggagctgta ttaattgtaa cggcgtctta taacggtcat   1620
ccgcctgata acgcaaagca atttgtcgac tggttagacc aagcgtctgc tgatgaagta   1680
aaaggcgttc gctactccgt atttggatgc ggcgataaaa actgggctac tacgtatcaa   1740
aaagtgcctg cttttatcga tgaaacgctt gccgctaaag gggcagaaaa catcgctgac   1800
cgcggtgaag cagatgcaag cgacgacttt gaaggcacat atgaagtatg cgtgagcat   1860 atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctggaa gcagaagaag aaaaattagc tcatttgcca   2220
ctcgctaaaa cagtatccgt agaagagctt ctgcaatacg tggagcttca agatcctgcg   2280
acgcgcacgc agcttcgcgc aatggctgct aaaacggtct gcccgccgca taagtagag   2340 cttgaagcct tgcttgaaaa gcaagcctac aaagaacaag tgctggcaaa acgtttaaca   2400
atgcttgaac tgcttgaaaa ataccccggcg tgtgaaatga aattcagcga atttatcgcc   2460
cttctgccaa gcatacgccc gcgctattac tcgatttctt catcacctcg tgtcgatgaa   2520
aaacaagcaa gcatcacggt cagcgttgtc tcaggagaag cgtggagcgg atatggagaa   2580
tataaaggaa ttgcgtcgaa ctatcttgcc gagctgcaag aaggagatac gattacgtgc   2640
tttatttcca caccgcagtc agaatttacg ctgccaaaag accctgaaac gccgcttatc   2700
atggtcggac cgggaacagg cgtcgcgccg tttagaggct ttgtgcaggc gcgcaaacag   2760
ctaaaagaac aaggacagtc acttggagaa gcacatttat acttcggctg ccgttcacct   2820
catgaagact atctgtatca agaagagctt gaaaacgccc aaagcgaagg catcattacg   2880
cttcataccg ctttttctcg catgccaaat cagccgaaaa catacgttca gcacgtaatg   2940
gaacaagacg gcaagaaatt gattgaactt cttgatcaag gagcgcactt ctatatttgc   3000
ggagacggaa gccaaatggc acctgccgtt gaagcaacgc ttatgaaaag ctatgctgac   3060
gttcaccaag tgagtgaagc agacgctcgc ttatggctgc agcagctaga agaaaaaggc   3120
cgatacgcaa aagacgtgtg ggctgggtaa                                     3150
```

<210> SEQ ID NO 34
<211> LENGTH: 1049
<212> TYPE: PRT
<213> ORGANISM: Artificial Sequence
<220> FEATURE:
<223> OTHER INFORMATION: synthetic P450-BM3 variant polypeptide

<400> SEQUENCE: 34

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Leu
        35                  40                  45

Val Thr Ile Phe Leu Ser Ser Gln Arg Leu Ile Lys Glu Ala Cys Asp
```

```
            50                  55                  60
Glu Ser Arg Phe Asp Lys Asn Leu Ser Gln Ala Met Lys Phe Ala Arg
 65                  70                  75                  80

Asp Phe Leu Gly Asp Gly Leu Ala Thr Ser Thr His Glu Ile Asn
                 85                  90                  95

Trp Lys Lys Ala His Asn Ile Leu Leu Pro Ser Phe Ser Gln Gln Ala
                100                 105                 110

Met Lys Gly Tyr His Ala Met Met Val Asp Ile Ala Val Gln Leu Val
                115                 120                 125

Gln Lys Trp Glu Arg Leu Asn Ala Asp Glu His Ile Glu Val Ser Glu
        130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Ala Leu Asp Glu Val Met Asn Lys Arg Gln Arg Ala
                180                 185                 190

Asn Pro Asp Asp Pro Ala Tyr Asp Glu Asn Lys Arg Gln Cys Gln Glu
                195                 200                 205

Asp Ile Lys Val Met Asn Asp Tyr Val Asp Arg Ile Ala Asp Arg
210                 215                 220

Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
                260                 265                 270

Leu Leu Ser Phe Ala Leu Tyr Phe Leu Val Lys Asn Pro His Val Leu
                275                 280                 285

Gln Lys Val Ala Glu Glu Ala Ala Arg Val Leu Val Asp Pro Val Pro
                290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
                340                 345                 350

Glu Val Asn Val Leu Ile Pro Gln Leu His Arg Asp Lys Thr Ile Trp
                355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
                420                 425                 430

Arg Ile Lys Glu Thr Leu Thr Leu Lys Pro Glu Gly Phe Val Val Lys
                435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn
465                 470                 475                 480
```

```
Thr Pro Leu Leu Val Leu Tyr Gly Ser Asn Met Gly Thr Ala Glu Gly
            485                 490                 495

Thr Ala Arg Asp Leu Ala Asp Ile Ala Met Ser Lys Gly Phe Ala Pro
        500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
        530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Val Trp Arg Glu His Met Trp Ser Asp
        610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
        690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Ala Thr Arg Thr Gln Leu Arg Ala Met
        755                 760                 765

Ala Ala Lys Thr Val Cys Pro Pro His Lys Val Glu Leu Glu Ala Leu
        770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
            835                 840                 845

Val Val Ser Gly Glu Ala Trp Ser Gly Tyr Gly Glu Tyr Lys Gly Ile
        850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895
```

Thr Pro Leu Ile Met Val Gly Pro Gly Thr Gly Val Ala Pro Phe Arg
            900                 905                 910
Gly Phe Val Gln Ala Arg Lys Gln Leu Lys Glu Gln Gly Gln Ser Leu
        915                 920                 925
Gly Glu Ala His Leu Tyr Phe Gly Cys Arg Ser Pro His Glu Asp Tyr
    930                 935                 940
Leu Tyr Gln Glu Glu Leu Glu Asn Ala Gln Ser Glu Gly Ile Ile Thr
945                 950                 955                 960
Leu His Thr Ala Phe Ser Arg Met Pro Asn Gln Pro Lys Thr Tyr Val
                965                 970                 975
Gln His Val Met Glu Gln Asp Gly Lys Lys Leu Ile Glu Leu Leu Asp
            980                 985                 990
Gln Gly Ala His Phe Tyr Ile Cys Gly Asp Gly Ser Gln Met Ala Pro
        995                 1000                1005
Ala Val Glu Ala Thr Leu Met Lys Ser Tyr Ala Asp Val His Gln
    1010                1015                1020
Val Ser Glu Ala Asp Ala Arg Leu Trp Leu Gln Gln Leu Glu Glu
    1025                1030                1035
Lys Gly Arg Tyr Ala Lys Asp Val Trp Ala Gly
    1040                1045

<210> SEQ ID NO 35
<211> LENGTH: 3150
<212> TYPE: DNA
<213> ORGANISM: Artificial Sequence
<220> FEATURE:
<223> OTHER INFORMATION: synthetic P450-BM3 variant polynucleotide

<400> SEQUENCE: 35

| | | | | |
|---|---|---|---|---|
| atgacaataa aggaaatgcc gcagccgaaa acgtttggag aacttaaaaa tttaccgtta | 60 |
| ttaaacacag ataaaccggt tcaagctttg atgcgtattg cggatgaatt aggagaaatc | 120 |
| tttaaattcg aggcgcctgg tttggtaacg atttacttat caagtcagcg tctaattaaa | 180 |
| gaagcatgcg atgaatcacg ctttgataaa aacttaagtc aggcgatgaa atttgcacgt | 240 |
| gattttctgg agacggggtt agcaacaagc tggacgcatg aaccgaattg gaaaaaagcg | 300 |
| cataatatct tacttccaag ctttagtcag caggcaatga acgttatca tgcgatgatg | 360 |
| gtcgatatcg ccgtgcagct tgttcaaaag tgggagcgtc taaatgcaga tgagcatatt | 420 |
| gaagtatcgg aagacatgac acgtttaacg cttgatacaa ttggtctttg cggctttaac | 480 |
| tatcgcttta cagcttttta ccgagatcag cctcatccat ttattgtgag tatggtccgt | 540 |
| gcactggatg aagtaatgaa caagcgtcag cgagcaaatc cagacgaccc agcttatgat | 600 |
| gaaaacaagc gccagtgtca agaagatatc aaggtgatga cgacctagt agataaaatt | 660 |
| attgcagatc gcaaagcaag gggtgaacaa agccatgatt tattaacgca gatgctaaac | 720 |
| ggaaaagatc cagaaacggg tgagccgctt gatgacggga acattagcta tcaaattatt | 780 |
| acattcttaa ttgcgggaca cgaaacaaca agtggtcttt atcatttgc gctgtatttc | 840 |
| ttagtgaaaa atccacatgt attacaaaaa gtagcagaag aagcagcacg agttctagta | 900 |
| gatcctgttc caagctacaa acaagtcaaa cagcttaaat atgtcggcat ggtcttaaac | 960 |
| gaagcgctgc gcttatggcc aactgctcct gcgttttccc tatatgcaaa agaagatacg | 1020 |
| gtgcttggag gagaatatcc tttagaaaaa ggcgacgaag taatgttct gattcctcag | 1080 |
| cttcaccgtg ataaacaat tggggagac gatgtggagg agttccgtcc agagcgtttt | 1140 |
| gaaaatccaa gtgcgattcc gcagcatgcg tttaaaccgt ttggaaacgg tcagcgtgcg | 1200 |

```
tgtatcggtc agcagttcgc tcttcatgaa gcaacgctgg tacttggtat gatgctaaaa    1260
cactttgact ttgaagatca tacaaactac gagctcgata ttaaagaaac tttaacgtta    1320
aaacctgaag ctttgtggt aaaagcaaaa tcgaaaaaaa ttccgcttgg cggtattcct    1380
tcacctagca ctgaacagtc tgctaaaaaa gtacgcaaaa aggcagaaaa cgctcataat    1440
acgccgctgc ttgtgctata cggttcaaat gcgggaacag ctgaaggaac ggcgcgtgat    1500
ttagcagata ttgcaatgag caaaggattt gcaccgcagg tcgcaacgct tgattcacac    1560
gccggaaatc ttccgcgcga aggagctgta ttaattgtaa cggcgtctta taacggtcat    1620
ccgcctgata acgcaaagca atttgtcgac tggttagacc aagcgtctgc tgatgaagta    1680
aaaggcgttc gctactccgt atttggatgc ggcgataaaa actgggctac tacgtatcaa    1740
aaagtgcctg cttttatcga tgaaacgctt gccgctaaag gggcagaaaa catcgctgac    1800
cgcggtgaag cagatgcaag cgacgacttt gaaggcacat atgaagaatg cgtgaacat     1860
atgtggagtg acgtagcagc ctactttaac ctcgacattg aaaacagtga agataataaa    1920
tctactcttt cacttcaatt tgtcgacagc gccgcggata tgccgcttgc gaaaatgcac    1980
ggtgcgtttt caacgaacgt cgtagcaagc aaagaacttc aacagccagg cagtgcacga    2040
agcacgcgac atcttgaaat tgaacttcca aaagaagctt cttatcaaga aggagatcat    2100
ttaggtgtta ttcctcgcaa ctatgaagga atagtaaacc gtgtaacagc aaggttcggc    2160
ctagatgcat cacagcaaat ccgtctggaa gcagaagaag aaaaattagc tcatttgcca    2220
ctcgctaaaa cagtatccgt agaagagctt ctgcaatacg tggagcttca agatcctgcg    2280
acgcgcacgc agcttcgcgc aatggctgct aaaacggtct gcccgccgca taagtagag     2340
cttgaagcct tgcttgaaaa gcaagcctac aaagaacaag tgctggcaaa cgtttaaca    2400
atgcttgaac tgcttgaaaa ataccccggcg tgtgaaatga attcagcga tttatcgcc    2460
cttctgccaa gcatacgccc gcgctattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct ttgtgcaggc gcgcaaacag    2760
ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg cttttttctcg catgccaaat cagccgaaaa catacgttca gcacgtaatg    2940
gaacaagacg caagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctgggtaa                                     3150
```

<210> SEQ ID NO 36
<211> LENGTH: 1049
<212> TYPE: PRT
<213> ORGANISM: Artificial Sequence
<220> FEATURE:
<223> OTHER INFORMATION: synthetic P450-BM3 variant polypeptide

<400> SEQUENCE: 36

Met Thr Ile Lys Glu Met Pro Gln Pro Lys Thr Phe Gly Glu Leu Lys
1               5                   10                  15

```
Asn Leu Pro Leu Leu Asn Thr Asp Lys Pro Val Gln Ala Leu Met Arg
             20                  25                  30

Ile Ala Asp Glu Leu Gly Glu Ile Phe Lys Phe Glu Ala Pro Gly Leu
         35                  40                  45

Val Thr Ile Tyr Leu Ser Ser Gln Arg Leu Ile Lys Glu Ala Cys Asp
 50                  55                  60

Glu Ser Arg Phe Asp Lys Asn Leu Ser Gln Ala Met Lys Phe Ala Arg
 65                  70                  75                  80

Asp Phe Leu Gly Asp Gly Leu Ala Thr Ser Trp Thr His Glu Pro Asn
                 85                  90                  95

Trp Lys Lys Ala His Asn Ile Leu Leu Pro Ser Phe Ser Gln Gln Ala
                100                 105                 110

Met Lys Arg Tyr His Ala Met Met Val Asp Ile Ala Val Gln Leu Val
        115                 120                 125

Gln Lys Trp Glu Arg Leu Asn Ala Asp Glu His Ile Glu Val Ser Glu
130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Val
                165                 170                 175

Ser Met Val Arg Ala Leu Asp Glu Val Met Asn Lys Arg Gln Arg Ala
            180                 185                 190

Asn Pro Asp Asp Pro Ala Tyr Asp Glu Asn Lys Arg Gln Cys Gln Glu
        195                 200                 205

Asp Ile Lys Val Met Asn Asp Leu Val Asp Lys Ile Ile Ala Asp Arg
    210                 215                 220

Lys Ala Arg Gly Glu Gln Ser His Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
                260                 265                 270

Leu Leu Ser Phe Ala Leu Tyr Phe Leu Val Lys Asn Pro His Val Leu
            275                 280                 285

Gln Lys Val Ala Glu Glu Ala Ala Arg Val Leu Val Asp Pro Val Pro
        290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
                340                 345                 350

Glu Val Asn Val Leu Ile Pro Gln Leu His Arg Asp Lys Thr Ile Trp
            355                 360                 365

Gly Asp Asp Val Glu Glu Phe Arg Pro Glu Arg Phe Glu Asn Pro Ser
        370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430
```

-continued

```
Asp Ile Lys Glu Thr Leu Thr Leu Lys Pro Gly Phe Val Val Lys
        435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Ala Gly Thr Ala Glu Gly
                485                 490                 495

Thr Ala Arg Asp Leu Ala Asp Ile Ala Met Ser Lys Gly Phe Ala Pro
                500                 505                 510

Gln Val Ala Thr Leu Asp Ser His Ala Gly Asn Leu Pro Arg Glu Gly
                515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
                580                 585                 590

Lys Gly Ala Glu Asn Ile Ala Asp Arg Gly Glu Ala Asp Ala Ser Asp
                595                 600                 605

Asp Phe Glu Gly Thr Tyr Glu Glu Trp Arg Glu His Met Trp Ser Asp
                610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
                660                 665                 670

Leu Gln Gln Pro Gly Ser Ala Arg Ser Thr Arg His Leu Glu Ile Glu
                675                 680                 685

Leu Pro Lys Glu Ala Ser Tyr Gln Glu Gly Asp His Leu Gly Val Ile
                690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
                740                 745                 750

Tyr Val Glu Leu Gln Asp Pro Ala Thr Arg Thr Gln Leu Arg Ala Met
                755                 760                 765

Ala Ala Lys Thr Val Cys Pro Pro His Lys Val Glu Leu Glu Ala Leu
770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
                820                 825                 830

Ser Ser Ser Pro Arg Val Asp Glu Lys Gln Ala Ser Ile Thr Val Ser
                835                 840                 845

Val Val Ser Gly Glu Ala Trp Ser Gly Tyr Gly Glu Tyr Lys Gly Ile
```

```
Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
            885                 890                 895

Thr Pro Leu Ile Met Val Gly Pro Gly Thr Gly Val Ala Pro Phe Arg
        900                 905                 910

Gly Phe Val Gln Ala Arg Lys Gln Leu Lys Glu Gln Gly Gln Ser Leu
            915                 920                 925

Gly Glu Ala His Leu Tyr Phe Gly Cys Arg Ser Pro His Glu Asp Tyr
        930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
            965                 970                 975

Gln His Val Met Glu Gln Asp Gly Lys Lys Leu Ile Glu Leu Leu Asp
        980                 985                 990

Gln Gly Ala His Phe Tyr Ile Cys  Gly Asp Gly Ser Gln  Met Ala Pro
            995                 1000                 1005

Ala Val  Glu Ala Thr Leu Met  Lys Ser Tyr Ala Asp  Val His Gln
    1010                 1015                 1020

Val Ser  Glu Ala Asp Ala Arg  Leu Trp Leu Gln Gln  Leu Glu Glu
    1025                 1030                 1035

Lys Gly  Arg Tyr Ala Lys Asp  Val Trp Ala Gly
    1040                 1045

<210> SEQ ID NO 37
<211> LENGTH: 3150
<212> TYPE: DNA
<213> ORGANISM: Artificial Sequence
<220> FEATURE:
<223> OTHER INFORMATION: synthetic P450-BM3 variant polynucleotide

<400> SEQUENCE: 37
atgacaataa aggaaatgcc gcagccgaaa acgtttggag aacttaaaaa tttaccgtta      60
ttaaacacag ataaaccggt tcaagctttg atgcgtattg cggatgaatt aggagaaatc     120
tttaaattcg aggcgcctgg ttcagtaacg atttctctat caagtcagcg tctaattaaa     180
gaagcatgcg atgaatcacg ctttgataaa aacttaagtc aggcgatgaa atttgcacgt     240
gattttctgg agacgggtt agcaacaagc tggacgcatg aaccgaattg gaaaaaagcg     300
cataatatct tacttccaag ctttagtcag caggcaatga acgttatca tgcgatgatg     360 gtcgatatcg ccgtgcagct tgttcaaaag tgggagcgtc taaatgcaga tgagcatatt     420
gaagtatcgg aagacatgac acgtttaacg cttgatacaa ttggtctttg cggctttaac     480
tatcgcttta cagcttttta ccgagatcag cctcatccat ttattgtgag atggtccgt     540 gcactggatg aagtaatgaa caagcgtcag cgagcaaatc cagacgaccc agcttatgat     600
gaaaacaagc gccagtgtca agaagatatc aaggtgatga cgactatgt agataaaatt     660 attgcagatc gcaaagcaag gggtgaacaa agccatgatt tattaacgca gatgctaaac     720
ggaaaagatc cagaaacggg tgagccgctt gatgacggga cattagcta tcaaattatt     780 acattcttaa ttgcgggaca cgaaacaaca agtggtcttt atcatttgc gctgtatttc     840 ttagtgaaaa atccacatgt attacaaaaa gtagcagaag aagcagcacg agttctagta     900
gatcctgttc caagctacaa acaagtcaaa cagcttaaat atgtcggcat ggtcttaaac     960
```

```
gaagcgctgc gcttatggcc aactgctcct gcgttttccc tatatgcaaa agaagatacg    1020
gtgcttggag gagaatatcc tttaaagaaa ggcgacgaag taaatgttct gattcctcag    1080
cttcaccgtg ataaaacaat ttggggagac gatgtggagg agttccgtcc agagcgtttt    1140
gaaaatccaa gtgcgattcc gcagcatgcg tttaaaccgt ttggaaacgg tcagcgtgcg    1200
tgtatcggtc agcagttcgc tcttcatgaa gcaacgctgg tacttggtat gatgctaaaa    1260
cactttgact ttgaagatca tacaaactac gagctcgata ttaaagaaac tttaacgtta    1320
aaacctgaag gctttgtggt aaaagcaaaa tcgaaaaaaa ttccgcttgg cggtattcct    1380
tcacctagca ctgaacagtc tgctaaaaaa gtacgcaaaa aggcagaaaa cgctcataat    1440
acgccgctgc ttgtgctata cggttcaaat gcgggaacag ctgaaggaac ggcgcgtgat    1500
ttagcagata ttgcaatgag caaaggattt gcaccgcagg tcgcaacgct tgattcacac    1560
gccggaaatc ttccgcgcga aggagctgta ttaattgtaa cggcgtctta taacggtcat    1620
ccgcctgata acgcaaagca atttgtcgac tggttagacc aagcgtctgc tgatgaagta    1680
aaaggcgttc gctactccgt atttggatgc ggcgataaaa cctgggctgc tacgtatcaa    1740
aaagtgcctg cttttatcga tgaaacgctt gccgctaaag gggcagaaaa catcgctgac    1800
cgcggtgaag cagatgcaag cgacgacttt gaaggcacat atgaagaatg cgtgatcat    1860 atgtggagtg acgtagcagc ctactttaac ctcgacattg aaaacagtga agataataaa    1920
tctactcttt cacttcaatt tgtcgacagc gccgcggata tgccgcttgc gaaaatgcac    1980
ggtgcgtttt caacgaacgt cgtagcaagc aaagaacttc aacagccagg cagtgcacga    2040
agcacgcgac atcttgaaat tgaacttcca aaagaagctt cttatcaaga aggagatcat    2100
ttaggtgtta ttcctcgcaa ctatgaagga atagtaaacc gtgtaacagc aaggttcggc    2160
ctagatgcat cacagcaaat ccgtctggaa gcagaagaag aaaaattagc tcatttgcca    2220
ctcgctaaaa cagtatccgt agaagagctt ctgcaatacg tggagcttca agatcctgcg    2280
acgcgcacgc agcttcgcgc aatggctgct aaaacggtct gcccgccgca taagtagag    2340 cttgaagcct tgcttgaaaa gcaagcctac aaagaacaag tgctggcaaa acgtttaaca    2400
atgcttgaac tgcttgaaaa atacccggcg tgtgaaatga aattcagcga atttatcgcc    2460
cttctgccaa gcatacgccc gcgctattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct tgtgcaggc gcgcaaacag    2760 ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg cttttctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctgggtaa                                    3150
```

<210> SEQ ID NO 38
<211> LENGTH: 1049
<212> TYPE: PRT

<213> ORGANISM: Artificial Sequence
<220> FEATURE:
<223> OTHER INFORMATION: synthetic P450-BM3 variant polypeptide

<400> SEQUENCE: 38

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Arg
            20                  25                  30

Ile Ala Asp Glu Leu Gly Glu Ile Phe Lys Phe Glu Ala Pro Gly Ser
        35                  40                  45

Val Thr Ile Phe Leu Ser Ser Gln Arg Leu Ile Lys Glu Ala Cys Asp
    50                  55                  60

Glu Ser Arg Phe Asp Lys Asn Leu Ser Gln Ala Met Lys Phe Ala Arg
65                  70                  75                  80

Asp Phe Leu Gly Asp Gly Leu Ala Thr Ser Trp Thr His Glu Pro Asn
                85                  90                  95

Trp Lys Lys Ala His Asn Ile Leu Leu Pro Ser Phe Ser Gln Gln Ala
            100                 105                 110

Met Lys Arg Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Val
                165                 170                 175

Ser Met Val Arg Ala Leu Asp Glu Val Met Asn Lys Arg Gln Arg Ala
            180                 185                 190

Asn Pro Asp Asp Pro Ala Tyr Asp Glu Asn Lys Arg Gln Cys Gln Glu
        195                 200                 205

Asp Ile Lys Val Met Asn Asp Tyr Val Asp Lys Ile Ile Ala Asp Arg
    210                 215                 220

Lys Ala Arg Gly Glu Gln Ser His Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Val Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Lys Lys Gly Asp
            340                 345                 350

Glu Val Asn Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
```

```
385                 390                 395                 400

Cys Ile Gly Gln Gln Phe Ala Leu His Glu Ala Thr Leu Val Leu Gly
            405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
            435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Ala Glu Asn Ala His Asn
465                 470                 475                 480

Thr Pro Leu Leu Val Leu Tyr Gly Ser Asn Ala Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Thr Trp Ala
                565                 570                 575

Ala Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
            595                 600                 605

Asp Phe Glu Gly Thr Tyr Glu Glu Trp Arg Asp His Met Trp Ser Asp
            610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
            675                 680                 685

Leu Pro Lys Glu Ala Ser Tyr Gln Glu Gly Asp His Leu Gly Val Ile
            690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Ala Thr Arg Thr Gln Leu Arg Ala Met
            755                 760                 765

Ala Ala Lys Thr Val Cys Pro Pro His Lys Val Glu Leu Glu Ala Leu
            770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815
```

```
Glu Phe Ile Ala Leu Leu Pro Ser Ile Arg Pro Arg Tyr Tyr Ser Ile
                820                 825                 830

Ser Ser Ser Pro Arg Val Asp Glu Lys Gln Ala Ser Ile Thr Val Ser
            835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Ala Gly
    1040                1045

<210> SEQ ID NO 39
<211> LENGTH: 3150
<212> TYPE: DNA
<213> ORGANISM: Artificial Sequence
<220> FEATURE:
<223> OTHER INFORMATION: synthetic P450-BM3 variant polynucleotide

<400> SEQUENCE: 39
atgacaataa aggaaatgcc gcagccgaaa acgtttggag aacttaaaaa tttaccgtta      60
ttaaacacag ataaaccggt tcaagctttg atgcgtattg cggatgaatt aggagaaatc     120
tttaaattcg aggcgcctgg ttcagtaacg atttacttat caagtcagcg tctaattaaa     180
gaagcatgcg atgaatcacg ctttgataaa aacttaagtc aggcgatgaa atttgcacgt     240
gattttctgg agacgggtt agcaacaagc tggacgcatg aaccgaattg gaaaaaagcg     300
cataatatct acttccaag ctttagtcag caggcaatga acgttatca tgcgatgatg     360 gtcgatatcg ccgtgcagct tgttcaaaag tgggagcgtc taaatgcaga tgagcatatt     420
gaagtatcgg aagacatgac acgtttaacg cttgatacaa ttggtctttg cggctttaac     480
tatcgcttta cagctttta ccgagatcag cctcatccat ttattgtgag tatggtccgt     540
gcactggatg aagtaatgaa caagcgtcag cgagcaaatc cagacgaccc agcttatgat     600
gaaaacaagc gccagtgtca agaagatatc aaggtgatga cgacctagt agataaaatt     660 attgcagatc gcaaagcaag gggtgaacaa agccatgatt tattaacgca gatgctaaac     720
```

-continued

```
ggaaaagatc cagaaacggg tgagccgctt gatgacggga acattagcta tcaaattatt    780
acattcttaa ttgcgggaca cgaaacaaca agtggtcttt tatcatttgc gctgtatttc    840
ttagtgaaaa atccacatgt attacaaaaa gtagcagaag aagcagcacg agttctagta    900
gatcctgttc caagctacaa acaagtcaaa cagcttaaat atgtcggcat ggtcttaaac    960
gaagcgctgc gcttatggcc aactgctcct gcgttttccc tatatgcaaa agaagatacg   1020
gtgcttggag gagaatatcc tttaaagaaa ggcgacgaag taaatgttct gattcctcag   1080
cttcaccgtg ataaaacaat tggggagac gatgtggagg agttccgtcc agagcgtttt   1140
gaaaatccaa gtgcgattcc gcagcatgcg tttaaaccgt tggaaacgg tcagcgtgcg   1200
tgtatcggtc agcagttcgc tcttcatgaa gcaacgctgg tacttggtat gatgctaaaa   1260
cactttgact tgaagatca tacaaactac gagctcgata ttaaagaaac tttaacgtta   1320
aaacctgaag gctttgtggt aaaagcaaaa tcgaaaggta ttccgcttgg cggtattcct   1380
tcacctagca ctgaacagtc tgctaaaaaa gtacgcaaaa aggcagaaaa cgctcataat   1440
acgccgctgc ttgtgctata cggttcaaat gcgggaacag ctgaaggaac ggcgcgtgat   1500
ttagcagata ttgcaatgag caaaggattt gcaccgcagg tcgcaacgct tgattcacac   1560
gccggaaatc ttccgcgcga aggagctgta ttaattgtaa cggcgtctta taacggtcat   1620
ccgcctgata cgcaaagca atttgtcgac tggttagacc aagcgtctgc tgatgaagta   1680
aaaggcgttc gctactccgt atttggatgc ggcgataaaa actgggctgc tacgtatcaa   1740
aaagtgcctg cttttatcga tgaaacgctt gccgctaaag gggcagaaaa catcgctgac   1800
cgcggtgaag cagatgcaag cgacgacttt gaaggcacat atgaagaatg gcgtgatcat   1860
atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctggaa gcagaagaag aaaaattagc tcatttgcca   2220
ctcgctaaaa cagtatccgt agaagagctt ctgcaatacg tggagcttca agatcctgcg   2280
acgcgcacgc agcttcgcgc aatggctgct aaaacggtct gcccgccgca taagtagag   2340
cttgaagcct tgcttgaaaa gcaagcctac aaagaacaag tgctggcaaa acgtttaaca   2400
atgcttgaac tgcttgaaaa ataccccggcg tgtgaaatga aattcagcga atttatcgcc   2460
cttctgccaa gcatacgccc gcgctattac tcgatttctt catcacctcg tgtcgatgaa   2520
aaacaagcaa gcatcacggt cagcgttgtc tcaggagaa cgtggagcgg atatggagaa   2580
tataaggaa ttgcgtcgaa ctatcttgcc gagctgcaag aaggagatac gattacgtgc   2640
tttatttcca caccgcagtc agaatttacg ctgccaaaag accctgaaac gccgcttatc   2700
atggtcggac cgggaacagg cgtcgcgccg tttagaggct tgtgcaggc gcgcaaacag   2760
ctaaaagaac aaggacagtc acttggagaa gcacatttat acttcggctg ccgttcacct   2820
catgaagact atctgtatca agaagagctt gaaaacgccc aaagcgaagg catcattacg   2880
cttcataccg cttttctctcg catgccaaat cagccgaaaa catacgttca gcacgtaatg   2940
gaacaagacg gcaagaaatt gattgaactt cttgatcaag gagcgcactt ctatatttgc   3000
ggagacggaa gccaaatggc acctgccgtt gaagcaacgc ttatgaaaag ctatgctgac   3060
```

```
gttcaccaag tgagtgaagc agacgctcgc ttatggctgc agcagctaga agaaaaaggc    3120
cgatacgcaa aagacgtgtg ggctgggtaa                                    3150
```

<210> SEQ ID NO 40
<211> LENGTH: 1049
<212> TYPE: PRT
<213> ORGANISM: Artificial Sequence
<220> FEATURE:
<223> OTHER INFORMATION: synthetic P450-BM3 variant polypeptide

<400> SEQUENCE: 40

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Arg
            20                  25                  30

Ile Ala Asp Glu Leu Gly Glu Ile Phe Lys Phe Glu Ala Pro Gly Ser
        35                  40                  45

Val Thr Ile Tyr Leu Ser Ser Gln Arg Leu Ile Lys Glu Ala Cys Asp
    50                  55                  60

Glu Ser Arg Phe Asp Lys Asn Leu Ser Gln Ala Met Lys Phe Ala Arg
65                  70                  75                  80

Asp Phe Leu Gly Asp Gly Leu Ala Thr Ser Trp Thr His Glu Pro Asn
                85                  90                  95

Trp Lys Lys Ala His Asn Ile Leu Leu Pro Ser Phe Ser Gln Gln Ala
            100                 105                 110

Met Lys Arg Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Val
                165                 170                 175

Ser Met Val Arg Ala Leu Asp Glu Val Met Asn Lys Arg Gln Arg Ala
            180                 185                 190

Asn Pro Asp Asp Pro Ala Tyr Asp Glu Asn Lys Arg Gln Cys Gln Glu
        195                 200                 205

Asp Ile Lys Val Met Asn Asp Leu Val Asp Lys Ile Ile Ala Asp Arg
    210                 215                 220

Lys Ala Arg Gly Glu Gln Ser His Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Val Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Lys Lys Gly Asp
            340                 345                 350
```

```
Glu Val Asn Val Leu Ile Pro Gln Leu His Arg Asp Lys Thr Ile Trp
            355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
                435                 440                 445

Ala Lys Ser Lys Gly Ile Pro Leu Gly Gly Ile Pro Ser Pro Ser Thr
            450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Ala Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
                515                 520                 525

Ala Val Leu Ile Val Thr Ala Ser Tyr Asn Gly His Pro Pro Asp Asn
            530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Ala Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
                595                 600                 605

Asp Phe Glu Gly Thr Tyr Glu Glu Trp Arg Asp His Met Trp Ser Asp
    610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
                675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Ala Thr Arg Thr Gln Leu Arg Ala Met
            755                 760                 765
```

```
Ala Ala Lys Thr Val Cys Pro Pro His Lys Val Glu Leu Glu Ala Leu
    770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
                820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
                900                 905                 910

Gly Phe Val Gln Ala Arg Lys Gln Leu Lys Glu Gln Gly Gln Ser Leu
                915                 920                 925

Gly Glu Ala His Leu Tyr Phe Gly Cys Arg Ser Pro His Glu Asp Tyr
        930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
                980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Ala Gly
    1040                1045

<210> SEQ ID NO 41
<211> LENGTH: 3150
<212> TYPE: DNA
<213> ORGANISM: Artificial Sequence
<220> FEATURE:
<223> OTHER INFORMATION: synthetic P450-BM3 variant polynucleotide

<400> SEQUENCE: 41
atgacaataa aggaaatgcc gcagccgaaa acgtttggag aacttaaaaa tttaccgtta      60
ttaaacacag ataaaccggt tcaagctttg atgaaaattg cggatgaatt aggagaaatc     120
tttaaattcg aggcgcctgg ttgtgtaacg cgctacttat caagtcagcg tctaattaaa     180
gaagcatgcg atgaatcacg ctttgataaa aacttaagtc aagcgcttaa atttgcacgt     240
gattttgcag agacgggtt ggtgacaagc tggacgcatg aaataaattg gaaaaaagcg     300
cataatatct tacttccaag ctttagtcag caggcaatga aaggctatca tgcgatgatg     360
gtcgatatcg ccgtgcagct tgttcaaaag tgggagcgtc taaatgcaga tgagcatatt     420
gaagtatcgg aagacatgac acgtttaacg cttgatacaa ttggtctttg cggctttaac     480
```

| | |
|---|---|
| tatcgcttta acagcttta ccgagatcag cctcatccat ttattataag tatggtccgt | 540 |
| gcactggatg aagtaatgaa caagctgcag cgagcaaatc cagacgaccc agcttatgat | 600 |
| gaaaacaagc gccagtgtca agaagatatc aaggtgatga acgacctagt agataaaatt | 660 |
| attgcagatc gcaaagcaag gggtgaacaa agcgatgatt tattaacgca gatgctaaac | 720 |
| ggaaaagatc cagaaacggg tgagccgctt gatgacggga acattagcta tcaaattatt | 780 |
| acattcttaa ttgcgggaca cgaaacaaca agtggtcttt tatcatttgc gctgtatttc | 840 |
| ttagtgaaaa atccacatgt attacaaaaa gtagcagaag aagcagcacg agttctagta | 900 |
| gatcctgttc caagctacaa acaagtcaaa cagcttaaat atgtcggcat ggtcttaaac | 960 |
| gaagcgctgc gcttatggcc aactgctcct gcgttttccc tatatgcaaa agaagatacg | 1020 |
| gtgcttggag gagaatatcc tttagaaaaa ggcgacgaag taatggttct gattcctcag | 1080 |
| cttcaccgtg ataaaacaat ttggggagac gatgtggagg agttccgtcc agagcgtttt | 1140 |
| gaaaatccaa gtgcgattcc gcagcatgcg tttaaaccgt tggaaacggt cagcgtgcg | 1200 |
| tgtatcggtc agcagttcgc tcttcatgaa gcaacgctgg tacttggtat gatgctaaaa | 1260 |
| cactttgact tgaagatca tacaaactac gagctcgata ttaaagaaac tttaacgtta | 1320 |
| aaacctgaag gctttgtggt aaaagcaaaa tcgaaaaaaa ttccgcttgg cggtattcct | 1380 |
| tcacctagca ctgaacagtc tgctaaaaaa gtacgcaaaa aggcagaaaa cgctcataat | 1440 |
| acgccgctgc ttgtgctata cggttcaaat atgggaacag ctgaaggaac ggcgcgtgat | 1500 |
| ttagcagata ttgcaatgag caaaggattt gcaccgcagg tcgcaacgct tgattcacac | 1560 |
| gccggaaatc ttccgcgcga aggagctgta ttaattgtaa cggcgtctta taacggtcat | 1620 |
| ccgcctgata acgcaaagca atttgtcgac tggttagacc aagcgtctgc tgatgaagta | 1680 |
| aaaggcgttc gctactccgt atttggatgc ggcgataaaa actgggctac tacgtatcaa | 1740 |
| aaagtgcctg ctttatcga tgaaacgctt gccgctaaag gggcagaaaa catcgctgac | 1800 |
| cgcggtgaag cagatgcaag cgacgacttt gaaggcacat atgaagaatg gcgtgaacat | 1860 |
| atgtggagtg acgtagcagc ctactttaac ctcgacattg aaaacagtga agataataaa | 1920 |
| tctactcttt cacttcaatt tgtcgacagc gccgcggata tgccgcttgc gaaaatgcac | 1980 |
| ggtgcgtttt caacgaacgt cgtagcaagc aaagaacttc aacagccagg cagtgcacga | 2040 |
| agcacgcgac atcttgaaat tgaacttcca aagaagcttc ttatcaaga aggagatcat | 2100 |
| ttaggtgtta ttcctcgcaa ctatgaagga atagtaaacc gtgtaacagc aaggttcggc | 2160 |
| ctagatgcat cacagcaaat ccgtctggaa gcagaagaag aaaaattagc tcatttgcca | 2220 |
| ctcgctaaaa cagtatccgt agaagagctt ctgcaatacg tggagcttca agatcctgtt | 2280 |
| acgcgcacgc agcttcgcgc aatggctgct aaaacggtct gcccgccgca taagtagag | 2340 |
| cttgaagcct tgcttgaaaa gcaagcctac aaagaacaag tgctggcaaa acgtttaaca | 2400 |
| atgcttgaac tgcttgaaaa ataccccggcg tgtgaaatga aattcagcga atttatcgcc | 2460 |
| cttctgccaa gcatacgccc gcgctattac tcgatttctt catcacctcg tgtcgatgaa | 2520 |
| aaacaagcaa gcatcacggt cagcgttgtc tcaggagaag cgtggagcgg atatggagaa | 2580 |
| tataaaggaa ttgcgtcgaa ctatcttgcc gagctgcaag aaggagatac gattacgtgc | 2640 |
| tttatttcca caccgcagtc agaatttacg ctgccaaaag accctgaaac gccgcttatc | 2700 |
| atggtcggac cggaacagg cgtcgcgccg tttagaggct ttgtgcaggc gcgcaaacag | 2760 |
| ctaaaagaac aaggacagtc acttggagaa gcacatttat acttcggctg ccgttcacct | 2820 |

```
catgaagact atctgtatca agaagagctt gaaaacgccc aaagcgaagg catcattacg    2880
cttcataccg cttttctcg catgccaaat cagccgaaaa catacgttca gcacgtaatg     2940
gaacaagacg gcaagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctgggtaa                                    3150
```

<210> SEQ ID NO 42
<211> LENGTH: 1049
<212> TYPE: PRT
<213> ORGANISM: Artificial Sequence
<220> FEATURE:
<223> OTHER INFORMATION: synthetic P450-BM3 variant polypeptide

<400> SEQUENCE: 42

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Cys
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Ala Arg
65                  70                  75                  80

Asp Phe Ala Gly Asp Gly Leu Val Thr Ser Trp Thr His Glu Ile Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Ala Leu Asp Glu Val Met Asn Lys Leu Gln Arg Ala
            180                 185                 190

Asn Pro Asp Asp Pro Ala Tyr Asp Glu Asn Lys Arg Gln Cys Gln Glu
        195                 200                 205

Asp Ile Lys Val Met Asn Asp Leu Val Asp Lys Ile Ile Ala Asp Arg
    210                 215                 220

Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Val Ala Glu Glu Ala Ala Arg Val Leu Val Asp Pro Val Pro
    290                 295                 300
```

```
Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Val Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
                420                 425                 430

Asp Ile Lys Glu Thr Leu Thr Leu Lys Pro Glu Gly Phe Val Val Lys
            435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
                500                 505                 510

Gln Val Ala Thr Leu Asp Ser His Ala Gly Asn Leu Pro Arg Glu Gly
                515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
                580                 585                 590

Lys Gly Ala Glu Asn Ile Ala Asp Arg Gly Glu Ala Asp Ala Ser Asp
                595                 600                 605

Asp Phe Glu Gly Thr Tyr Glu Glu Trp Arg Glu His Met Trp Ser Asp
        610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
                660                 665                 670

Leu Gln Gln Pro Gly Ser Ala Arg Ser Thr Arg His Leu Glu Ile Glu
            675                 680                 685

Leu Pro Lys Glu Ala Ser Tyr Gln Glu Gly Asp His Leu Gly Val Ile
            690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Glu Lys Leu
```

```
                    725                 730                 735
Ala His Leu Pro Leu Ala Lys Thr Val Ser Val Glu Glu Leu Leu Gln
                740                 745                 750
Tyr Val Glu Leu Gln Asp Pro Val Thr Arg Thr Gln Leu Arg Ala Met
                755                 760                 765
Ala Ala Lys Thr Val Cys Pro Pro His Lys Val Glu Leu Glu Ala Leu
            770                 775                 780
Leu Glu Lys Gln Ala Tyr Lys Glu Gln Val Leu Ala Lys Arg Leu Thr
785                 790                 795                 800
Met Leu Glu Leu Leu Glu Lys Tyr Pro Ala Cys Glu Met Lys Phe Ser
                805                 810                 815
Glu Phe Ile Ala Leu Leu Pro Ser Ile Arg Pro Arg Tyr Tyr Ser Ile
                820                 825                 830
Ser Ser Ser Pro Arg Val Asp Glu Lys Gln Ala Ser Ile Thr Val Ser
            835                 840                 845
Val Val Ser Gly Glu Ala Trp Ser Gly Tyr Gly Glu Tyr Lys Gly Ile
850                 855                 860
Ala Ser Asn Tyr Leu Ala Glu Leu Gln Glu Gly Asp Thr Ile Thr Cys
865                 870                 875                 880
Phe Ile Ser Thr Pro Gln Ser Glu Phe Thr Leu Pro Lys Asp Pro Glu
                885                 890                 895
Thr Pro Leu Ile Met Val Gly Pro Gly Thr Gly Val Ala Pro Phe Arg
                900                 905                 910
Gly Phe Val Gln Ala Arg Lys Gln Leu Lys Glu Gln Gly Gln Ser Leu
            915                 920                 925
Gly Glu Ala His Leu Tyr Phe Gly Cys Arg Ser Pro His Glu Asp Tyr
            930                 935                 940
Leu Tyr Gln Glu Glu Leu Glu Asn Ala Gln Ser Glu Gly Ile Ile Thr
945                 950                 955                 960
Leu His Thr Ala Phe Ser Arg Met Pro Asn Gln Pro Lys Thr Tyr Val
                965                 970                 975
Gln His Val Met Glu Gln Asp Gly Lys Lys Leu Ile Glu Leu Leu Asp
                980                 985                 990
Gln Gly Ala His Phe Tyr Ile Cys  Gly Asp Gly Ser Gln  Met Ala Pro
            995                 1000                1005
Ala Val Glu Ala Thr Leu Met  Lys Ser Tyr Ala Asp  Val His Gln
        1010                1015                1020
Val Ser Glu Ala Asp Ala Arg  Leu Trp Leu Gln Gln  Leu Glu Glu
        1025                1030                1035
Lys Gly Arg Tyr Ala Lys Asp  Val Trp Ala Gly
        1040                1045

<210> SEQ ID NO 43
<211> LENGTH: 3150
<212> TYPE: DNA
<213> ORGANISM: Artificial Sequence
<220> FEATURE:
<223> OTHER INFORMATION: synthetic P450-BM3 variant polynucleotide

<400> SEQUENCE: 43
atgacaataa aggaaatgcc gcagccgaaa acgtttggag aacttaaaaa tttaccgtta     60
ttaaacacag ataaaccggt tcaagctttg atgaaaattg cggatgaatt aggagaaatc    120
tttaaattcg aggcgcctgg ttgtgtaacg cgctacttat caagtcagcg tctaattaaa    180
gaagcatgcg atgaatcacg ctttgataaa aacttaagtc aagcgcttaa atttgcacgt    240
```

```
gattttgcag gagacgggtt ggtgacaagc tggacgcatg aaccgaattg gaaaaaagcg      300
cataatatct tacttccaag ctttagtcag caggcaatga aacgctatca tgcgatgatg      360
gtcgatatcg ccgtgcagct tgttcaaaag tgggagcgtc taaatgcaga tgagcatatt      420
gaagtatcgg aagacatgac acgtttaacg cttgatacaa ttggtctttg cggctttaac      480
tatcgcttta acagctttta ccgagatcag cctcatccat ttattgtgag tatggtccgt      540
gcactggatg aagtaatgaa caagctgcag cgagcaaatc cagacgaccc agcttatgat      600
gaaaacaagc gccagtgtca agaagatatc aaggtgatga acgacctagt agataaaatt      660
attgcagatc gcaaagcaag gggtgaacaa agccacgatt tattaacgca gatgctaaac      720
ggaaaagatc cagaaacggg tgagccgctt gatgacggga acattagcta tcaaattatt      780
acattcttaa ttgcgggaca cgaaacaaca agtggtcttt tatcatttgc gctgtatttc      840
ttagtgaaaa atccacatgt attacaaaaa gtagcagaag aagcagcacg agttctagta      900
gatcctgttc caagctacaa acaagtcaaa cagcttaaat atgtcggcat ggtcttaaac      960
gaagcgctgc gcttatggcc aactgctcct gcgttttccc tatatgcaaa agaagatacg     1020
gtgcttggag gagaatatcc tttagaaaaa ggcgacgaag taatggttct gattcctcag     1080
cttcaccgtg ataaaacaat ttggggagac gatgtggagg agttccgtcc agagcgtttt     1140
gaaaatccaa gtgcgattcc gcagcatgcg tttaaaccgt ttggaaacgg tcagcgtgcg     1200
tgtatcggtc agcagttcgc tcttcatgaa gcaacgctgg tacttggtat gatgctaaaa     1260
cactttgact ttgaagatca tacaaactac gagctcgata ttaaagaaac tttaacgtta     1320
aaacctgaag gctttgtggt aaaagcaaaa tcgaaaaaaa ttccgcttgg cggtattcct     1380
tcacctagca ctgaacagtc tgctaaaaaa gtacgcaaaa aggcagaaaa cgctcataat     1440
acgccgctgc ttgtgctata cggttcaaat atgggaacag ctgaaggaac ggcgcgtgat     1500
ttagcagata ttgcaatgag caaaggattt gcaccgcagg tcgcaacgct tgattcacac     1560
gccggaaatc ttccgcgcga aggagctgta ttaattgtaa cggcgtctta taacggtcat     1620
ccgcctgata acgcaaagca atttgtcgac tggttagacc aagcgtctgc tgatgaagta     1680
aaaggcgttc gctactccgt atttggatgc ggcgataaaa actgggctac tacgtatcaa     1740
aaagtgcctg ctttttatcga tgaaacgctt gccgctaaag gggcagaaaa catcgctgac     1800
cgcggtgaag cagatgcaag cgacgacttt gaaggcacat atgaagaatg gcgtgaacat     1860
atgtggagtg acgtagcagc ctactttaac ctcgacattg aaaacagtga agataataaa     1920
tctactcttt cacttcaatt tgtcgacagc gccgcggata tgccgcttgc gaaaatgcac     1980
ggtgcgtttt caacgaacgt cgtagcaagc aaagaacttc aacagccagg cagtgcacga     2040
agcacgcgac atcttgaaat tgaacttcca aaagaagctt cttatcaaga aggagatcat     2100
ttaggtgtta ttcctcgcaa ctatgaagga atagtaaacc gtgtaacagc aaggttcggc     2160
ctagatgcat cacagcaaat ccgtctggaa gcagaagaag aaaaattagc tcatttgcca     2220
ctcgctaaaa cagtatccgt agaagagctt ctgcaatacg tggagcttca agatcctgtt     2280
acgcgcacgc agcttcgcgc aatggctgct aaaacggtct gcccgccgca taaagtagag     2340
cttgaagcct tgcttgaaaa gcaagcctac aaagaacaag tgctggcaaa acgtttaaca     2400
atgcttgaac tgcttgaaaa atacccggcg tgtgaaatga aattcagcga atttatcgcc     2460
cttctgccaa gcatacgccc gcgctattac tcgatttctt catcacctcg tgtcgatgaa     2520
aaacaagcaa gcatcacggt cagcgttgtc tcaggagaag cgtggagcgg atatggagaa     2580
```

```
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct ttgtgcaggc gcgcaaacag    2760
ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg cttttctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctgggtaa                                    3150
```

<210> SEQ ID NO 44
<211> LENGTH: 1049
<212> TYPE: PRT
<213> ORGANISM: Artificial Sequence
<220> FEATURE:
<223> OTHER INFORMATION: synthetic P450-BM3 variant polypeptide

<400> SEQUENCE: 44

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Cys
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Ala Arg
65                  70                  75                  80

Asp Phe Ala Gly Asp Gly Leu Val Thr Ser Trp Thr His Glu Pro Asn
                85                  90                  95

Trp Lys Lys Ala His Asn Ile Leu Leu Pro Ser Phe Ser Gln Gln Ala
            100                 105                 110

Met Lys Arg Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Val
                165                 170                 175

Ser Met Val Arg Ala Leu Asp Glu Val Met Asn Lys Leu Gln Arg Ala
            180                 185                 190

Asn Pro Asp Asp Pro Ala Tyr Asp Glu Asn Lys Arg Gln Cys Gln Glu
        195                 200                 205

Asp Ile Lys Val Met Asn Asp Leu Val Asp Lys Ile Ala Asp Arg
    210                 215                 220

Lys Ala Arg Gly Glu Gln Ser His Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
```

-continued

```
                260                 265                 270
Leu Leu Ser Phe Ala Leu Tyr Phe Leu Val Lys Asn Pro His Val Leu
            275                 280                 285
Gln Lys Val Ala Glu Ala Ala Arg Val Leu Val Asp Pro Val Pro
        290                 295                 300
Ser Tyr Lys Gln Val Lys Gln Leu Lys Tyr Val Gly Met Val Leu Asn
305                 310                 315                 320
Glu Ala Leu Arg Leu Trp Pro Thr Ala Pro Ala Phe Ser Leu Tyr Ala
                325                 330                 335
Lys Glu Asp Thr Val Leu Gly Gly Glu Tyr Pro Leu Glu Lys Gly Asp
            340                 345                 350
Glu Val Met Val Leu Ile Pro Gln Leu His Arg Asp Lys Thr Ile Trp
        355                 360                 365
Gly Asp Asp Val Glu Glu Phe Arg Pro Glu Arg Phe Glu Asn Pro Ser
        370                 375                 380
Ala Ile Pro Gln His Ala Phe Lys Pro Phe Gly Asn Gly Gln Arg Ala
385                 390                 395                 400
Cys Ile Gly Gln Gln Phe Ala Leu His Glu Ala Thr Leu Val Leu Gly
                405                 410                 415
Met Met Leu Lys His Phe Asp Phe Glu Asp His Thr Asn Tyr Glu Leu
            420                 425                 430
Asp Ile Lys Glu Thr Leu Thr Leu Lys Pro Glu Gly Phe Val Val Lys
        435                 440                 445
Ala Lys Ser Lys Lys Ile Pro Leu Gly Gly Ile Pro Ser Pro Ser Thr
        450                 455                 460
Glu Gln Ser Ala Lys Lys Val Arg Lys Lys Ala Glu Asn Ala His Asn
465                 470                 475                 480
Thr Pro Leu Leu Val Leu Tyr Gly Ser Asn Met Gly Thr Ala Glu Gly
                485                 490                 495
Thr Ala Arg Asp Leu Ala Asp Ile Ala Met Ser Lys Gly Phe Ala Pro
            500                 505                 510
Gln Val Ala Thr Leu Asp Ser His Ala Gly Asn Leu Pro Arg Glu Gly
        515                 520                 525
Ala Val Leu Ile Val Thr Ala Ser Tyr Asn Gly His Pro Pro Asp Asn
        530                 535                 540
Ala Lys Gln Phe Val Asp Trp Leu Asp Gln Ala Ser Ala Asp Glu Val
545                 550                 555                 560
Lys Gly Val Arg Tyr Ser Val Phe Gly Cys Gly Asp Lys Asn Trp Ala
                565                 570                 575
Thr Thr Tyr Gln Lys Val Pro Ala Phe Ile Asp Glu Thr Leu Ala Ala
            580                 585                 590
Lys Gly Ala Glu Asn Ile Ala Asp Arg Gly Glu Ala Asp Ala Ser Asp
        595                 600                 605
Asp Phe Glu Gly Thr Tyr Glu Glu Trp Arg Glu His Met Trp Ser Asp
        610                 615                 620
Val Ala Ala Tyr Phe Asn Leu Asp Ile Glu Asn Ser Glu Asp Asn Lys
625                 630                 635                 640
Ser Thr Leu Ser Leu Gln Phe Val Asp Ser Ala Asp Met Pro Leu
                645                 650                 655
Ala Lys Met His Gly Ala Phe Ser Thr Asn Val Val Ala Ser Lys Glu
            660                 665                 670
Leu Gln Gln Pro Gly Ser Ala Arg Ser Thr Arg His Leu Glu Ile Glu
        675                 680                 685
```

Leu Pro Lys Glu Ala Ser Tyr Gln Glu Gly Asp His Leu Gly Val Ile
690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
            725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
            755                 760                 765

Ala Ala Lys Thr Val Cys Pro Pro His Lys Val Glu Leu Glu Ala Leu
770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
            805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
            835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
            885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
            915                 920                 925

Gly Glu Ala His Leu Tyr Phe Gly Cys Arg Ser Pro His Glu Asp Tyr
            930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
            965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
            995                 1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Ala Gly
    1040                1045

<210> SEQ ID NO 45
<211> LENGTH: 3150
<212> TYPE: DNA
<213> ORGANISM: Artificial Sequence
<220> FEATURE:
<223> OTHER INFORMATION: synthetic P450-BM3 variant polynucleotide

<400> SEQUENCE: 45

-continued

```
atgacaataa aggaaatgcc gcagccgaaa acgtttggag aacttaaaaa tttaccgtta      60
ttaaacacag ataaaccggt tcaagctttg atgcgcattg cggatgaatt aggagaaatc     120
tttaaattcg aggcgcctgg ttgtgtaacg cgctacttat caagtcagcg tctaattaaa     180
gaagcatgcg atgaatcacg ctttgataaa aacttaagtc aagcgcttaa atttgcacgt     240
gattttgcag gagacgggtt ggtgacaagc tggacgcatg aaccgaattg gaaaaaagcg     300
cataatatct tacttccaag ctttagtcag caggcaatga aacgctatca tgcgatgatg     360
gtcgatatcg ccgtgcagct tgttcaaaag tgggagcgtc taaatgcaga tgagcatatt     420
gaagtatcgg aagacatgac acgtttaacg cttgatacaa ttggtctttg cggctttaac     480
tatcgcttta acagctttta ccgagatcag cctcatccat ttattgtgag tatggtccgt     540
gcactggatg aagtaatgaa caagctgcag cgagcaaatc cagacgaccc agcttatgat     600
gaaaacaagc gccagtgtca agaagatatc aaggtgatga acgacctagt agataaaatt     660
attgcagatc gcaaagcaag gggtgaacaa agcgatgatt tattaacgca gatgctaaac     720
ggaaaagatc cagaaacggg tgagccgctt gatgacggga acattagcta tcaaattatt     780
acattcttaa ttgcgggaca cgaaacaaca agtggtcttt tatcatttgc gctgtatttc     840
ttagtgaaaa atccacatgt attacaaaaa gtagcagaag aagcagcacg agttctagta     900
gatcctgttc caagctacaa acaagtcaaa cagcttaaat atgtcggcat ggtcttaaac     960
gaagcgctgc gcttatggcc aactgctcct gcgttttccc tatatgcaaa agaagatacg    1020
gtgcttggag gagaatatcc tttagaaaaa ggcgacgaag taatggttct gattcctcag    1080
cttcaccgtg ataaaacaat tggggagac gatgtggagg agttccgtcc agagcgtttt    1140
gaaaatccaa gtgcgattcc gcagcatgcg tttaaaccgt ttggaaacgg tcagcgtgcg    1200
tgtatcggtc agcagttcgc tcttcatgaa gcaacgctgg tacttggtat gatgctaaaa    1260
cactttgact ttgaagatca tacaaactac gagctcgata ttaaagaaac tttaacgtta    1320
aaacctgaag gctttgtggt aaaagcaaaa tcgaaaaaaa ttccgcttgg cggtattcct    1380
tcacctagca ctgaacagtc tgctaaaaaa gtacgcaaaa aggcagaaaa cgctcataat    1440
acgccgctgc ttgtgctata cggttcaaat gccggaacag ctgaaggaac ggcgcgtgat    1500
ttagcagata ttgcaatgag caaaggattt gcaccgcagg tcgcaacgct tgattcacac    1560
gccggaaatc ttccgcgcga aggagctgta ttaattgtaa cggcgtctta taacggtcat    1620
ccgcctgata acgcaaagca atttgtcgac tggttagacc aagcgtctgc tgatgaagta    1680
aaaggcgttc gctactccgt atttggatgc ggcgataaaa actgggctac tacgtatcaa    1740
aaagtgcctg cttttatcga tgaaacgctt gccgctaaag gggcagaaaa catcgctgac    1800
cgcggtgaag cagatgcaag cgacgacttt gaaggcacat atgaagaatg gcgtgaacat    1860
atgtggagtg acgtagcagc ctactttaac ctcgacattg aaaacagtga agataataaa    1920
tctactcttt cacttcaatt tgtcgacagc gccgcggata tgccgcttgc gaaaatgcac    1980
ggtgcgtttt caacgaacgt cgtagcaagc aaagaacttc aacagccagg cagtgcacga    2040
agcacgcgac atcttgaaat tgaacttcca aaagaagctt cttatcaaga aggagatcat    2100
ttaggtgtta ttcctcgcaa ctatgaagga atagtaaacc gtgtaacagc aaggttcggc    2160
ctagatgcat cacagcaaat ccgtctggaa gcagaagaag aaaaattagc tcatttgcca    2220
ctcgctaaaa cagtatccgt agaagagctt ctgcaatacg tggagcttca agatcctgtt    2280
acgcgcacgc agcttcgcgc aatggctgct aaaacggtct gcccgccgca taagtagag    2340
```

-continued

| | |
|---|---|
| cttgaagcct tgcttgaaaa gcaagcctac aaagaacaag tgctggcaaa acgtttaaca | 2400 |
| atgcttgaac tgcttgaaaa atacccggcg tgtgaaatga aattcagcga atttatcgcc | 2460 |
| cttctgccaa gcatacgccc gcgctattac tcgatttctt catcacctcg tgtcgatgaa | 2520 |
| aaacaagcaa gcatcacggt cagcgttgtc tcaggagaag cgtggagcgg atatggagaa | 2580 |
| tataaggaa ttgcgtcgaa ctatcttgcc gagctgcaag aaggagatac gattacgtgc | 2640 |
| tttatttcca caccgcagtc agaatttacg ctgccaaaag accctgaaac gccgcttatc | 2700 |
| atggtcggac cgggaacagg cgtcgcgccg tttagaggct ttgtgcaggc gcgcaaacag | 2760 |
| ctaaaagaac aaggacagtc acttggagaa gcacatttat acttcggctg ccgttcacct | 2820 |
| catgaagact atctgtatca agaagagctt gaaaacgccc aaagcgaagg catcattacg | 2880 |
| cttcataccg cttttctcg catgccaaat cagccgaaaa catacgttca gcacgtaatg | 2940 |
| gaacaagacg gcaagaaatt gattgaactt cttgatcaag gagcgcactt ctatatttgc | 3000 |
| ggagacggaa gccaaatggc acctgccgtt gaagcaacgc ttatgaaaag ctatgctgac | 3060 |
| gttcaccaag tgagtgaagc agacgctcgc ttatggctgc agcagctaga agaaaaaggc | 3120 |
| cgatacgcaa aagacgtgtg ggctgggtaa | 3150 |

<210> SEQ ID NO 46
<211> LENGTH: 1049
<212> TYPE: PRT
<213> ORGANISM: Artificial Sequence
<220> FEATURE:
<223> OTHER INFORMATION: synthetic P450-BM3 variant polypeptide

<400> SEQUENCE: 46

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Arg
            20                  25                  30

Ile Ala Asp Glu Leu Gly Glu Ile Phe Lys Phe Glu Ala Pro Gly Cys
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Ala Arg
65                  70                  75                  80

Asp Phe Ala Gly Asp Gly Leu Val Thr Ser Trp Thr His Glu Pro Asn
                85                  90                  95

Trp Lys Lys Ala His Asn Ile Leu Leu Pro Ser Phe Ser Gln Gln Ala
            100                 105                 110

Met Lys Arg Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Val
                165                 170                 175

Ser Met Val Arg Ala Leu Asp Glu Val Met Asn Lys Leu Gln Arg Ala
            180                 185                 190

Asn Pro Asp Asp Pro Ala Tyr Asp Glu Asn Lys Arg Gln Cys Gln Glu
        195                 200                 205

Asp Ile Lys Val Met Asn Asp Leu Val Asp Lys Ile Ile Ala Asp Arg
    210                 215                 220

```
Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Ser
            245                 250                 255

Tyr Gln Ile Ile Thr Phe Leu Ile Ala Gly His Glu Thr Thr Ser Gly
        260                 265                 270

Leu Leu Ser Phe Ala Leu Tyr Phe Leu Val Lys Asn Pro His Val Leu
    275                 280                 285

Gln Lys Val Ala Glu Ala Ala Arg Val Leu Val Asp Pro Val Pro
290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
            325                 330                 335

Lys Glu Asp Thr Val Leu Gly Gly Tyr Pro Leu Glu Lys Gly Asp
            340                 345                 350

Glu Val Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
            405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
            435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Ala Gly Thr Ala Glu Gly
            485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
            530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
            565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
            595                 600                 605

Asp Phe Glu Gly Thr Tyr Glu Glu Trp Arg Glu His Met Trp Ser Asp
            610                 615                 620

Val Ala Ala Tyr Phe Asn Leu Asp Ile Glu Asn Ser Glu Asp Asn Lys
625                 630                 635                 640
```

-continued

```
Ser Thr Leu Ser Leu Gln Phe Val Asp Ser Ala Ala Asp Met Pro Leu
                645                 650                 655
Ala Lys Met His Gly Ala Phe Ser Thr Asn Val Val Ala Ser Lys Glu
            660                 665                 670
Leu Gln Gln Pro Gly Ser Ala Arg Ser Thr Arg His Leu Glu Ile Glu
        675                 680                 685
Leu Pro Lys Glu Ala Ser Tyr Gln Glu Gly Asp His Leu Gly Val Ile
    690                 695                 700
Pro Arg Asn Tyr Glu Gly Ile Val Asn Arg Val Thr Ala Arg Phe Gly
705                 710                 715                 720
Leu Asp Ala Ser Gln Gln Ile Arg Leu Glu Ala Glu Glu Lys Leu
                725                 730                 735
Ala His Leu Pro Leu Ala Lys Thr Val Ser Val Glu Glu Leu Leu Gln
            740                 745                 750
Tyr Val Glu Leu Gln Asp Pro Val Thr Arg Thr Gln Leu Arg Ala Met
        755                 760                 765
Ala Ala Lys Thr Val Cys Pro His Lys Val Glu Leu Glu Ala Leu
    770                 775                 780
Leu Glu Lys Gln Ala Tyr Lys Glu Gln Val Leu Ala Lys Arg Leu Thr
785                 790                 795                 800
Met Leu Glu Leu Leu Glu Lys Tyr Pro Ala Cys Glu Met Lys Phe Ser
                805                 810                 815
Glu Phe Ile Ala Leu Leu Pro Ser Ile Arg Pro Arg Tyr Tyr Ser Ile
            820                 825                 830
Ser Ser Ser Pro Arg Val Asp Glu Lys Gln Ala Ser Ile Thr Val Ser
        835                 840                 845
Val Val Ser Gly Glu Ala Trp Ser Gly Tyr Gly Glu Tyr Lys Gly Ile
    850                 855                 860
Ala Ser Asn Tyr Leu Ala Glu Leu Gln Glu Gly Asp Thr Ile Thr Cys
865                 870                 875                 880
Phe Ile Ser Thr Pro Gln Ser Glu Phe Thr Leu Pro Lys Asp Pro Glu
                885                 890                 895
Thr Pro Leu Ile Met Val Gly Pro Gly Thr Gly Val Ala Pro Phe Arg
            900                 905                 910
Gly Phe Val Gln Ala Arg Lys Gln Leu Lys Glu Gln Gly Gln Ser Leu
        915                 920                 925
Gly Glu Ala His Leu Tyr Phe Gly Cys Arg Ser Pro His Glu Asp Tyr
    930                 935                 940
Leu Tyr Gln Glu Glu Leu Glu Asn Ala Gln Ser Glu Gly Ile Ile Thr
945                 950                 955                 960
Leu His Thr Ala Phe Ser Arg Met Pro Asn Gln Pro Lys Thr Tyr Val
                965                 970                 975
Gln His Val Met Glu Gln Asp Gly Lys Lys Leu Ile Glu Leu Leu Asp
            980                 985                 990
Gln Gly Ala His Phe Tyr Ile Cys Gly Asp Gly Ser Gln Met Ala Pro
        995                 1000                1005
Ala Val Glu Ala Thr Leu Met Lys Ser Tyr Ala Asp Val His Gln
    1010                1015                1020
Val Ser Glu Ala Asp Ala Arg Leu Trp Leu Gln Gln Leu Glu Glu
    1025                1030                1035
Lys Gly Arg Tyr Ala Lys Asp Val Trp Ala Gly
    1040                1045
```

<210> SEQ ID NO 47
<211> LENGTH: 3150
<212> TYPE: DNA
<213> ORGANISM: Artificial Sequence
<220> FEATURE:
<223> OTHER INFORMATION: synthetic P450-BM3 variant polynucleotide

<400> SEQUENCE: 47

| | | | | | |
|---|---|---|---|---|---|
| atgacaataa | aggaaatgcc | gcagccgaaa | acgtttggag | aacttaaaaa | tttaccgtta | 60 |
| ttaaacacag | ataaaccggt | tcaagctttg | atgaaaattg | cggatgaatt | aggagaaatc | 120 |
| tttaaattcg | aggcgcctgg | ttgtgtaacg | cgctacttat | caagtcagcg | tctaattaaa | 180 |
| gaagcatgcg | atgaatcacg | ctttgataaa | aacttaagtc | aagcgcttaa | atttgcacgt | 240 |
| gattttgcag | agacgggtt | ggtgacaagc | tggacgcatg | aaccgaattg | gaaaaaagcg | 300 |
| cataatatct | tacttccaag | ctttagtcag | caggcaatga | aacgctatca | tgcgatgatg | 360 |
| gtcgatatcg | ccgtgcagct | tgttcaaaag | tgggagcgtc | taaatgcaga | tgagcatatt | 420 |
| gaagtatcgg | aagacatgac | acgtttaacg | cttgatacaa | ttggtctttg | cggctttaac | 480 |
| tatcgcttta | acagctttta | ccgagatcag | cctcatccat | ttattataag | tatggtccgt | 540 |
| gcactggatg | aagtaatgaa | caagctgcag | cgagcaaatc | cagacgaccc | agcttatgat | 600 |
| gaaaacaagc | gccagtgtca | agaagatatc | aaggtgatga | cgacctagt | agataaaatt | 660 |
| attgcagatc | gcaaagcaag | gggtgaacaa | agcgatgatt | tattaacgca | gatgctaaac | 720 |
| ggaaaagatc | cagaaacggg | tgagccgctt | gatgacggga | cattagcta | tcaaattatt | 780 |
| acattcttaa | ttgcgggaca | cgaaacaaca | agtggtcttt | tatcatttgc | gctgtatttc | 840 |
| ttagtgaaaa | atccacatgt | attacaaaaa | gtagcagaag | aagcagcacg | agttctagta | 900 |
| gatcctgttc | caagctacaa | acaagtcaaa | cagcttaaat | atgtcggcat | ggtcttaaac | 960 |
| gaagcgctgc | gcttatggcc | aactgctcct | gcgttttccc | tatatgcaaa | agaagatacg | 1020 |
| gtgcttggag | agaatatcc | tttagaaaaa | ggcgacgaag | taatggttct | gattcctcag | 1080 |
| cttcaccgtg | ataaaacaat | tggggagac | gatgtggagg | agttccgtcc | agagcgtttt | 1140 |
| gaaaatccaa | gtgcgattcc | gcagcatgcg | tttaaaccgt | ttggaaacgg | tcagcgtgcg | 1200 |
| tgtatcggtc | agcagttcgc | tcttcatgaa | gcaacgctgg | tacttggtat | gatgctaaaa | 1260 |
| cactttgact | ttgaagatca | tacaaactac | gagctcgata | ttaaagaaac | tttaacgtta | 1320 |
| aaacctgaag | gctttgtggt | aaaagcaaaa | tcgaaaaaaa | ttccgcttgg | cggtattcct | 1380 |
| tcacctagca | ctgaacagtc | tgctaaaaaa | gtacgcaaaa | aggcagaaaa | cgctcataat | 1440 |
| acgccgctgc | ttgtgctata | cggttcaaat | gccggaacag | ctgaaggaac | ggcgcgtgat | 1500 |
| ttagcagata | ttgcaatgag | caaaggattt | gcaccgcagg | tcgcaacgct | tgattcacac | 1560 |
| gccggaaatc | ttccgcgcga | aggagctgta | ttaattgtaa | cggcgtctta | taacggtcat | 1620 |
| ccgcctgata | acgcaaagca | atttgtcgac | tggttagacc | aagcgtctgc | tgatgaagta | 1680 |
| aaaggcgttc | gctactccgt | atttggatgc | ggcgataaaa | actgggctac | tacgtatcaa | 1740 |
| aaagtgcctg | cttttatcga | tgaaacgctt | gccgctaaag | ggcagaaaa | catcgctgac | 1800 |
| cgcggtgaag | cagatgcaag | cgacgacttt | gaaggcacat | atgaagaatg | gcgtgaacat | 1860 |
| atgtggagtg | acgtagcagc | ctactttaac | ctcgacattg | aaacagtga | agataataaa | 1920 |
| tctactcttt | cacttcaatt | tgtcgacagc | gccgcggata | tgccgcttgc | gaaaatgcac | 1980 |
| ggtgcgtttt | caacgaacgt | cgtagcaagc | aaagaacttc | aacagccagg | cagtgcacga | 2040 |
| agcacgcgac | atcttgaaat | tgaacttcca | aaagaagctt | cttatcaaga | aggagatcat | 2100 |

```
ttaggtgtta ttcctcgcaa ctatgaagga atagtaaacc gtgtaacagc aaggttcggc    2160
ctagatgcat cacagcaaat ccgtctggaa gcagaagaag aaaaattagc tcatttgcca    2220
ctcgctaaaa cagtatccgt agaagagctt ctgcaatacg tggagcttca agatcctgtt    2280
acgcgcacgc agcttcgcgc aatggctgct aaaacggtct gcccgccgca taaagtagag    2340
cttgaagcct tgcttgaaaa gcaagcctac aaagaacaag tgctggcaaa acgtttaaca    2400
atgcttgaac tgcttgaaaa atacccggcg tgtgaaatga aattcagcga atttatcgcc    2460
cttctgccaa gcatacgccc gcgctattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct ttgtgcaggc gcgcaaacag    2760
ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg cttttctcg catgccaaat cagccgaaaa catacgttca gcacgtaatg    2940
gaacaagacg gcaagaaatt gattgaactt cttgatcaag agcgcacttt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctgggtaa                                    3150
```

<210> SEQ ID NO 48
<211> LENGTH: 1049
<212> TYPE: PRT
<213> ORGANISM: Artificial Sequence
<220> FEATURE:
<223> OTHER INFORMATION: synthetic P450-BM3 variant polypeptide

<400> SEQUENCE: 48

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Cys
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Ala Arg
65                  70                  75                  80

Asp Phe Ala Gly Asp Gly Leu Val Thr Ser Trp Thr His Glu Pro Asn
                85                  90                  95

Trp Lys Lys Ala His Asn Ile Leu Leu Pro Ser Phe Ser Gln Gln Ala
            100                 105                 110

Met Lys Arg Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175
```

```
Ser Met Val Arg Ala Leu Asp Glu Val Met Asn Lys Leu Gln Arg Ala
                180                 185                 190
Asn Pro Asp Asp Pro Ala Tyr Asp Glu Asn Lys Arg Gln Cys Gln Glu
            195                 200                 205
Asp Ile Lys Val Met Asn Asp Leu Val Asp Lys Ile Ile Ala Asp Arg
        210                 215                 220
Lys Ala Arg Gly Glu Gln Ser Asp Asp Leu Leu Thr Gln Met Leu Asn
225                 230                 235                 240
Gly Lys Asp Pro Glu Thr Gly Glu Pro Leu Asp Asp Gly Asn Ile Ser
                245                 250                 255
Tyr Gln Ile Ile Thr Phe Leu Ile Ala Gly His Glu Thr Thr Ser Gly
            260                 265                 270
Leu Leu Ser Phe Ala Leu Tyr Phe Leu Val Lys Asn Pro His Val Leu
        275                 280                 285
Gln Lys Val Ala Glu Glu Ala Ala Arg Val Leu Val Asp Pro Val Pro
    290                 295                 300
Ser Tyr Lys Gln Val Lys Gln Leu Lys Tyr Val Gly Met Val Leu Asn
305                 310                 315                 320
Glu Ala Leu Arg Leu Trp Pro Thr Ala Pro Ala Phe Ser Leu Tyr Ala
                325                 330                 335
Lys Glu Asp Thr Val Leu Gly Gly Glu Tyr Pro Leu Glu Lys Gly Asp
            340                 345                 350
Glu Val Met Val Leu Ile Pro Gln Leu His Arg Asp Lys Thr Ile Trp
        355                 360                 365
Gly Asp Asp Val Glu Glu Phe Arg Pro Glu Arg Phe Glu Asn Pro Ser
    370                 375                 380
Ala Ile Pro Gln His Ala Phe Lys Pro Phe Gly Asn Gly Gln Arg Ala
385                 390                 395                 400
Cys Ile Gly Gln Gln Phe Ala Leu His Glu Ala Thr Leu Val Leu Gly
                405                 410                 415
Met Met Leu Lys His Phe Asp Phe Glu Asp His Thr Asn Tyr Glu Leu
            420                 425                 430
Asp Ile Lys Glu Thr Leu Thr Leu Lys Pro Glu Gly Phe Val Val Lys
        435                 440                 445
Ala Lys Ser Lys Lys Ile Pro Leu Gly Gly Ile Pro Ser Pro Ser Thr
    450                 455                 460
Glu Gln Ser Ala Lys Lys Val Arg Lys Lys Ala Glu Asn Ala His Asn
465                 470                 475                 480
Thr Pro Leu Leu Val Leu Tyr Gly Ser Asn Ala Gly Thr Ala Glu Gly
                485                 490                 495
Thr Ala Arg Asp Leu Ala Asp Ile Ala Met Ser Lys Gly Phe Ala Pro
            500                 505                 510
Gln Val Ala Thr Leu Asp Ser His Ala Gly Asn Leu Pro Arg Glu Gly
        515                 520                 525
Ala Val Leu Ile Val Thr Ala Ser Tyr Asn Gly His Pro Pro Asp Asn
    530                 535                 540
Ala Lys Gln Phe Val Asp Trp Leu Asp Gln Ala Ser Ala Asp Glu Val
545                 550                 555                 560
Lys Gly Val Arg Tyr Ser Val Phe Gly Cys Gly Asp Lys Asn Trp Ala
                565                 570                 575
Thr Thr Tyr Gln Lys Val Pro Ala Phe Ile Asp Glu Thr Leu Ala Ala
            580                 585                 590
Lys Gly Ala Glu Asn Ile Ala Asp Arg Gly Glu Ala Asp Ala Ser Asp
```

```
                595                 600                 605
Asp Phe Glu Gly Thr Tyr Glu Glu Trp Arg Glu His Met Trp Ser Asp
            610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
                675                 680                 685

Leu Pro Lys Glu Ala Ser Tyr Gln Glu Gly Asp His Leu Gly Val Ile
            690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
                755                 760                 765

Ala Ala Lys Thr Val Cys Pro Pro His Lys Val Glu Leu Glu Ala Leu
770                 775                 780

Leu Glu Lys Gln Ala Tyr Lys Glu Gln Val Leu Ala Lys Arg Leu Thr
            785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
                835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
            915                 920                 925

Gly Glu Ala His Leu Tyr Phe Gly Cys Arg Ser Pro His Glu Asp Tyr
            930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
            995                 1000                1005

Ala Val Glu Ala Thr Leu Met Lys Ser Tyr Ala Asp Val His Gln
      1010                1015                1020
```

```
Val Ser Glu Ala Asp Ala Arg Leu Trp Leu Gln Gln Leu Glu Glu
    1025                1030                1035
Lys Gly Arg Tyr Ala Lys Asp Val Trp Ala Gly
    1040                1045
```

<210> SEQ ID NO 49
<211> LENGTH: 3150
<212> TYPE: DNA
<213> ORGANISM: Artificial Sequence
<220> FEATURE:
<223> OTHER INFORMATION: synthetic P450-BM3 variant polynucleotide

<400> SEQUENCE: 49

```
atgacaataa aggaaatgcc gcagccgaaa acgtttggag aacttaaaaa tttaccgtta      60
ttaaacacag ataaaccggt tcaagctttg atgaaaattg cggatgaatt aggagaaatc     120
tttaaattcg aggcgcctgg ttgtgtaacg cgctacttat caagtcagcg tctaattaaa     180
gaagcatgcg atgaatcacg ctttgataaa aacttaagtc aagcgcttaa atttgcacgt     240
gattttgcag gagacgggtt ggtgacaagc tggacgcatg aaccgaattg gaaaaaagcg     300
cataatatct acttccaagc ttttagtcag caggcaatga acgctatca tgcgatgatg     360
gtcgatatcg ccgtgcagct tgttcaaaag tgggagcgtc taaatgcaga tgagcatatt     420
gaagtatcgg aagacatgac acgtttaacg cttgatacaa ttggtctttg cggctttaac     480
tatcgcttta cagcttttta ccgagatcag cctcatccat ttattgtgag tatggtccgt     540
gcactggatg aagtaatgaa caagctgcag cgagcaaatc cagacgaccc agcttatgat     600
gaaaacaagc gccagtgtca agaagatatc aaggtgatga cgacctagt agataaaatt     660
attgcagatc gcaaagcaag gggtgaacaa agccacgatt tattaacgca gatgctaaac     720
ggaaaagatc cagaaacggg tgagccgctt gatgacggga cattagcta tcaaattatt     780
acattcttaa ttgcgggaca cgaaacaaca agtggtcttt tatcatttgc gctgtatttc     840
ttagtgaaaa atccacatgt attacaaaaa gtagcagaag aagcagcacg agttctagta     900
gatcctgttc caagctacaa acaagtcaaa cagcttaaat atgtcggcat ggtcttaaac     960
gaagcgctgc gcttatggcc aactgctcct gcgttttccc tatatgcaaa agaagatacg    1020
gtgcttggag agaatatcc tttagaaaaa ggcgacgaag taatggttct gattcctcag    1080
cttcaccgtg ataaaacaat tgggggagac gatgtggagg agttccgtcc agagcgtttt    1140
gaaaatccaa gtgcgattcc gcagcatgcg tttaaaccgt ttggaaacgg tcagcgtgcg    1200
tgtatcggtc agcagttcgc tcttcatgaa gcaacgctgg tacttggtat gatgctaaaa    1260
cactttgact ttgaagatca tacaaactac gagctcgata ttaagaaac tttaacgtta    1320
aaacctgaag gctttgtggt aaaagcaaaa tcgaaaaaaa ttccgcttgg cggtattcct    1380
tcacctagca ctgaacagtc tgctaaaaaa gtacgcaaaa aggcagaaaa cgctcataat    1440
acgccgctgc ttgtgctata cggttcaaat atgggaacag ctgaaggaac ggcgcgtgat    1500
ttagcagata ttgcaatgag caaaggattt gcaccgcagg tcgcaacgct tgattcacac    1560
gccggaaatc ttccgcgcga aggagctgta ttaattgtaa cggcgtctta taacggtcat    1620
ccgcctgata acgcaaagca atttgtcgac tggttagacc aagcgtctgc tgatgaagta    1680
aaaggcgttc gctactccgt atttggatgc ggcgataaaa actgggctac tacgtatcaa    1740
aaagtgcctg ctttatcga tgaaacgctt gccgctaaag ggcagaaaaa catcgctgac    1800
cgcggtgaag cagatgcaag cgacgacttt gaaggcacat atgaagaatg gcgtgaacat    1860
```

```
atgtggagtg acgtagcagc ctactttaac ctcgacattg aaaacagtga agataataaa    1920
tctactcttt cacttcaatt tgtcgacagc gccgcggata tgccgcttgc gaaaatgcac    1980
ggtgcgtttt caacgaacgt cgtagcaagc aaagaacttc aacagccagg cagtgcacga    2040
agcacgcgac atcttgaaat tgaacttcca aaagaagctt cttatcaaga aggagatcat    2100
ttaggtgtta ttcctcgcaa ctatgaagga atagtaaacc gtgtaacagc aaggttcggc    2160
ctagatgcat cacagcaaat ccgtctggaa gcagaagaag aaaaattagc tcatttgcca    2220
ctcgctaaaa cagtatccgt agaagagctt ctgcaatacg tggagcttca agatcctgtt    2280
acgcgcacgc agcttcgcgc aatggctgct aaaacggtct gcccgccgca taaagtagag    2340
cttgaagcct tgcttgaaaa gcaagcctac aaagaacaag tgctggcaaa acgtttaaca    2400
atgcttgaac tgcttgaaaa ataccccggcg tgtgaaatga aattcagcga atttatcgcc    2460
cttctgccaa gcatacgccc gcgctattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct ttgtgcaggc gcgcaaacag    2760
ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg cttttttctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctgggtaa                                     3150
```

<210> SEQ ID NO 50
<211> LENGTH: 1049
<212> TYPE: PRT
<213> ORGANISM: Artificial Sequence
<220> FEATURE:
<223> OTHER INFORMATION: synthetic P450-BM3 variant polypeptide

<400> SEQUENCE: 50

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Cys
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Ala Arg
65                  70                  75                  80

Asp Phe Ala Gly Asp Gly Leu Val Thr Ser Trp Thr His Glu Pro Asn
                85                  90                  95

Trp Lys Lys Ala His Asn Ile Leu Leu Pro Ser Phe Ser Gln Gln Ala
            100                 105                 110

Met Lys Arg Tyr His Ala Met Met Val Asp Ile Ala Val Gln Leu Val
        115                 120                 125

Gln Lys Trp Glu Arg Leu Asn Ala Asp Glu His Ile Glu Val Ser Glu
```

```
            130                 135                 140
Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Val
                165                 170                 175

Ser Met Val Arg Ala Leu Asp Glu Val Met Asn Lys Leu Gln Arg Ala
            180                 185                 190

Asn Pro Asp Asp Pro Ala Tyr Asp Glu Asn Lys Arg Gln Cys Gln Glu
            195                 200                 205

Asp Ile Lys Val Met Asn Asp Leu Val Asp Lys Ile Ile Ala Asp Arg
210                 215                 220

Lys Ala Arg Gly Glu Gln Ser His Asp Leu Leu Thr Gln Met Leu Asn
225                 230                 235                 240

Gly Lys Asp Pro Glu Thr Gly Glu Pro Leu Asp Asp Gly Asn Ile Ser
            245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Val Ala Glu Glu Ala Arg Val Leu Val Asp Pro Val Pro
290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Val Met Val Leu Ile Pro Gln Leu His Arg Asp Lys Thr Ile Trp
            355                 360                 365

Gly Asp Asp Val Glu Glu Phe Arg Pro Glu Arg Phe Glu Asn Pro Ser
        370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
            435                 440                 445

Ala Lys Ser Lys Lys Ile Pro Leu Gly Gly Ile Pro Ser Pro Ser Thr
        450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Ala Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
        530                 535                 540

Ala Lys Gln Phe Val Asp Trp Leu Asp Gln Ala Ser Ala Asp Glu Val
545                 550                 555                 560
```

```
Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
                580                 585                 590

Lys Gly Ala Glu Asn Ile Ala Asp Arg Gly Glu Ala Asp Ala Ser Asp
                595                 600                 605

Asp Phe Glu Gly Thr Tyr Glu Glu Trp Arg Glu His Met Trp Ser Asp
            610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
                660                 665                 670

Leu Gln Gln Pro Gly Ser Ala Arg Ser Thr Arg His Leu Glu Ile Glu
            675                 680                 685

Leu Pro Lys Glu Ala Ser Tyr Gln Glu Gly Asp His Leu Gly Val Ile
            690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
                740                 745                 750

Tyr Val Glu Leu Gln Asp Pro Val Thr Arg Thr Gln Leu Arg Ala Met
                755                 760                 765

Ala Ala Lys Thr Val Cys Pro Pro His Lys Val Glu Leu Glu Ala Leu
                770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
                820                 825                 830

Ser Ser Ser Pro Arg Val Asp Glu Lys Gln Ala Ser Ile Thr Val Ser
                835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
                900                 905                 910

Gly Phe Val Gln Ala Arg Lys Gln Leu Lys Glu Gln Gly Gln Ser Leu
                915                 920                 925

Gly Glu Ala His Leu Tyr Phe Gly Cys Arg Ser Pro His Glu Asp Tyr
            930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975
```

Gln His Val Met Glu Gln Asp Gly Lys Lys Leu Ile Glu Leu Leu Asp
                980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln
        1010                1015                1020

Val Ser Glu Ala Asp Ala Arg Leu Trp Leu Gln Gln Leu Glu Glu
        1025                1030                1035

Lys Gly Arg Tyr Ala Lys Asp Val Trp Ala Gly
        1040                1045

<210> SEQ ID NO 51
<211> LENGTH: 3150
<212> TYPE: DNA
<213> ORGANISM: Artificial Sequence
<220> FEATURE:
<223> OTHER INFORMATION: synthetic P450-BM3 variant polynucleotide

<400> SEQUENCE: 51

| | |
|---|---:|
| atgacaataa aggaaatgcc gcagccgaaa acgtttggag aacttaaaaa tttaccgtta | 60 |
| ttaaacacag ataaaccggt tcaagctttg atgcgcattg cggatgaatt aggagaaatc | 120 |
| tttaaattcg aggcgcctgg ttgtgtaacg cgctacttat caagtcagcg tctaattaaa | 180 |
| gaagcatgcg atgaatcacg ctttgataaa aacttaagtc aagcgcttaa atttgcacgt | 240 |
| gattttgcag gagacgggtt ggtgacaagc tggacgcatg aaataaattg gaaaaaagcg | 300 |
| cataatatct tacttccaag ctttagtcag caggcaatga acgctatca tgcgatgatg | 360 |
| gtcgatatcg ccgtgcagct tgttcaaaag tgggagcgtc taaatgcaga tgagcatatt | 420 |
| gaagtatcgg aagacatgac acgtttaacg cttgatacaa ttggtctttg cggctttaac | 480 |
| tatcgcttta acagctttta ccgagatcag cctcatccat tattataag tatggtccgt | 540 |
| gcactggatg aagtaatgaa caagctgcag cgagcaaatc cagacgaccc agcttatgat | 600 |
| gaaaacaagc gccagtgtca agaagatatc aaggtgatga cgaccctagt agataaaatt | 660 |
| attgcagatc gcaaagcaag gggtgaacaa agccacgatt tattaacgca gatgctaaac | 720 |
| ggaaaagatc cagaaacggg tgagccgctt gatgacggga acattagcta tcaaattatt | 780 |
| acattcttaa ttgcgggaca cgaaacaaca agtggtcttt tatcatttgc gctgtatttc | 840 |
| ttagtgaaaa atccacatgt attacaaaaa gtagcagaag aagcagcacg agttctagta | 900 |
| gatcctgttc caagctacaa acaagtcaaa cagcttaaat atgtcggcat ggtcttaaac | 960 |
| gaagcgctgc gcttatggcc aactgctcct gcgttttccc tatatgcaaa agaagatacg | 1020 |
| gtgcttggag gagaatatcc tttagaaaaa ggcgacgaag taatggttct gattcctcag | 1080 |
| cttcaccgtg ataaacaat tggggagac gatgtgagg agttccgtcc agagcgtttt | 1140 |
| gaaaatccaa gtgcgattcc gcagcatgcg tttaaaccgt ttggaaacgg tcagcgtgcg | 1200 |
| tgtatcggtc agcagttcgc tcttcatgaa gcaacgctgg tacttggtat gatgctaaaa | 1260 |
| cactttgact ttgaagatca tacaaactac gagctcgata ttaagaaac tttaacgtta | 1320 |
| aaacctgaag cttttgtggt aaaagcaaaa tcgaaaaaaa ttccgcttgg cggtattcct | 1380 |
| tcacctagca ctgaacagtc tgctaaaaaa gtacgcaaaa aggcagaaaa cgctcataat | 1440 |
| acgccgctgc ttgtgctata cggttcaaat atgggaacag ctgaaggaac ggcgcgtgat | 1500 |
| ttagcagata ttgcaatgag caaaggattt gcaccgcagg tcgcaacgct tgattcacac | 1560 |
| gccggaaatc ttccgcgcga aggagctgta ttaattgtaa cggcgtctta taacggtcat | 1620 |

-continued

```
ccgcctgata acgcaaagca atttgtcgac tggttagacc aagcgtctgc tgatgaagta    1680
aaaggcgttc gctactccgt atttggatgc ggcgataaaa actgggctac tacgtatcaa    1740
aaagtgcctg cttttatcga tgaaacgctt gccgctaaag gggcagaaaa catcgctgac    1800
cgcggtgaag cagatgcaag cgacgacttt gaaggcacat atgaagaatg cgtgaacat     1860 atgtggagtg acgtagcagc ctactttaac ctcgacattg aaaacagtga agataataaa    1920
tctactcttt cacttcaatt tgtcgacagc gccgcggata tgccgcttgc gaaaatgcac    1980
ggtgcgtttt caacgaacgt cgtagcaagc aaagaacttc aacagccagg cagtgcacga    2040
agcacgcgac atcttgaaat tgaacttcca aaagaagctt cttatcaaga aggagatcat    2100
ttaggtgtta ttcctcgcaa ctatgaagga atagtaaacc gtgtaacagc aaggttcggc    2160
ctagatgcat cacagcaaat ccgtctggaa gcagaagaag aaaaattagc tcatttgcca    2220
ctcgctaaaa cagtatccgt agaagagctt ctgcaatacg tggagcttca agatcctgtt    2280
acgcgcacgc agcttcgcgc aatggctgct aaaacggtct gcccgccgca taagtagag    2340 cttgaagcct tgcttgaaaa gcaagcctac aaagaacaag tgctggcaaa acgtttaaca    2400
atgcttgaac tgcttgaaaa atacccggcg tgtgaaatga aattcagcga atttatcgcc    2460
cttctgccaa gcatacgccc cgctattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct ttgtgcaggc gcgcaaacag    2760
ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg ctttttctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctgggtaa                                    3150
```

<210> SEQ ID NO 52
<211> LENGTH: 1049
<212> TYPE: PRT
<213> ORGANISM: Artificial Sequence
<220> FEATURE:
<223> OTHER INFORMATION: synthetic P450-BM3 variant polypeptide

<400> SEQUENCE: 52

```
Met Thr Ile Lys Glu Met Pro Gln Pro Lys Thr Phe Gly Glu Leu Lys
1               5                  10                  15

Asn Leu Pro Leu Leu Asn Thr Asp Lys Pro Val Gln Ala Leu Met Arg
            20                  25                  30

Ile Ala Asp Glu Leu Gly Glu Ile Phe Lys Phe Glu Ala Pro Gly Cys
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Ala Arg
65                  70                  75                  80

Asp Phe Ala Gly Asp Gly Leu Val Thr Ser Trp Thr His Glu Ile Asn
                85                  90                  95
```

```
Trp Lys Lys Ala His Asn Ile Leu Leu Pro Ser Phe Ser Gln Gln Ala
            100                 105                 110

Met Lys Arg Tyr His Ala Met Val Asp Ile Ala Val Gln Leu Val
            115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Ala Leu Asp Glu Val Met Asn Lys Leu Gln Arg Ala
            180                 185                 190

Asn Pro Asp Asp Pro Ala Tyr Asp Glu Asn Lys Arg Gln Cys Gln Glu
            195                 200                 205

Asp Ile Lys Val Met Asn Asp Leu Val Asp Lys Ile Ile Ala Asp Arg
    210                 215                 220

Lys Ala Arg Gly Glu Gln Ser His Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
            275                 280                 285

Gln Lys Val Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Val Met Val Leu Ile Pro Gln Leu His Arg Asp Lys Thr Ile Trp
            355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
            435                 440                 445

Ala Lys Ser Lys Lys Ile Pro Leu Gly Gly Ile Pro Ser Pro Ser Thr
    450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Ala Gly Thr Ala Glu Gly
                485                 490                 495

Thr Ala Arg Asp Leu Ala Asp Ile Ala Met Ser Lys Gly Phe Ala Pro
            500                 505                 510
```

```
Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
            565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
            595                 600                 605

Asp Phe Glu Gly Thr Tyr Glu Glu Trp Arg Glu His Met Trp Ser Asp
610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
            645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
            675                 680                 685

Leu Pro Lys Glu Ala Ser Tyr Gln Glu Gly Asp His Leu Gly Val Ile
            690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
            725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
            755                 760                 765

Ala Ala Lys Thr Val Cys Pro Pro His Lys Val Glu Leu Glu Ala Leu
770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
            805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
            835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
            885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
            915                 920                 925

Gly Glu Ala His Leu Tyr Phe Gly Cys Arg Ser Pro His Glu Asp Tyr
```

```
                930             935             940
Leu Tyr Gln Glu Glu Leu Glu Asn Ala Gln Ser Glu Gly Ile Ile Thr
945             950             955             960

Leu His Thr Ala Phe Ser Arg Met Pro Asn Gln Pro Lys Thr Tyr Val
            965             970             975

Gln His Val Met Glu Gln Asp Gly Lys Lys Leu Ile Glu Leu Leu Asp
            980             985             990

Gln Gly Ala His Phe Tyr Ile Cys Gly Asp Gly Ser Gln Met Ala Pro
            995             1000            1005

Ala Val Glu Ala Thr Leu Met Lys Ser Tyr Ala Asp Val His Gln
    1010            1015            1020

Val Ser Glu Ala Asp Ala Arg Leu Trp Leu Gln Gln Leu Glu Glu
    1025            1030            1035

Lys Gly Arg Tyr Ala Lys Asp Val Trp Ala Gly
    1040            1045

<210> SEQ ID NO 53
<211> LENGTH: 3150
<212> TYPE: DNA
<213> ORGANISM: Artificial Sequence
<220> FEATURE:
<223> OTHER INFORMATION: synthetic P450-BM3 variant polynucleotide

<400> SEQUENCE: 53
atgacaataa aggaaatgcc gcagccgaaa acgtttggag aacttaaaaa tttaccgtta      60
ttaaacacag ataaaccggt tcaagctttg atgcgcattg cggatgaatt aggagaaatc     120
tttaaattcg aggcgcctgg ttgtgtaacg cgctacttat caagtcagcg tctaattaaa     180
gaagcatgcg atgaatcacg ctttgataaa aacttaagtc aagcgcttaa atttgcacgt     240
gattttgcag gagacgggtt ggtgacaagc tggacgcatg aaataaattg gaaaaaagcg     300
cataatatct tacttccaag ctttagtcag caggcaatga acgctatca tgcgatgatg     360
gtcgatatcg ccgtgcagct tgttcaaaag tgggagcgtc taaatgcaga tgagcatatt     420
gaagtatcgg aagacatgac acgtttaacg cttgatacaa ttggtctttg cggctttaac     480
tatcgcttta acagcttta ccgagatcag cctcatccat tattataag tatggtccgt     540
gcactggatg aagtaatgaa caagctgcag cgagcaaatc cagacgaccc agcttatgat     600
gaaaacaagc gccagtgtca agaagatatc aaggtgatga cgacctagt agataaaatt     660
attgcagatc gcaaagcaag gggtgaacaa agcgatgatt tattaacgca gatgctaaac     720
ggaaaagatc cagaaacggg tgagccgctt gatgacggga acattagcta tcaaattatt     780
acattcttaa ttgcgggaca cgaaacaaca gtggtctttt atcatttgc gctgtatttc     840
ttagtgaaaa atccacatgt attacaaaaa gtagcagaag aagcagcacg agttctagta     900
gatcctgttc aagctacaa acaagtcaaa cagcttaaat atgtcggcat ggtcttaaac     960
gaagcgctgc gcttatggcc aactgctcct gcgttttccc tatatgcaaa agaagatacg    1020
gtgcttggag gagaatatcc tttagaaaaa ggcgacgaag taatggttct gattcctcag    1080
cttcaccgtg ataaaacaat tgggggagac gatgtggagg agttccgtcc agagcgtttt    1140
gaaaatccaa gtgcgattcc gcagcatgcg tttaaaccgt ttggaaacgg tcagcgtgcg    1200
tgtatcggtc agcagttcgc tcttcatgaa gcaacgctgg tacttggtat gatgctaaaa    1260
cactttgact ttgaagatca tacaaactac gagctcgata ttaagaaac tttaacgtta    1320
aaacctgaag gctttgtggt aaaagcaaaa tcgaaaaaaa ttccgcttgg cggtattcct    1380
```

| | |
|---|---|
| tcacctagca ctgaacagtc tgctaaaaaa gtacgcaaaa aggcagaaaa cgctcataat | 1440 |
| acgccgctgc ttgtgctata cggttcaaat gccggaacag ctgaaggaac ggcgcgtgat | 1500 |
| ttagcagata ttgcaatgag caaaggattt gcaccgcagg tcgcaacgct tgattcacac | 1560 |
| gccggaaatc ttccgcgcga aggagctgta ttaattgtaa cggcgtctta taacggtcat | 1620 |
| ccgcctgata acgcaaagca atttgtcgac tggttagacc aagcgtctgc tgatgaagta | 1680 |
| aaaggcgttc gctactccgt atttggatgc ggcgataaaa actgggctac tacgtatcaa | 1740 |
| aaagtgcctg cttttatcga tgaaacgctt gtcgctaaag gggcagaaaa catcgctgac | 1800 |
| cgcggtgaag cagatgcaag cgacgacttt gaaggcacat atgaagaatg gcgtgaacat | 1860 |
| atgtggagtg acgtagcagc ctactttaac ctcgacattg aaacagtga agataataaa | 1920 |
| tctactcttt cacttcaatt tgtcgacagc gccgcggata tgccgcttgc gaaaatgcac | 1980 |
| ggtgcgtttt caacgaacgt cgtagcaagc aaagaacttc aacagccagg cagtgcacga | 2040 |
| agcacgcgac atcttgaaat tgaacttcca aaagaagctt cttatcaaga aggagatcat | 2100 |
| ttaggtgtta ttcctcgcaa ctatgaagga atagtaaacc gtgtaacagc aaggttcggc | 2160 |
| ctagatgcat cacagcaaat ccgtctggaa gcagaagaag aaaaattagc tcatttgcca | 2220 |
| ctcgctaaaa cagtatccgt agaagagctt ctgcaatacg tggagcttca agatcctgtt | 2280 |
| acgcgcacgc agcttcgcgc aatggctgct aaaacggtct gcccgccgca taagtagag | 2340 |
| cttgaagcct tgcttgaaaa gcaagcctac aagaacaag tgctggcaaa acgtttaaca | 2400 |
| atgcttgaac tgcttgaaaa ataccccggcg tgtgaaatga aattcagcga atttatcgcc | 2460 |
| cttctgccaa gcatacgccc gcgctattac tcgatttctt catcacctcg tgtcgatgaa | 2520 |
| aaacaagcaa gcatcacggt cagcgttgtc tcaggagaag cgtggagcgg atatgagaa | 2580 |
| tataaaggaa ttgcgtcgaa ctatcttgcc gagctgcaag aaggagatac gattacgtgc | 2640 |
| tttatttcca caccgcagtc agaatttacg ctgccaaaag accctgaaac gccgcttatc | 2700 |
| atggtcggac cgggaacagg cgtcgcgccg tttagaggct ttgtgcaggc cgcaaacag | 2760 |
| ctaaaagaac aaggacagtc acttggagaa gcacatttat acttcggctg ccgttcacct | 2820 |
| catgaagact atctgtatca agaagagctt gaaaacgccc aaagcgaagg catcattacg | 2880 |
| cttcataccg cttttttctcg catgccaaat cagccgaaaa catacgttca gcacgtaatg | 2940 |
| gaacaagacg gcaagaaatt gattgaactt cttgatcaag gagcgcactt ctatatttgc | 3000 |
| ggagacggaa gccaaatggc acctgccgtt gaagcaacgc ttatgaaaag ctatgctgac | 3060 |
| gttcaccaag tgagtgaagc agacgctcgc ttatggctgc agcagctaga agaaaaggc | 3120 |
| cgatacgcaa aagacgtgtg ggctgggtaa | 3150 |

<210> SEQ ID NO 54
<211> LENGTH: 1049
<212> TYPE: PRT
<213> ORGANISM: Artificial Sequence
<220> FEATURE:
<223> OTHER INFORMATION: synthetic P450-BM3 variant polypeptide

<400> SEQUENCE: 54

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Arg
            20                  25                  30

Ile Ala Asp Glu Leu Gly Glu Ile Phe Lys Phe Glu Ala Pro Gly Cys
        35                  40                  45

Val Thr Arg Tyr Leu Ser Ser Gln Arg Leu Ile Lys Glu Ala Cys Asp
 50                     55                      60

Glu Ser Arg Phe Asp Lys Asn Leu Ser Gln Ala Leu Lys Phe Ala Arg
 65                  70                  75                  80

Asp Phe Ala Gly Asp Gly Leu Val Thr Ser Trp Thr His Glu Ile Asn
                 85                  90                  95

Trp Lys Lys Ala His Asn Ile Leu Leu Pro Ser Phe Ser Gln Gln Ala
                100                 105                 110

Met Lys Arg Tyr His Ala Met Met Val Asp Ile Ala Val Gln Leu Val
            115                 120                 125

Gln Lys Trp Glu Arg Leu Asn Ala Asp Glu His Ile Glu Val Ser Glu
            130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Ala Leu Asp Glu Val Met Asn Lys Leu Gln Arg Ala
            180                 185                 190

Asn Pro Asp Asp Pro Ala Tyr Asp Glu Asn Lys Arg Gln Cys Gln Glu
            195                 200                 205

Asp Ile Lys Val Met Asn Asp Leu Val Asp Lys Ile Ala Asp Arg
210                 215                 220

Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
            275                 280                 285

Gln Lys Val Ala Glu Glu Ala Ala Arg Val Leu Val Asp Pro Val Pro
            290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Val Met Val Leu Ile Pro Gln Leu His Arg Asp Lys Thr Ile Trp
            355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
            435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn

```
            465                 470                 475                 480
        Thr Pro Leu Leu Val Leu Tyr Gly Ser Asn Ala Gly Thr Ala Glu Gly
                        485                 490                 495

Thr Ala Arg Asp Leu Ala Asp Ile Ala Met Ser Lys Gly Phe Ala Pro
                    500                 505                 510

Gln Val Ala Thr Leu Asp Ser His Ala Gly Asn Leu Pro Arg Glu Gly
                    515                 520                 525

Ala Val Leu Ile Val Thr Ala Ser Tyr Asn Gly His Pro Pro Asp Asn
        530                 535                 540

Ala Lys Gln Phe Val Asp Trp Leu Asp Gln Ala Ser Ala Asp Glu Val
        545                 550                 555                 560

Lys Gly Val Arg Tyr Ser Val Phe Gly Cys Gly Asp Lys Asn Trp Ala
                        565                 570                 575

Thr Thr Tyr Gln Lys Val Pro Ala Phe Ile Asp Glu Thr Leu Val Ala
                    580                 585                 590

Lys Gly Ala Glu Asn Ile Ala Asp Arg Gly Glu Ala Asp Ala Ser Asp
                    595                 600                 605

Asp Phe Glu Gly Thr Tyr Glu Glu Trp Arg Glu His Met Trp Ser Asp
            610                 615                 620

Val Ala Ala Tyr Phe Asn Leu Asp Ile Glu Asn Ser Glu Asp Asn Lys
        625                 630                 635                 640

Ser Thr Leu Ser Leu Gln Phe Val Asp Ser Ala Ala Asp Met Pro Leu
                        645                 650                 655

Ala Lys Met His Gly Ala Phe Ser Thr Asn Val Val Ala Ser Lys Glu
                        660                 665                 670

Leu Gln Gln Pro Gly Ser Ala Arg Ser Thr Arg His Leu Glu Ile Glu
                    675                 680                 685

Leu Pro Lys Glu Ala Ser Tyr Gln Glu Gly Asp His Leu Gly Val Ile
            690                 695                 700

Pro Arg Asn Tyr Glu Gly Ile Val Asn Arg Val Thr Ala Arg Phe Gly
        705                 710                 715                 720

Leu Asp Ala Ser Gln Gln Ile Arg Leu Glu Ala Glu Glu Lys Leu
                        725                 730                 735

Ala His Leu Pro Leu Ala Lys Thr Val Ser Val Glu Glu Leu Leu Gln
                        740                 745                 750

Tyr Val Glu Leu Gln Asp Pro Val Thr Arg Thr Gln Leu Arg Ala Met
                    755                 760                 765

Ala Ala Lys Thr Val Cys Pro Pro His Lys Val Glu Leu Glu Ala Leu
                    770                 775                 780

Leu Glu Lys Gln Ala Tyr Lys Glu Gln Val Leu Ala Lys Arg Leu Thr
        785                 790                 795                 800

Met Leu Glu Leu Leu Glu Lys Tyr Pro Ala Cys Glu Met Lys Phe Ser
                        805                 810                 815

Glu Phe Ile Ala Leu Leu Pro Ser Ile Arg Pro Arg Tyr Tyr Ser Ile
                        820                 825                 830

Ser Ser Ser Pro Arg Val Asp Glu Lys Gln Ala Ser Ile Thr Val Ser
                    835                 840                 845

Val Val Ser Gly Glu Ala Trp Ser Gly Tyr Gly Glu Tyr Lys Gly Ile
                    850                 855                 860

Ala Ser Asn Tyr Leu Ala Glu Leu Gln Glu Gly Asp Thr Ile Thr Cys
        865                 870                 875                 880

Phe Ile Ser Thr Pro Gln Ser Glu Phe Thr Leu Pro Lys Asp Pro Glu
                        885                 890                 895
```

```
Thr Pro Leu Ile Met Val Gly Pro Gly Thr Gly Val Ala Pro Phe Arg
            900                 905                 910

Gly Phe Val Gln Ala Arg Lys Gln Leu Lys Glu Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys  Gly Asp Gly Ser Gln  Met Ala Pro
            995                 1000                1005

Ala Val  Glu Ala Thr Leu Met  Lys Ser Tyr Ala Asp  Val His Gln
    1010                1015                1020

Val Ser  Glu Ala Asp Ala Arg  Leu Trp Leu Gln Gln  Leu Glu Glu
    1025                1030                1035

Lys Gly  Arg Tyr Ala Lys Asp  Val Trp Ala Gly
    1040                1045
```

<210> SEQ ID NO 55
<211> LENGTH: 3150
<212> TYPE: DNA
<213> ORGANISM: Artificial Sequence
<220> FEATURE:
<223> OTHER INFORMATION: synthetic P450-BM3 variant polynucleotide

<400> SEQUENCE: 55

```
atgacaataa aggaaatgcc gcagccgaaa acgtttggag aacttaaaaa tttaccgtta      60
ttaaacacag ataaaccggt tcaagctttg atgcgcattg cggatgaatt aggagaaatc     120
tttaaattcg aggcgcctgg ttgtgtaacg cgctacttat caagtcagcg tctaattaaa     180
gaagcatgcg atgaatcacg ctttgataaa aacttaagtc aagcgcttaa atttgcacgt     240
gattttgcag agacgggtt ggtgacaagc tggacgcatg aaccgaattg gaaaaaagcg      300
cataatatct tacttccaag ctttagtcag caggcaatga acgctatca tgcgatgatg      360 gtcgatatcg ccgtgcagct tgttcaaaag tgggagcgtc taaatgcaga tgagcatatt     420
gaagtatcgg aagacatgac acgtttaacg cttgatacaa ttggtctttg cggctttaac     480
tatcgcttta acagctttta ccgagatcag cctcatccat ttattataag tatggtccgt     540
gcactggatg aagtaatgaa caagctgcag cgagcaaatc agacgaccc agcttatgat      600 gaaaacaagc gccagtgtca agaagatatc aaggtgatga cgacctagt agataaaatt      660 attgcagatc gcaaagcaag gggtgaacaa agccacgatt tattaacgca gatgctaaac     720
ggaaaagatc cagaaacggg tgagccgctt gatgacggga cattagcta tcaaattat       780 acattcttaa ttgcgggaca cgaaacaaca agtggtcttt atcatttgc gctgtatttc      840 ttagtgaaaa atccacatgt attacaaaaa gtagcagaag aagcagcacg agttctagta     900
gatcctgttc caagctacaa acaagtcaaa cagcttaaat atgtcggcat ggtcttaaac     960
gaagcgctgc gcttatggcc aactgctcct gcgttttccc tatatgcaaa agaagatacg    1020
gtgcttggag gagaatatcc tttagaaaaa ggcgacgaag taatggttct gattcctcag    1080
cttcaccgtg ataaaacaat ttggggagac gatgtggagg agttccgtcc agagcgtttt    1140
```

```
gaaaatccaa gtgcgattcc gcagcatgcg tttaaaccgt ttggaaacgg tcagcgtgcg      1200
tgtatcggtc agcagttcgc tcttcatgaa gcaacgctgg tacttggtat gatgctaaaa      1260
cactttgact ttgaagatca tacaaactac gagctcgata ttaaagaaac tttaacgtta      1320
aaacctgaag ctttgtggt aaaagcaaaa tcgaaaaaaa ttccgcttgg cggtattcct       1380
tcacctagca ctgaacagtc tgctaaaaaa gtacgcaaaa aggcagaaaa cgctcataat      1440
acgccgctgc ttgtgctata cggttcaaat gccggaacag ctgaaggaac ggcgcgtgat      1500
ttagcagata ttgcaatgag caaaggattt gcaccgcagg tcgcaacgct tgattcacac      1560
gccggaaatc ttccgcgcga aggagctgta ttaattgtaa cggcgtctta taacggtcat      1620
ccgcctgata acgcaaagca atttgtcgac tggttagacc aagcgtctgc tgatgaagta      1680
aaaggcgttc gctactccgt atttggatgc ggcgataaaa actgggctac tacgtatcaa      1740
aaagtgcctg cttttatcga tgaaacgctt gccgctaaag gggcagaaaa catcgctgac      1800
cgcggtgaag cagatgcaag cgacgacttt gaaggcacat atgaagaatg gcgtgaacat      1860
atgtggagtg acgtagcagc ctactttaac ctcgacattg aaaacagtga agataataaa      1920
tctactcttt cacttcaatt tgtcgacagc gccgcggata tgccgcttgc gaaaatgcac      1980
ggtgcgtttt caacgaacgt cgtagcaagc aaagaacttc aacagccagg cagtgcacga      2040
agcacgcgac atcttgaaat tgaacttcca aaagaagctt cttatcaaga aggagatcat      2100
ttaggtgtta ttcctcgcaa ctatgaagga atagtaaacc gtgtaacagc aaggttcggc      2160
ctagatgcat cacagcaaat ccgtctggaa gcagaagaag aaaaattagc tcatttgcca      2220
ctcgctaaaa cagtatccgt agaagagctt ctgcaatacg tggagcttca agatcctgtt      2280
acgcgcacgc agcttcgcgc aatggctgct aaaacggtct gcccgccgca taaagtagag      2340
cttgaagcct tgcttgaaaa gcaagcctac aaagaacaag tgctggcaaa acgtttaaca      2400
atgcttgaac tgcttgaaaa atacccggcg tgtgaaatga aattcagcga atttatcgcc      2460
cttctgccaa gcatacgccc gcgctattac tcgatttctt catcacctcg tgtcgatgaa      2520
aaacaagcaa gcatcacggt cagcgttgtc tcaggagaag cgtggagcgg atatgagaa       2580 tataaaggaa ttgcgtcgaa ctatcttgcc gagctgcaag aaggagatac gattacgtgc      2640
tttatttcca caccgcagtc agaatttacg ctgccaaaag accctgaaac gccgcttatc      2700
atggtcggac cggaacagg cgtcgcgccg tttagaggct ttgtgcaggc gcgcaaacag      2760
ctaaaagaac aaggacagtc acttggagaa gcacatttat acttcggctg ccgttcacct      2820
catgaagact atctgtatca agaagagctt gaaaacgccc aaagcgaagg catcattacg      2880
cttcataccg cttttctcg catgccaaat cagccgaaaa catacgttca gcacgtaatg      2940
gaacaagacg gcaagaaatt gattgaactt cttgatcaag gagcgcactt ctatatttgc      3000
ggagacggaa gccaaatggc acctgccgtt gaagcaacgc ttatgaaaag ctatgctgac      3060
gttcaccaag tgagtgaagc agacgctcgc ttatggctgc agcagctaga agaaaaaggc      3120
cgatacgcaa aagacgtgtg ggctgggtaa                                       3150
```

<210> SEQ ID NO 56
<211> LENGTH: 1049
<212> TYPE: PRT
<213> ORGANISM: Artificial Sequence
<220> FEATURE:
<223> OTHER INFORMATION: synthetic P450-BM3 variant polypeptide

<400> SEQUENCE: 56

Met Thr Ile Lys Glu Met Pro Gln Pro Lys Thr Phe Gly Glu Leu Lys

```
1               5                   10                  15
Asn Leu Pro Leu Leu Asn Thr Asp Lys Pro Val Gln Ala Leu Met Arg
                20                  25                  30

Ile Ala Asp Glu Leu Gly Glu Ile Phe Lys Phe Glu Ala Pro Gly Cys
                35                  40                  45

Val Thr Arg Tyr Leu Ser Ser Gln Arg Leu Ile Lys Glu Ala Cys Asp
                50                  55                  60

Glu Ser Arg Phe Asp Lys Asn Leu Ser Gln Ala Leu Lys Phe Ala Arg
65                  70                  75                  80

Asp Phe Ala Gly Asp Gly Leu Val Thr Ser Trp Thr His Glu Pro Asn
                85                  90                  95

Trp Lys Lys Ala His Asn Ile Leu Leu Pro Ser Phe Ser Gln Gln Ala
                100                 105                 110

Met Lys Arg Tyr His Ala Met Met Val Asp Ile Ala Val Gln Leu Val
                115                 120                 125

Gln Lys Trp Glu Arg Leu Asn Ala Asp Glu His Ile Glu Val Ser Glu
                130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Ala Leu Asp Glu Val Met Asn Lys Leu Gln Arg Ala
                180                 185                 190

Asn Pro Asp Asp Pro Ala Tyr Asp Glu Asn Lys Arg Gln Cys Gln Glu
                195                 200                 205

Asp Ile Lys Val Met Asn Asp Leu Val Asp Lys Ile Ile Ala Asp Arg
210                 215                 220

Lys Ala Arg Gly Glu Gln Ser His Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
                260                 265                 270

Leu Leu Ser Phe Ala Leu Tyr Phe Leu Val Lys Asn Pro His Val Leu
                275                 280                 285

Gln Lys Val Ala Glu Glu Ala Ala Arg Val Leu Val Asp Pro Val Pro
                290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
                340                 345                 350

Glu Val Met Val Leu Ile Pro Gln Leu His Arg Asp Lys Thr Ile Trp
                355                 360                 365

Gly Asp Asp Val Glu Glu Phe Arg Pro Glu Arg Phe Glu Asn Pro Ser
                370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
                420                 425                 430
```

```
Asp Ile Lys Glu Thr Leu Thr Leu Lys Pro Glu Gly Phe Val Val Lys
            435                 440                 445

Ala Lys Ser Lys Lys Ile Pro Leu Gly Gly Ile Pro Ser Pro Ser Thr
        450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Ala Gly Thr Ala Glu Gly
                485                 490                 495

Thr Ala Arg Asp Leu Ala Asp Ile Ala Met Ser Lys Gly Phe Ala Pro
                500                 505                 510

Gln Val Ala Thr Leu Asp Ser His Ala Gly Asn Leu Pro Arg Glu Gly
                515                 520                 525

Ala Val Leu Ile Val Thr Ala Ser Tyr Asn Gly His Pro Pro Asp Asn
                530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
                580                 585                 590

Lys Gly Ala Glu Asn Ile Ala Asp Arg Gly Glu Ala Asp Ala Ser Asp
                595                 600                 605

Asp Phe Glu Gly Thr Tyr Glu Glu Trp Arg Glu His Met Trp Ser Asp
                610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
                660                 665                 670

Leu Gln Gln Pro Gly Ser Ala Arg Ser Thr Arg His Leu Glu Ile Glu
                675                 680                 685

Leu Pro Lys Glu Ala Ser Tyr Gln Glu Gly Asp His Leu Gly Val Ile
                690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
                740                 745                 750

Tyr Val Glu Leu Gln Asp Pro Val Thr Arg Thr Gln Leu Arg Ala Met
                755                 760                 765

Ala Ala Lys Thr Val Cys Pro Pro His Lys Val Glu Leu Glu Ala Leu
                770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
                820                 825                 830

Ser Ser Ser Pro Arg Val Asp Glu Lys Gln Ala Ser Ile Thr Val Ser
                835                 840                 845
```

```
Val Val Ser Gly Glu Ala Trp Ser Gly Tyr Gly Tyr Lys Gly Ile
    850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
                900                 905                 910

Gly Phe Val Gln Ala Arg Lys Gln Leu Lys Glu Gln Gly Gln Ser Leu
            915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
                980                 985                 990

Gln Gly Ala His Phe Tyr Ile Cys Gly Asp Gly Ser Gln Met Ala Pro
            995                 1000                1005

Ala Val Glu Ala Thr Leu Met Lys Ser Tyr Ala Asp Val His Gln
    1010            1015                1020

Val Ser Glu Ala Asp Ala Arg Leu Trp Leu Gln Gln Leu Glu Glu
    1025            1030                1035

Lys Gly Arg Tyr Ala Lys Asp Val Trp Ala Gly
    1040            1045
```

<210> SEQ ID NO 57
<211> LENGTH: 3150
<212> TYPE: DNA
<213> ORGANISM: Artificial Sequence
<220> FEATURE:
<223> OTHER INFORMATION: synthetic P450-BM3 variant polynucleotide

<400> SEQUENCE: 57

```
atgacaataa aggaaatgcc gcagccgaaa acgtttggag aacttaaaaa tttaccgtta    60
ttaaacacag ataaaccggt tcaagctttg atgcgcattg cggatgaatt aggagaaatc   120
tttaaattcg aggcgcctgg ttgtgtaacg cgctacttat caagtcagcg tctaattaaa   180
gaagcatgcg atgaatcacg ctttgataaa aacttaagtc aagcgcttaa atttgcacgt   240
gattttgcag agacgggtt ggtgacaagc tggacgcatg aaccgaattg gaaaaagcg    300 cataatatct tacttccaag ctttagtcag caggcaatga acgctatca tgcgatgatg    360 gtcgatatcg ccgtgcagct tgttcaaaag tgggagcgtc taaatgcaga tgagcatatt   420
gaagtatcgg aagacatgac acgtttaacg cttgatacaa ttggtctttg cggctttaac   480
tatcgcttta acagcttta ccgagatcag cctcatccat ttattgtgag tatggtccgt   540
gcactggatg aagtaatgaa caagctgcag cgagcaaatc cagacgaccc agcttatgat   600
gaaaacaagc gccagtgtca agaagatatc aaggtgatga cgacctagt agataaaatt   660 attgcagatc gcaaagcaag gggtgaacaa agccacgatt tattaacgca gatgctaaac   720
ggaaaagatc cagaaacggg tgagccgctt gatgacggga cattagcta tcaaattatt   780 acattcttaa ttgcgggaca cgaaacaaca agtggtcttt tatcatttgc gctgtatttc   840
ttagtgaaaa atccacatgt attacaaaaa gtagcagaag aagcagcacg agttctagta   900
```

```
gatcctgttc caagctacaa acaagtcaaa cagcttaaat atgtcggcat ggtcttaaac      960
gaagcgctgc gcttatggcc aactgctcct gcgttttccc tatatgcaaa agaagatacg     1020
gtgcttggag gagaatatcc tttagaaaaa ggcgacgaag taatggttct gattcctcag     1080
cttcaccgtg ataaaacaat tggggagac gatgtggagg agttccgtcc agagcgtttt      1140
gaaaatccaa gtgcgattcc gcagcatgcg tttaaaccgt ttggaaacgg tcagcgtgcg     1200
tgtatcggtc agcagttcgc tcttcatgaa gcaacgctgg tacttggtat gatgctaaaa     1260
cactttgact ttgaagatca tacaaactac gagctcgata ttaaagaaac tttaacgtta     1320
aaacctgaag gctttgtggt aaaagcaaaa tcgaaaaaaa ttccgcttgg cggtattcct     1380
tcacctagca ctgaacagtc tgctaaaaaa gtacgcaaaa aggcagaaaa cgctcataat     1440
acgccgctgc ttgtgctata cggttcaaat gccggaacag ctgaaggaac ggcgcgtgat     1500
ttagcagata ttgcaatgag caaaggattt gcaccgcagg tcgcaacgct tgattcacac     1560
gccggaaatc ttccgcgcga aggagctgta ttaattgtaa cggcgtctta taacggtcat     1620
ccgcctgata acgcaaagca atttgtcgac tggttagacc aagcgtctgc tgatgaagta     1680
aaaggcgttc gctactccgt atttggatgc ggcgataaaa actgggctac tacgtatcaa     1740
aaagtgcctg cttttatcga tgaaacgctt gccgctaaag gggcagaaaa catcgctgac     1800
cgcggtgaag cagatgcaag cgacgacttt gaaggcacat atgaagaatg gcgtgaacat     1860
atgtggagtg acgtagcagc ctactttaac ctcgacattg aaaacagtga agataataaa     1920
tctactcttt cacttcaatt tgtcgacagc gccgcggata tgccgcttgc gaaaatgcac     1980
ggtgcgtttt caacgaacgt cgtagcaagc aaagaacttc aacagccagg cagtgcacga     2040
agcacgcgac atcttgaaat tgaacttcca aaagaagctt cttatcaaga aggagatcat     2100
ttaggtgtta ttcctcgcaa ctatgaagga atagtaaacc gtgtaacagc aaggttcggc     2160
ctagatgcat cacagcaaat ccgtctggaa gcagaagaag aaaaattagc tcatttgcca     2220
ctcgctaaaa cagtatccgt agaagagctt ctgcaatacg tggagcttca agatcctgtt     2280
acgcgcacgc agcttcgcgc aatggctgct aaaacggtct gcccgccgca taagtagag      2340
cttgaagcct tgcttgaaaa gcaagcctac aaagaacaag tgctggcaaa acgtttaaca     2400
atgcttgaac tgcttgaaaa atacccggcg tgtgaaatga aattcagcga atttatcgcc     2460
cttctgccaa gcatacgccc gcgctattac tcgatttctt catcacctcg tgtcgatgaa     2520
aaacaagcaa gcatcacggt cagcgttgtc tcaggagaag cgtggagcgg atatggagaa     2580
tataaaggaa ttgcgtcgaa ctatcttgcc gagctgcaag aaggagatac gattacgtgc     2640
tttatttcca caccgcagtc agaatttacg ctgccaaaag accctgaaac gccgcttatc     2700
atggtcggac cgggaacagg cgtcgcgccg tttagaggct ttgtgcaggc gcgcaaacag     2760
ctaaaagaac aaggacagtc acttggagaa gcacatttat acttcggctg ccgttcacct     2820
catgaagact atctgtatca agaagagctt gaaaacgccc aaagcgaagg catcattacg     2880
cttcataccg cttttctcg catgccaaat cagccgaaaa catacgttca gcacgtaatg     2940
gaacaagacg gcaagaaatt gattgaactt cttgatcaag gagcgcactt ctatatttgc     3000
ggagacggaa gccaaatggc acctgccgtt gaagcaacgc ttatgaaaag ctatgctgac     3060
gttcaccaag tgagtgaagc agacgctcgc ttatggctgc agcagctaga agaaaaaggc     3120
cgatacgcaa aagacgtgtg ggctgggtaa                                       3150
```

<210> SEQ ID NO 58
<211> LENGTH: 1049

```
<212> TYPE: PRT
<213> ORGANISM: Artificial Sequence
<220> FEATURE:
<223> OTHER INFORMATION: synthetic P450-BM3 variant polypeptide

<400> SEQUENCE: 58

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Arg
            20                  25                  30

Ile Ala Asp Glu Leu Gly Glu Ile Phe Lys Phe Glu Ala Pro Gly Cys
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Ala Arg
65                  70                  75                  80

Asp Phe Ala Gly Asp Gly Leu Val Thr Ser Trp Thr His Glu Pro Asn
                85                  90                  95

Trp Lys Lys Ala His Asn Ile Leu Leu Pro Ser Phe Ser Gln Gln Ala
            100                 105                 110

Met Lys Arg Tyr His Ala Met Met Val Asp Ile Ala Val Gln Leu Val
        115                 120                 125

Gln Lys Trp Glu Arg Leu Asn Ala Asp Glu His Ile Glu Val Ser Glu
130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Val
                165                 170                 175

Ser Met Val Arg Ala Leu Asp Glu Val Met Asn Lys Leu Gln Arg Ala
            180                 185                 190

Asn Pro Asp Asp Pro Ala Tyr Asp Glu Asn Lys Arg Gln Cys Gln Glu
        195                 200                 205

Asp Ile Lys Val Met Asn Asp Leu Val Asp Lys Ile Ile Ala Asp Arg
    210                 215                 220

Lys Ala Arg Gly Glu Gln Ser His Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Val Ala Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Val Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
    370                 375                 380
```

-continued

```
Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
            405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
            435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Ala Gly Thr Ala Glu Gly
            485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
            565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
            595                 600                 605

Asp Phe Glu Gly Thr Tyr Glu Glu Trp Arg Glu His Met Trp Ser Asp
            610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
            645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
            675                 680                 685

Leu Pro Lys Glu Ala Ser Tyr Gln Glu Gly Asp His Leu Gly Val Ile
            690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
            725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
            755                 760                 765

Ala Ala Lys Thr Val Cys Pro Pro His Lys Val Glu Leu Glu Ala Leu
            770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
```

```
                805                 810                 815
Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
            835                 840                 845

Val Val Ser Gly Glu Ala Trp Ser Gly Tyr Gly Glu Tyr Lys Gly Ile
        850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Ala Gly
    1040                1045
```

<210> SEQ ID NO 59
<211> LENGTH: 3150
<212> TYPE: DNA
<213> ORGANISM: Artificial Sequence
<220> FEATURE:
<223> OTHER INFORMATION: synthetic P450-BM3 variant polynucleotide

<400> SEQUENCE: 59

```
atgacaataa aggaaatgcc gcagccgaaa acgtttggag aacttaaaaa tttaccgtta      60
ttaaacacag ataaaccggt tcaagctttg atgaaaattg cggatgaatt aggagaaatc     120
tttaaattcg aggcgcctgg ttgtgtaacg cgctacttat caagtcagcg tctaattaaa     180
gaagcatgcg atgaatcacg ctttgataaa aacttaagtc aagcgcttaa atttgcacgt     240
gattttgcag agacggggtt ggtgacaagc tggacgcatg aaataaattg gaaaaaagcg     300
cataatatct acttccaagc ttttagtcag caggcaatga acgctatca tgcgatgatg     360 gtcgatatcg ccgtgcagct tgttcaaaag tgggagcgtc taaatgcaga tgagcatatt     420
gaagtatcgg aagacatgac acgtttaacg cttgatacaa ttggtctttg cggctttaac     480
tatcgcttta acagctttta ccgagatcag cctcatccat ttattgtgag tatggtccgt     540
gcactggatg aagtaatgaa caagctgcag cgagcaaatc cagacgaccc agcttatgat     600
gaaaacaagc gccagtgtca agaagatatc aaggtgatga cgaccctagt agataaaatt     660
```

```
attgcagatc gcaaagcaag gggtgaacaa agccacgatt tattaacgca gatgctaaac    720
ggaaaagatc cagaaacggg tgagccgctt gatgacggga acattagcta tcaaattatt    780
acattcttaa ttgcgggaca cgaaacaaca agtggtcttt tatcatttgc gctgtatttc    840
ttagtgaaaa atccacatgt attacaaaaa gtagcagaag aagcagcacg agttctagta    900
gatcctgttc caagctacaa acaagtcaaa cagcttaaat atgtcggcat ggtcttaaac    960
gaagcgctgc gcttatggcc aactgctcct gcgttttccc tatatgcaaa agaagatacg   1020
gtgcttggag gagaatatcc tttagaaaaa ggcgacgaag taatggttct gattcctcag   1080
cttcaccgtg ataaaacaat tggggagac gatgtggagg agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact ttgaagatca tacaaactac gagctcgata ttaaagaaac tttaacgtta   1320
aaacctgaag gctttgtggt aaaagcaaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat gccggaacag ctgaaggaac ggcgcgtgat   1500
ttagcagata ttgcaatgag caaaggattt gcaccgcagg tcgcaacgct tgattcacac   1560
gccggaaatc ttccgcgcga aggagctgta ttaattgtaa cggcgtctta taacggtcat   1620
ccgcctgata acgcaaagca atttgtcgac tggttagacc aagcgtctgc tgatgaagta   1680
aaaggcgttc gctactccgt atttggatgc ggcgataaaa actgggctac tacgtatcaa   1740
aaagtgcctg cttttatcga tgaaacgctt gccgctaaag gggcagaaaa catcgctgac   1800
cgcggtgaag cagatgcaag cgacgacttt gaaggcacat atgaagaatg gcgtgaacat   1860
atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctggaa gcagaagaag aaaaattagc tcatttgcca   2220
ctcgctaaaa cagtatccgt agaagagctt ctgcaatacg tggagcttca agatcctgtt   2280
acgcgcacgc agcttcgcgc aatggctgct aaaacggtct gcccgccgca taagtagag   2340
cttgaagcct tgcttgaaaa gcaagcctac aaagaacaag tgctggcaaa acgtttaaca   2400
atgcttgaac tgcttgaaaa atacccggcg tgtgaaatga aattcagcga atttatcgcc   2460
cttctgccaa gcatacgccc gcgctattac tcgatttctt catcacctcg tgtcgatgaa   2520
aaacaagcaa gcatcacggt cagcgttgtc tcaggagaag cgtggagcgg atatggagaa   2580
tataaaggaa ttgcgtcgaa ctatcttgcc gagctgcaag aaggagatac gattacgtgc   2640
tttatttcca caccgcagtc agaatttacg ctgccaaaag accctgaaac gccgcttatc   2700
atggtcggac cgggaacagg cgtcgcgccg tttagaggct tgtgcaggc gcgcaaacag   2760
ctaaaagaac aaggacagtc acttggagaa gcacatttat acttcggctg ccgttcacct   2820
catgaagact atctgtatca agaagagctt gaaaacgccc aaagcgaagg catcattacg   2880
cttcataccg cttttctcg catgccaaat cagccgaaaa catacgttca gcacgtaatg   2940
gaacaagacg gcaagaaatt gattgaactt cttgatcaag gagcgcactt ctatatttgc   3000
ggagacggaa gccaaatggc acctgccgtt gaagcaacgc ttatgaaaag ctatgctgac   3060
```

```
gttcaccaag tgagtgaagc agacgctcgc ttatggctgc agcagctaga agaaaaaggc    3120
cgatacgcaa aagacgtgtg ggctgggtaa                                     3150
```

<210> SEQ ID NO 60
<211> LENGTH: 1049
<212> TYPE: PRT
<213> ORGANISM: Artificial Sequence
<220> FEATURE:
<223> OTHER INFORMATION: synthetic P450-BM3 variant polypeptide

<400> SEQUENCE: 60

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Cys
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Ala Arg
65                  70                  75                  80

Asp Phe Ala Gly Asp Gly Leu Val Thr Ser Trp Thr His Glu Ile Asn
                85                  90                  95

Trp Lys Lys Ala His Asn Ile Leu Leu Pro Ser Phe Ser Gln Gln Ala
            100                 105                 110

Met Lys Arg Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Val
                165                 170                 175

Ser Met Val Arg Ala Leu Asp Glu Val Met Asn Lys Leu Gln Arg Ala
            180                 185                 190

Asn Pro Asp Asp Pro Ala Tyr Asp Glu Asn Lys Arg Gln Cys Gln Glu
        195                 200                 205

Asp Ile Lys Val Met Asn Asp Leu Val Asp Lys Ile Ile Ala Asp Arg
    210                 215                 220

Lys Ala Arg Gly Glu Gln Ser His Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Val Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
```

-continued

```
                340                 345                 350
Glu Val Met Val Leu Ile Pro Gln Leu His Arg Asp Lys Thr Ile Trp
                355                 360                 365
Gly Asp Asp Val Glu Glu Phe Arg Pro Glu Arg Phe Glu Asn Pro Ser
            370                 375                 380
Ala Ile Pro Gln His Ala Phe Lys Pro Phe Gly Asn Gly Gln Arg Ala
385                 390                 395                 400
Cys Ile Gly Gln Gln Phe Ala Leu His Glu Ala Thr Leu Val Leu Gly
                405                 410                 415
Met Met Leu Lys His Phe Asp Phe Glu Asp His Thr Asn Tyr Glu Leu
                420                 425                 430
Asp Ile Lys Glu Thr Leu Thr Leu Lys Pro Glu Gly Phe Val Val Lys
            435                 440                 445
Ala Lys Ser Lys Lys Ile Pro Leu Gly Gly Ile Pro Ser Pro Ser Thr
            450                 455                 460
Glu Gln Ser Ala Lys Lys Val Arg Lys Lys Ala Glu Asn Ala His Asn
465                 470                 475                 480
Thr Pro Leu Leu Val Leu Tyr Gly Ser Asn Ala Gly Thr Ala Glu Gly
                485                 490                 495
Thr Ala Arg Asp Leu Ala Asp Ile Ala Met Ser Lys Gly Phe Ala Pro
            500                 505                 510
Gln Val Ala Thr Leu Asp Ser His Ala Gly Asn Leu Pro Arg Glu Gly
            515                 520                 525
Ala Val Leu Ile Val Thr Ala Ser Tyr Asn Gly His Pro Pro Asp Asn
            530                 535                 540
Ala Lys Gln Phe Val Asp Trp Leu Asp Gln Ala Ser Ala Asp Glu Val
545                 550                 555                 560
Lys Gly Val Arg Tyr Ser Val Phe Gly Cys Gly Asp Lys Asn Trp Ala
                565                 570                 575
Thr Thr Tyr Gln Lys Val Pro Ala Phe Ile Asp Glu Thr Leu Ala Ala
            580                 585                 590
Lys Gly Ala Glu Asn Ile Ala Asp Arg Gly Glu Ala Asp Ala Ser Asp
            595                 600                 605
Asp Phe Glu Gly Thr Tyr Glu Glu Trp Arg Glu His Met Trp Ser Asp
            610                 615                 620
Val Ala Ala Tyr Phe Asn Leu Asp Ile Glu Asn Ser Glu Asp Asn Lys
625                 630                 635                 640
Ser Thr Leu Ser Leu Gln Phe Val Asp Ser Ala Ala Asp Met Pro Leu
                645                 650                 655
Ala Lys Met His Gly Ala Phe Ser Thr Asn Val Val Ala Ser Lys Glu
                660                 665                 670
Leu Gln Gln Pro Gly Ser Ala Arg Ser Thr Arg His Leu Glu Ile Glu
            675                 680                 685
Leu Pro Lys Glu Ala Ser Tyr Gln Glu Gly Asp His Leu Gly Val Ile
            690                 695                 700
Pro Arg Asn Tyr Glu Gly Ile Val Asn Arg Val Thr Ala Arg Phe Gly
705                 710                 715                 720
Leu Asp Ala Ser Gln Gln Ile Arg Leu Glu Ala Glu Glu Lys Leu
                725                 730                 735
Ala His Leu Pro Leu Ala Lys Thr Val Ser Val Glu Glu Leu Leu Gln
            740                 745                 750
Tyr Val Glu Leu Gln Asp Pro Val Thr Arg Thr Gln Leu Arg Ala Met
            755                 760                 765
```

```
Ala Ala Lys Thr Val Cys Pro Pro His Lys Val Glu Leu Glu Ala Leu
        770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Ala Gly
    1040                1045

<210> SEQ ID NO 61
<211> LENGTH: 3150
<212> TYPE: DNA
<213> ORGANISM: Artificial Sequence
<220> FEATURE:
<223> OTHER INFORMATION: synthetic P450-BM3 variant polynucleotide

<400> SEQUENCE: 61
atgacaataa aggaaatgcc gcagccgaaa acgtttggag aacttaaaaa tttaccgtta      60
ttaaacacag ataaaccggt tcaagctttg atgaaaattg cggatgaatt aggagaaatc     120
tttaaattcg aggcgcctgg ttgtgtaacg cgctacttat caagtcagcg tctaattaaa     180
gaagcatgcg atgaatcacg ctttgataaa aacttaagtc aagcgcttaa atttgcacgt     240
gattttgcag gagacgggtt ggtgacaagc tggacgcatg aaataaattg gaaaaaagcg     300
cataatatct tacttccaag ctttagtcag caggcaatga aaggctatca tgcgatgatg     360
gtcgatatcg ccgtgcagct tgttcaaaag tgggagcgtc taaatgcaga tgagcatatt     420
```

```
gaagtatcgg aagacatgac acgtttaacg cttgatacaa ttggtctttg cggctttaac    480
tatcgcttta acagctttta ccgagatcag cctcatccat ttattgtgag tatggtccgt    540
gcactggatg aagtaatgaa caagctgcag cgagcaaatc cagacgaccc agcttatgat    600
gaaaacaagc gccagtgtca agaagatatc aaggtgatga cgacctagt agataaaatt    660
attgcagatc gcaaagcaag gggtgaacaa agcgatgatt tattaacgca gatgctaaac    720
ggaaaagatc cagaaacggg tgagccgctt gatgacggga acattagcta tcaaattatt    780
acattcttaa ttgcgggaca cgaaacaaca agtggtcttt tatcatttgc gctgtatttc    840
ttagtgaaaa atccacatgt attacaaaaa gtagcagaag aagcagcacg agttctagta    900
gatcctgttc caagctacaa acaagtcaaa cagcttaaat atgtcggcat ggtcttaaac    960
gaagcgctgc gcttatggcc aactgctcct gcgttttccc tatatgcaaa agaagatacg   1020
gtgcttggag gagaatatcc tttagaaaaa ggcgacgaag taatggttct gattcctcag   1080
cttcaccgtg ataaaacaat ttggggagac gatgtggagg agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact ttgaagatca tacaaactac gagctcgata ttaaagaaac tttaacgtta   1320
aaacctgaag gctttgtggt aaaagcaaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat gccggaacag ctgaaggaac ggcgcgtgat   1500
ttagcagata ttgcaatgag caaaggattt gcaccgcagg tcgcaacgct tgattcacac   1560
gccggaaatc ttccgcgcga aggagctgta ttaattgtaa cggcgtctta taacggtcat   1620
ccgcctgata acgcaaagca atttgtcgac tggttagacc aagcgtctgc tgatgaagta   1680
aaaggcgttc gctactccgt atttggatgc ggcgataaaa actgggctac tacgtatcaa   1740
aaagtgcctg cttttatcga tgaaacgctt gccgctaaag gggcagaaaa catcgctgac   1800
cgcggtgaag cagatgcaag cgacgacttt gaaggcacat atgaagaatg cgtgaacat   1860
atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctggaa gcagaagaag aaaaattagc tcatttgcca   2220
ctcgctaaaa cagtatccgt agaagagctt ctgcaatacg tggagcttca agatcctgtt   2280
acgcgcacgc agcttcgcgc aatggctgct aaaacggtct gcccgccgca taagtagag    2340
cttgaagcct tgcttgaaaa gcaagcctac aaagaacaag tgctggcaaa acgtttaaca   2400
atgcttgaac tgcttgaaaa ataccccggcg tgtgaaatga aattcagcga atttatcgcc   2460
cttctgccaa gcatacgccc gcgctattac tcgatttctt catcacctcg tgtcgatgaa   2520
aaacaagcaa gcatcacggt cagcgttgtc tcaggagaag cgtggagcgg atatggagaa   2580
tataaaggaa ttgcgtcgaa ctatcttgcc gagctgcaag aaggagatac gattacgtgc   2640
tttatttcca caccgcagtc agaatttacg ctgccaaaag accctgaaac gccgcttatc   2700
atggtcggac cgggaacagg cgtcgcgccg tttagaggct ttgtgcaggc gcgcaaacag   2760
ctaaaagaac aaggacagtc acttggagaa gcacatttat acttcggctg ccgttcacct   2820
```

```
catgaagact atctgtatca agaagagctt gaaaacgccc aaagcgaagg catcattacg    2880
cttcataccg cttttctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctgggtaa                                    3150
```

<210> SEQ ID NO 62
<211> LENGTH: 1049
<212> TYPE: PRT
<213> ORGANISM: Artificial Sequence
<220> FEATURE:
<223> OTHER INFORMATION: synthetic P450-BM3 variant polypeptide

<400> SEQUENCE: 62

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Cys
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Ala Arg
65                  70                  75                  80

Asp Phe Ala Gly Asp Gly Leu Val Thr Ser Trp Thr His Glu Ile Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Val
                165                 170                 175

Ser Met Val Arg Ala Leu Asp Glu Val Met Asn Lys Leu Gln Arg Ala
            180                 185                 190

Asn Pro Asp Asp Pro Ala Tyr Asp Glu Asn Lys Arg Gln Cys Gln Glu
        195                 200                 205

Asp Ile Lys Val Met Asn Asp Leu Val Asp Lys Ile Ile Ala Asp Arg
    210                 215                 220

Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Val Ala Glu Glu Ala Ala Arg Val Leu Val Asp Pro Val Pro
    290                 295                 300
```

```
Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Val Met Val Leu Ile Pro Gln Leu His Arg Asp Lys Thr Ile Trp
            355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
            435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Ala Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
            595                 600                 605

Asp Phe Glu Gly Thr Tyr Glu Glu Trp Arg Glu His Met Trp Ser Asp
            610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
            675                 680                 685

Leu Pro Lys Glu Ala Ser Tyr Gln Glu Gly Asp His Leu Gly Val Ile
            690                 695                 700

Pro Arg Asn Tyr Glu Gly Ile Val Asn Arg Val Thr Ala Arg Phe Gly
705                 710                 715                 720
```

Leu Asp Ala Ser Gln Gln Ile Arg Leu Glu Ala Glu Glu Lys Leu
             725                 730                 735

Ala His Leu Pro Leu Ala Lys Thr Val Ser Val Glu Glu Leu Leu Gln
         740                 745                 750

Tyr Val Glu Leu Gln Asp Pro Val Thr Arg Thr Gln Leu Arg Ala Met
             755                 760                 765

Ala Ala Lys Thr Val Cys Pro Pro His Lys Val Glu Leu Glu Ala Leu
         770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
             805                 810                 815

Glu Phe Ile Ala Leu Leu Pro Ser Ile Arg Pro Arg Tyr Tyr Ser Ile
             820                 825                 830

Ser Ser Ser Pro Arg Val Asp Glu Lys Gln Ala Ser Ile Thr Val Ser
         835                 840                 845

Val Val Ser Gly Glu Ala Trp Ser Gly Tyr Gly Glu Tyr Lys Gly Ile
         850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
             885                 890                 895

Thr Pro Leu Ile Met Val Gly Pro Gly Thr Gly Val Ala Pro Phe Arg
             900                 905                 910

Gly Phe Val Gln Ala Arg Lys Gln Leu Lys Glu Gln Gly Gln Ser Leu
             915                 920                 925

Gly Glu Ala His Leu Tyr Phe Gly Cys Arg Ser Pro His Glu Asp Tyr
         930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
             965                 970                 975

Gln His Val Met Glu Gln Asp Gly Lys Lys Leu Ile Glu Leu Leu Asp
             980                 985                 990

Gln Gly Ala His Phe Tyr Ile Cys Gly Asp Gly Ser Gln Met Ala Pro
         995                 1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Ala Gly
    1040                1045

<210> SEQ ID NO 63
<211> LENGTH: 3150
<212> TYPE: DNA
<213> ORGANISM: Artificial Sequence
<220> FEATURE:
<223> OTHER INFORMATION: synthetic P450-BM3 variant polynucleotide

<400> SEQUENCE: 63
atgacaataa aggaaatgcc gcagccgaaa acgtttggag aacttaaaaa tttaccgtta    60
ttaaacacag ataaaccggt tcaagctttg atgaaaattg cggatgaatt aggagaaatc   120
tttaaattcg aggcgcctgg ttgtgtaacg cgctactat caagtcagcg tctaattaaa   180

```
gaagcatgcg atgaatcacg ctttgataaa aacttaagtc aagcgcttaa atttgcacgt    240
gattttgcag gagacgggtt ggtgacaagc tggacgcatg aaccgaattg gaaaaaagcg    300
cataatatct tacttccaag ctttagtcag caggcaatga aacgctatca tgcgatgatg    360
gtcgatatcg ccgtgcagct tgttcaaaag tgggagcgtc taaatgcaga tgagcatatt    420
gaagtatcgg aagacatgac acgtttaacg cttgatacaa ttggtctttg cggctttaac    480
tatcgcttta acagctttta ccgagatcag cctcatccat ttattataag tatggtccgt    540
gcactggatg aagtaatgaa caagctgcag cgagcaaatc cagacgaccc agcttatgat    600
gaaaacaagc gccagtgtca agaagatatc aaggtgatga acgacctagt agataaaatt    660
attgcagatc gcaaagcaag gggtgaacaa agccacgatt tattaacgca gatgctaaac    720
ggaaaagatc cagaaacggg tgagccgctt gatgacggga acattagcta tcaaattatt    780
acattcttaa ttgcgggaca cgaaacaaca agtggtcttt tatcatttgc gctgtatttc    840
ttagtgaaaa atccacatgt attacaaaaa gtagcagaag aagcagcacg agttctagta    900
gatcctgttc caagctacaa acaagtcaaa cagcttaaat atgtcggcat ggtcttaaac    960
gaagcgctgc gcttatggcc aactgctcct gcgttttccc tatatgcaaa agaagatacg    1020
gtgcttggag gagaatatcc tttagaaaaa ggcgacgaag taatggttct gattcctcag    1080
cttcaccgtg ataaaacaat ttggggagac gatgtggagg agttccgtcc agagcgtttt    1140
gaaaatccaa gtgcgattcc gcagcatgcg tttaaaccgt ttggaaacgg tcagcgtgcg    1200
tgtatcggtc agcagttcgc tcttcatgaa gcaacgctgg tacttggtat gatgctaaaa    1260
cactttgact ttgaagatca tacaaactac gagctcgata ttaaagaaac tttaacgtta    1320
aaacctgaag gctttgtggt aaaagcaaaa tcgaaaaaaa ttccgcttgg cggtattcct    1380
tcacctagca ctgaacagtc tgctaaaaaa gtacgcaaaa aggcagaaaa cgctcataat    1440
acgccgctgc ttgtgctata cggttcaaat atgggaacag ctgaaggaac ggcgcgtgat    1500
ttagcagata ttgcaatgag caaaggattt gcaccgcagg tcgcaacgct tgattccacac   1560 gccggaaatc ttccgcgcga aggagctgta ttaattgtaa cggcgtctta taacggtcat    1620
ccgcctgata acgcaaagca atttgtcgac tggttagacc aagcgtctgc tgatgaagta    1680
aaaggcgttc gctactccgt atttggatgc ggcgataaaa actgggctac tacgtatcaa    1740
aaagtgcctg cttttatcga tgaaacgctt gccgctaaag gggcagaaaa catcgctgac    1800
cgcggtgaag cagatgcaag cgacgacttt gaaggcacat atgaagaatg cgtgaacat    1860 atgtggagtg acgtagcagc ctactttaac ctcgacattg aaaacagtga agataataaa    1920
tctactcttt cacttcaatt tgtcgacagc gccgcggata tgccgcttgc gaaaatgcac    1980
ggtgcgtttt caacgaacgt cgtagcaagc aaagaacttc aacagccagg cagtgcacga    2040
agcacgcgac atcttgaaat tgaacttcca aaagaagctt cttatcaaga aggagatcat    2100
ttaggtgtta ttcctcgcaa ctatgaagga atagtaaacc gtgtaacagc aaggttcggc    2160
ctagatgcat cacagcaaat ccgtctggaa gcagaagaag aaaaattagc tcatttgcca    2220
ctcgctaaaa cagtatccgt agaagagctt ctgcaatacg tggagcttca agatcctgtt    2280
acgcgcacgc agcttcgcgc aatgctgct aaaacggtct gcccgccgca taagtagag     2340 cttgaagcct tgcttgaaaa gcaagcctac aaagaacaag tgctggcaaa acgtttaaca    2400
atgcttgaac tgcttgaaaa atacccggcg tgtgaaatga aattcagcga atttatcgcc    2460
cttctgccaa gcatacgccc gcgctattac tcgatttctt catcacctcg tgtcgatgaa    2520
aaacaagcaa gcatcacggt cagcgttgtc tcaggagaag cgtggagcgg atatggagaa    2580
```

```
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct ttgtgcaggc gcgcaaacag    2760
ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg cttttctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc aacctgccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctgggtaa                                     3150
```

<210> SEQ ID NO 64
<211> LENGTH: 1049
<212> TYPE: PRT
<213> ORGANISM: Artificial Sequence
<220> FEATURE:
<223> OTHER INFORMATION: synthetic P450-BM3 variant polypeptide

<400> SEQUENCE: 64

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Cys
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Ala Arg
65                  70                  75                  80

Asp Phe Ala Gly Asp Gly Leu Val Thr Ser Trp Thr His Glu Pro Asn
                85                  90                  95

Trp Lys Lys Ala His Asn Ile Leu Leu Pro Ser Phe Ser Gln Gln Ala
            100                 105                 110

Met Lys Arg Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Ala Leu Asp Glu Val Met Asn Lys Leu Gln Arg Ala
            180                 185                 190

Asn Pro Asp Asp Pro Ala Tyr Asp Glu Asn Lys Arg Gln Cys Gln Glu
        195                 200                 205

Asp Ile Lys Val Met Asn Asp Leu Val Asp Lys Ile Ile Ala Asp Arg
    210                 215                 220

Lys Ala Arg Gly Glu Gln Ser His Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255
```

```
Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Val Ala Glu Ala Ala Arg Val Leu Val Asp Pro Val Pro
290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
            325                 330                 335

Lys Glu Asp Thr Val Leu Gly Gly Tyr Pro Leu Glu Lys Gly Asp
            340                 345                 350

Glu Val Met Val Leu Ile Pro Gln Leu His Arg Asp Lys Thr Ile Trp
            355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
            405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
            435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
            565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
            595                 600                 605

Asp Phe Glu Gly Thr Tyr Glu Glu Trp Arg Glu His Met Trp Ser Asp
            610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
```

675                 680                 685

Leu Pro Lys Glu Ala Ser Tyr Gln Glu Gly Asp His Leu Gly Val Ile
            690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Leu Leu Gln
            740                 745                 750

Tyr Val Glu Leu Gln Asp Pro Val Thr Arg Thr Gln Leu Arg Ala Met
            755                 760                 765

Ala Ala Lys Thr Val Cys Pro Pro His Lys Val Glu Leu Glu Ala Leu
770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
915                 920                 925

Gly Glu Ala His Leu Tyr Phe Gly Cys Arg Ser Pro His Glu Asp Tyr
930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
995                 1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Ala Gly
    1040                1045

<210> SEQ ID NO 65
<211> LENGTH: 3150
<212> TYPE: DNA
<213> ORGANISM: Artificial Sequence
<220> FEATURE:
<223> OTHER INFORMATION: synthetic P450-BM3 variant polynucleotide

```
<400> SEQUENCE: 65
atgacaataa aggaaatgcc gcagccgaaa acgtttggag aacttaaaaa tttaccgtta      60
ttaaacacag ataaaccggt tcaagctttg atgaaaattg cggatgaatt aggagaaatc     120
tttaaattcg aggcgcctgg ttgtgtaacg cgctacttat caagtcagcg tctaattaaa     180
gaagcatgcg atgaatcacg cttttgataaa aacttaagtc aagcgcttaa atttgcacgt    240
gattttgcag gagacgggtt ggtgacaagc tggacgcatg aaccgaattg gaaaaaagcg    300
cataatatct tacttccaag ctttagtcag caggcaatga aacgctatca tgcgatgatg     360
gtcgatatcg ccgtgcagct tgttcaaaag tgggagcgtc taaatgcaga tgagcatatt     420
gaagtatcgg aagacatgac acgtttaacg cttgatacaa ttggtctttg cggctttaac     480
tatcgcttta acagctttta ccgagatcag cctcatccat ttattgtgag tatggtccgt     540
gcactggatg aagtaatgaa caagctgcag cgagcaaatc cagacgaccc agcttatgat     600
gaaaacaagc gccagtgtca agaagatatc aaggtgatga cgacctagt agataaaatt      660
attgcagatc gcaaagcaag gggtgaacaa agccacgatt tattaacgca gatgctaaac     720
ggaaaagatc cagaaacggg tgagccgctt gatgacggga acattagcta tcaaattatt     780
acattcttaa ttgcgggaca cgaaacaaca agtggtctt tatcatttgc gctgtatttc      840
ttagtgaaaa atccacatgt attacaaaaa gtagcagaag aagcagcacg agttctagta     900
gatcctgttc caagctacaa acaagtcaaa cagcttaaat atgtcggcat ggtcttaaac     960
gaagcgctgc gcttatggcc aactgctcct gcgttttccc tatatgcaaa agaagatacg    1020
gtgcttggag gagaatatcc tttagaaaaa ggcgacgaag taatggttct gattcctcag    1080
cttcaccgtg ataaaacaat ttggggagac gatgtggagg agttccgtcc agagcgtttt    1140
gaaaatccaa gtgcgattcc gcagcatgcg tttaaaccgt ttggaaacgg tcagcgtgcg    1200
tgtatcggtc agcagttcgc tcttcatgaa gcaacgctgg tacttggtat gatgctaaaa    1260
cactttgact ttgaagatca tacaaactac gagctcgata ttaaagaaac tttaacgtta    1320
aaacctgaag gctttgtggt aaaagcaaaa tcgaaaaaaa ttccgcttgg cggtattcct    1380
tcacctagca ctgaacagtc tgctaaaaaa gtacgcaaaa aggcagaaaa cgctcataat    1440
acgccgctgc ttgtgctata cggttcaaat atgggaacag ctgaaggaac ggcgcgtgat    1500
ttagcagata ttgcaatgag caaaggattt gcaccgcagg tcgcaccgct tgattcacac    1560
gccggaaatc ttccgcgcga aggagctgta ttaattgtaa cggcgtctta taacggtcat    1620
ccgcctgata acgcaaagca atttgtcgac tggttagacc aagcgtctgc tgatgaagta    1680
aaaggcgttc gctactccgt atttggatgc ggcgataaaa actgggctac tacgtatcaa    1740
aaagtgcctg cttttatcga tgaaacgctt gccgctaaag gggcagaaaa catcgctgac    1800
cgcggtgaag cagatgcaag cgacgacttt gaaggcacat atgaagaatg gcgtgaacat    1860
atgtggagtg acgtagcagc ctactttaac ctcgacattg aaaacagtga agataataaa    1920
tctactcttt cacttcaatt tgtcgacagc gccgcggata tgccgcttgc gaaaatgcac    1980
ggtgcgtttt caacgaacgt cgtagcaagc aaagaacttc aacagccagg cagtgcacga    2040
agcacgcgac atcttgaaat tgaacttcca aaagaagctt cttatcaaga aggagatcat    2100
ttaggtgtta ttcctcgcaa ctatgaagga atagtaaacc gtgtaacagc aaggttcggc    2160
ctagatgcat cacagcaaat ccgtctggaa gcagaagaag aaaaattagc tcatttgcca    2220
ctcgctaaaa cagtatccgt agaagagctt ctgcaatacg tggagcttca agatcctgtt    2280
acgcgcacgc agcttcgcgc aatggctgct aaaacggtct gcccgccgca taaagtagag    2340
```

```
cttgaagcct tgcttgaaaa gcaagcctac aaagaacaag tgctggcaaa acgtttaaca    2400
atgcttgaac tgcttgaaaa atacccggcg tgtgaaatga aattcagcga atttatcgcc    2460
cttctgccaa gcatacgccc gcgctattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct tgtgcaggc gcgcaaacag    2760 ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg cttttctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc aactgccgtt gaagcaacgc ttatgaaaag ctatgctgac    3060
gttcaccaag tgagtgaagc agacgctcgc ttatggctgc agcagctaga agaaaaggc    3120 cgatacgcaa aagacgtgtg ggctgggtaa                                    3150
```

<210> SEQ ID NO 66
<211> LENGTH: 1049
<212> TYPE: PRT
<213> ORGANISM: Artificial Sequence
<220> FEATURE:
<223> OTHER INFORMATION: synthetic P450-BM3 variant polypeptide

<400> SEQUENCE: 66

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Cys
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Ala Arg
65                  70                  75                  80

Asp Phe Ala Gly Asp Gly Leu Val Thr Ser Trp Thr His Glu Pro Asn
                85                  90                  95

Trp Lys Lys Ala His Asn Ile Leu Leu Pro Ser Phe Ser Gln Gln Ala
            100                 105                 110

Met Lys Arg Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Val
                165                 170                 175

Ser Met Val Arg Ala Leu Asp Glu Val Met Asn Lys Leu Gln Arg Ala
            180                 185                 190

Asn Pro Asp Asp Pro Ala Tyr Asp Glu Asn Lys Arg Gln Cys Gln Glu
        195                 200                 205

Asp Ile Lys Val Met Asn Asp Leu Val Asp Lys Ile Ile Ala Asp Arg
```

-continued

```
            210                 215                 220
Lys Ala Arg Gly Glu Gln Ser His Asp Leu Leu Thr Gln Met Leu Asn
225                 230                 235                 240

Gly Lys Asp Pro Glu Thr Gly Glu Pro Leu Asp Asp Gly Asn Ile Ser
                245                 250                 255

Tyr Gln Ile Ile Thr Phe Leu Ile Ala Gly His Glu Thr Thr Ser Gly
                260                 265                 270

Leu Leu Ser Phe Ala Leu Tyr Phe Leu Val Lys Asn Pro His Val Leu
            275                 280                 285

Gln Lys Val Ala Glu Ala Ala Arg Val Leu Val Asp Pro Val Pro
        290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Tyr Pro Leu Glu Lys Gly Asp
                340                 345                 350

Glu Val Met Val Leu Ile Pro Gln Leu His Arg Asp Lys Thr Ile Trp
            355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
                420                 425                 430

Asp Ile Lys Glu Thr Leu Thr Leu Lys Pro Gly Phe Val Val Lys
            435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
                500                 505                 510

Gln Val Ala Pro Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
                580                 585                 590

Lys Gly Ala Glu Asn Ile Ala Asp Arg Gly Glu Ala Asp Ala Ser Asp
            595                 600                 605

Asp Phe Glu Gly Thr Tyr Glu Glu Trp Arg Glu His Met Trp Ser Asp
        610                 615                 620

Val Ala Ala Tyr Phe Asn Leu Asp Ile Glu Asn Ser Glu Asp Asn Lys
625                 630                 635                 640
```

```
Ser Thr Leu Ser Leu Gln Phe Val Asp Ser Ala Ala Asp Met Pro Leu
            645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
            675                 680                 685

Leu Pro Lys Glu Ala Ser Tyr Gln Glu Gly Asp His Leu Gly Val Ile
            690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
            725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
            755                 760                 765

Ala Ala Lys Thr Val Cys Pro Pro His Lys Val Glu Leu Glu Ala Leu
            770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
            805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
            835                 840                 845

Val Val Ser Gly Glu Ala Trp Ser Gly Tyr Gly Glu Tyr Lys Gly Ile
            850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
            885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
            915                 920                 925

Gly Glu Ala His Leu Tyr Phe Gly Cys Arg Ser Pro His Glu Asp Tyr
            930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
            965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
            995                 1000                1005

Ala Val Glu Ala Thr Leu Met Lys Ser Tyr Ala Asp Val His Gln
            1010                1015                1020

Val Ser Glu Ala Asp Ala Arg Leu Trp Leu Gln Gln Leu Glu Glu
            1025                1030                1035

Lys Gly Arg Tyr Ala Lys Asp Val Trp Ala Gly
            1040                1045
```

<210> SEQ ID NO 67
<211> LENGTH: 3150
<212> TYPE: DNA
<213> ORGANISM: Artificial Sequence
<220> FEATURE:
<223> OTHER INFORMATION: synthetic P450-BM3 variant polynucleotide

<400> SEQUENCE: 67

```
atgacaataa aggaaatgcc gcagccgaaa acgtttggag aacttaaaaa tttaccgtta      60
ttaaacacag ataaaccggt tcaagctttg atgaaaattg cggatgaatt aggagaaatc     120
tttaaattcg aggcgcctgg ttgtgtaacg cgctacttat caagtcagcg tctaattaaa     180
gaagcatgcg atgaatcacg ctttgataaa aacttaagtc aagcgcttaa atttgcacgt     240
gattttgcag gagacgggtt ggtgacaagc tggacgcatg aaccgaattg gaaaaaagcg     300
cataatatct tacttccaag ctttagtcag caggcaatga aaggctatca tgcgatgatg     360
gtcgatatcg ccgtgcagct tgttcaaaag tgggagcgtc taaatgcaga tgagcatatt     420
gaagtatcgg aagacatgac acgtttaacg cttgatacaa ttggtctttg cggctttaac     480
tatcgcttta acagcttta ccgagatcag cctcatccat ttattgtgag tatggtccgt     540
gcactggatg aagtaatgaa caagctgcag cgagcaaatc cagacgaccc agcttatgat     600
gaaaacaagc gccagtgtca agaagatatc aaggtgatga cgacctagt agataaaatt     660
attgcagatc gcaaagcaag gggtgaacaa agccacgatt tattaacgca gatgctaaac     720
ggaaaagatc cagaaacggg tgagccgctt gatgacggga cattagcta tcaaattatt     780
acattcttaa ttgcgggaca cgaaacaaca agtggtcttt tatcatttgc gctgtatttc     840
ttagtgaaaa atccacatgt attacaaaaa gtagcagaag aagcagcacg agttctagta     900
gatcctgttc caagctacaa acaagtcaaa cagcttaaat atgtcggcat ggtcttaaac     960
gaagcgctgc gcttatggcc aactgctcct gcgttttccc tatatgcaaa agaagatacg    1020
gtgcttggag gagaatatcc tttagaaaaa ggcgacgaag taatggttct gattcctcag    1080
cttcaccgtg ataaaacaat ttggggagac gatgtggagg agttccgtcc agagcgtttt    1140
gaaaatccaa gtgcgattcc gcagcatgcg tttaaaccgt ttggaaacgg tcagcgtgcg    1200
tgtatcggtc agcagttcgc tcttcatgaa gcaacgctgg tacttggtat gatgctaaaa    1260
cactttgact tgaagatca tacaaactac gagctcgata ttaaagaaac tttaacgtta    1320
aaacctgaag gctttgtggt aaaagcaaaa tcgaaaaaaa ttccgcttgg cggtattcct    1380
tcacctagca ctgaacagtc tgctaaaaaa gtacgcaaaa aggcagaaaa cgctcataat    1440
acgccgctgc ttgtgctata cggttcaaat atgccggaac ag ctgaaggaac ggcgcgtgat    1500
ttagcagata ttgcaatgag caaaggattt gcaccgcagg tcgcaacgct tgattcacac    1560
gccggaaatc ttccgcgcga aggagctgta ttaattgtaa cggcgtctta taacggtcat    1620
ccgcctgata cgcaaagca atttgtcgac tggttagacc aagcgtctgc tgatgaagta    1680
aaaggcgttc gctactccgt atttggatgc ggcgataaaa actgggctac tacgtatcaa    1740
aaagtgcctg ctttttatcga tgaaacgctt gccgctaaag gggcagaaaa catcgctgac    1800
cgcggtgaag cagatgcaag cgacgacttt gaaggcacat atgaagaatg gcgtgaacat    1860
atgtggagtg acgtagcagc ctactttaac ctcgacattg aaaacagtga agataataaa    1920
tctactcttt cacttcaatt tgtcgacagc gccgcggata tgccgcttgc gaaaatgcac    1980
ggtgcgtttt caacgaacgt cgtagcaagc aaagaacttc aacagccagg cagtgcacga    2040
agcacgcgac atcttgaaat tgaacttcca aaagaagctt cttatcaaga aggagatcat    2100
```

```
ttaggtgtta ttcctcgcaa ctatgaagga atagtaaacc gtgtaacagc aaggttcggc    2160
ctagatgcat cacagcaaat ccgtctggaa gcagaagaag aaaaattagc tcatttgcca    2220
ctcgctaaaa cagtatccgt agaagagctt ctgcaatacg tggagcttca agatcctgtt    2280
acgcgcacgc agcttcgcgc aatggctgct aaaacggtct gcccgccgca taaagtagag    2340
cttgaagcct tgcttgaaaa gcaagcctac aaagaacaag tgctggcaaa acgtttaaca    2400
atgcttgaac tgcttgaaaa atacccggcg tgtgaaatga aattcagcga atttatcgcc    2460
cttctgccaa gcatacgccc gcgctattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct tgtgcaggc gcgcaaacag    2760 ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg cttttctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctgggtaa                                    3150
```

<210> SEQ ID NO 68
<211> LENGTH: 1049
<212> TYPE: PRT
<213> ORGANISM: Artificial Sequence
<220> FEATURE:
<223> OTHER INFORMATION: synthetic P450-BM3 variant polypeptide

<400> SEQUENCE: 68

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Cys
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Ala Arg
65                  70                  75                  80

Asp Phe Ala Gly Asp Gly Leu Val Thr Ser Trp Thr His Glu Pro Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Val
                165                 170                 175
```

```
Ser Met Val Arg Ala Leu Asp Glu Val Met Asn Lys Leu Gln Arg Ala
            180                 185                 190

Asn Pro Asp Asp Pro Ala Tyr Asp Glu Asn Lys Arg Gln Cys Gln Glu
            195                 200                 205

Asp Ile Lys Val Met Asn Asp Leu Val Asp Lys Ile Ile Ala Asp Arg
210                 215                 220

Lys Ala Arg Gly Glu Gln Ser His Asp Leu Leu Thr Gln Met Leu Asn
225                 230                 235                 240

Gly Lys Asp Pro Glu Thr Gly Glu Pro Leu Asp Asp Gly Asn Ile Ser
            245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
            275                 280                 285

Gln Lys Val Ala Glu Glu Ala Ala Arg Val Leu Val Asp Pro Val Pro
            290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Val Met Val Leu Ile Pro Gln Leu His Arg Asp Lys Thr Ile Trp
            355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
            405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
            435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Ala Gly Thr Ala Glu Gly
            485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
            530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
            565                 570                 575

Thr Thr Tyr Gln Lys Val Pro Ala Phe Ile Asp Glu Thr Leu Ala Ala
            580                 585                 590
```

```
Lys Gly Ala Glu Asn Ile Ala Asp Arg Gly Glu Ala Asp Ala Ser Asp
            595                 600                 605

Asp Phe Glu Gly Thr Tyr Glu Glu Trp Arg Glu His Met Trp Ser Asp
610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
            645                 650                 655

Ala Lys Met His Gly Ala Phe Ser Thr Asn Val Val Ala Ser Lys Glu
                660                 665                 670

Leu Gln Gln Pro Gly Ser Ala Arg Ser Thr Arg His Leu Glu Ile Glu
            675                 680                 685

Leu Pro Lys Glu Ala Ser Tyr Gln Glu Gly Asp His Leu Gly Val Ile
            690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
                740                 745                 750

Tyr Val Glu Leu Gln Asp Pro Val Thr Arg Thr Gln Leu Arg Ala Met
            755                 760                 765

Ala Ala Lys Thr Val Cys Pro Pro His Lys Val Glu Leu Glu Ala Leu
                770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
                820                 825                 830

Ser Ser Ser Pro Arg Val Asp Glu Lys Gln Ala Ser Ile Thr Val Ser
                835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
            915                 920                 925

Gly Glu Ala His Leu Tyr Phe Gly Cys Arg Ser Pro His Glu Asp Tyr
            930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
                980                 985                 990

Gln Gly Ala His Phe Tyr Ile Cys Gly Asp Gly Ser Gln Met Ala Pro
            995                 1000                1005

Ala Val Glu Ala Thr Leu Met Lys Ser Tyr Ala Asp Val His Gln
```

-continued

```
            1010                1015                1020
Val  Ser  Glu  Ala  Asp  Ala  Arg  Leu  Trp  Leu  Gln  Gln  Leu  Glu  Glu
       1025                1030                1035

Lys  Gly  Arg  Tyr  Ala  Lys  Asp  Val  Trp  Ala  Gly
       1040                1045
```